(12) United States Patent
Hafner et al.

(10) Patent No.: US 9,340,580 B2
(45) Date of Patent: May 17, 2016

(54) PEPTIDE WITH MULTIPLE EPITOPES

(75) Inventors: Roderick Peter Hafner, Oxford (GB); Mark Larche, Ontario (CA)

(73) Assignee: Circassia Limited, Oxford (GB)

( * ) Notice: Subject to any disclaimer, the term of this patent is extended or adjusted under 35 U.S.C. 154(b) by 711 days.

(21) Appl. No.: 12/673,386

(22) PCT Filed: Aug. 15, 2008

(86) PCT No.: PCT/GB2008/002778
§ 371 (c)(1),
(2), (4) Date: Mar. 11, 2010

(87) PCT Pub. No.: WO2009/022154
PCT Pub. Date: Feb. 19, 2009

(65) Prior Publication Data
US 2010/0298239 A1    Nov. 25, 2010

(30) Foreign Application Priority Data

Aug. 15, 2007  (GB) .................. 0715949.4
Aug. 20, 2007  (GB) .................. 0716224.1
Nov. 28, 2007  (GB) .................. 0723337.2

(51) Int. Cl.
| | | |
|---|---|---|
| *A61K 39/00* | (2006.01) |
| *A61K 45/00* | (2006.01) |
| *C07K 7/08* | (2006.01) |
| *A61K 39/35* | (2006.01) |
| *A61K 39/36* | (2006.01) |
| *C07K 14/415* | (2006.01) |
| *C07K 14/435* | (2006.01) |
| *G01N 33/569* | (2006.01) |
| *C07K 16/16* | (2006.01) |
| *C07K 16/18* | (2006.01) |
| *C07K 7/06* | (2006.01) |
| *A61K 39/39* | (2006.01) |

(52) U.S. Cl.
CPC .............. *C07K 7/08* (2013.01); *A61K 39/0005* (2013.01); *A61K 39/0008* (2013.01); *A61K 39/35* (2013.01); *A61K 39/36* (2013.01); *C07K 7/06* (2013.01); *C07K 14/415* (2013.01); *C07K 14/435* (2013.01); *C07K 14/43531* (2013.01); *C07K 16/16* (2013.01); *C07K 16/18* (2013.01); *G01N 33/56977* (2013.01); *A61K 39/0002* (2013.01); *A61K 39/39* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,906,564 A | 3/1990 | Lyon et al. |
| 5,114,713 A | 5/1992 | Sinigaglia |
| 5,126,399 A | 6/1992 | Arlinghaus et al. |
| 5,547,669 A | 8/1996 | Rogers et al. |
| 5,820,862 A | 10/1998 | Garman et al. |
| 5,968,526 A | 10/1999 | Garman et al. |
| 6,982,326 B1 | 1/2006 | Griffith et al. |
| 2002/0192705 A1 | 12/2002 | Matsushita et al. |
| 2004/0071718 A1 | 4/2004 | Tsai |
| 2004/0265342 A1 | 12/2004 | Larche et al. |
| 2006/0057641 A1 | 3/2006 | Morgenstern et al. |
| 2006/0084789 A1 | 4/2006 | O'Hehir et al. |
| 2008/0075725 A1 | 3/2008 | O'Hehir et al. |
| 2010/0239599 A1 | 9/2010 | Hafner et al. |
| 2010/0260805 A1 | 10/2010 | Hafner et al. |
| 2011/0217325 A1 | 9/2011 | O'Hehir et al. |

FOREIGN PATENT DOCUMENTS

| | | |
|---|---|---|
| EP | 0340109 A2 | 11/1989 |
| EP | 0367306 A2 | 5/1990 |
| GB | 2455108 | 6/2009 |
| JP | 6-16695 | 1/1994 |
| WO | 91/06571 A1 | 5/1991 |
| WO | 92/04445 A1 | 3/1992 |
| WO | 93/08279 | 4/1993 |
| WO | 93/20842 A1 | 10/1993 |
| WO | 94/04572 A1 | 3/1994 |
| WO | 94/21675 A3 | 9/1994 |
| WO | 94/24281 | 10/1994 |
| WO | 94/27634 | 12/1994 |
| WO | 95/06728 A3 | 3/1995 |
| WO | 95/20599 | 8/1995 |
| WO | 95/28424 | 10/1995 |
| WO | 96/13517 A1 | 5/1996 |
| WO | 97/00027 A1 | 1/1997 |
| WO | 97/35193 A1 | 9/1997 |
| WO | 00/44781 A1 | 8/2000 |
| WO | 01/70772 A2 | 9/2001 |
| WO | 02/16410 A2 | 2/2002 |
| WO | 02/50250 A2 | 6/2002 |
| WO | 02/056905 A2 | 7/2002 |
| WO | 02/062834 A3 | 8/2002 |

(Continued)

OTHER PUBLICATIONS

Web-based tools (2003).*

(Continued)

*Primary Examiner* — Gerald R Ewoldt
*Assistant Examiner* — Marianne Dibrino
(74) *Attorney, Agent, or Firm* — Nelson Mullins Riley & Scarborough LLP; Jane E. Remillard, Esq.; Jeanne M. DiGiorgio, Esq.

(57) ABSTRACT

The present invention relates to peptides comprising multiple MHC Class II-binding T cell epitopes for tolerization therapy.

4 Claims, 1 Drawing Sheet

(56) References Cited

FOREIGN PATENT DOCUMENTS

| WO | 02/080848 | | 10/2002 |
|---|---|---|---|
| WO | 02/081512 | A1 | 10/2002 |
| WO | 03/047618 | A2 | 6/2003 |
| WO | 03/082924 | A1 | 10/2003 |
| WO | 2004/005334 | A2 | 1/2004 |
| WO | 2004/007538 | A2 | 1/2004 |
| WO | 2004/078098 | A2 | 9/2004 |
| WO | 2005/000891 | A2 | 1/2005 |
| WO | 2005/103082 | A2 | 11/2005 |
| WO | 2006/035725 | A1 | 4/2006 |
| WO | 2006/082313 | A3 | 8/2006 |
| WO | 2007/031080 | A1 | 3/2007 |
| WO | 2007/098934 | A1 | 9/2007 |
| WO | 2007/129093 | A2 | 11/2007 |
| WO | 2007/140505 | A2 | 12/2007 |
| WO | 2008/017517 | A1 | 2/2008 |
| WO | 2008/145998 | A1 | 12/2008 |
| WO | 2009/067191 | A2 | 5/2009 |

OTHER PUBLICATIONS

Karin et al (J. Exp. Med. 1994, 180: 2227-2237).*
Thibodeau (OncoImmunology 1:6, 908-916; Sep. 2012, Landes Bioscience).*
Roche and Furata (Nature Reviews/Immunology, 2015, 15: 203-216).*
Wheeler and Woroniecki (Allergology Int. 2001, 50: 295-301).*
Huggins and Looney (2004, aafp.org/afp, 2004, 70(4): 689-696).*
Berzofsky, Jay A., "Structural Basis of Antigen Recognition by T Lymphocytes, Implications for Vaccines," The Journal of Clinical Investigation, Inc., vol. 82:1811-1817 (1988).
Brett, Sara J. et al., "Differential pattern of T cell recognition of the 65-kDa mycobacterial antigen following immunization with the whole protein or peptides," Eur. J. Immunol., vol. 19:1303-1310 (1989).
Briner, Thomas J. et al., "Peripheral T-cell tolerance induced in naive and primed mice by subcutaneous injection of peptides from the major cat allergen Fel k I," Proc. Natl. Acad. Sci. USA, vol. 90:7608-7612 (1993).
Chua, K.Y. et al., "Expression of Dermatophagoides pteronyssinus Allergen, Der p II, in *Escherichia coli* and the Binding Studies with Human IgE," Int. Arch. Allergy Appl. Immunol., vol. 91:124-129 (1990).
Cromwell, Oliver et al., "Transition of recombinant allergens from bench to clinical application," Methods, vol. 32:300-312 (2004).
Ebner, Christof et al., "Nonallergic Individuals Recognize the Same T Cell Epitopes of Bet v 1, the Major Birch Pollen Allergen, as Atopic Patients," The Journal of Immunology, vol. 154:1932-1940 (1995).
Evans, Ronald M., "The Steroid and Thyroid Hormone Receptor Superfamily," Science, vol. 240(4854):889-895 (1988).
Francis, Michael J. et al., "Peptide Vaccines BAsed on Enhanced Immunogenicity of Peptide Epitopes Presented with T-Cell Determinants or Hepatitis B Core Protein," Methods in Enzymology, vol. 178:659-676 (1989).
Greene, W.K. et al., "Antigenic Analysis of Group I House Dust Mite Allergens Using Random Fragments of Der p I Expressed by Recombinant DNA Libraries," Int. Arch. Allergy Immunol., vol. 92:30-38 (1990).
Gurka, Gary et al., "Allergen-specific human T cell clones: Derivation, specificity, and activation requirements," J. Allergy Clin. Immunol., vol. 83:945-954 (1989).
Hogervorst, Els J.M. et al., "Efficient recognition by rat T cell clones of an epitope of mycobacterial hsp 65 inserted in *Escherichia coli* outer membrane protein PhoE," Eur. J. Immunol., vol. 20:2763-2768 (1990).
Horiuchi, Takashi et al., "Core Sequence of Two Separable Terminus Sites of the R6K Plasmid That Exhibit Polar Inhibition of Replication Is a 20 bp Inverted Repeat," Cell, vol. 54:515-523 (1988).
Jeannin, Pascale et al., "Immunogenicity and Antigenicity of Synthetic Peptides Derived from the Mite Allergen Der p I," Molecular Immunology, vol. 30(16):1511-1518 (1993).

Kudo, Koichiro et al., "IgE antibody response to mite antigen in the mouse, Suppression of an established IgE antibody response by chemically modified antigen," The Journal of Allergy and Clinical Immunology, vol. 61(1):1-9 (1977).
Lai, Ming-Zong et al., "T Lymphocyte Response to Bacteriophage I Repressor cl protein, Recognition of the Same Peptide Presented by la Molecules of Different Haplotypes," The Journal of Immunology, vol. 139(12):3973-3980 (1987).
Lamb, Jonathan R. et al., "Mapping of T cell epitopes using recombinant antigens and synthetic peptides," The EMBO Journal, vol. 6(5):1245-1249 (1987).
Larche, Mark et al., "Peptide-based Therapeutic vaccines for allergic and autoimmune diseases," Nature Medicine, vol. 11(4):S69-S76 (2005).
Leitermann, Kathleen et al., "Cat allergen 1: Biochemical, antigenic, and allergenic properties," J. Allergy Clin. Immunol., vol. 74:147-153 (1984).
Michael, J.G. et al., "Modulation of the immune response to ragweed allergens by peptic fragments," Clinical and Experimental Allergy, vol. 20:669-674 (1990).
Munesinghe, Dona Yamuna et al., "Immunogenicity of multiple antigen peptides (MAP) containing T and B cell epitopes of the repeat region of the P. falciparum circumsporozoite protein," Eur. J. Immunol., vol. 21:3015-3020 (1991).
O'Hehir, Robin E. et al., "The Specificity and Regulation of T-Cell Responsiveness to Allergens," Annu. Rev. Immunol., vol. 9:67-95 (1991).
Ota, Kohei et al., "T-cell recognition of an immuno-dominant myelin basic protein epitope in multiple sclerosis," Nature, vol. 346:183-187 (1990).
Perez, Mary et al., "cDNA Cloning and Immunological Characterization of the Rye Grass Allergen Lol p I," The Journal of Biological Chemistry, vol. 265(27):16210-16215 (1990).
Rogers, B.L. et al., "Fel d I Genes: Genomic Structure and Expression in Cat Tissues," J. Allergy Clin. Immunol., vol. 87(1 pt. 2):327, abstract 750 (1991).
Rothbard, Jonathan B. et al., "A sequence pattern common to T cell epitopes," The EMBO Journal, vol. 7(1):93-100 (1988).
Rothbard, Jonathan B. et al., "Structural Model of HLA-DR1 Restricted T Cell Antigen Recognition," Cell, vol. 52:515-523 (1988).
Schad, V.C. et al., "The potential use of T cell epitopes to alter the immune response," Seminars in Immunology, vol. 3:217-224 (1991).
Shastri, Nilabh et al., "Molecule-Associated Selectivity in T Cell Recognition of a 23-Amino-Acid Peptide of Lysozyme," J. Exp. Med., vol. 164:882-896 (1986).
Shen, Shi-Hsiang, "Multiple joined genes prevent product degradation in *Escherichia coli*," Proc. Natl. Acad. Sci. USA, vol. 81:4627-4631 (1984).
Shimonkevitz, Richard et al., "Antigen Recognition by H-2-Restricted T Cells. II. A Tryptic Ovalbumin Peptide that Substitutes for Processed Antigen," The Journal of Immunology, vol. 133(4):2067-2074 (1984).
Sinigaglia, Francesco et al., "Selection of T Cell Epitopes and Vaccine Engineering," Methods in Enzymology, vol. 203:370-386 (1991).
Tam, James P., "Synthetic peptide vaccine design: Synthesis and properties of a high-density multiple antigenic peptide system," Proc. Natl. Acad. Sci. USA, vol. 85:5409-5413 (1988).
Tamborini, Elena et al., "Biochemical and immunological characterization of recombinant allergen Lol p 1," Eur. J. Biochem., vol. 249:886-894 (1997).
Texier, Catherine et al., "Emerging principles for the design of promiscuous HLA-DR-restricted peptides: an example from the major bee venom allergen," Eur. J. Immunol., vol. 32:3699-3707 (2002).
van de Wal, Yvonne et al., "Peptide binding characteristics of the coeliac disease-associated DQ(a1*0501, b1*0201) molecule," Immunogenetics, vol. 44:246-253 (1996).
Walker, P.R. et al., "Mapping major and minor T-cell epitopes in vitro and their immunogenic and tolerogenic effect in vivo in non-human primates," Immunology, vol. 80:209-216 (1993).
Young, Richard A. et al., "Efficient isolation of genes by using antibody probes," Proc. Natl. Acad. Sci. USA, vol. 80:1194-1198 (1983).

(56) References Cited

OTHER PUBLICATIONS

Yssel, Hans et al., "T Cell Activation-Inducing Epitopes of the House Dust Mite Allergen Der p 1, Proliferation and Lymphokine Production Patterns by Der p I-Specific CD4+ T Cell Clones," The Journal of Immunology, vol. 148 (3):738-745 (1992).

Zamvil, Scott S. et al., "T-cell epitope of the autoantigen myelin basic protein that induces encephalomyelitis," Nature, vol. 324:258-260 (1986).

Zhu, Xiaojiu et al., "T Cell Epitope Mapping of Ragweed Pollen Allergen Ambrosia artemisiifolia (Amb a 5) and Ambrosia trifida (Amb t 5) and the Role of Free Sulfhydryl Groups in T Cell Recognition," The Journal of Immunology, vol. 155:5064-5073 (1995).

Harris, D.P. et al., "Permissive recognition of a mycobacterial T-cell epitope: localization of overlapping epitope core sequences recognized in association with multiple major histocompatibility complex class II I-A molecules," Immunology, vol. 84:555-561 (1995).

Krco, Christopher J. et al., "Immune Response of HLA-DQ Transgenic Mice to House Dust Mite Allergen p2: Identification of HLA-DQ Restricted Minimal Epitopes and Critical Residues," Clinical Immunology, vol. 97(2):154-161 (2000).

Kristensen, Nanna M. et al., "Induction of T cell responses to the invariant chain derived peptide CLIP in mice immunized with the group 1 allergen of house dust mite," International Immunology, vol. 8(7):1091-1098 (1996).

Mustafa, Abu Salim et al., "Identification of Mycobacterial Peptide Epitopes Recognized by CD4+ T Cells in Association With Multiple Major Histocompatibility Complex Class II Molecules," Supplement to Nutrition, vol. 11 (5):657-660 (1995).

Nagato, Toshihiro et al., "Functional Analysis of Birch Pollen Allergen Bet v 1-Specific Regulatory T Cells," The Journal of Immunology, vol. 178:1189-1198 (2007).

Ohkuri, Takayuki et al., "Identification of a novel NY-ESO-1 promiscuous helper epitope presented by multiple MHC class II molecules found frequently in the Japanese population," Cancer Sci., vol. 98:1092-1098 (2007).

Rao, Varada P. et al., "Mapping of thyroglobulin epitopes: presentation of a 9mer pathogenic peptide by different mouse MHC class II isotypes," Immunogenetics, vol. 40:352-359 (1994).

Schafer, James Robert A. et al., "Prediction of well-conserved HIV-1 ligands using a matrix-based algorithm, EpiMatrix," Vaccine, vol. 16(19):1880-1884 (1998).

Verhoef, Adrienne et al., "Threshold Signaling of Human Th0 Cells in Activation and Anergy: Modulation of Effector Function by Altered TCR Ligand," The Journal of Immunology, vol. 164:6034-6040 (2000).

Banga, et al., "Stability of Therapeutic Peptides and Proteins," Therapeutic Peptides and Proteins Formulation, Processing, and Delivery Systems, 2nd Edition, Chapter 3, pp. 67-89 (2005).

Burkhart, Christoph et al., "Peptide-induced T cell regulation of experimental autoimmune encephalomyelitis: a role for IL-10," International Immunology, vol. 11(10):1625-1634 (1999).

Campbell, John D. et al., "Peptide immunotherapy in allergic asthma generates IL-10-dependent immunological tolerance associated with linked epitope suppression," J. Exp. Med., vol. 206(7):1535-1547 (2009).

Dick, Lawrence R. et al., "Proteolytic Processing in Ovalbumin and beta-galactosidase by the Proteasome to Yield Antigenic Peptides," J. Immunol., vol. 152(8):3884-3894 (1994).

Higgins, Julie A. et al., "Overlapping T-cell epitopes in the group I allergen of Dermatophagoides species restricted by HLA-DP and HLA-DR class II molecules," J. Allergy Clin. Immunol., vol. 93:891-899 (1994).

Hoyne, Gerard F. et al., "Inhibition of T Cell and Antibody Responses to House Dust Mite Allergen by Inhalation of the Dominant T Cell Epitope in Naive and Sensitized Mice," J. Exp. Med., vol. 178:1783-1788 (1993).

Larche, Mark et al., "Peptide-based therapeutic vaccines for allergic and autoimmune diseases," Nature Medicine Supplement, vol. 11(4):S69-S76 (2005).

O'Brien, R.M. et al., "An immunogenetic analysis of the T-cell recognition of the major house dust mite allergen Der p 2: identification of high- and low-responder HLA-DQ alleles and localization of T-cell epitopes," Immunology, vol. 86:176-182 (1995).

Oldfield, William L.G. et al., "Allergen-Derived T Cell Peptide-Induced Late Asthmatic Reactions Precede the Induction of Antigen-Specific Hyporesponsiveness in Atopic Allergic Asthmatic Subjects," The Journal of Immunology, vol. 167:1734-1739 (2001).

Oldfield, William L.G. et al., "Effect of T-cell peptides derived from Fel d 1 on allergic reactions and cytokine production in patients sensitive to cats: a randomised controlled trial," The Lancet, vol. 360:47-53 (2002).

Tarzi, M. et al., "Induction of interleukin-10 and suppressor of cytokine signalling-3 gene expression following peptide immunotherapy," Clinical and Experimental Allergy, vol. 36:465-474 (2006).

Thrower, S.L. et al., "Proinsulin peptide immunotherapy in type 1 diabetes: report of a first-in-man Phase I safety study," Clinical & Experimental Immunology, vol. 155:156-165 (2008).

Verhoef, Adrienne et al., "Clonal analysis of the atopic immune response to the group 2 allergen of Dermatophagoides spp.: identification of HLA-DR and -DQ restricted T cell epitopes," International Immunology, vol. 5 (12):1589-1597 (1993).

Worm, Margitta et al., "Development and preliminary clinical evaluation of a peptide immunotherapy vaccine for cat allergy," J. Allergy Clin. Immunol., vol. 127:89-97 (2011).

Zuleger, Cindy L. et al., "Peptide induces CD4+CD25+ and IL-10+ T cells and protection in airway allergy models," Vaccine, vol. 23:3181-3186 (2005).

U.S. Appl. No. 12/673,412: Non-Final Office Action dated Oct. 9, 2012, 18 pages.

U.S. Appl. No. 12/673,412: Non-Final Office Action dated Mar. 19, 2012, 9 pages.

U.S. Appl. No. 10/809,689: Non-Final Office Action dated Jun. 22, 2010, 11 pages.

U.S. Appl. No. 10/809,689: Final Office Action dated Jun. 9, 2009, 22 pages.

U.S. Appl. No. 10/809,689: Non-Final Office Action dated Aug. 20, 2008, 14 pages.

U.S. Appl. No. 10/809,689: Final Office Action dated Nov. 19, 2007, 19 pages.

U.S. Appl. No. 10/809,689: Non-Final Office Action dated Mar. 28, 2007, 25 pages.

U.S. Appl. No. 10/809,689: Non-Final Office Action dated Oct. 10, 2006, 10 pages.

U.S. Appl. No. 11/629,336: Notice of Allowance dated Jun. 27, 2011, 5 pages.

U.S. Appl. No. 11/629,336: Final Office Action dated Sep. 22, 2010, 8 pages.

U.S. Appl. No. 11/629,336: Non-Final Office Action dated Mar. 31, 2010, 19 pages.

U.S. Appl. No. 11/629,336: Non-Final Office Action dated Sep. 29, 2009, 6 pages.

U.S. Appl. No. 11/629,336: Non-Final Office Action dated Jun. 19, 2009, 6 pages.

U.S. Appl. No. 12/871,575: Final Office Action dated Mar. 29, 2012, 27 pages.

U.S. Appl. No. 12/871,575: Non-Final Office Action dated Oct. 26, 2011, 28 pages.

U.S. Appl. No. 12/871,575: Non-Final Office Action dated Aug. 26, 2011, 9 pages.

U.S. Appl. No. 10/510,276: Non-Final Office Action dated Jun. 22, 2010, 5 pages.

U.S. Appl. No. 10/510,276: Final Office Action dated Mar. 9, 2010, 14 pages.

U.S. Appl. No. 10/510,276: Non-Final Office Action dated May 14, 2009, 25 pages.

U.S. Appl. No. 10/510,276: Non-Final Office Action dated Sep. 22, 2008, 11 pages.

U.S. Appl. No. 10/510,276: Non-Final Office Action dated Mar. 19, 2008, 9 pages.

* cited by examiner

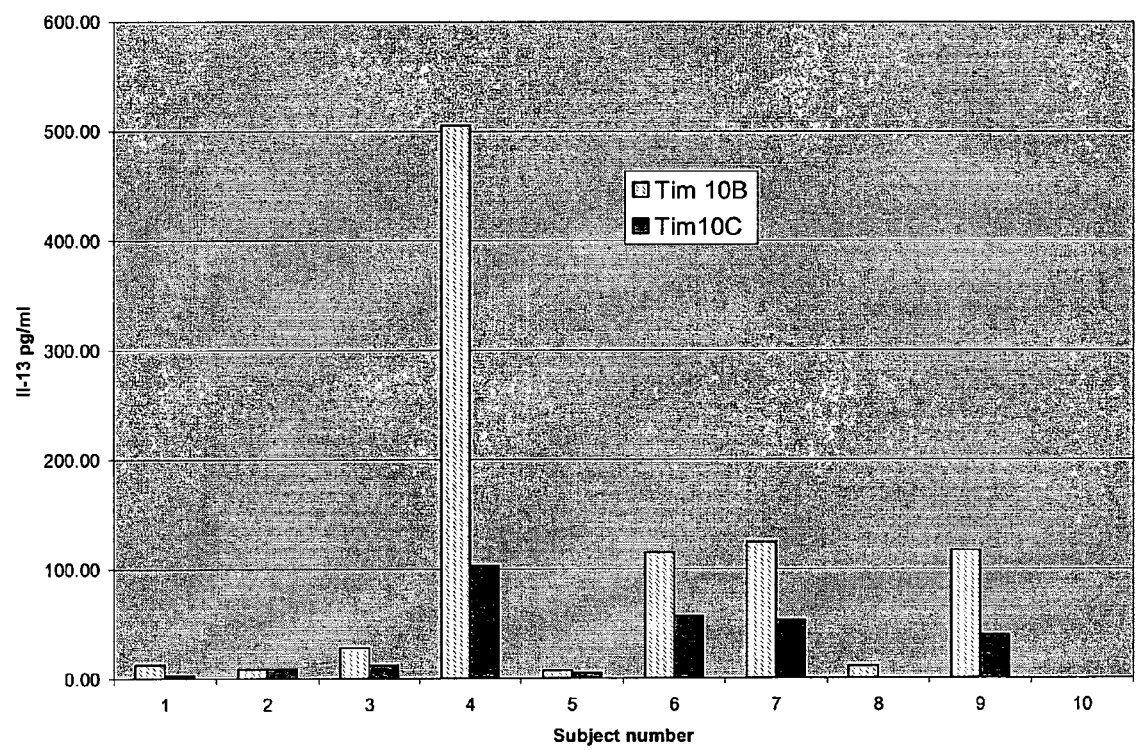

SEQUENCE LISTING

<160> NUMBER OF SEQ ID NOS: 420

<210> SEQ ID NO 1
<211> LENGTH: 13
<212> TYPE: PRT

-continued

```
<213> ORGANISM: Influenza virus

<400> SEQUENCE: 1

Pro Lys Tyr Val Lys Gln Asn Thr Leu Lys Leu Ala Thr
1               5                   10

<210> SEQ ID NO 2
<211> LENGTH: 15
<212> TYPE: PRT
<213> ORGANISM: Mycobacterium tuberculosis

<400> SEQUENCE: 2

Ala Lys Thr Ile Ala Tyr Asp Glu Glu Ala Arg Arg Gly Leu Glu
1               5                   10                  15

<210> SEQ ID NO 3
<211> LENGTH: 16
<212> TYPE: PRT
<213> ORGANISM: Homo sapiens

<400> SEQUENCE: 3

Thr Glu Arg Val Arg Leu Val Thr Arg His Ile Tyr Asn Arg Glu Glu
1               5                   10                  15

<210> SEQ ID NO 4
<211> LENGTH: 15
<212> TYPE: PRT
<213> ORGANISM: Homo sapiens

<400> SEQUENCE: 4

Glu Asn Pro Val Val His Phe Phe Lys Asn Ile Val Thr Pro Arg
1               5                   10                  15

<210> SEQ ID NO 5
<211> LENGTH: 15
<212> TYPE: PRT
<213> ORGANISM: Homo sapiens

<400> SEQUENCE: 5

Phe Val Asn Gln His Leu Cys Gly Ser His Leu Val Glu Ala Leu
1               5                   10                  15

<210> SEQ ID NO 6
<211> LENGTH: 16
<212> TYPE: PRT
<213> ORGANISM: Felis catus

<400> SEQUENCE: 6

Glu Gln Val Ala Gln Tyr Lys Ala Leu Pro Val Val Leu Glu Asn Ala
1               5                   10                  15

<210> SEQ ID NO 7
<211> LENGTH: 19
<212> TYPE: PRT
<213> ORGANISM: Artificial sequence
<220> FEATURE:
<223> OTHER INFORMATION: HDM01A synthetic peptide

<400> SEQUENCE: 7

Ile Asp Leu Arg Gln Met Arg Thr Val Thr Pro Ile Arg Met Gln Gly
1               5                   10                  15

Gly Ser Gly

<210> SEQ ID NO 8
```

-continued

<210> SEQ ID NO 8
<211> LENGTH: 18
<212> TYPE: PRT
<213> ORGANISM: Artificial sequence
<220> FEATURE:
<223> OTHER INFORMATION: HDM207 synthetic peptide

<400> SEQUENCE: 8

Asp Met Arg Asn Ile Gln Val Arg Gly Leu Lys Gln Met Lys Arg Val
1               5                   10                  15

Gly Asp

<210> SEQ ID NO 9
<211> LENGTH: 13
<212> TYPE: PRT
<213> ORGANISM: Dermatophagoides pteronyssinus

<400> SEQUENCE: 9

Ile Asp Leu Arg Gln Met Arg Thr Val Thr Pro Ile Arg
1               5                   10

<210> SEQ ID NO 10
<211> LENGTH: 13
<212> TYPE: PRT
<213> ORGANISM: Dermatophagoides pteronyssinus

<400> SEQUENCE: 10

Arg Thr Val Thr Pro Ile Arg Met Gln Gly Gly Cys Gly
1               5                   10

<210> SEQ ID NO 11
<211> LENGTH: 19
<212> TYPE: PRT
<213> ORGANISM: Dermatophagoides pteronyssinus

<400> SEQUENCE: 11

Arg Asn Gln Ser Leu Asp Leu Ala Glu Gln Glu Leu Val Asp Cys Ala
1               5                   10                  15

Ser Gln His

<210> SEQ ID NO 12
<211> LENGTH: 13
<212> TYPE: PRT
<213> ORGANISM: Dermatophagoides pteronyssinus

<400> SEQUENCE: 12

Glu Tyr Ile Gln His Asn Gly Val Val Gln Glu Ser Tyr
1               5                   10

<210> SEQ ID NO 13
<211> LENGTH: 13
<212> TYPE: PRT
<213> ORGANISM: Dermatophagoides pteronyssinus

<400> SEQUENCE: 13

Arg Tyr Val Ala Arg Glu Gln Ser Cys Arg Arg Pro Asn
1               5                   10

<210> SEQ ID NO 14
<211> LENGTH: 13
<212> TYPE: PRT
<213> ORGANISM: Dermatophagoides pteronyssinus

<400> SEQUENCE: 14

Pro Asn Val Asn Lys Ile Arg Glu Ala Leu Ala Gln Thr

```
<210> SEQ ID NO 15
<211> LENGTH: 13
<212> TYPE: PRT
<213> ORGANISM: Dermatophagoides pteronyssinus

<400> SEQUENCE: 15

Asn Lys Ile Arg Glu Ala Leu Ala Gln Thr His Ser Ala
1               5                   10

<210> SEQ ID NO 16
<211> LENGTH: 14
<212> TYPE: PRT
<213> ORGANISM: Dermatophagoides pteronyssinus

<400> SEQUENCE: 16

Arg Glu Ala Leu Ala Gln Thr His Ser Ala Ile Ala Val Ile
1               5                   10

<210> SEQ ID NO 17
<211> LENGTH: 13
<212> TYPE: PRT
<213> ORGANISM: Dermatophagoides pteronyssinus

<400> SEQUENCE: 17

Ile Gly Ile Lys Asp Leu Asp Ala Phe Arg His Tyr Asp
1               5                   10

<210> SEQ ID NO 18
<211> LENGTH: 13
<212> TYPE: PRT
<213> ORGANISM: Dermatophagoides pteronyssinus

<400> SEQUENCE: 18

Lys Asp Leu Asp Ala Phe Arg His Tyr Asp Gly Arg Thr
1               5                   10

<210> SEQ ID NO 19
<211> LENGTH: 14
<212> TYPE: PRT
<213> ORGANISM: Dermatophagoides pteronyssinus

<400> SEQUENCE: 19

Arg Thr Ile Ile Gln Arg Asp Asn Gly Tyr Gln Pro Asn Tyr
1               5                   10

<210> SEQ ID NO 20
<211> LENGTH: 14
<212> TYPE: PRT
<213> ORGANISM: Dermatophagoides pteronyssinus

<400> SEQUENCE: 20

Arg Asn Ser Trp Asp Thr Asn Trp Gly Asp Asn Gly Tyr Gly
1               5                   10

<210> SEQ ID NO 21
<211> LENGTH: 16
<212> TYPE: PRT
<213> ORGANISM: Dermatophagoides farinae

<400> SEQUENCE: 21

Asn Ser Val Asn Val Pro Ser Glu Leu Asp Leu Arg Ser Leu Arg Thr
1               5                   10                  15
```

<210> SEQ ID NO 22
<211> LENGTH: 15
<212> TYPE: PRT
<213> ORGANISM: Dermatophagoides pteronyssinus

<400> SEQUENCE: 22

Asp Gln Val Asp Val Lys Asp Cys Ala Asn His Glu Ile Lys Lys
1               5                   10                  15

<210> SEQ ID NO 23
<211> LENGTH: 13
<212> TYPE: PRT
<213> ORGANISM: Dermatophagoides pteronyssinus

<400> SEQUENCE: 23

Cys Ile Ile His Arg Gly Lys Pro Phe Gln Leu Glu Ala
1               5                   10

<210> SEQ ID NO 24
<211> LENGTH: 15
<212> TYPE: PRT
<213> ORGANISM: Dermatophagoides pteronyssinus

<400> SEQUENCE: 24

Lys Pro Phe Gln Leu Glu Ala Val Phe Glu Ala Asn Gln Asn Thr
1               5                   10                  15

<210> SEQ ID NO 25
<211> LENGTH: 16
<212> TYPE: PRT
<213> ORGANISM: Dermatophagoides pteronyssinus

<400> SEQUENCE: 25

Lys Pro Phe Gln Leu Glu Ala Val Phe Glu Ala Asn Gln Asn Thr Lys
1               5                   10                  15

<210> SEQ ID NO 26
<211> LENGTH: 17
<212> TYPE: PRT
<213> ORGANISM: Dermatophagoides pteronyssinus

<400> SEQUENCE: 26

Arg Gly Lys Pro Phe Gln Leu Glu Ala Val Phe Glu Ala Asn Gln Asn
1               5                   10                  15

Thr

<210> SEQ ID NO 27
<211> LENGTH: 14
<212> TYPE: PRT
<213> ORGANISM: Dermatophagoides pteronyssinus

<400> SEQUENCE: 27

Glu Ala Val Phe Glu Ala Asn Gln Asn Thr Lys Thr Ala Lys
1               5                   10

<210> SEQ ID NO 28
<211> LENGTH: 16
<212> TYPE: PRT
<213> ORGANISM: Dermatophagoides pteronyssinus

<400> SEQUENCE: 28

Asp Gly Leu Glu Val Asp Val Pro Gly Ile Asp Pro Asn Ala Cys His
1               5                   10                  15

<210> SEQ ID NO 29
<211> LENGTH: 15
<212> TYPE: PRT
<213> ORGANISM: Dermatophagoides pteronyssinus

<400> SEQUENCE: 29

Asp Gly Val Leu Ala Cys Ala Ile Ala Thr His Ala Lys Ile Arg
1               5                   10                  15

<210> SEQ ID NO 30
<211> LENGTH: 13
<212> TYPE: PRT
<213> ORGANISM: Dermatophagoides pteronyssinus

<400> SEQUENCE: 30

Ala Lys Ile Glu Ile Lys Ala Ser Leu Asp Gly Leu Glu
1               5                   10

<210> SEQ ID NO 31
<211> LENGTH: 13
<212> TYPE: PRT
<213> ORGANISM: Dermatophagoides pteronyssinus

<400> SEQUENCE: 31

Lys Ala Val Asp Glu Ala Val Ala Ala Ile Glu Lys Ser
1               5                   10

<210> SEQ ID NO 32
<211> LENGTH: 13
<212> TYPE: PRT
<213> ORGANISM: Dermatophagoides pteronyssinus

<400> SEQUENCE: 32

Glu Thr Phe Asp Pro Met Lys Val Pro Asp His Ser Asp
1               5                   10

<210> SEQ ID NO 33
<211> LENGTH: 14
<212> TYPE: PRT
<213> ORGANISM: Dermatophagoides pteronyssinus

<400> SEQUENCE: 33

Glu Thr Phe Asp Pro Met Lys Val Pro Asp His Ser Asp Lys
1               5                   10

<210> SEQ ID NO 34
<211> LENGTH: 15
<212> TYPE: PRT
<213> ORGANISM: Dermatophagoides pteronyssinus

<400> SEQUENCE: 34

Lys Ser Glu Thr Phe Asp Pro Met Lys Val Pro Asp His Ser Asp
1               5                   10                  15

<210> SEQ ID NO 35
<211> LENGTH: 13
<212> TYPE: PRT
<213> ORGANISM: Dermatophagoides pteronyssinus

<400> SEQUENCE: 35

Asp Lys Phe Glu Arg His Ile Gly Ile Ile Asp Leu Lys
1               5                   10

<210> SEQ ID NO 36

```
<211> LENGTH: 14
<212> TYPE: PRT
<213> ORGANISM: Dermatophagoides pteronyssinus

<400> SEQUENCE: 36

Ile Gly Ile Ile Asp Leu Lys Gly Glu Leu Asp Met Arg Asn
1               5                   10

<210> SEQ ID NO 37
<211> LENGTH: 15
<212> TYPE: PRT
<213> ORGANISM: Dermatophagoides pteronyssinus

<400> SEQUENCE: 37

His Ile Gly Ile Ile Asp Leu Lys Gly Glu Leu Asp Met Arg Asn
1               5                   10                  15

<210> SEQ ID NO 38
<211> LENGTH: 13
<212> TYPE: PRT
<213> ORGANISM: Dermatophagoides pteronyssinus

<400> SEQUENCE: 38

Ile Asp Leu Lys Gly Glu Leu Asp Met Arg Asn Ile Gln
1               5                   10

<210> SEQ ID NO 39
<211> LENGTH: 15
<212> TYPE: PRT
<213> ORGANISM: Dermatophagoides pteronyssinus

<400> SEQUENCE: 39

Ile Asp Leu Lys Gly Glu Leu Asp Met Arg Asn Ile Gln Val Arg
1               5                   10                  15

<210> SEQ ID NO 40
<211> LENGTH: 13
<212> TYPE: PRT
<213> ORGANISM: Dermatophagoides pteronyssinus

<400> SEQUENCE: 40

Leu Asp Met Arg Asn Ile Gln Val Arg Gly Leu Lys Gln
1               5                   10

<210> SEQ ID NO 41
<211> LENGTH: 15
<212> TYPE: PRT
<213> ORGANISM: Dermatophagoides pteronyssinus

<400> SEQUENCE: 41

Arg Asn Ile Gln Val Arg Gly Leu Lys Gln Met Lys Arg Val Gly
1               5                   10                  15

<210> SEQ ID NO 42
<211> LENGTH: 13
<212> TYPE: PRT
<213> ORGANISM: Dermatophagoides pteronyssinus

<400> SEQUENCE: 42

Arg Gly Leu Lys Gln Met Lys Arg Val Gly Asp Ala Asn
1               5                   10

<210> SEQ ID NO 43
<211> LENGTH: 13
<212> TYPE: PRT
```

<213> ORGANISM: Dermatophagoides pteronyssinus

<400> SEQUENCE: 43

Lys Arg Val Gly Asp Ala Asn Val Lys Ser Glu Asp Gly
1               5                   10

<210> SEQ ID NO 44
<211> LENGTH: 13
<212> TYPE: PRT
<213> ORGANISM: Dermatophagoides farinae

<400> SEQUENCE: 44

Ala Asn Val Lys Ser Glu Asp Gly Val Val Lys Ala His
1               5                   10

<210> SEQ ID NO 45
<211> LENGTH: 13
<212> TYPE: PRT
<213> ORGANISM: Dermatophagoides pteronyssinus

<400> SEQUENCE: 45

Asp Asp Val Val Ser Met Glu Tyr Asp Leu Ala Tyr Lys
1               5                   10

<210> SEQ ID NO 46
<211> LENGTH: 15
<212> TYPE: PRT
<213> ORGANISM: Dermatophagoides pteronyssinus

<400> SEQUENCE: 46

His Asp Asp Val Val Ser Met Glu Tyr Asp Leu Ala Tyr Lys Leu
1               5                   10                  15

<210> SEQ ID NO 47
<211> LENGTH: 15
<212> TYPE: PRT
<213> ORGANISM: Dermatophagoides pteronyssinus

<400> SEQUENCE: 47

Val Ser Met Glu Tyr Asp Leu Ala Tyr Lys Leu Gly Asp Leu His
1               5                   10                  15

<210> SEQ ID NO 48
<211> LENGTH: 14
<212> TYPE: PRT
<213> ORGANISM: Dermatophagoides pteronyssinus

<400> SEQUENCE: 48

Thr Ala Ile Phe Gln Asp Thr Val Arg Ala Glu Met Thr Lys
1               5                   10

<210> SEQ ID NO 49
<211> LENGTH: 13
<212> TYPE: PRT
<213> ORGANISM: Dermatophagoides pteronyssinus

<400> SEQUENCE: 49

Asp Thr Val Arg Ala Glu Met Thr Lys Val Leu Ala Pro
1               5                   10

<210> SEQ ID NO 50
<211> LENGTH: 18
<212> TYPE: PRT
<213> ORGANISM: Phleum pratense

```
<400> SEQUENCE: 50

Lys Tyr Thr Val Phe Glu Thr Ala Leu Lys Lys Ala Ile Thr Ala Met
1               5                   10                  15

Ser Glu

<210> SEQ ID NO 51
<211> LENGTH: 9
<212> TYPE: PRT
<213> ORGANISM: Phleum pratense

<400> SEQUENCE: 51

Leu Lys Lys Ala Ile Thr Ala Met Ser
1               5

<210> SEQ ID NO 52
<211> LENGTH: 9
<212> TYPE: PRT
<213> ORGANISM: Dermatophagoides pteronyssinus

<400> SEQUENCE: 52

Leu Glu Ser Val Lys Tyr Val Gln Ser
1               5

<210> SEQ ID NO 53
<211> LENGTH: 9
<212> TYPE: PRT
<213> ORGANISM: Dermatophagoides pteronyssinus

<400> SEQUENCE: 53

Glu Ser Val Lys Tyr Val Gln Ser Asn
1               5

<210> SEQ ID NO 54
<211> LENGTH: 9
<212> TYPE: PRT
<213> ORGANISM: Dermatophagoides pteronyssinus

<400> SEQUENCE: 54

Ser Val Lys Tyr Val Gln Ser Asn Gly
1               5

<210> SEQ ID NO 55
<211> LENGTH: 9
<212> TYPE: PRT
<213> ORGANISM: Dermatophagoides pteronyssinus

<400> SEQUENCE: 55

Val Lys Tyr Val Gln Ser Asn Gly Gly
1               5

<210> SEQ ID NO 56
<211> LENGTH: 9
<212> TYPE: PRT
<213> ORGANISM: Dermatophagoides pteronyssinus

<400> SEQUENCE: 56

Lys Tyr Val Gln Ser Asn Gly Gly Ala
1               5

<210> SEQ ID NO 57
<211> LENGTH: 9
<212> TYPE: PRT
<213> ORGANISM: Dermatophagoides pteronyssinus
```

```
<400> SEQUENCE: 57

Tyr Val Gln Ser Asn Gly Gly Ala Ile
1               5

<210> SEQ ID NO 58
<211> LENGTH: 9
<212> TYPE: PRT
<213> ORGANISM: Dermatophagoides pteronyssinus

<400> SEQUENCE: 58

Val Gln Ser Asn Gly Gly Ala Ile Asn
1               5

<210> SEQ ID NO 59
<211> LENGTH: 9
<212> TYPE: PRT
<213> ORGANISM: Dermatophagoides pteronyssinus

<400> SEQUENCE: 59

Gln Ser Asn Gly Gly Ala Ile Asn His
1               5

<210> SEQ ID NO 60
<211> LENGTH: 11
<212> TYPE: PRT
<213> ORGANISM: Dermatophagoides pteronyssinus

<400> SEQUENCE: 60

Val Lys Tyr Val Gln Ser Asn Gly Gly Ala Ile
1               5                   10

<210> SEQ ID NO 61
<211> LENGTH: 9
<212> TYPE: PRT
<213> ORGANISM: Dermatophagoides pteronyssinus

<400> SEQUENCE: 61

Leu Asp Glu Phe Lys Asn Arg Phe Leu
1               5

<210> SEQ ID NO 62
<211> LENGTH: 9
<212> TYPE: PRT
<213> ORGANISM: Dermatophagoides pteronyssinus

<400> SEQUENCE: 62

Asp Glu Phe Lys Asn Arg Phe Leu Met
1               5

<210> SEQ ID NO 63
<211> LENGTH: 9
<212> TYPE: PRT
<213> ORGANISM: Dermatophagoides pteronyssinus

<400> SEQUENCE: 63

Glu Phe Lys Asn Arg Phe Leu Met Ser
1               5

<210> SEQ ID NO 64
<211> LENGTH: 9
<212> TYPE: PRT
<213> ORGANISM: Dermatophagoides pteronyssinus

<400> SEQUENCE: 64
```

Phe Lys Asn Arg Phe Leu Met Ser Ala
1               5

<210> SEQ ID NO 65
<211> LENGTH: 9
<212> TYPE: PRT
<213> ORGANISM: Dermatophagoides pteronyssinus

<400> SEQUENCE: 65

Lys Asn Arg Phe Leu Met Ser Ala Glu
1               5

<210> SEQ ID NO 66
<211> LENGTH: 9
<212> TYPE: PRT
<213> ORGANISM: Dermatophagoides pteronyssinus

<400> SEQUENCE: 66

Asn Arg Phe Leu Met Ser Ala Glu Ala
1               5

<210> SEQ ID NO 67
<211> LENGTH: 9
<212> TYPE: PRT
<213> ORGANISM: Dermatophagoides pteronyssinus

<400> SEQUENCE: 67

Arg Phe Leu Met Ser Ala Glu Ala Phe
1               5

<210> SEQ ID NO 68
<211> LENGTH: 9
<212> TYPE: PRT
<213> ORGANISM: Dermatophagoides pteronyssinus

<400> SEQUENCE: 68

Phe Leu Met Ser Ala Glu Ala Phe Glu
1               5

<210> SEQ ID NO 69
<211> LENGTH: 11
<212> TYPE: PRT
<213> ORGANISM: Dermatophagoides pteronyssinus

<400> SEQUENCE: 69

Phe Lys Asn Arg Phe Leu Met Ser Ala Glu Ala
1               5                   10

<210> SEQ ID NO 70
<211> LENGTH: 9
<212> TYPE: PRT
<213> ORGANISM: Dermatophagoides pteronyssinus

<400> SEQUENCE: 70

Leu Arg Gln Met Arg Thr Val Thr Pro
1               5

<210> SEQ ID NO 71
<211> LENGTH: 9
<212> TYPE: PRT
<213> ORGANISM: Dermatophagoides pteronyssinus

<400> SEQUENCE: 71

Arg Gln Met Arg Thr Val Thr Pro Ile
1               5

<210> SEQ ID NO 72
<211> LENGTH: 9
<212> TYPE: PRT
<213> ORGANISM: Dermatophagoides pteronyssinus

<400> SEQUENCE: 72

Gln Met Arg Thr Val Thr Pro Ile Arg
1               5

<210> SEQ ID NO 73
<211> LENGTH: 9
<212> TYPE: PRT
<213> ORGANISM: Dermatophagoides pteronyssinus

<400> SEQUENCE: 73

Met Arg Thr Val Thr Pro Ile Arg Met
1               5

<210> SEQ ID NO 74
<211> LENGTH: 9
<212> TYPE: PRT
<213> ORGANISM: Dermatophagoides pteronyssinus

<400> SEQUENCE: 74

Arg Thr Val Thr Pro Ile Arg Met Gln
1               5

<210> SEQ ID NO 75
<211> LENGTH: 9
<212> TYPE: PRT
<213> ORGANISM: Dermatophagoides pteronyssinus

<400> SEQUENCE: 75

Thr Val Thr Pro Ile Arg Met Gln Gly
1               5

<210> SEQ ID NO 76
<211> LENGTH: 9
<212> TYPE: PRT
<213> ORGANISM: Dermatophagoides pteronyssinus

<400> SEQUENCE: 76

Val Thr Pro Ile Arg Met Gln Gly Gly
1               5

<210> SEQ ID NO 77
<211> LENGTH: 9
<212> TYPE: PRT
<213> ORGANISM: Dermatophagoides pteronyssinus

<400> SEQUENCE: 77

Thr Pro Ile Arg Met Gln Gly Gly Cys
1               5

<210> SEQ ID NO 78
<211> LENGTH: 9
<212> TYPE: PRT
<213> ORGANISM: Dermatophagoides pteronyssinus

<400> SEQUENCE: 78

Pro Ile Arg Met Gln Gly Gly Cys Gly
1               5

```
<210> SEQ ID NO 79
<211> LENGTH: 9
<212> TYPE: PRT
<213> ORGANISM: Dermatophagoides pteronyssinus

<400> SEQUENCE: 79

Ile Arg Met Gln Gly Gly Cys Gly Ser
1               5

<210> SEQ ID NO 80
<211> LENGTH: 9
<212> TYPE: PRT
<213> ORGANISM: Dermatophagoides pteronyssinus

<400> SEQUENCE: 80

Arg Met Gln Gly Gly Cys Gly Ser Cys
1               5

<210> SEQ ID NO 81
<211> LENGTH: 18
<212> TYPE: PRT
<213> ORGANISM: Dermatophagoides pteronyssinus

<400> SEQUENCE: 81

Leu Arg Gln Met Arg Thr Val Thr Pro Ile Arg Met Gln Gly Gly Cys
1               5                   10                  15

Gly Ser

<210> SEQ ID NO 82
<211> LENGTH: 9
<212> TYPE: PRT
<213> ORGANISM: Dermatophagoides pteronyssinus

<400> SEQUENCE: 82

Ala Tyr Leu Ala Tyr Arg Asn Gln Ser
1               5

<210> SEQ ID NO 83
<211> LENGTH: 9
<212> TYPE: PRT
<213> ORGANISM: Dermatophagoides pteronyssinus

<400> SEQUENCE: 83

Tyr Leu Ala Tyr Arg Asn Gln Ser Leu
1               5

<210> SEQ ID NO 84
<211> LENGTH: 9
<212> TYPE: PRT
<213> ORGANISM: Dermatophagoides pteronyssinus

<400> SEQUENCE: 84

Leu Ala Tyr Arg Asn Gln Ser Leu Asp
1               5

<210> SEQ ID NO 85
<211> LENGTH: 9
<212> TYPE: PRT
<213> ORGANISM: Dermatophagoides pteronyssinus

<400> SEQUENCE: 85

Ala Tyr Arg Asn Gln Ser Leu Asp Leu
1               5
```

```
<210> SEQ ID NO 86
<211> LENGTH: 9
<212> TYPE: PRT
<213> ORGANISM: Dermatophagoides pteronyssinus

<400> SEQUENCE: 86

Tyr Arg Asn Gln Ser Leu Asp Leu Ala
1               5

<210> SEQ ID NO 87
<211> LENGTH: 9
<212> TYPE: PRT
<213> ORGANISM: Dermatophagoides pteronyssinus

<400> SEQUENCE: 87

Arg Asn Gln Ser Leu Asp Leu Ala Glu
1               5

<210> SEQ ID NO 88
<211> LENGTH: 13
<212> TYPE: PRT
<213> ORGANISM: Dermatophagoides pteronyssinus

<400> SEQUENCE: 88

Ala Tyr Leu Ala Tyr Arg Asn Gln Ser Leu Asp Leu Ala
1               5                   10

<210> SEQ ID NO 89
<211> LENGTH: 9
<212> TYPE: PRT
<213> ORGANISM: Dermatophagoides pteronyssinus

<400> SEQUENCE: 89

Ser Tyr Tyr Arg Tyr Val Ala Arg Glu
1               5

<210> SEQ ID NO 90
<211> LENGTH: 9
<212> TYPE: PRT
<213> ORGANISM: Dermatophagoides pteronyssinus

<400> SEQUENCE: 90

Tyr Tyr Arg Tyr Val Ala Arg Glu Gln
1               5

<210> SEQ ID NO 91
<211> LENGTH: 9
<212> TYPE: PRT
<213> ORGANISM: Dermatophagoides pteronyssinus

<400> SEQUENCE: 91

Tyr Arg Tyr Val Ala Arg Glu Gln Ser
1               5

<210> SEQ ID NO 92
<211> LENGTH: 9
<212> TYPE: PRT
<213> ORGANISM: Dermatophagoides pteronyssinus

<400> SEQUENCE: 92

Arg Tyr Val Ala Arg Glu Gln Ser Cys
1               5

<210> SEQ ID NO 93
<211> LENGTH: 9
```

```
<212> TYPE: PRT
<213> ORGANISM: Dermatophagoides pteronyssinus

<400> SEQUENCE: 93

Tyr Val Ala Arg Glu Gln Ser Cys Arg
1               5

<210> SEQ ID NO 94
<211> LENGTH: 9
<212> TYPE: PRT
<213> ORGANISM: Dermatophagoides pteronyssinus

<400> SEQUENCE: 94

Val Ala Arg Glu Gln Ser Cys Arg Arg
1               5

<210> SEQ ID NO 95
<211> LENGTH: 9
<212> TYPE: PRT
<213> ORGANISM: Dermatophagoides pteronyssinus

<400> SEQUENCE: 95

Ala Arg Glu Gln Ser Cys Arg Arg Pro
1               5

<210> SEQ ID NO 96
<211> LENGTH: 9
<212> TYPE: PRT
<213> ORGANISM: Dermatophagoides pteronyssinus

<400> SEQUENCE: 96

Arg Glu Gln Ser Cys Arg Arg Pro Asn
1               5

<210> SEQ ID NO 97
<211> LENGTH: 9
<212> TYPE: PRT
<213> ORGANISM: Dermatophagoides pteronyssinus

<400> SEQUENCE: 97

Glu Gln Ser Cys Arg Arg Pro Asn Ala
1               5

<210> SEQ ID NO 98
<211> LENGTH: 9
<212> TYPE: PRT
<213> ORGANISM: Dermatophagoides pteronyssinus

<400> SEQUENCE: 98

Gln Ser Cys Arg Arg Pro Asn Ala Gln
1               5

<210> SEQ ID NO 99
<211> LENGTH: 16
<212> TYPE: PRT
<213> ORGANISM: Dermatophagoides pteronyssinus

<400> SEQUENCE: 99

Tyr Tyr Arg Tyr Val Ala Arg Glu Gln Ser Cys Arg Arg Pro Asn Ala
1               5                   10                  15

<210> SEQ ID NO 100
<211> LENGTH: 9
<212> TYPE: PRT
<213> ORGANISM: Dermatophagoides pteronyssinus
```

```
<400> SEQUENCE: 100

Gly Tyr Gly Tyr Phe Ala Ala Asn Ile
1               5

<210> SEQ ID NO 101
<211> LENGTH: 9
<212> TYPE: PRT
<213> ORGANISM: Dermatophagoides pteronyssinus

<400> SEQUENCE: 101

Tyr Gly Tyr Phe Ala Ala Asn Ile Asp
1               5

<210> SEQ ID NO 102
<211> LENGTH: 9
<212> TYPE: PRT
<213> ORGANISM: Dermatophagoides pteronyssinus

<400> SEQUENCE: 102

Gly Tyr Phe Ala Ala Asn Ile Asp Leu
1               5

<210> SEQ ID NO 103
<211> LENGTH: 9
<212> TYPE: PRT
<213> ORGANISM: Dermatophagoides pteronyssinus

<400> SEQUENCE: 103

Tyr Phe Ala Ala Asn Ile Asp Leu Met
1               5

<210> SEQ ID NO 104
<211> LENGTH: 9
<212> TYPE: PRT
<213> ORGANISM: Dermatophagoides pteronyssinus

<400> SEQUENCE: 104

Phe Ala Ala Asn Ile Asp Leu Met Met
1               5

<210> SEQ ID NO 105
<211> LENGTH: 9
<212> TYPE: PRT
<213> ORGANISM: Dermatophagoides pteronyssinus

<400> SEQUENCE: 105

Ala Ala Asn Ile Asp Leu Met Met Ile
1               5

<210> SEQ ID NO 106
<211> LENGTH: 9
<212> TYPE: PRT
<213> ORGANISM: Dermatophagoides pteronyssinus

<400> SEQUENCE: 106

Ala Asn Ile Asp Leu Met Met Ile Glu
1               5

<210> SEQ ID NO 107
<211> LENGTH: 12
<212> TYPE: PRT
<213> ORGANISM: Dermatophagoides pteronyssinus

<400> SEQUENCE: 107
```

Tyr Gly Tyr Phe Ala Ala Asn Ile Asp Leu Met Met
1               5                   10

<210> SEQ ID NO 108
<211> LENGTH: 9
<212> TYPE: PRT
<213> ORGANISM: Betula pendula

<400> SEQUENCE: 108

Pro Ala Ala Arg Met Phe Lys Ala Phe
1               5

<210> SEQ ID NO 109
<211> LENGTH: 9
<212> TYPE: PRT
<213> ORGANISM: Betula pendula

<400> SEQUENCE: 109

Ala Ala Arg Met Phe Lys Ala Phe Ile
1               5

<210> SEQ ID NO 110
<211> LENGTH: 9
<212> TYPE: PRT
<213> ORGANISM: Betula pendula

<400> SEQUENCE: 110

Ala Arg Met Phe Lys Ala Phe Ile Leu
1               5

<210> SEQ ID NO 111
<211> LENGTH: 9
<212> TYPE: PRT
<213> ORGANISM: Betula pendula

<400> SEQUENCE: 111

Arg Met Phe Lys Ala Phe Ile Leu Asp
1               5

<210> SEQ ID NO 112
<211> LENGTH: 10
<212> TYPE: PRT
<213> ORGANISM: Betula pendula

<400> SEQUENCE: 112

Ala Ala Arg Met Phe Lys Ala Phe Ile Leu
1               5                   10

<210> SEQ ID NO 113
<211> LENGTH: 9
<212> TYPE: PRT
<213> ORGANISM: Betula pendula

<400> SEQUENCE: 113

Val Phe Asn Tyr Glu Ile Gly Ala Thr
1               5

<210> SEQ ID NO 114
<211> LENGTH: 9
<212> TYPE: PRT
<213> ORGANISM: Betula pendula

<400> SEQUENCE: 114

Phe Asn Tyr Glu Ile Gly Ala Thr Ser

-continued

```
<210> SEQ ID NO 115
<211> LENGTH: 9
<212> TYPE: PRT
<213> ORGANISM: Betula pendula

<400> SEQUENCE: 115

Asn Tyr Glu Ile Gly Ala Thr Ser Val
1               5

<210> SEQ ID NO 116
<211> LENGTH: 9
<212> TYPE: PRT
<213> ORGANISM: Betula pendula

<400> SEQUENCE: 116

Tyr Glu Ile Gly Ala Thr Ser Val Ile
1               5

<210> SEQ ID NO 117
<211> LENGTH: 9
<212> TYPE: PRT
<213> ORGANISM: Betula pendula

<400> SEQUENCE: 117

Glu Ile Gly Ala Thr Ser Val Ile Pro
1               5

<210> SEQ ID NO 118
<211> LENGTH: 9
<212> TYPE: PRT
<213> ORGANISM: Betula pendula

<400> SEQUENCE: 118

Ile Gly Ala Thr Ser Val Ile Pro Ala
1               5

<210> SEQ ID NO 119
<211> LENGTH: 9
<212> TYPE: PRT
<213> ORGANISM: Betula pendula

<400> SEQUENCE: 119

Gly Ala Thr Ser Val Ile Pro Ala Ala
1               5

<210> SEQ ID NO 120
<211> LENGTH: 14
<212> TYPE: PRT
<213> ORGANISM: Betula pendula

<400> SEQUENCE: 120

Val Phe Asn Tyr Glu Ile Gly Ala Thr Ser Val Ile Pro Ala
1               5                   10

<210> SEQ ID NO 121
<211> LENGTH: 9
<212> TYPE: PRT
<213> ORGANISM: Betula pendula

<400> SEQUENCE: 121

Ser Pro Phe Lys Tyr Val Lys Glu Arg
1               5
```

```
<210> SEQ ID NO 122
<211> LENGTH: 9
<212> TYPE: PRT
<213> ORGANISM: Betula pendula

<400> SEQUENCE: 122

Pro Phe Lys Tyr Val Lys Glu Arg Val
1               5

<210> SEQ ID NO 123
<211> LENGTH: 9
<212> TYPE: PRT
<213> ORGANISM: Betula pendula

<400> SEQUENCE: 123

Phe Lys Tyr Val Lys Glu Arg Val Asp
1               5

<210> SEQ ID NO 124
<211> LENGTH: 9
<212> TYPE: PRT
<213> ORGANISM: Betula pendula

<400> SEQUENCE: 124

Lys Tyr Val Lys Glu Arg Val Asp Glu
1               5

<210> SEQ ID NO 125
<211> LENGTH: 9
<212> TYPE: PRT
<213> ORGANISM: Betula pendula

<400> SEQUENCE: 125

Tyr Val Lys Glu Arg Val Asp Glu Val
1               5

<210> SEQ ID NO 126
<211> LENGTH: 9
<212> TYPE: PRT
<213> ORGANISM: Betula pendula

<400> SEQUENCE: 126

Val Lys Glu Arg Val Asp Glu Val Asp
1               5

<210> SEQ ID NO 127
<211> LENGTH: 9
<212> TYPE: PRT
<213> ORGANISM: Betula pendula

<400> SEQUENCE: 127

Lys Glu Arg Val Asp Glu Val Asp His
1               5

<210> SEQ ID NO 128
<211> LENGTH: 9
<212> TYPE: PRT
<213> ORGANISM: Betula pendula

<400> SEQUENCE: 128

Asn Phe Lys Tyr Ser Tyr Ser Met Ile
1               5

<210> SEQ ID NO 129
```

```
<211> LENGTH: 9
<212> TYPE: PRT
<213> ORGANISM: Betula pendula

<400> SEQUENCE: 129

Phe Lys Tyr Ser Tyr Ser Met Ile Glu
1               5

<210> SEQ ID NO 130
<211> LENGTH: 9
<212> TYPE: PRT
<213> ORGANISM: Betula pendula

<400> SEQUENCE: 130

Lys Tyr Ser Tyr Ser Met Ile Glu Gly
1               5

<210> SEQ ID NO 131
<211> LENGTH: 9
<212> TYPE: PRT
<213> ORGANISM: Betula pendula

<400> SEQUENCE: 131

Tyr Ser Tyr Ser Met Ile Glu Gly Gly
1               5

<210> SEQ ID NO 132
<211> LENGTH: 9
<212> TYPE: PRT
<213> ORGANISM: Betula pendula

<400> SEQUENCE: 132

Ser Tyr Ser Met Ile Glu Gly Gly Ala
1               5

<210> SEQ ID NO 133
<211> LENGTH: 9
<212> TYPE: PRT
<213> ORGANISM: Betula pendula

<400> SEQUENCE: 133

Tyr Ser Met Ile Glu Gly Gly Ala Leu
1               5

<210> SEQ ID NO 134
<211> LENGTH: 9
<212> TYPE: PRT
<213> ORGANISM: Betula pendula

<400> SEQUENCE: 134

Ser Met Ile Glu Gly Gly Ala Leu Gly
1               5

<210> SEQ ID NO 135
<211> LENGTH: 13
<212> TYPE: PRT
<213> ORGANISM: Betula pendula

<400> SEQUENCE: 135

Phe Lys Tyr Ser Tyr Ser Met Ile Glu Gly Gly Ala Leu
1               5                   10

<210> SEQ ID NO 136
<211> LENGTH: 9
<212> TYPE: PRT
```

<213> ORGANISM: Betula pendula

<400> SEQUENCE: 136

Ala Leu Leu Arg Ala Val Glu Ser Tyr
1               5

<210> SEQ ID NO 137
<211> LENGTH: 9
<212> TYPE: PRT
<213> ORGANISM: Betula pendula

<400> SEQUENCE: 137

Leu Leu Arg Ala Val Glu Ser Tyr Leu
1               5

<210> SEQ ID NO 138
<211> LENGTH: 9
<212> TYPE: PRT
<213> ORGANISM: Betula pendula

<400> SEQUENCE: 138

Leu Arg Ala Val Glu Ser Tyr Leu Leu
1               5

<210> SEQ ID NO 139
<211> LENGTH: 9
<212> TYPE: PRT
<213> ORGANISM: Betula pendula

<400> SEQUENCE: 139

Arg Ala Val Glu Ser Tyr Leu Leu Ala
1               5

<210> SEQ ID NO 140
<211> LENGTH: 9
<212> TYPE: PRT
<213> ORGANISM: Betula pendula

<400> SEQUENCE: 140

Ala Val Glu Ser Tyr Leu Leu Ala His
1               5

<210> SEQ ID NO 141
<211> LENGTH: 9
<212> TYPE: PRT
<213> ORGANISM: Betula pendula

<400> SEQUENCE: 141

Val Glu Ser Tyr Leu Leu Ala His Ser
1               5

<210> SEQ ID NO 142
<211> LENGTH: 9
<212> TYPE: PRT
<213> ORGANISM: Betula pendula

<400> SEQUENCE: 142

Glu Ser Tyr Leu Leu Ala His Ser Asp
1               5

<210> SEQ ID NO 143
<211> LENGTH: 9
<212> TYPE: PRT
<213> ORGANISM: Betula pendula

```
<400> SEQUENCE: 143

Ser Tyr Leu Leu Ala His Ser Asp Ala
1               5

<210> SEQ ID NO 144
<211> LENGTH: 9
<212> TYPE: PRT
<213> ORGANISM: Betula pendula

<400> SEQUENCE: 144

Tyr Leu Leu Ala His Ser Asp Ala Tyr
1               5

<210> SEQ ID NO 145
<211> LENGTH: 16
<212> TYPE: PRT
<213> ORGANISM: Betula pendula

<400> SEQUENCE: 145

Leu Leu Arg Ala Val Glu Ser Tyr Leu Leu Ala His Ser Asp Ala Tyr
1               5                   10                  15

<210> SEQ ID NO 146
<211> LENGTH: 9
<212> TYPE: PRT
<213> ORGANISM: Phleum pratense

<400> SEQUENCE: 146

Gly Asp Glu Gln Lys Leu Arg Ser Ala
1               5

<210> SEQ ID NO 147
<211> LENGTH: 9
<212> TYPE: PRT
<213> ORGANISM: Phleum pratense

<400> SEQUENCE: 147

Asp Glu Gln Lys Leu Arg Ser Ala Gly
1               5

<210> SEQ ID NO 148
<211> LENGTH: 9
<212> TYPE: PRT
<213> ORGANISM: Phleum pratense

<400> SEQUENCE: 148

Glu Gln Lys Leu Arg Ser Ala Gly Glu
1               5

<210> SEQ ID NO 149
<211> LENGTH: 9
<212> TYPE: PRT
<213> ORGANISM: Phleum pratense

<400> SEQUENCE: 149

Gln Lys Leu Arg Ser Ala Gly Glu Leu
1               5

<210> SEQ ID NO 150
<211> LENGTH: 9
<212> TYPE: PRT
<213> ORGANISM: Phleum pratense

<400> SEQUENCE: 150
```

```
Lys Leu Arg Ser Ala Gly Glu Leu Glu
1               5
```

<210> SEQ ID NO 151
<211> LENGTH: 9
<212> TYPE: PRT
<213> ORGANISM: Phleum pratense

<400> SEQUENCE: 151

```
Leu Arg Ser Ala Gly Glu Leu Glu Leu
1               5
```

<210> SEQ ID NO 152
<211> LENGTH: 9
<212> TYPE: PRT
<213> ORGANISM: Phleum pratense

<400> SEQUENCE: 152

```
Arg Ser Ala Gly Glu Leu Glu Leu Gln
1               5
```

<210> SEQ ID NO 153
<211> LENGTH: 13
<212> TYPE: PRT
<213> ORGANISM: Phleum pratense

<400> SEQUENCE: 153

```
Asp Glu Gln Lys Leu Arg Ser Ala Gly Glu Leu Glu Leu
1               5                   10
```

<210> SEQ ID NO 154
<211> LENGTH: 9
<212> TYPE: PRT
<213> ORGANISM: Phleum pratense

<400> SEQUENCE: 154

```
Asn Tyr Leu Ala Leu Leu Val Lys Tyr
1               5
```

<210> SEQ ID NO 155
<211> LENGTH: 9
<212> TYPE: PRT
<213> ORGANISM: Phleum pratense

<400> SEQUENCE: 155

```
Tyr Leu Ala Leu Leu Val Lys Tyr Val
1               5
```

<210> SEQ ID NO 156
<211> LENGTH: 9
<212> TYPE: PRT
<213> ORGANISM: Phleum pratense

<400> SEQUENCE: 156

```
Leu Ala Leu Leu Val Lys Tyr Val Asn
1               5
```

<210> SEQ ID NO 157
<211> LENGTH: 9
<212> TYPE: PRT
<213> ORGANISM: Phleum pratense

<400> SEQUENCE: 157

```
Ala Leu Leu Val Lys Tyr Val Asn Gly
1               5
```

<210> SEQ ID NO 158
<211> LENGTH: 10
<212> TYPE: PRT
<213> ORGANISM: Phleum pratense

<400> SEQUENCE: 158

Tyr Leu Ala Leu Leu Val Lys Tyr Val Asn
1               5                   10

<210> SEQ ID NO 159
<211> LENGTH: 9
<212> TYPE: PRT
<213> ORGANISM: Phleum pratense

<400> SEQUENCE: 159

Ser Trp Gly Ala Ile Trp Arg Ile Asp
1               5

<210> SEQ ID NO 160
<211> LENGTH: 9
<212> TYPE: PRT
<213> ORGANISM: Phleum pratense

<400> SEQUENCE: 160

Trp Gly Ala Ile Trp Arg Ile Asp Thr
1               5

<210> SEQ ID NO 161
<211> LENGTH: 9
<212> TYPE: PRT
<213> ORGANISM: Phleum pratense

<400> SEQUENCE: 161

Gly Ala Ile Trp Arg Ile Asp Thr Pro
1               5

<210> SEQ ID NO 162
<211> LENGTH: 9
<212> TYPE: PRT
<213> ORGANISM: Phleum pratense

<400> SEQUENCE: 162

Ala Ile Trp Arg Ile Asp Thr Pro Asp
1               5

<210> SEQ ID NO 163
<211> LENGTH: 9
<212> TYPE: PRT
<213> ORGANISM: Phleum pratense

<400> SEQUENCE: 163

Ile Trp Arg Ile Asp Thr Pro Asp Lys
1               5

<210> SEQ ID NO 164
<211> LENGTH: 9
<212> TYPE: PRT
<213> ORGANISM: Phleum pratense

<400> SEQUENCE: 164

Trp Arg Ile Asp Thr Pro Asp Lys Leu
1               5

```
<210> SEQ ID NO 165
<211> LENGTH: 9
<212> TYPE: PRT
<213> ORGANISM: Phleum pratense

<400> SEQUENCE: 165

Arg Ile Asp Thr Pro Asp Lys Leu Thr
1               5

<210> SEQ ID NO 166
<211> LENGTH: 13
<212> TYPE: PRT
<213> ORGANISM: Phleum pratense

<400> SEQUENCE: 166

Trp Gly Ala Ile Trp Arg Ile Asp Thr Pro Asp Lys Leu
1               5                   10

<210> SEQ ID NO 167
<211> LENGTH: 9
<212> TYPE: PRT
<213> ORGANISM: Phleum pratense

<400> SEQUENCE: 167

Gly Asp Glu Gln Lys Leu Arg Ser Ala
1               5

<210> SEQ ID NO 168
<211> LENGTH: 9
<212> TYPE: PRT
<213> ORGANISM: Phleum pratense

<400> SEQUENCE: 168

Asp Glu Gln Lys Leu Arg Ser Ala Gly
1               5

<210> SEQ ID NO 169
<211> LENGTH: 9
<212> TYPE: PRT
<213> ORGANISM: Phleum pratense

<400> SEQUENCE: 169

Glu Gln Lys Leu Arg Ser Ala Gly Glu
1               5

<210> SEQ ID NO 170
<211> LENGTH: 9
<212> TYPE: PRT
<213> ORGANISM: Phleum pratense

<400> SEQUENCE: 170

Gln Lys Leu Arg Ser Ala Gly Glu Leu
1               5

<210> SEQ ID NO 171
<211> LENGTH: 9
<212> TYPE: PRT
<213> ORGANISM: Phleum pratense

<400> SEQUENCE: 171

Lys Leu Arg Ser Ala Gly Glu Leu Glu
1               5

<210> SEQ ID NO 172
<211> LENGTH: 9
```

```
<212> TYPE: PRT
<213> ORGANISM: Phleum pratense

<400> SEQUENCE: 172

Leu Arg Ser Ala Gly Glu Leu Glu Leu
1               5

<210> SEQ ID NO 173
<211> LENGTH: 9
<212> TYPE: PRT
<213> ORGANISM: Phleum pratense

<400> SEQUENCE: 173

Arg Ser Ala Gly Glu Leu Glu Leu Gln
1               5

<210> SEQ ID NO 174
<211> LENGTH: 9
<212> TYPE: PRT
<213> ORGANISM: Phleum pratense

<400> SEQUENCE: 174

Lys Ile Asn Ala Gly Phe Lys Ala Ala
1               5

<210> SEQ ID NO 175
<211> LENGTH: 9
<212> TYPE: PRT
<213> ORGANISM: Phleum pratense

<400> SEQUENCE: 175

Ile Asn Ala Gly Phe Lys Ala Ala Leu
1               5

<210> SEQ ID NO 176
<211> LENGTH: 9
<212> TYPE: PRT
<213> ORGANISM: Phleum pratense

<400> SEQUENCE: 176

Asn Ala Gly Phe Lys Ala Ala Leu Ala
1               5

<210> SEQ ID NO 177
<211> LENGTH: 9
<212> TYPE: PRT
<213> ORGANISM: Phleum pratense

<400> SEQUENCE: 177

Ala Gly Phe Lys Ala Ala Leu Ala Ala
1               5

<210> SEQ ID NO 178
<211> LENGTH: 9
<212> TYPE: PRT
<213> ORGANISM: Phleum pratense

<400> SEQUENCE: 178

Gly Phe Lys Ala Ala Leu Ala Ala Ala
1               5

<210> SEQ ID NO 179
<211> LENGTH: 9
<212> TYPE: PRT
<213> ORGANISM: Phleum pratense
```

<400> SEQUENCE: 179

Phe Lys Ala Ala Leu Ala Ala Ala Ala
1               5

<210> SEQ ID NO 180
<211> LENGTH: 9
<212> TYPE: PRT
<213> ORGANISM: Phleum pratense

<400> SEQUENCE: 180

Lys Ala Ala Leu Ala Ala Ala Ala Gly
1               5

<210> SEQ ID NO 181
<211> LENGTH: 9
<212> TYPE: PRT
<213> ORGANISM: Phleum pratense

<400> SEQUENCE: 181

Ala Ala Leu Ala Ala Ala Ala Gly Val
1               5

<210> SEQ ID NO 182
<211> LENGTH: 9
<212> TYPE: PRT
<213> ORGANISM: Phleum pratense

<400> SEQUENCE: 182

Ala Leu Ala Ala Ala Ala Gly Val Gln
1               5

<210> SEQ ID NO 183
<211> LENGTH: 15
<212> TYPE: PRT
<213> ORGANISM: Phleum pratense

<400> SEQUENCE: 183

Ile Asn Ala Gly Phe Lys Ala Ala Leu Ala Ala Ala Ala Gly Val
1               5                   10                  15

<210> SEQ ID NO 184
<211> LENGTH: 9
<212> TYPE: PRT
<213> ORGANISM: Phleum pratense

<400> SEQUENCE: 184

Lys Tyr Arg Thr Phe Val Ala Thr Phe
1               5

<210> SEQ ID NO 185
<211> LENGTH: 9
<212> TYPE: PRT
<213> ORGANISM: Phleum pratense

<400> SEQUENCE: 185

Tyr Arg Thr Phe Val Ala Thr Phe Gly
1               5

<210> SEQ ID NO 186
<211> LENGTH: 9
<212> TYPE: PRT
<213> ORGANISM: Phleum pratense

<400> SEQUENCE: 186

Arg Thr Phe Val Ala Thr Phe Gly Ala
1               5

<210> SEQ ID NO 187
<211> LENGTH: 9
<212> TYPE: PRT
<213> ORGANISM: Phleum pratense

<400> SEQUENCE: 187

Phe Val Ala Thr Phe Gly Ala Ala Ser
1               5

<210> SEQ ID NO 188
<211> LENGTH: 9
<212> TYPE: PRT
<213> ORGANISM: Phleum pratense

<400> SEQUENCE: 188

Val Ala Thr Phe Gly Ala Ala Ser Asn
1               5

<210> SEQ ID NO 189
<211> LENGTH: 12
<212> TYPE: PRT
<213> ORGANISM: Phleum pratense

<400> SEQUENCE: 189

Tyr Arg Thr Phe Val Ala Thr Phe Gly Ala Ala Ser
1               5                   10

<210> SEQ ID NO 190
<211> LENGTH: 9
<212> TYPE: PRT
<213> ORGANISM: Phleum pratense

<400> SEQUENCE: 190

Thr Ser Lys Leu Asp Ala Ala Tyr Lys
1               5

<210> SEQ ID NO 191
<211> LENGTH: 9
<212> TYPE: PRT
<213> ORGANISM: Phleum pratense

<400> SEQUENCE: 191

Ser Lys Leu Asp Ala Ala Tyr Lys Leu
1               5

<210> SEQ ID NO 192
<211> LENGTH: 9
<212> TYPE: PRT
<213> ORGANISM: Phleum pratense

<400> SEQUENCE: 192

Lys Leu Asp Ala Ala Tyr Lys Leu Ala
1               5

<210> SEQ ID NO 193
<211> LENGTH: 9
<212> TYPE: PRT
<213> ORGANISM: Phleum pratense

<400> SEQUENCE: 193

Leu Asp Ala Ala Tyr Lys Leu Ala Tyr

```
<210> SEQ ID NO 194
<211> LENGTH: 9
<212> TYPE: PRT
<213> ORGANISM: Phleum pratense

<400> SEQUENCE: 194

Asp Ala Ala Tyr Lys Leu Ala Tyr Lys
1               5

<210> SEQ ID NO 195
<211> LENGTH: 9
<212> TYPE: PRT
<213> ORGANISM: Phleum pratense

<400> SEQUENCE: 195

Ala Ala Tyr Lys Leu Ala Tyr Lys Thr
1               5

<210> SEQ ID NO 196
<211> LENGTH: 9
<212> TYPE: PRT
<213> ORGANISM: Phleum pratense

<400> SEQUENCE: 196

Ala Tyr Lys Leu Ala Tyr Lys Thr Ala
1               5

<210> SEQ ID NO 197
<211> LENGTH: 9
<212> TYPE: PRT
<213> ORGANISM: Phleum pratense

<400> SEQUENCE: 197

Tyr Lys Leu Ala Tyr Lys Thr Ala Glu
1               5

<210> SEQ ID NO 198
<211> LENGTH: 9
<212> TYPE: PRT
<213> ORGANISM: Phleum pratense

<400> SEQUENCE: 198

Lys Leu Ala Tyr Lys Thr Ala Glu Gly
1               5

<210> SEQ ID NO 199
<211> LENGTH: 9
<212> TYPE: PRT
<213> ORGANISM: Phleum pratense

<400> SEQUENCE: 199

Leu Ala Tyr Lys Thr Ala Glu Gly Ala
1               5

<210> SEQ ID NO 200
<211> LENGTH: 16
<212> TYPE: PRT
<213> ORGANISM: Phleum pratense

<400> SEQUENCE: 200

Ser Lys Leu Asp Ala Ala Tyr Lys Leu Ala Tyr Lys Thr Ala Glu Gly
1               5                   10                  15
```

<210> SEQ ID NO 201
<211> LENGTH: 9
<212> TYPE: PRT
<213> ORGANISM: Phleum pratense

<400> SEQUENCE: 201

Lys Val Asp Ala Ala Phe Lys Val Ala
1               5

<210> SEQ ID NO 202
<211> LENGTH: 9
<212> TYPE: PRT
<213> ORGANISM: Phleum pratense

<400> SEQUENCE: 202

Val Asp Ala Ala Phe Lys Val Ala Ala
1               5

<210> SEQ ID NO 203
<211> LENGTH: 9
<212> TYPE: PRT
<213> ORGANISM: Phleum pratense

<400> SEQUENCE: 203

Asp Ala Ala Phe Lys Val Ala Ala Thr
1               5

<210> SEQ ID NO 204
<211> LENGTH: 9
<212> TYPE: PRT
<213> ORGANISM: Phleum pratense

<400> SEQUENCE: 204

Ala Ala Phe Lys Val Ala Ala Thr Ala
1               5

<210> SEQ ID NO 205
<211> LENGTH: 9
<212> TYPE: PRT
<213> ORGANISM: Phleum pratense

<400> SEQUENCE: 205

Ala Phe Lys Val Ala Ala Thr Ala Ala
1               5

<210> SEQ ID NO 206
<211> LENGTH: 9
<212> TYPE: PRT
<213> ORGANISM: Phleum pratense

<400> SEQUENCE: 206

Phe Lys Val Ala Ala Thr Ala Ala Asn
1               5

<210> SEQ ID NO 207
<211> LENGTH: 9
<212> TYPE: PRT
<213> ORGANISM: Phleum pratense

<400> SEQUENCE: 207

Lys Val Ala Ala Thr Ala Ala Asn Ala
1               5

<210> SEQ ID NO 208

```
<211> LENGTH: 9
<212> TYPE: PRT
<213> ORGANISM: Phleum pratense

<400> SEQUENCE: 208

Val Ala Ala Thr Ala Ala Asn Ala Ala
1               5

<210> SEQ ID NO 209
<211> LENGTH: 9
<212> TYPE: PRT
<213> ORGANISM: Phleum pratense

<400> SEQUENCE: 209

Ala Ala Thr Ala Ala Asn Ala Ala Pro
1               5

<210> SEQ ID NO 210
<211> LENGTH: 15
<212> TYPE: PRT
<213> ORGANISM: Phleum pratense

<400> SEQUENCE: 210

Val Asp Ala Ala Phe Lys Val Ala Ala Thr Ala Ala Asn Ala Ala
1               5                   10                  15

<210> SEQ ID NO 211
<211> LENGTH: 9
<212> TYPE: PRT
<213> ORGANISM: Phleum pratense

<400> SEQUENCE: 211

Ser Tyr Lys Phe Ile Pro Ala Leu Glu
1               5

<210> SEQ ID NO 212
<211> LENGTH: 9
<212> TYPE: PRT
<213> ORGANISM: Phleum pratense

<400> SEQUENCE: 212

Tyr Lys Phe Ile Pro Ala Leu Glu Ala
1               5

<210> SEQ ID NO 213
<211> LENGTH: 9
<212> TYPE: PRT
<213> ORGANISM: Phleum pratense

<400> SEQUENCE: 213

Lys Phe Ile Pro Ala Leu Glu Ala Ala
1               5

<210> SEQ ID NO 214
<211> LENGTH: 9
<212> TYPE: PRT
<213> ORGANISM: Phleum pratense

<400> SEQUENCE: 214

Phe Ile Pro Ala Leu Glu Ala Ala Val
1               5

<210> SEQ ID NO 215
<211> LENGTH: 9
<212> TYPE: PRT
```

<213> ORGANISM: Phleum pratense

<400> SEQUENCE: 215

Ile Pro Ala Leu Glu Ala Ala Val Lys
1               5

<210> SEQ ID NO 216
<211> LENGTH: 9
<212> TYPE: PRT
<213> ORGANISM: Phleum pratense

<400> SEQUENCE: 216

Pro Ala Leu Glu Ala Ala Val Lys Gln
1               5

<210> SEQ ID NO 217
<211> LENGTH: 9
<212> TYPE: PRT
<213> ORGANISM: Phleum pratense

<400> SEQUENCE: 217

Ala Leu Glu Ala Ala Val Lys Gln Ala
1               5

<210> SEQ ID NO 218
<211> LENGTH: 9
<212> TYPE: PRT
<213> ORGANISM: Phleum pratense

<400> SEQUENCE: 218

Leu Glu Ala Ala Val Lys Gln Ala Tyr
1               5

<210> SEQ ID NO 219
<211> LENGTH: 9
<212> TYPE: PRT
<213> ORGANISM: Phleum pratense

<400> SEQUENCE: 219

Glu Ala Ala Val Lys Gln Ala Tyr Ala
1               5

<210> SEQ ID NO 220
<211> LENGTH: 15
<212> TYPE: PRT
<213> ORGANISM: Phleum pratense

<400> SEQUENCE: 220

Tyr Lys Phe Ile Pro Ala Leu Glu Ala Ala Val Lys Gln Ala Tyr
1               5                   10                  15

<210> SEQ ID NO 221
<211> LENGTH: 9
<212> TYPE: PRT
<213> ORGANISM: Phleum pratense

<400> SEQUENCE: 221

Lys Tyr Thr Val Phe Glu Thr Ala Leu
1               5

<210> SEQ ID NO 222
<211> LENGTH: 9
<212> TYPE: PRT
<213> ORGANISM: Phleum pratense

```
<400> SEQUENCE: 222

Tyr Thr Val Phe Glu Thr Ala Leu Lys
1               5

<210> SEQ ID NO 223
<211> LENGTH: 9
<212> TYPE: PRT
<213> ORGANISM: Phleum pratense

<400> SEQUENCE: 223

Thr Val Phe Glu Thr Ala Leu Lys Lys
1               5

<210> SEQ ID NO 224
<211> LENGTH: 9
<212> TYPE: PRT
<213> ORGANISM: Phleum pratense

<400> SEQUENCE: 224

Val Phe Glu Thr Ala Leu Lys Lys Ala
1               5

<210> SEQ ID NO 225
<211> LENGTH: 9
<212> TYPE: PRT
<213> ORGANISM: Phleum pratense

<400> SEQUENCE: 225

Phe Glu Thr Ala Leu Lys Lys Ala Ile
1               5

<210> SEQ ID NO 226
<211> LENGTH: 9
<212> TYPE: PRT
<213> ORGANISM: Phleum pratense

<400> SEQUENCE: 226

Glu Thr Ala Leu Lys Lys Ala Ile Thr
1               5

<210> SEQ ID NO 227
<211> LENGTH: 9
<212> TYPE: PRT
<213> ORGANISM: Phleum pratense

<400> SEQUENCE: 227

Thr Ala Leu Lys Lys Ala Ile Thr Ala
1               5

<210> SEQ ID NO 228
<211> LENGTH: 9
<212> TYPE: PRT
<213> ORGANISM: Phleum pratense

<400> SEQUENCE: 228

Ala Leu Lys Lys Ala Ile Thr Ala Met
1               5

<210> SEQ ID NO 229
<211> LENGTH: 9
<212> TYPE: PRT
<213> ORGANISM: Phleum pratense

<400> SEQUENCE: 229
```

```
Leu Lys Lys Ala Ile Thr Ala Met Ser
1               5

<210> SEQ ID NO 230
<211> LENGTH: 9
<212> TYPE: PRT
<213> ORGANISM: Phleum pratense

<400> SEQUENCE: 230

Lys Lys Ala Ile Thr Ala Met Ser Glu
1               5

<210> SEQ ID NO 231
<211> LENGTH: 16
<212> TYPE: PRT
<213> ORGANISM: Phleum pratense

<400> SEQUENCE: 231

Tyr Thr Val Phe Glu Thr Ala Leu Lys Lys Ala Ile Thr Ala Met Ser
1               5                   10                  15

<210> SEQ ID NO 232
<211> LENGTH: 9
<212> TYPE: PRT
<213> ORGANISM: Alternaria alternata

<400> SEQUENCE: 232

Gln Leu Leu Met Leu Ser Ala Lys Arg
1               5

<210> SEQ ID NO 233
<211> LENGTH: 9
<212> TYPE: PRT
<213> ORGANISM: Alternaria alternata

<400> SEQUENCE: 233

Leu Leu Met Leu Ser Ala Lys Arg Met
1               5

<210> SEQ ID NO 234
<211> LENGTH: 9
<212> TYPE: PRT
<213> ORGANISM: Alternaria alternata

<400> SEQUENCE: 234

Leu Met Leu Ser Ala Lys Arg Met Lys
1               5

<210> SEQ ID NO 235
<211> LENGTH: 9
<212> TYPE: PRT
<213> ORGANISM: Alternaria alternata

<400> SEQUENCE: 235

Met Leu Ser Ala Lys Arg Met Lys Val
1               5

<210> SEQ ID NO 236
<211> LENGTH: 9
<212> TYPE: PRT
<213> ORGANISM: Alternaria alternata

<400> SEQUENCE: 236

Leu Ser Ala Lys Arg Met Lys Val Ala
1               5
```

```
<210> SEQ ID NO 237
<211> LENGTH: 9
<212> TYPE: PRT
<213> ORGANISM: Alternaria alternata

<400> SEQUENCE: 237

Ser Ala Lys Arg Met Lys Val Ala Phe
1               5

<210> SEQ ID NO 238
<211> LENGTH: 9
<212> TYPE: PRT
<213> ORGANISM: Alternaria alternata

<400> SEQUENCE: 238

Ala Lys Arg Met Lys Val Ala Phe Lys
1               5

<210> SEQ ID NO 239
<211> LENGTH: 9
<212> TYPE: PRT
<213> ORGANISM: Alternaria alternata

<400> SEQUENCE: 239

Lys Arg Met Lys Val Ala Phe Lys Leu
1               5

<210> SEQ ID NO 240
<211> LENGTH: 9
<212> TYPE: PRT
<213> ORGANISM: Alternaria alternata

<400> SEQUENCE: 240

Arg Met Lys Val Ala Phe Lys Leu Asp
1               5

<210> SEQ ID NO 241
<211> LENGTH: 9
<212> TYPE: PRT
<213> ORGANISM: Alternaria alternata

<400> SEQUENCE: 241

Met Lys Val Ala Phe Lys Leu Asp Ile
1               5

<210> SEQ ID NO 242
<211> LENGTH: 9
<212> TYPE: PRT
<213> ORGANISM: Alternaria alternata

<400> SEQUENCE: 242

Lys Val Ala Phe Lys Leu Asp Ile Glu
1               5

<210> SEQ ID NO 243
<211> LENGTH: 11
<212> TYPE: PRT
<213> ORGANISM: Alternaria alternata

<400> SEQUENCE: 243

Leu Leu Met Leu Ser Ala Lys Arg Met Lys Val
1               5                   10
```

-continued

```
<210> SEQ ID NO 244
<211> LENGTH: 12
<212> TYPE: PRT
<213> ORGANISM: Alternaria alternata

<400> SEQUENCE: 244

Ala Lys Arg Met Lys Val Ala Phe Lys Leu Asp Ile
1               5                   10

<210> SEQ ID NO 245
<211> LENGTH: 17
<212> TYPE: PRT
<213> ORGANISM: Alternaria alternata

<400> SEQUENCE: 245

Leu Leu Met Leu Ser Ala Lys Arg Met Lys Val Ala Phe Lys Leu Asp
1               5                   10                  15

Ile

<210> SEQ ID NO 246
<211> LENGTH: 9
<212> TYPE: PRT
<213> ORGANISM: Alternaria alternata

<400> SEQUENCE: 246

Gly Phe Lys Arg Cys Leu Gln Phe Thr
1               5

<210> SEQ ID NO 247
<211> LENGTH: 9
<212> TYPE: PRT
<213> ORGANISM: Alternaria alternata

<400> SEQUENCE: 247

Phe Lys Arg Cys Leu Gln Phe Thr Leu
1               5

<210> SEQ ID NO 248
<211> LENGTH: 9
<212> TYPE: PRT
<213> ORGANISM: Alternaria alternata

<400> SEQUENCE: 248

Lys Arg Cys Leu Gln Phe Thr Leu Tyr
1               5

<210> SEQ ID NO 249
<211> LENGTH: 9
<212> TYPE: PRT
<213> ORGANISM: Alternaria alternata

<400> SEQUENCE: 249

Arg Cys Leu Gln Phe Thr Leu Tyr Arg
1               5

<210> SEQ ID NO 250
<211> LENGTH: 9
<212> TYPE: PRT
<213> ORGANISM: Alternaria alternata

<400> SEQUENCE: 250

Cys Leu Gln Phe Thr Leu Tyr Arg Pro
1               5
```

<210> SEQ ID NO 251
<211> LENGTH: 9
<212> TYPE: PRT
<213> ORGANISM: Alternaria alternata

<400> SEQUENCE: 251

Leu Gln Phe Thr Leu Tyr Arg Pro Arg
1               5

<210> SEQ ID NO 252
<211> LENGTH: 9
<212> TYPE: PRT
<213> ORGANISM: Alternaria alternata

<400> SEQUENCE: 252

Gln Phe Thr Leu Tyr Arg Pro Arg Asp
1               5

<210> SEQ ID NO 253
<211> LENGTH: 9
<212> TYPE: PRT
<213> ORGANISM: Alternaria alternata

<400> SEQUENCE: 253

Phe Thr Leu Tyr Arg Pro Arg Asp Leu
1               5

<210> SEQ ID NO 254
<211> LENGTH: 9
<212> TYPE: PRT
<213> ORGANISM: Alternaria alternata

<400> SEQUENCE: 254

Thr Leu Tyr Arg Pro Arg Asp Leu Leu
1               5

<210> SEQ ID NO 255
<211> LENGTH: 9
<212> TYPE: PRT
<213> ORGANISM: Alternaria alternata

<400> SEQUENCE: 255

Leu Tyr Arg Pro Arg Asp Leu Leu Ser
1               5

<210> SEQ ID NO 256
<211> LENGTH: 9
<212> TYPE: PRT
<213> ORGANISM: Alternaria alternata

<400> SEQUENCE: 256

Tyr Arg Pro Arg Asp Leu Leu Ser Leu
1               5

<210> SEQ ID NO 257
<211> LENGTH: 9
<212> TYPE: PRT
<213> ORGANISM: Alternaria alternata

<400> SEQUENCE: 257

Arg Pro Arg Asp Leu Leu Ser Leu Leu
1               5

<210> SEQ ID NO 258
<211> LENGTH: 15

```
<212> TYPE: PRT
<213> ORGANISM: Alternaria alternata

<400> SEQUENCE: 258

Phe Lys Arg Cys Leu Gln Phe Thr Leu Tyr Arg Pro Arg Asp Leu
1               5                   10                  15

<210> SEQ ID NO 259
<211> LENGTH: 12
<212> TYPE: PRT
<213> ORGANISM: Alternaria alternata

<400> SEQUENCE: 259

Phe Thr Leu Tyr Arg Pro Arg Asp Leu Leu Ser Leu
1               5                   10

<210> SEQ ID NO 260
<211> LENGTH: 18
<212> TYPE: PRT
<213> ORGANISM: Alternaria alternata

<400> SEQUENCE: 260

Phe Lys Arg Cys Leu Gln Phe Thr Leu Tyr Arg Pro Arg Asp Leu Leu
1               5                   10                  15

Ser Leu

<210> SEQ ID NO 261
<211> LENGTH: 9
<212> TYPE: PRT
<213> ORGANISM: Alternaria alternata

<400> SEQUENCE: 261

Thr Tyr Tyr Asn Ser Leu Gly Phe Asn
1               5

<210> SEQ ID NO 262
<211> LENGTH: 9
<212> TYPE: PRT
<213> ORGANISM: Alternaria alternata

<400> SEQUENCE: 262

Tyr Tyr Asn Ser Leu Gly Phe Asn Ile
1               5

<210> SEQ ID NO 263
<211> LENGTH: 9
<212> TYPE: PRT
<213> ORGANISM: Alternaria alternata

<400> SEQUENCE: 263

Tyr Asn Ser Leu Gly Phe Asn Ile Lys
1               5

<210> SEQ ID NO 264
<211> LENGTH: 9
<212> TYPE: PRT
<213> ORGANISM: Alternaria alternata

<400> SEQUENCE: 264

Asn Ser Leu Gly Phe Asn Ile Lys Ala
1               5

<210> SEQ ID NO 265
<211> LENGTH: 9
```

```
<212> TYPE: PRT
<213> ORGANISM: Alternaria alternata

<400> SEQUENCE: 265

Ser Leu Gly Phe Asn Ile Lys Ala Thr
1               5

<210> SEQ ID NO 266
<211> LENGTH: 9
<212> TYPE: PRT
<213> ORGANISM: Alternaria alternata

<400> SEQUENCE: 266

Leu Gly Phe Asn Ile Lys Ala Thr Asn
1               5

<210> SEQ ID NO 267
<211> LENGTH: 9
<212> TYPE: PRT
<213> ORGANISM: Alternaria alternata

<400> SEQUENCE: 267

Gly Phe Asn Ile Lys Ala Thr Asn Gly
1               5

<210> SEQ ID NO 268
<211> LENGTH: 9
<212> TYPE: PRT
<213> ORGANISM: Alternaria alternata

<400> SEQUENCE: 268

Phe Asn Ile Lys Ala Thr Asn Gly Gly
1               5

<210> SEQ ID NO 269
<211> LENGTH: 9
<212> TYPE: PRT
<213> ORGANISM: Alternaria alternata

<400> SEQUENCE: 269

Asn Ile Lys Ala Thr Asn Gly Gly Thr
1               5

<210> SEQ ID NO 270
<211> LENGTH: 9
<212> TYPE: PRT
<213> ORGANISM: Alternaria alternata

<400> SEQUENCE: 270

Ile Lys Ala Thr Asn Gly Gly Thr Leu
1               5

<210> SEQ ID NO 271
<211> LENGTH: 9
<212> TYPE: PRT
<213> ORGANISM: Alternaria alternata

<400> SEQUENCE: 271

Lys Ala Thr Asn Gly Gly Thr Leu Asp
1               5

<210> SEQ ID NO 272
<211> LENGTH: 17
<212> TYPE: PRT
<213> ORGANISM: Alternaria alternata
```

```
<400> SEQUENCE: 272

Tyr Tyr Asn Ser Leu Gly Phe Asn Ile Lys Ala Thr Asn Gly Gly Thr
1               5                   10                  15
Leu

<210> SEQ ID NO 273
<211> LENGTH: 9
<212> TYPE: PRT
<213> ORGANISM: Alternaria alternata

<400> SEQUENCE: 273

Asp Ile Thr Tyr Val Ala Thr Ala Thr
1               5

<210> SEQ ID NO 274
<211> LENGTH: 9
<212> TYPE: PRT
<213> ORGANISM: Alternaria alternata

<400> SEQUENCE: 274

Ile Thr Tyr Val Ala Thr Ala Thr Leu
1               5

<210> SEQ ID NO 275
<211> LENGTH: 9
<212> TYPE: PRT
<213> ORGANISM: Alternaria alternata

<400> SEQUENCE: 275

Thr Tyr Val Ala Thr Ala Thr Leu Pro
1               5

<210> SEQ ID NO 276
<211> LENGTH: 9
<212> TYPE: PRT
<213> ORGANISM: Alternaria alternata

<400> SEQUENCE: 276

Tyr Val Ala Thr Ala Thr Leu Pro Asn
1               5

<210> SEQ ID NO 277
<211> LENGTH: 9
<212> TYPE: PRT
<213> ORGANISM: Alternaria alternata

<400> SEQUENCE: 277

Val Ala Thr Ala Thr Leu Pro Asn Tyr
1               5

<210> SEQ ID NO 278
<211> LENGTH: 9
<212> TYPE: PRT
<213> ORGANISM: Alternaria alternata

<400> SEQUENCE: 278

Ala Thr Ala Thr Leu Pro Asn Tyr Cys
1               5

<210> SEQ ID NO 279
<211> LENGTH: 12
<212> TYPE: PRT
<213> ORGANISM: Alternaria alternata
```

```
<400> SEQUENCE: 279

Ile Thr Tyr Val Ala Thr Ala Thr Leu Pro Asn Tyr
1               5                   10

<210> SEQ ID NO 280
<211> LENGTH: 9
<212> TYPE: PRT
<213> ORGANISM: Alternaria alternata

<400> SEQUENCE: 280

Ala Tyr Ile Thr Leu Val Thr Leu Pro
1               5

<210> SEQ ID NO 281
<211> LENGTH: 9
<212> TYPE: PRT
<213> ORGANISM: Alternaria alternata

<400> SEQUENCE: 281

Tyr Ile Thr Leu Val Thr Leu Pro Lys
1               5

<210> SEQ ID NO 282
<211> LENGTH: 9
<212> TYPE: PRT
<213> ORGANISM: Alternaria alternata

<400> SEQUENCE: 282

Ile Thr Leu Val Thr Leu Pro Lys Ser
1               5

<210> SEQ ID NO 283
<211> LENGTH: 9
<212> TYPE: PRT
<213> ORGANISM: Alternaria alternata

<400> SEQUENCE: 283

Thr Leu Val Thr Leu Pro Lys Ser Ser
1               5

<210> SEQ ID NO 284
<211> LENGTH: 10
<212> TYPE: PRT
<213> ORGANISM: Alternaria alternata

<400> SEQUENCE: 284

Tyr Ile Thr Leu Val Thr Leu Pro Lys Ser
1               5                   10

<210> SEQ ID NO 285
<211> LENGTH: 9
<212> TYPE: PRT
<213> ORGANISM: Alternaria alternata

<400> SEQUENCE: 285

Glu Val Tyr Gln Lys Leu Lys Ala Leu
1               5

<210> SEQ ID NO 286
<211> LENGTH: 9
<212> TYPE: PRT
<213> ORGANISM: Alternaria alternata

<400> SEQUENCE: 286
```

Val Tyr Gln Lys Leu Lys Ala Leu Ala
1               5

<210> SEQ ID NO 287
<211> LENGTH: 9
<212> TYPE: PRT
<213> ORGANISM: Alternaria alternata

<400> SEQUENCE: 287

Tyr Gln Lys Leu Lys Ala Leu Ala Lys
1               5

<210> SEQ ID NO 288
<211> LENGTH: 9
<212> TYPE: PRT
<213> ORGANISM: Alternaria alternata

<400> SEQUENCE: 288

Gln Lys Leu Lys Ala Leu Ala Lys Lys
1               5

<210> SEQ ID NO 289
<211> LENGTH: 9
<212> TYPE: PRT
<213> ORGANISM: Alternaria alternata

<400> SEQUENCE: 289

Lys Leu Lys Ala Leu Ala Lys Lys Thr
1               5

<210> SEQ ID NO 290
<211> LENGTH: 9
<212> TYPE: PRT
<213> ORGANISM: Alternaria alternata

<400> SEQUENCE: 290

Leu Lys Ala Leu Ala Lys Lys Thr Tyr
1               5

<210> SEQ ID NO 291
<211> LENGTH: 9
<212> TYPE: PRT
<213> ORGANISM: Alternaria alternata

<400> SEQUENCE: 291

Lys Ala Leu Ala Lys Lys Thr Tyr Gly
1               5

<210> SEQ ID NO 292
<211> LENGTH: 13
<212> TYPE: PRT
<213> ORGANISM: Alternaria alternata

<400> SEQUENCE: 292

Val Tyr Gln Lys Leu Lys Ala Leu Ala Lys Lys Thr Tyr
1               5                   10

<210> SEQ ID NO 293
<211> LENGTH: 9
<212> TYPE: PRT
<213> ORGANISM: Alternaria alternata

<400> SEQUENCE: 293

Gly Tyr Thr Gly Lys Ile Lys Ile Ala

```
1               5

<210> SEQ ID NO 294
<211> LENGTH: 9
<212> TYPE: PRT
<213> ORGANISM: Alternaria alternata

<400> SEQUENCE: 294

Tyr Thr Gly Lys Ile Lys Ile Ala Met
1               5

<210> SEQ ID NO 295
<211> LENGTH: 9
<212> TYPE: PRT
<213> ORGANISM: Alternaria alternata

<400> SEQUENCE: 295

Thr Gly Lys Ile Lys Ile Ala Met Asp
1               5

<210> SEQ ID NO 296
<211> LENGTH: 9
<212> TYPE: PRT
<213> ORGANISM: Alternaria alternata

<400> SEQUENCE: 296

Gly Lys Ile Lys Ile Ala Met Asp Val
1               5

<210> SEQ ID NO 297
<211> LENGTH: 9
<212> TYPE: PRT
<213> ORGANISM: Alternaria alternata

<400> SEQUENCE: 297

Lys Ile Lys Ile Ala Met Asp Val Ala
1               5

<210> SEQ ID NO 298
<211> LENGTH: 9
<212> TYPE: PRT
<213> ORGANISM: Alternaria alternata

<400> SEQUENCE: 298

Ile Lys Ile Ala Met Asp Val Ala Ser
1               5

<210> SEQ ID NO 299
<211> LENGTH: 9
<212> TYPE: PRT
<213> ORGANISM: Alternaria alternata

<400> SEQUENCE: 299

Lys Ile Ala Met Asp Val Ala Ser Ser
1               5

<210> SEQ ID NO 300
<211> LENGTH: 9
<212> TYPE: PRT
<213> ORGANISM: Alternaria alternata

<400> SEQUENCE: 300

Ile Ala Met Asp Val Ala Ser Ser Glu
1               5
```

<210> SEQ ID NO 301
<211> LENGTH: 9
<212> TYPE: PRT
<213> ORGANISM: Alternaria alternata

<400> SEQUENCE: 301

Ala Met Asp Val Ala Ser Ser Glu Phe
1               5

<210> SEQ ID NO 302
<211> LENGTH: 15
<212> TYPE: PRT
<213> ORGANISM: Alternaria alternata

<400> SEQUENCE: 302

Tyr Thr Gly Lys Ile Lys Ile Ala Met Asp Val Ala Ser Ser Glu
1               5                   10                  15

<210> SEQ ID NO 303
<211> LENGTH: 9
<212> TYPE: PRT
<213> ORGANISM: Alternaria alternata

<400> SEQUENCE: 303

Ala Phe Gly Ala Gly Trp Gly Val Met
1               5

<210> SEQ ID NO 304
<211> LENGTH: 9
<212> TYPE: PRT
<213> ORGANISM: Alternaria alternata

<400> SEQUENCE: 304

Phe Gly Ala Gly Trp Gly Val Met Val
1               5

<210> SEQ ID NO 305
<211> LENGTH: 9
<212> TYPE: PRT
<213> ORGANISM: Alternaria alternata

<400> SEQUENCE: 305

Gly Ala Gly Trp Gly Val Met Val Ser
1               5

<210> SEQ ID NO 306
<211> LENGTH: 9
<212> TYPE: PRT
<213> ORGANISM: Alternaria alternata

<400> SEQUENCE: 306

Ala Gly Trp Gly Val Met Val Ser His
1               5

<210> SEQ ID NO 307
<211> LENGTH: 9
<212> TYPE: PRT
<213> ORGANISM: Alternaria alternata

<400> SEQUENCE: 307

Gly Trp Gly Val Met Val Ser His Arg
1               5

<210> SEQ ID NO 308

<211> LENGTH: 9
<212> TYPE: PRT
<213> ORGANISM: Alternaria alternata

<400> SEQUENCE: 308

Trp Gly Val Met Val Ser His Arg Ser
1 5

<210> SEQ ID NO 309
<211> LENGTH: 9
<212> TYPE: PRT
<213> ORGANISM: Alternaria alternata

<400> SEQUENCE: 309

Gly Val Met Val Ser His Arg Ser Gly
1 5

<210> SEQ ID NO 310
<211> LENGTH: 9
<212> TYPE: PRT
<213> ORGANISM: Alternaria alternata

<400> SEQUENCE: 310

Val Met Val Ser His Arg Ser Gly Glu
1 5

<210> SEQ ID NO 311
<211> LENGTH: 9
<212> TYPE: PRT
<213> ORGANISM: Alternaria alternata

<400> SEQUENCE: 311

Met Val Ser His Arg Ser Gly Glu Thr
1 5

<210> SEQ ID NO 312
<211> LENGTH: 9
<212> TYPE: PRT
<213> ORGANISM: Alternaria alternata

<400> SEQUENCE: 312

Val Ser His Arg Ser Gly Glu Thr Glu
1 5

<210> SEQ ID NO 313
<211> LENGTH: 16
<212> TYPE: PRT
<213> ORGANISM: Alternaria alternata

<400> SEQUENCE: 313

Phe Gly Ala Gly Trp Gly Val Met Val Ser His Arg Ser Gly Glu Thr
1 5 10 15

<210> SEQ ID NO 314
<211> LENGTH: 11
<212> TYPE: PRT
<213> ORGANISM: Betula pendula

<400> SEQUENCE: 314

Phe Lys Tyr Val Lys Glu Arg Val Asp Glu Val
1 5 10

<210> SEQ ID NO 315
<211> LENGTH: 9
<212> TYPE: PRT

```
<213> ORGANISM: Phleum pratense

<400> SEQUENCE: 315

Thr Phe Val Ala Thr Phe Gly Ala Ala
1               5

<210> SEQ ID NO 316
<211> LENGTH: 320
<212> TYPE: PRT
<213> ORGANISM: Dermatophagoides pteronyssinus

<400> SEQUENCE: 316

Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
    130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
    210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
        275                 280                 285

Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu
305                 310                 315                 320

<210> SEQ ID NO 317
<211> LENGTH: 146
<212> TYPE: PRT
```

<213> ORGANISM: Dermatophagoides pteronyssinus

<400> SEQUENCE: 317

```
Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
            20                  25                  30

Val Leu Val Pro Gly Cys His Gly Ser Glu Pro Cys Ile Ile His Arg
        35                  40                  45

Gly Lys Pro Phe Gln Leu Glu Ala Val Phe Glu Ala Asn Gln Asn Thr
    50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Val Met
        115                 120                 125

Gly Asp Asp Gly Val Leu Ala Cys Ala Ile Ala Thr His Ala Lys Ile
    130                 135                 140

Arg Asp
145
```

<210> SEQ ID NO 318
<211> LENGTH: 261
<212> TYPE: PRT
<213> ORGANISM: Dermatophagoides pteronyssinus

<400> SEQUENCE: 318

```
Met Ile Ile Tyr Asn Ile Leu Ile Val Leu Leu Ala Ile Asn Thr
1               5                   10                  15

Leu Ala Asn Pro Ile Leu Pro Ala Ser Pro Asn Ala Thr Ile Val Gly
            20                  25                  30

Gly Glu Lys Ala Leu Ala Gly Glu Cys Pro Tyr Gln Ile Ser Leu Gln
        35                  40                  45

Ser Ser Ser His Phe Cys Gly Gly Thr Ile Leu Asp Glu Tyr Trp Ile
    50                  55                  60

Leu Thr Ala Ala His Cys Val Ala Gly Gln Thr Ala Ser Lys Leu Ser
65                  70                  75                  80

Ile Arg Tyr Asn Ser Leu Lys His Ser Leu Gly Gly Glu Lys Ile Ser
                85                  90                  95

Val Ala Lys Ile Phe Ala His Glu Lys Tyr Asp Ser Tyr Gln Ile Asp
            100                 105                 110

Asn Asp Ile Ala Leu Ile Lys Leu Lys Ser Pro Met Lys Leu Asn Gln
        115                 120                 125

Lys Asn Ala Lys Ala Val Gly Leu Pro Ala Lys Gly Ser Asp Val Lys
    130                 135                 140

Val Gly Asp Gln Val Arg Val Ser Gly Trp Gly Tyr Leu Glu Glu Gly
145                 150                 155                 160

Ser Tyr Ser Leu Pro Ser Glu Leu Arg Arg Val Asp Ile Ala Val Val
                165                 170                 175

Ser Arg Lys Glu Cys Asn Glu Leu Tyr Ser Lys Ala Asn Ala Glu Val
            180                 185                 190

Thr Asp Asn Met Ile Cys Gly Gly Asp Val Ala Asn Gly Gly Lys Asp
```

```
                 195                 200                 205

Ser Cys Gln Gly Asp Ser Gly Gly Pro Val Val Asp Val Lys Asn Asn
210                 215                 220

Gln Val Val Gly Ile Val Ser Trp Gly Tyr Gly Cys Ala Arg Lys Gly
225                 230                 235                 240

Tyr Pro Gly Val Tyr Thr Arg Val Gly Asn Phe Ile Asp Trp Ile Glu
                245                 250                 255

Ser Lys Arg Ser Gln
            260

<210> SEQ ID NO 319
<211> LENGTH: 19
<212> TYPE: PRT
<213> ORGANISM: Dermatophagoides pteronyssinus
<220> FEATURE:
<221> NAME/KEY: UNSURE
<222> LOCATION: (3)..(3)
<223> OTHER INFORMATION: Xaa = unknown
<220> FEATURE:
<221> NAME/KEY: UNSURE
<222> LOCATION: (10)..(10)
<223> OTHER INFORMATION: Xaa = unknown
<220> FEATURE:
<221> NAME/KEY: UNSURE
<222> LOCATION: (16)..(16)
<223> OTHER INFORMATION: Xaa = unknown

<400> SEQUENCE: 319

Lys Tyr Xaa Asn Pro His Phe Ile Gly Xaa Arg Ser Val Ile Thr Xaa
1               5                   10                  15

Leu Met Glu

<210> SEQ ID NO 320
<211> LENGTH: 132
<212> TYPE: PRT
<213> ORGANISM: Dermatophagoides pteronyssinus

<400> SEQUENCE: 320

Met Lys Phe Ile Ile Ala Phe Phe Val Ala Thr Leu Ala Val Met Thr
1               5                   10                  15

Val Ser Gly Glu Asp Lys Lys His Asp Tyr Gln Asn Glu Phe Asp Phe
                20                  25                  30

Leu Leu Met Glu Arg Ile His Glu Gln Ile Lys Lys Gly Glu Leu Ala
            35                  40                  45

Leu Phe Tyr Leu Gln Glu Gln Ile Asn His Phe Glu Glu Lys Pro Thr
        50                  55                  60

Lys Glu Met Lys Asp Lys Ile Val Ala Glu Met Asp Thr Ile Ile Ala
65                  70                  75                  80

Met Ile Asp Gly Val Arg Gly Val Leu Asp Arg Leu Met Gln Arg Lys
                85                  90                  95

Asp Leu Asp Ile Phe Glu Gln Tyr Asn Leu Glu Met Ala Lys Lys Ser
            100                 105                 110

Gly Asp Ile Leu Glu Arg Asp Leu Lys Lys Glu Glu Ala Arg Val Lys
        115                 120                 125

Lys Ile Glu Val
    130

<210> SEQ ID NO 321
<211> LENGTH: 20
<212> TYPE: PRT
<213> ORGANISM: Dermatophagoides pteronyssinus
```

```
<220> FEATURE:
<221> NAME/KEY: UNSURE
<222> LOCATION: (4)..(4)
<223> OTHER INFORMATION: Xaa = unknown

<400> SEQUENCE: 321

Ala Ile Gly Xaa Gln Pro Ala Ala Glu Ala Glu Ala Pro Phe Gln Ile
1               5                   10                  15

Ser Leu Met Lys
            20

<210> SEQ ID NO 322
<211> LENGTH: 215
<212> TYPE: PRT
<213> ORGANISM: Dermatophagoides pteronyssinus

<400> SEQUENCE: 322

Met Met Lys Leu Leu Leu Ile Ala Ala Ala Phe Val Ala Val Ser
1               5                   10                  15

Ala Asp Pro Ile His Tyr Asp Lys Ile Thr Glu Glu Ile Asn Lys Ala
            20                  25                  30

Val Asp Glu Ala Val Ala Ala Ile Glu Lys Ser Glu Thr Phe Asp Pro
        35                  40                  45

Met Lys Val Pro Asp His Ser Asp Lys Phe Glu Arg His Ile Gly Ile
    50                  55                  60

Ile Asp Leu Lys Gly Glu Leu Asp Met Arg Asn Ile Gln Val Arg Gly
65                  70                  75                  80

Leu Lys Gln Met Lys Arg Val Gly Asp Ala Asn Val Lys Ser Glu Asp
                85                  90                  95

Gly Val Val Lys Ala His Leu Leu Val Gly Val His Asp Asp Val Val
            100                 105                 110

Ser Met Glu Tyr Asp Leu Ala Tyr Lys Leu Gly Asp Leu His Pro Asn
        115                 120                 125

Thr His Val Ile Ser Asp Ile Gln Asp Phe Val Val Glu Leu Ser Leu
    130                 135                 140

Glu Val Ser Glu Glu Gly Asn Met Thr Leu Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Ala Val Leu Ser Asp Val Leu Thr Ala Ile Phe Gln Asp
            180                 185                 190

Thr Val Arg Ala Glu Met Thr Lys Val Leu Ala Pro Ala Phe Lys Lys
        195                 200                 205

Glu Leu Glu Arg Asn Asn Gln
    210                 215

<210> SEQ ID NO 323
<211> LENGTH: 18
<212> TYPE: PRT
<213> ORGANISM: Dermatophagoides pteronyssinus

<400> SEQUENCE: 323

Ile Val Gly Gly Ser Asn Ala Ser Pro Gly Asp Ala Val Tyr Gln Ile
1               5                   10                  15

Ala Leu

<210> SEQ ID NO 324
<211> LENGTH: 319
```

```
<212> TYPE: PRT
<213> ORGANISM: Dermatophagoides farinae

<400> SEQUENCE: 324

Met Lys Phe Val Leu Ala Ile Ala Ser Leu Leu Val Leu Thr Val Tyr
1               5                   10                  15

Ala Arg Pro Ala Ser Ile Lys Thr Phe Glu Phe Lys Lys Ala Phe Asn
            20                  25                  30

Lys Asn Tyr Ala Thr Val Glu Glu Glu Val Ala Arg Lys Asn Phe
        35                  40                  45

Leu Glu Ser Leu Lys Tyr Val Glu Ala Asn Lys Gly Ala Ile Asn His
    50                  55                  60

Leu Ser Asp Leu Ser Leu Asp Glu Phe Lys Asn Arg Tyr Leu Met Ser
65                  70                  75                  80

Ala Glu Ala Phe Glu Gln Leu Lys Thr Gln Phe Asp Leu Asn Ala Glu
                85                  90                  95

Thr Ser Ala Cys Arg Ile Asn Ser Val Asn Val Pro Ser Glu Leu Asp
            100                 105                 110

Leu Arg Ser Leu Arg Thr Val Thr Pro Ile Arg Met Gln Gly Gly Cys
        115                 120                 125

Gly Ser Cys Trp Ala Phe Ser Gly Val Ala Ala Thr Glu Ser Ala Tyr
    130                 135                 140

Leu Ala Tyr Arg Asn Thr Ser Leu Asp Leu Ser Glu Gln Glu Leu Val
145                 150                 155                 160

Asp Cys Ala Ser Gln His Gly Cys His Gly Asp Thr Ile Pro Arg Gly
                165                 170                 175

Ile Glu Tyr Ile Gln Gln Asn Gly Val Val Glu Glu Arg Ser Tyr Pro
            180                 185                 190

Tyr Val Ala Arg Glu Gln Arg Cys Arg Arg Pro Asn Ser Gln His Tyr
        195                 200                 205

Gly Ile Ser Asn Tyr Cys Gln Ile Tyr Pro Pro Asp Val Lys Gln Ile
    210                 215                 220

Arg Glu Ala Leu Thr Gln Thr His Thr Ala Ile Ala Val Ile Ile Gly
225                 230                 235                 240

Ile Lys Asp Leu Arg Ala Phe Gln His Tyr Asp Gly Arg Thr Ile Ile
                245                 250                 255

Gln His Asp Asn Gly Tyr Gln Pro Asn Tyr His Ala Val Asn Ile Val
            260                 265                 270

Gly Tyr Gly Ser Thr Gln Gly Asp Asp Tyr Trp Ile Val Arg Asn Ser
        275                 280                 285

Trp Asp Thr Thr Trp Gly Asp Ser Gly Tyr Gly Tyr Phe Gln Ala Gly
    290                 295                 300

Asn Asn Leu Met Met Ile Glu Gln Tyr Pro Tyr Val Val Ile Met
305                 310                 315

<210> SEQ ID NO 325
<211> LENGTH: 146
<212> TYPE: PRT
<213> ORGANISM: Dermatophagoides farinae

<400> SEQUENCE: 325

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30
```

```
Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
 50                  55                  60

Lys Thr Ala Lys Ile Glu Ile Lys Ala Ser Leu Asp Gly Leu Glu Ile
 65                  70                  75                  80

Asp Val Pro Gly Ile Asp Thr Asn Ala Cys His Phe Met Lys Cys Pro
                 85                  90                  95

Leu Val Lys Gly Gln Gln Tyr Asp Ile Lys Tyr Thr Trp Asn Val Pro
                100                 105                 110

Lys Ile Ala Pro Lys Ser Glu Asn Val Val Thr Val Lys Leu Ile
        115                 120                 125

Gly Asp Asn Gly Val Leu Ala Cys Ala Ile Ala Thr His Gly Lys Ile
        130                 135                 140

Arg Asp
145

<210> SEQ ID NO 326
<211> LENGTH: 259
<212> TYPE: PRT
<213> ORGANISM: Dermatophagoides farinae

<400> SEQUENCE: 326

Met Met Ile Leu Thr Ile Val Val Leu Leu Ala Ala Asn Ile Leu Ala
 1               5                  10                  15

Thr Pro Ile Leu Pro Ser Ser Pro Asn Ala Thr Ile Val Gly Gly Val
             20                  25                  30

Lys Ala Gln Ala Gly Asp Cys Pro Tyr Gln Ile Ser Leu Gln Ser Ser
        35                  40                  45

Ser His Phe Cys Gly Gly Ser Ile Leu Asp Glu Tyr Trp Ile Leu Thr
 50                  55                  60

Ala Ala His Cys Val Asn Gly Gln Ser Ala Lys Lys Leu Ser Ile Arg
 65                  70                  75                  80

Tyr Asn Thr Leu Lys His Ala Ser Gly Gly Glu Lys Ile Gln Val Ala
                 85                  90                  95

Glu Ile Tyr Gln His Glu Asn Tyr Asp Ser Met Thr Ile Asp Asn Asp
                100                 105                 110

Val Ala Leu Ile Lys Leu Lys Thr Pro Met Thr Leu Asp Gln Thr Asn
            115                 120                 125

Ala Lys Pro Val Pro Leu Pro Ala Gln Gly Ser Asp Val Lys Val Gly
        130                 135                 140

Asp Lys Ile Arg Val Ser Gly Trp Gly Tyr Leu Gln Glu Gly Ser Tyr
145                 150                 155                 160

Ser Leu Pro Ser Glu Leu Gln Arg Val Asp Ile Asp Val Val Ser Arg
                165                 170                 175

Glu Gln Cys Asp Gln Leu Tyr Ser Lys Ala Gly Ala Asp Val Ser Glu
                180                 185                 190

Asn Met Ile Cys Gly Gly Asp Val Ala Asn Gly Gly Val Asp Ser Cys
            195                 200                 205

Gln Gly Asp Ser Gly Gly Pro Val Val Asp Val Ala Thr Lys Gln Ile
        210                 215                 220

Val Gly Ile Val Ser Trp Gly Tyr Gly Cys Ala Arg Lys Gly Tyr Pro
225                 230                 235                 240

Gly Val Tyr Thr Arg Val Gly Asn Phe Val Asp Trp Ile Glu Ser Lys
                245                 250                 255
```

Arg Ser Gln

<210> SEQ ID NO 327
<211> LENGTH: 20
<212> TYPE: PRT
<213> ORGANISM: Dermatophagoides farinae

<400> SEQUENCE: 327

Ala Val Gly Gly Gln Asp Ala Asp Leu Ala Glu Ala Pro Phe Gln Ile
1               5                   10                  15

Ser Leu Leu Lys
            20

<210> SEQ ID NO 328
<211> LENGTH: 213
<212> TYPE: PRT
<213> ORGANISM: Dermatophagoides farinae

<400> SEQUENCE: 328

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
            20                  25                  30

Ile Asp Asp Ala Ile Ala Ala Ile Glu Gln Ser Glu Thr Ile Asp Pro
        35                  40                  45

Met Lys Val Pro Asp His Ala Asp Lys Phe Glu Arg His Val Gly Ile
    50                  55                  60

Val Asp Phe Lys Gly Glu Leu Ala Met Arg Asn Ile Glu Ala Arg Gly
65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
            100                 105                 110

Ser Met Glu Tyr Asp Leu Ala Tyr Lys Leu Gly Asp Leu His Pro Thr
        115                 120                 125

Thr His Val Ile Ser Asp Ile Gln Asp Phe Val Val Ala Leu Ser Leu
    130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
        195                 200                 205

Glu Leu Glu Lys Asn
    210

<210> SEQ ID NO 329
<211> LENGTH: 138
<212> TYPE: PRT
<213> ORGANISM: Hevea brasiliensis

<400> SEQUENCE: 329

Met Ala Glu Asp Glu Asp Asn Gln Gln Gly Gln Gly Glu Gly Leu Lys
1               5                   10                  15

Tyr Leu Gly Phe Val Gln Asp Ala Ala Thr Tyr Ala Val Thr Thr Phe

```
                20                  25                  30
Ser Asn Val Tyr Leu Phe Ala Lys Asp Lys Ser Gly Pro Leu Gln Pro
                35                  40                  45

Gly Val Asp Ile Ile Glu Gly Pro Val Lys Asn Val Ala Val Pro Leu
            50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Ser Ala Ile Arg Ala Ala
                100                 105                 110

Pro Glu Ala Ala Arg Ser Leu Ala Ser Ser Leu Pro Gly Gln Thr Lys
                115                 120                 125

Ile Leu Ala Lys Val Phe Tyr Gly Glu Asn
                130                 135

<210> SEQ ID NO 330
<211> LENGTH: 204
<212> TYPE: PRT
<213> ORGANISM: Hevea brasiliensis

<400> SEQUENCE: 330

Met Ala Glu Glu Val Glu Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
                20                  25                  30

Tyr Ala Lys Asp Ile Ser Gly Pro Leu Lys Pro Gly Val Asp Thr Ile
                35                  40                  45

Glu Asn Val Val Lys Thr Val Val Thr Pro Val Tyr Tyr Ile Pro Leu
            50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
                100                 105                 110

Ser Val Phe Asn Thr Gly Val Gln Glu Gly Ala Lys Ala Leu Tyr Ala
                115                 120                 125

Asn Leu Glu Pro Lys Ala Glu Gln Tyr Ala Val Ile Thr Trp Arg Ala
            130                 135                 140

Leu Asn Lys Leu Pro Leu Val Pro Gln Val Ala Asn Val Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
                180                 185                 190

Glu Lys Ile Thr Lys Val Phe Gly Asp Glu Ala Ser
                195                 200

<210> SEQ ID NO 331
<211> LENGTH: 263
<212> TYPE: PRT
<213> ORGANISM: Lolium perenne

<400> SEQUENCE: 331

Met Ala Ser Ser Ser Ser Val Leu Leu Val Val Ala Leu Phe Ala Val
```

```
  1               5                  10                 15
Phe Leu Gly Ser Ala His Gly Ile Ala Lys Val Pro Gly Pro Asn
                20                 25                 30

Ile Thr Ala Glu Tyr Gly Asp Lys Trp Leu Asp Ala Lys Ser Thr Trp
                35                 40                 45

Tyr Gly Lys Pro Thr Gly Ala Gly Pro Lys Asp Asn Gly Gly Ala Cys
 50                 55                 60

Gly Tyr Lys Asn Val Asp Lys Ala Pro Phe Asn Gly Met Thr Gly Cys
 65                 70                 75                 80

Gly Asn Thr Pro Ile Phe Lys Asp Gly Arg Gly Cys Gly Ser Cys Phe
                85                 90                 95

Glu Ile Lys Cys Thr Lys Pro Glu Ser Cys Ser Gly Glu Ala Val Thr
                100                105                110

Val Thr Ile Thr Asp Asp Asn Glu Glu Pro Ile Ala Pro Tyr His Phe
                115                120                125

Asp Leu Ser Gly His Ala Phe Gly Ser Met Ala Lys Lys Gly Glu Glu
                130                135                140

Gln Asn Val Arg Ser Ala Gly Glu Leu Glu Leu Gln Phe Arg Arg Val
145                 150                155                160

Lys Cys Lys Tyr Pro Asp Asp Thr Lys Pro Thr Phe His Val Glu Lys
                165                170                175

Ala Ser Asn Pro Asn Tyr Leu Ala Ile Leu Val Lys Tyr Val Asp Gly
                180                185                190

Asp Gly Asp Val Val Ala Val Asp Ile Lys Glu Lys Gly Lys Asp Lys
                195                200                205

Trp Ile Glu Leu Lys Glu Ser Trp Gly Ala Val Trp Arg Ile Asp Thr
210                 215                220

Pro Asp Lys Leu Thr Gly Pro Phe Thr Val Arg Tyr Thr Thr Glu Gly
225                 230                235                240

Gly Thr Lys Ser Glu Phe Glu Asp Val Ile Pro Glu Gly Trp Lys Ala
                245                250                255

Asp Thr Ser Tyr Ser Ala Lys
                260

<210> SEQ ID NO 332
<211> LENGTH: 97
<212> TYPE: PRT
<213> ORGANISM: Lolium perenne

<400> SEQUENCE: 332

Ala Ala Pro Val Glu Phe Thr Val Glu Lys Gly Ser Asp Glu Lys Asn
1               5                  10                 15

Leu Ala Leu Ser Ile Lys Tyr Asn Lys Glu Gly Asp Ser Met Ala Glu
                20                 25                 30

Val Glu Leu Lys Glu His Gly Ser Asn Glu Trp Leu Ala Leu Lys Lys
                35                 40                 45

Asn Gly Asp Gly Val Trp Glu Ile Lys Ser Asp Lys Pro Leu Lys Gly
                50                 55                 60

Pro Phe Asn Phe Arg Phe Val Ser Glu Lys Gly Met Arg Asn Val Phe
65                  70                 75                 80

Asp Asp Val Val Pro Ala Asp Phe Lys Val Gly Thr Thr Tyr Lys Pro
                85                 90                 95

Glu
```

<210> SEQ ID NO 333
<211> LENGTH: 97
<212> TYPE: PRT
<213> ORGANISM: Lolium perenne

<400> SEQUENCE: 333

```
Thr Lys Val Asp Leu Thr Val Glu Lys Gly Ser Asp Ala Lys Thr Leu
1               5                   10                  15

Val Leu Asn Ile Lys Tyr Thr Arg Pro Gly Asp Thr Leu Ala Glu Val
            20                  25                  30

Glu Leu Arg Gln His Gly Ser Glu Glu Trp Glu Pro Met Thr Lys Lys
        35                  40                  45

Gly Asn Leu Trp Glu Val Lys Ser Ala Lys Pro Leu Thr Gly Pro Met
    50                  55                  60

Asn Phe Arg Phe Leu Ser Lys Gly Gly Met Lys Asn Val Phe Asp Glu
65                  70                  75                  80

Val Ile Pro Thr Ala Phe Thr Val Gly Lys Thr Tyr Thr Pro Glu Tyr
                85                  90                  95

Asn
```

<210> SEQ ID NO 334
<211> LENGTH: 308
<212> TYPE: PRT
<213> ORGANISM: Lolium perenne

<400> SEQUENCE: 334

```
Met Ala Val Gln Lys Tyr Thr Val Ala Leu Phe Leu Arg Arg Gly Pro
1               5                   10                  15

Arg Gly Gly Pro Gly Arg Ser Tyr Ala Ala Asp Ala Gly Tyr Thr Pro
            20                  25                  30

Ala Ala Ala Ala Thr Pro Ala Thr Pro Ala Ala Thr Pro Ala Gly Gly
        35                  40                  45

Trp Arg Glu Gly Asp Asp Arg Arg Ala Glu Ala Ala Gly Gly Arg Gln
    50                  55                  60

Arg Leu Ala Ser Arg Gln Pro Trp Pro Pro Leu Pro Thr Pro Leu Arg
65                  70                  75                  80

Arg Thr Ser Ser Arg Ser Ser Arg Pro Pro Ser Pro Ser Pro Pro Arg
                85                  90                  95

Ala Ser Ser Pro Thr Ser Ala Ala Lys Ala Pro Gly Leu Ile Pro Lys
                100                 105                 110

Leu Asp Thr Ala Tyr Asp Val Ala Tyr Lys Ala Ala Glu Ala His Pro
            115                 120                 125

Arg Gly Gln Val Arg Arg Leu Arg His Cys Pro His Arg Ser Leu Arg
        130                 135                 140

Val Ile Ala Gly Ala Leu Glu Val His Ala Val Lys Pro Ala Thr Glu
145                 150                 155                 160

Glu Val Leu Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
            180                 185                 190

Pro Thr Asn Asp Lys Phe Thr Val Phe Glu Ser Ala Phe Asn Lys Ala
        195                 200                 205

Leu Asn Glu Cys Thr Gly Gly Ala Met Arg Pro Thr Ser Ser Ser Pro
    210                 215                 220

Pro Ser Arg Pro Arg Ser Ser Arg Pro Thr Pro Pro Ser Pro Ala
225                 230                 235                 240
```

```
Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
            260                 265                 270

Ala Ala Thr Ala Ala Ala Thr Val Ala Thr Ala Ala Thr Ala Ala
        275                 280                 285

Ala Val Leu Pro Pro Pro Leu Leu Val Val Gln Ser Leu Ile Ser Leu
        290                 295                 300

Leu Ile Tyr Tyr
305

<210> SEQ ID NO 335
<211> LENGTH: 339
<212> TYPE: PRT
<213> ORGANISM: Lolium perenne

<400> SEQUENCE: 335

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
            20                  25                  30

Ala Thr Pro Ala Thr Pro Ala Ala Pro Ala Thr Ala Ala Thr Pro Ala
        35                  40                  45

Thr Pro Ala Thr Pro Ala Thr Pro Ala Ala Val Pro Ser Gly Lys Ala
50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
                100                 105                 110

Gly Leu Ala Ser Gly Tyr Ala Asp Gln Ser Lys Asn Gln Leu Thr Ser
                115                 120                 125

Lys Leu Asp Ala Ala Leu Lys Leu Ala Tyr Glu Ala Ala Gln Gly Ala
            130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
            180                 185                 190

Ile Asp Lys Val Asp Ala Ala Tyr Arg Thr Ala Ala Thr Ala Ala Asn
        195                 200                 205

Ala Ala Pro Ala Asn Asp Lys Phe Thr Val Phe Glu Asn Thr Phe Asn
    210                 215                 220

Asn Ala Ile Lys Val Ser Leu Gly Ala Ala Tyr Asp Ser Tyr Lys Phe
225                 230                 235                 240

Ile Pro Thr Leu Val Ala Ala Val Lys Gln Ala Tyr Ala Ala Lys Gln
                245                 250                 255

Ala Thr Ala Pro Glu Val Lys Tyr Val Ser Glu Thr Ala Leu Lys
            260                 265                 270

Lys Ala Val Thr Ala Met Ser Glu Ala Glu Lys Glu Ala Thr Pro Ala
        275                 280                 285

Ala Ala Ala Thr Ala Thr Pro Thr Pro Ala Ala Ala Thr Ala Thr Ala
```

```
            290                 295                 300
Thr Pro Ala Ala Ala Tyr Ala Thr Ala Thr Pro Ala Ala Ala Thr Ala
305                 310                 315                 320

Thr Ala Thr Pro Ala Ala Ala Thr Ala Thr Pro Ala Ala Ala Gly Gly
                325                 330                 335

Tyr Lys Val

<210> SEQ ID NO 336
<211> LENGTH: 339
<212> TYPE: PRT
<213> ORGANISM: Lolium perenne

<400> SEQUENCE: 336

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Thr Pro Ala Ala Pro Ala Thr Ala Ala Thr Pro Ala
            35                  40                  45

Thr Pro Ala Thr Pro Ala Thr Pro Ala Ala Val Pro Ser Gly Lys Ala
50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
            100                 105                 110

Gly Leu Ala Ser Gly Tyr Ala Asp Gln Ser Lys Asn Gln Leu Thr Ser
        115                 120                 125

Lys Leu Asp Ala Ala Leu Lys Leu Ala Tyr Glu Ala Ala Gln Gly Ala
130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
            180                 185                 190

Ile Asp Lys Val Asp Ala Ala Tyr Arg Thr Ala Ala Thr Ala Ala Asn
        195                 200                 205

Ala Ala Pro Ala Asn Asp Lys Phe Thr Val Phe Glu Asn Thr Phe Asn
210                 215                 220

Asn Ala Ile Lys Val Ser Leu Gly Ala Ala Tyr Asp Ser Tyr Lys Phe
225                 230                 235                 240

Ile Pro Thr Leu Val Ala Ala Val Lys Gln Ala Tyr Ala Ala Lys Gln
                245                 250                 255

Ala Thr Ala Pro Glu Val Lys Tyr Thr Val Ser Glu Thr Ala Leu Lys
            260                 265                 270

Lys Ala Val Thr Ala Met Ser Glu Ala Glu Lys Glu Ala Thr Pro Ala
        275                 280                 285

Ala Ala Ala Thr Ala Thr Pro Thr Pro Ala Ala Thr Ala Thr Ala
290                 295                 300

Thr Pro Ala Ala Ala Tyr Ala Thr Ala Thr Pro Ala Ala Ala Thr Ala
305                 310                 315                 320

Thr Ala Thr Pro Ala Ala Ala Thr Ala Thr Pro Ala Ala Ala Gly Gly
```

-continued

```
            325                 330                 335
Tyr Lys Val

<210> SEQ ID NO 337
<211> LENGTH: 134
<212> TYPE: PRT
<213> ORGANISM: Lolium perenne
<220> FEATURE:
<221> NAME/KEY: UNSURE
<222> LOCATION: (103)..(103)
<223> OTHER INFORMATION: Xaa = unknown

<400> SEQUENCE: 337

Asp Lys Gly Pro Gly Phe Val Val Thr Gly Arg Val Tyr Cys Asp Pro
1               5                   10                  15

Cys Arg Ala Gly Phe Glu Thr Asn Val Ser His Asn Val Glu Gly Ala
            20                  25                  30

Thr Val Ala Val Asp Cys Arg Pro Phe Asp Gly Gly Glu Ser Lys Leu
        35                  40                  45

Lys Ala Glu Ala Thr Thr Asp Lys Asp Gly Trp Tyr Lys Ile Glu Ile
    50                  55                  60

Asp Gln Asp His Gln Glu Glu Ile Cys Glu Val Val Leu Ala Lys Ser
65                  70                  75                  80

Pro Asp Lys Ser Cys Ser Glu Ile Glu Glu Phe Arg Asp Arg Ala Arg
                85                  90                  95

Val Pro Leu Thr Ser Asn Xaa Gly Ile Lys Gln Gln Gly Ile Arg Tyr
            100                 105                 110

Ala Asn Pro Ile Ala Phe Phe Arg Lys Glu Pro Leu Lys Glu Cys Gly
        115                 120                 125

Gly Ile Leu Gln Ala Tyr
    130

<210> SEQ ID NO 338
<211> LENGTH: 145
<212> TYPE: PRT
<213> ORGANISM: Olea europaea

<400> SEQUENCE: 338

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30

Phe Ile Pro Gly Ala Ser Leu Arg Leu Gln Cys Lys Asp Lys Glu Asn
        35                  40                  45

Gly Asp Val Thr Phe Thr Glu Val Gly Tyr Thr Arg Ala Glu Gly Leu
    50                  55                  60

Tyr Ser Met Leu Val Glu Arg Asp His Lys Asn Glu Phe Cys Glu Ile
65                  70                  75                  80

Thr Leu Ile Ser Ser Gly Arg Lys Asp Cys Asn Glu Ile Pro Thr Glu
                85                  90                  95

Gly Trp Ala Lys Pro Ser Leu Lys Phe Lys Leu Asn Thr Val Asn Gly
            100                 105                 110

Thr Thr Arg Thr Val Asn Pro Leu Gly Phe Phe Lys Lys Glu Ala Leu
        115                 120                 125

Pro Lys Cys Ala Gln Val Tyr Asn Lys Leu Gly Met Tyr Pro Pro Asn
    130                 135                 140

Met
```

<210> SEQ ID NO 339
<211> LENGTH: 133
<212> TYPE: PRT
<213> ORGANISM: Parietaria judaica

<400> SEQUENCE: 339

```
Met Arg Thr Val Ser Met Ala Ala Leu Val Val Ile Ala Ala Ala Leu
1               5                   10                  15

Ala Trp Thr Ser Ser Ala Glu Pro Ala Pro Ala Pro Ala Pro Gly Glu
            20                  25                  30

Glu Ala Cys Gly Lys Val Val Gln Asp Ile Met Pro Cys Leu His Phe
        35                  40                  45

Val Lys Gly Glu Glu Lys Glu Pro Ser Lys Glu Cys Cys Ser Gly Thr
    50                  55                  60

Lys Lys Leu Ser Glu Glu Val Lys Thr Thr Glu Gln Lys Arg Glu Ala
65                  70                  75                  80

Cys Lys Cys Ile Val Arg Ala Thr Lys Gly Ile Ser Gly Ile Lys Asn
                85                  90                  95

Glu Leu Val Ala Glu Val Pro Lys Lys Cys Asp Ile Lys Thr Thr Leu
            100                 105                 110

Pro Pro Ile Thr Ala Asp Phe Asp Cys Ser Lys Ile Gln Ser Thr Ile
        115                 120                 125

Phe Arg Gly Tyr Tyr
        130
```

<210> SEQ ID NO 340
<211> LENGTH: 133
<212> TYPE: PRT
<213> ORGANISM: Parietaria judaica

<400> SEQUENCE: 340

```
Met Val Arg Ala Leu Met Pro Cys Leu Pro Phe Val Gln Gly Lys Glu
1               5                   10                  15

Lys Glu Pro Ser Lys Gly Cys Cys Ser Gly Ala Lys Arg Leu Asp Gly
            20                  25                  30

Glu Thr Lys Thr Gly Pro Gln Arg Val His Ala Cys Glu Cys Ile Gln
        35                  40                  45

Thr Ala Met Lys Thr Tyr Ser Asp Ile Asp Gly Lys Leu Val Ser Glu
    50                  55                  60

Val Pro Lys His Cys Gly Ile Val Asp Ser Lys Leu Pro Pro Ile Asp
65                  70                  75                  80

Val Asn Met Asp Cys Lys Thr Val Gly Val Val Pro Arg Gln Pro Gln
                85                  90                  95

Leu Pro Val Ser Leu Arg His Gly Pro Val Thr Gly Pro Ser Asp Pro
            100                 105                 110

Ala His Lys Ala Arg Leu Glu Arg Pro Gln Ile Arg Val Pro Pro Pro
        115                 120                 125

Ala Pro Glu Lys Ala
        130
```

<210> SEQ ID NO 341
<211> LENGTH: 133
<212> TYPE: PRT
<213> ORGANISM: Parietaria judaica

<400> SEQUENCE: 341

```
Met Arg Thr Val Ser Met Ala Ala Leu Val Ile Ala Ala Ala Leu
1               5                   10                  15

Ala Trp Thr Ser Ser Ala Glu Leu Ala Ser Ala Pro Ala Pro Gly Glu
            20                  25                  30

Gly Pro Cys Gly Lys Val Val His His Ile Met Pro Cys Leu Lys Phe
        35                  40                  45

Val Lys Gly Glu Glu Lys Glu Pro Ser Lys Ser Cys Cys Ser Gly Thr
50                  55                  60

Lys Lys Leu Ser Glu Glu Val Lys Thr Thr Glu Gln Lys Arg Glu Ala
65                  70                  75                  80

Cys Lys Cys Ile Val Ala Ala Thr Lys Gly Ile Ser Gly Ile Lys Asn
                85                  90                  95

Glu Leu Val Ala Glu Val Pro Lys Lys Cys Gly Ile Thr Thr Thr Leu
            100                 105                 110

Pro Pro Ile Thr Ala Asp Phe Asp Cys Ser Lys Ile Glu Ser Thr Ile
        115                 120                 125

Phe Arg Gly Tyr Tyr
        130

<210> SEQ ID NO 342
<211> LENGTH: 176
<212> TYPE: PRT
<213> ORGANISM: Parietaria judaica

<400> SEQUENCE: 342

Met Arg Thr Val Ser Ala Pro Ser Ala Val Leu Val Val Ile Val
1               5                   10                  15

Ala Ala Gly Leu Ala Trp Thr Ser Leu Ala Ser Val Ala Pro Pro Ala
            20                  25                  30

Pro Ala Pro Gly Ser Glu Glu Thr Cys Gly Thr Val Arg Ala Leu
        35                  40                  45

Met Pro Cys Leu Pro Phe Val Gln Gly Lys Glu Lys Glu Pro Ser Lys
50                  55                  60

Gly Cys Cys Ser Gly Ala Lys Arg Leu Asp Gly Glu Thr Lys Thr Gly
65                  70                  75                  80

Leu Gln Arg Val His Ala Cys Glu Cys Ile Gln Thr Ala Met Lys Thr
                85                  90                  95

Tyr Ser Asp Ile Asp Gly Lys Leu Val Ser Glu Val Pro Lys His Cys
            100                 105                 110

Gly Ile Val Asp Ser Lys Leu Pro Pro Ile Asp Val Asn Met Asp Cys
        115                 120                 125

Lys Thr Leu Gly Val Val Pro Arg Gln Pro Gln Leu Pro Val Ser Leu
130                 135                 140

Arg His Gly Pro Val Thr Gly Pro Ser Asp Pro Ala His Lys Ala Arg
145                 150                 155                 160

Leu Glu Arg Pro Gln Ile Arg Val Pro Pro Ala Pro Glu Lys Ala
            165                 170                 175

<210> SEQ ID NO 343
<211> LENGTH: 138
<212> TYPE: PRT
<213> ORGANISM: Parietaria judaica

<400> SEQUENCE: 343

Met Arg Thr Val Ser Ala Arg Ser Ser Val Ala Leu Val Val Ile Val
1               5                   10                  15
```

```
Ala Ala Val Leu Val Trp Thr Ser Ser Ala Ser Val Ala Pro Ala Pro
            20                  25                  30

Ala Pro Gly Ser Glu Glu Thr Cys Gly Thr Val Val Gly Ala Leu Met
        35                  40                  45

Pro Cys Leu Pro Phe Val Gln Gly Lys Glu Lys Glu Pro Ser Lys Gly
 50                  55                  60

Cys Cys Ser Gly Ala Lys Arg Leu Asp Gly Thr Lys Thr Gly Pro
 65                  70                  75                  80

Gln Arg Val His Ala Cys Glu Cys Ile Gln Thr Ala Met Lys Thr Tyr
                85                  90                  95

Ser Asp Ile Asp Gly Lys Leu Val Ser Glu Val Pro Lys His Cys Gly
            100                 105                 110

Ile Val Asp Ser Lys Leu Pro Pro Ile Asp Val Asn Met Asp Cys Lys
            115                 120                 125

Thr Leu Gly Val Leu His Tyr Lys Gly Asn
            130                 135

<210> SEQ ID NO 344
<211> LENGTH: 143
<212> TYPE: PRT
<213> ORGANISM: Parietaria judaica

<400> SEQUENCE: 344

Met Val Arg Ala Leu Met Pro Cys Leu Pro Phe Val Gln Gly Lys Glu
 1               5                  10                  15

Lys Glu Pro Ser Lys Gly Cys Cys Ser Gly Ala Lys Arg Leu Asp Gly
            20                  25                  30

Glu Thr Lys Thr Gly Pro Gln Arg Val His Ala Cys Glu Cys Ile Gln
        35                  40                  45

Thr Ala Met Lys Thr Tyr Ser Asp Ile Asp Gly Lys Leu Val Ser Glu
 50                  55                  60

Val Pro Lys His Cys Gly Ile Val Asp Ser Lys Leu Pro Pro Ile Asp
 65                  70                  75                  80

Val Asn Met Asp Cys Lys Thr Val Gly Val Pro Arg Gln Pro Gln
                85                  90                  95

Leu Pro Val Ser Leu Arg His Gly Pro Val Thr Gly Pro Ser Arg Ser
            100                 105                 110

Arg Pro Pro Thr Lys His Gly Trp Arg Asp Pro Arg Leu Glu Phe Arg
            115                 120                 125

Pro Pro His Arg Lys Lys Pro Asn Pro Ala Phe Ser Thr Leu Gly
            130                 135                 140

<210> SEQ ID NO 345
<211> LENGTH: 263
<212> TYPE: PRT
<213> ORGANISM: Phleum pratense

<400> SEQUENCE: 345

Met Ala Ser Ser Ser Val Leu Leu Val Val Val Leu Phe Ala Val
 1               5                  10                  15

Phe Leu Gly Ser Ala Tyr Gly Ile Pro Lys Val Pro Pro Gly Pro Asn
            20                  25                  30

Ile Thr Ala Thr Tyr Gly Asp Lys Trp Leu Asp Ala Lys Ser Thr Trp
        35                  40                  45

Tyr Gly Lys Pro Thr Gly Ala Gly Pro Lys Asp Asn Gly Gly Ala Cys
 50                  55                  60
```

-continued

```
Gly Tyr Lys Asp Val Asp Lys Pro Pro Phe Ser Gly Met Thr Gly Cys
 65                  70                  75                  80

Gly Asn Thr Pro Ile Phe Lys Ser Gly Arg Gly Cys Gly Ser Cys Phe
                 85                  90                  95

Glu Ile Lys Cys Thr Lys Pro Glu Ala Cys Ser Gly Glu Pro Val Val
            100                 105                 110

Val His Ile Thr Asp Asp Asn Glu Glu Pro Ile Ala Pro Tyr His Phe
            115                 120                 125

Asp Leu Ser Gly His Ala Phe Gly Ala Met Ala Lys Lys Gly Asp Glu
        130                 135                 140

Gln Lys Leu Arg Ser Ala Gly Glu Leu Glu Leu Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
            180                 185                 190

Asp Gly Asp Val Val Ala Val Asp Ile Lys Glu Lys Gly Lys Asp Lys
            195                 200                 205

Trp Ile Glu Leu Lys Glu Ser Trp Gly Ala Ile Trp Arg Ile Asp Thr
        210                 215                 220

Pro Asp Lys Leu Thr Gly Pro Phe Thr Val Arg Tyr Thr Thr Glu Gly
225                 230                 235                 240

Gly Thr Lys Thr Glu Ala Glu Asp Val Ile Pro Glu Gly Trp Lys Ala
                245                 250                 255

Asp Thr Ser Tyr Glu Ser Lys
            260

<210> SEQ ID NO 346
<211> LENGTH: 262
<212> TYPE: PRT
<213> ORGANISM: Phleum pratense

<400> SEQUENCE: 346

Met Ala Ser Ser Ser Val Leu Leu Val Val Ala Leu Phe Ala Val
 1               5                  10                  15

Phe Leu Gly Ser Ala His Gly Ile Pro Lys Val Pro Pro Gly Pro Asn
                 20                  25                  30

Ile Thr Ala Thr Tyr Gly Asp Lys Trp Leu Asp Ala Lys Ser Thr Trp
             35                  40                  45

Tyr Gly Lys Pro Thr Ala Ala Gly Pro Lys Asp Asn Gly Gly Ala Cys
 50                  55                  60

Gly Tyr Lys Asp Val Asp Lys Pro Pro Phe Ser Gly Met Thr Gly Cys
 65                  70                  75                  80

Gly Asn Thr Pro Ile Phe Lys Ser Gly Arg Gly Cys Gly Ser Cys Phe
                 85                  90                  95

Glu Ile Lys Cys Thr Lys Pro Glu Ala Cys Ser Gly Glu Pro Val Val
            100                 105                 110

Val His Ile Thr Asp Asp Asn Glu Glu Pro Ile Ala Ala Tyr His Phe
            115                 120                 125

Asp Leu Ser Gly Ile Ala Phe Gly Ser Met Ala Lys Lys Gly Asp Glu
        130                 135                 140

Gln Lys Leu Arg Ser Ala Gly Glu Val Glu Ile Gln Phe Arg Arg Val
145                 150                 155                 160

Lys Cys Lys Tyr Pro Glu Gly Thr Lys Val Thr Phe His Val Glu Lys
```

```
                    165                 170                 175
Gly Ser Asn Pro Asn Tyr Leu Ala Leu Leu Val Lys Phe Ser Gly Asp
                180                 185                 190

Gly Asp Val Val Ala Val Asp Ile Lys Glu Gly Lys Asp Lys Trp
                195                 200                 205

Ile Ala Leu Lys Glu Ser Trp Gly Ala Ile Trp Arg Ile Asp Thr Pro
210                 215                 220

Glu Val Leu Lys Gly Pro Phe Thr Val Arg Tyr Thr Thr Gly Gly
225                 230                 235                 240

Thr Lys Ala Arg Ala Lys Asp Val Ile Pro Glu Gly Trp Lys Ala Asp
                245                 250                 255

Thr Ala Tyr Glu Ser Lys
                260

<210> SEQ ID NO 347
<211> LENGTH: 122
<212> TYPE: PRT
<213> ORGANISM: Phleum pratense

<400> SEQUENCE: 347

Met Ser Met Ala Ser Ser Ser Ser Ser Leu Leu Ala Met Ala Val
1               5                   10                  15

Leu Ala Ala Leu Phe Ala Gly Ala Trp Cys Val Pro Lys Val Thr Phe
                20                  25                  30

Thr Val Glu Lys Gly Ser Asn Glu Lys His Leu Ala Val Leu Val Lys
            35                  40                  45

Tyr Glu Gly Asp Thr Met Ala Glu Val Glu Leu Arg Glu His Gly Ser
    50                  55                  60

Asp Glu Trp Val Ala Met Thr Lys Gly Glu Gly Gly Val Trp Thr Phe
65                  70                  75                  80

Asp Ser Glu Glu Pro Leu Gln Gly Pro Phe Asn Phe Arg Phe Leu Thr
                85                  90                  95

Glu Lys Gly Met Lys Asn Val Phe Asp Asp Val Val Pro Glu Lys Tyr
            100                 105                 110

Thr Ile Gly Ala Thr Tyr Ala Pro Glu Glu
        115                 120

<210> SEQ ID NO 348
<211> LENGTH: 276
<212> TYPE: PRT
<213> ORGANISM: Phleum pratense

<400> SEQUENCE: 348

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
                20                  25                  30

Lys Ile Asn Asp Gly Phe Lys Ala Ala Leu Ala Ala Ala Ala Gly Val
            35                  40                  45

Pro Pro Ala Asp Lys Tyr Lys Thr Phe Val Ala Thr Phe Gly Ala Ala
    50                  55                  60

Ser Asn Lys Ala Phe Ala Glu Gly Leu Ser Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
```

-continued

```
                100               105                110
Tyr Asp Ala Tyr Val Ala Thr Leu Ser Glu Ala Leu Arg Ile Ile Ala
            115                 120                 125
Gly Thr Leu Glu Val His Ala Val Lys Pro Ala Ala Glu Glu Val Lys
        130                 135                 140
Val Ile Pro Ala Gly Glu Leu Gln Val Ile Glu Lys Val Asp Ser Ala
145                 150                 155                 160
Phe Lys Val Ala Ala Thr Ala Ala Asn Ala Ala Pro Ala Asn Asp Lys
                165                 170                 175
Phe Thr Val Phe Glu Ala Ala Phe Asn Asn Ala Ile Lys Ala Ser Thr
            180                 185                 190
Gly Gly Ala Tyr Glu Ser Tyr Lys Phe Ile Pro Ala Leu Glu Ala Ala
        195                 200                 205
Val Lys Gln Ala Tyr Ala Ala Thr Val Ala Thr Ala Pro Glu Val Lys
    210                 215                 220
Tyr Thr Val Phe Glu Thr Ala Leu Lys Lys Ala Phe Thr Ala Met Ser
225                 230                 235                 240
Glu Ala Gln Lys Ala Ala Lys Pro Ala Thr Glu Ala Thr Ala Thr Ala
                245                 250                 255
Thr Ala Ala Val Gly Ala Ala Thr Gly Ala Ala Thr Ala Ala Thr Gly
            260                 265                 270
Gly Tyr Lys Val
        275

<210> SEQ ID NO 349
<211> LENGTH: 276
<212> TYPE: PRT
<213> ORGANISM: Phleum pratense

<400> SEQUENCE: 349

Ala Asp Leu Gly Tyr Gly Gly Pro Ala Thr Pro Ala Ala Pro Ala Glu
1               5                   10                  15
Ala Ala Pro Ala Gly Lys Ala Thr Thr Glu Glu Gln Lys Leu Ile Glu
            20                  25                  30
Lys Ile Asn Asp Gly Phe Lys Ala Ala Leu Ala Ala Ala Ala Gly Val
        35                  40                  45
Pro Pro Ala Asp Lys Tyr Lys Thr Phe Val Ala Thr Phe Gly Ala Ala
    50                  55                  60
Ser Asn Lys Ala Phe Ala Glu Gly Leu Ser Ala Glu Pro Lys Gly Ala
65                  70                  75                  80
Ala Glu Ser Ser Ser Lys Ala Ala Leu Thr Ser Lys Leu Asp Ala Ala
                85                  90                  95
Tyr Lys Leu Ala Tyr Lys Thr Ala Glu Gly Ala Thr Pro Glu Ala Lys
            100                 105                 110
Tyr Asp Ala Tyr Val Ala Thr Leu Ser Glu Ala Leu Arg Ile Ile Ala
            115                 120                 125
Gly Thr Leu Glu Val His Ala Val Lys Pro Ala Ala Glu Glu Val Lys
        130                 135                 140
Val Ile Pro Ala Gly Glu Leu Gln Val Ile Glu Lys Val Asp Ser Ala
145                 150                 155                 160
Phe Lys Val Ala Ala Thr Ala Ala Asn Ala Ala Pro Ala Asn Asp Lys
                165                 170                 175
Phe Thr Val Phe Glu Ala Ala Phe Asn Asn Ala Ile Lys Ala Ser Thr
            180                 185                 190
```

```
Gly Gly Ala Tyr Glu Ser Tyr Lys Phe Ile Pro Ala Leu Glu Ala Ala
            195                 200                 205

Val Lys Gln Ala Tyr Ala Ala Thr Val Ala Thr Ala Pro Glu Val Lys
    210                 215                 220

Tyr Thr Val Phe Glu Thr Ala Leu Lys Lys Ala Ile Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Thr Gly
            260                 265                 270

Gly Tyr Lys Val
        275

<210> SEQ ID NO 350
<211> LENGTH: 284
<212> TYPE: PRT
<213> ORGANISM: Phleum pratense

<400> SEQUENCE: 350

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Thr Glu Glu Gln Lys Leu Ile Glu
        35                  40                  45

Asp Ile Asn Val Gly Phe Lys Ala Ala Val Ala Ala Ala Ala Ser Val
    50                  55                  60

Pro Ala Ala Asp Lys Phe Lys Thr Phe Glu Ala Ala Phe Thr Ser Ser
65                  70                  75                  80

Ser Lys Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
        115                 120                 125

Ile Ala Gly Ala Leu Glu Val His Ala Val Lys Pro Val Thr Glu Glu
    130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
        195                 200                 205

Leu Glu Ala Ala Val Lys Gln Ala Tyr Ala Ala Thr Val Ala Ala Ala
    210                 215                 220

Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
                245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
        275                 280
```

<210> SEQ ID NO 351
<211> LENGTH: 286
<212> TYPE: PRT
<213> ORGANISM: Phleum pratense

<400> SEQUENCE: 351

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Gly Ala Asp Ala Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Gly Ala Gly Val Gln Pro Ala Asp Lys Tyr
    50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
        115                 120                 125

Thr Leu Ser Glu Ala Leu Arg Ile Ile Ala Gly Thr Leu Glu Val His
    130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Thr Ala Thr Ala Thr Ala Val Gly Ala
            260                 265                 270

Ala Thr Gly Ala Ala Thr Ala Ala Thr Gly Gly Tyr Lys Val
        275                 280                 285

<210> SEQ ID NO 352
<211> LENGTH: 287
<212> TYPE: PRT
<213> ORGANISM: Phleum pratense

<400> SEQUENCE: 352

Met Ala Val Gln Lys Tyr Thr Val Ala Leu Phe Leu Ala Val Ala Leu
1               5                   10                  15

Val Ala Gly Pro Ala Ala Ser Tyr Ala Ala Asp Ala Gly Tyr Ala Pro
            20                  25                  30

Ala Thr Pro Ala Ala Ala Gly Ala Glu Ala Gly Lys Ala Thr Thr Glu
        35                  40                  45

```
Glu Gln Lys Leu Ile Glu Asp Ile Asn Val Gly Phe Lys Ala Ala Val
    50                  55                  60

Ala Ala Ala Ala Ser Val Pro Ala Ala Asp Lys Phe Lys Thr Phe Glu
 65              70                  75                  80

Ala Ala Phe Thr Ser Ser Ser Lys Ala Ala Thr Ala Lys Ala Pro Gly
                 85                  90                  95

Leu Val Pro Lys Leu Asp Ala Ala Tyr Ser Val Ser Tyr Lys Ala Ala
                100                 105                 110

Val Gly Ala Thr Pro Glu Ala Lys Phe Asp Ser Phe Val Ala Ser Leu
            115                 120                 125

Thr Glu Ala Leu Arg Val Ile Ala Gly Ala Leu Glu Val His Ala Val
        130                 135                 140

Lys Pro Val Thr Glu Glu Pro Gly Met Ala Lys Ile Pro Ala Gly Glu
145                 150                 155                 160

Leu Gln Ile Ile Asp Lys Ile Asp Ala Ala Phe Lys Val Ala Ala Thr
                165                 170                 175

Ala Ala Ala Thr Ala Pro Ala Asp Thr Val Phe Glu Ala Ala Phe Asn
            180                 185                 190

Lys Ala Ile Lys Glu Ser Thr Gly Gly Ala Tyr Asp Thr Tyr Lys Cys
        195                 200                 205

Ile Pro Ser Leu Glu Ala Ala Val Lys Gln Ala Tyr Ala Ala Thr Val
210                 215                 220

Ala Ala Ala Pro Gln Val Lys Tyr Ala Val Phe Glu Ala Ala Leu Thr
225                 230                 235                 240

Lys Ala Ile Thr Ala Met Ser Glu Val Gln Lys Val Ser Gln Pro Ala
                245                 250                 255

Thr Gly Ala Ala Thr Val Ala Ala Gly Ala Ala Thr Thr Ala Ala Gly
            260                 265                 270

Ala Ala Ser Gly Ala Ala Thr Val Ala Ala Gly Gly Tyr Lys Val
            275                 280                 285

<210> SEQ ID NO 353
<211> LENGTH: 290
<212> TYPE: PRT
<213> ORGANISM: Phleum pratense

<400> SEQUENCE: 353

Met Ala Val Gln Lys Tyr Thr Val Ala Leu Phe Leu Ala Val Ala Leu
 1               5                  10                  15

Val Ala Gly Pro Ala Ala Ser Tyr Ala Ala Asp Ala Gly Tyr Ala Pro
             20                  25                  30

Ala Thr Pro Ala Ala Ala Gly Ala Glu Ala Gly Lys Ala Thr Thr Glu
                 35                  40                  45

Glu Gln Lys Leu Ile Glu Asp Ile Asn Val Gly Phe Lys Ala Ala Val
    50                  55                  60

Ala Ala Ala Ala Ser Val Pro Ala Ala Asp Lys Phe Lys Thr Phe Glu
 65              70                  75                  80

Ala Ala Phe Thr Ser Ser Ser Lys Ala Ala Thr Ala Lys Ala Pro Gly
                 85                  90                  95

Leu Val Pro Lys Leu Asp Ala Ala Tyr Ser Val Ala Tyr Lys Ala Ala
                100                 105                 110

Val Gly Ala Thr Pro Glu Ala Lys Phe Asp Ser Phe Val Ala Ser Leu
            115                 120                 125

Thr Glu Ala Leu Arg Val Ile Ala Gly Ala Leu Glu Val His Ala Val
```

```
                130             135             140
Lys Pro Val Thr Glu Asp Pro Ala Trp Pro Lys Ile Pro Ala Gly Glu
145                 150                 155                 160

Leu Gln Ile Ile Asp Lys Ile Asp Ala Ala Phe Lys Val Ala Ala Thr
                165                 170                 175

Ala Ala Ala Thr Ala Pro Ala Asp Asp Lys Phe Thr Val Phe Glu Ala
            180                 185                 190

Ala Phe Asn Lys Ala Ile Lys Glu Ser Thr Gly Gly Ala Tyr Asp Thr
                195                 200                 205

Tyr Lys Cys Ile Pro Ser Leu Glu Ala Ala Val Lys Gln Ala Tyr Ala
            210                 215                 220

Ala Thr Val Ala Ala Pro Gln Val Lys Tyr Ala Val Phe Glu Ala
225                 230                 235                 240

Ala Leu Thr Lys Ala Ile Thr Ala Met Ser Glu Val Gln Lys Val Ser
                245                 250                 255

Gln Pro Ala Thr Gly Ala Ala Thr Val Ala Ala Gly Ala Ala Thr Thr
            260                 265                 270

Ala Thr Gly Ala Ala Ser Gly Ala Ala Thr Val Ala Ala Gly Gly Tyr
            275                 280                 285

Lys Val
    290

<210> SEQ ID NO 354
<211> LENGTH: 265
<212> TYPE: PRT
<213> ORGANISM: Phleum pratense

<400> SEQUENCE: 354

Ala Asp Ala Gly Tyr Ala Pro Ala Thr Pro Ala Ala Ala Gly Ala Glu
1               5                   10                  15

Ala Gly Lys Ala Thr Thr Glu Glu Gln Lys Leu Ile Glu Asp Ile Asn
                20                  25                  30

Val Gly Phe Lys Ala Ala Val Ala Ala Ala Ser Val Pro Ala Ala
            35                  40                  45

Asp Lys Phe Lys Thr Phe Glu Ala Ala Phe Thr Ser Ser Lys Ala
    50                  55                  60

Ala Thr Ala Lys Ala Pro Gly Leu Val Pro Lys Leu Asp Ala Ala Tyr
65                  70                  75                  80

Ser Val Ala Tyr Lys Ala Ala Val Gly Ala Thr Pro Glu Ala Lys Phe
                85                  90                  95

Asp Ser Phe Val Ala Ser Leu Thr Glu Ala Leu Arg Val Ile Ala Gly
            100                 105                 110

Ala Leu Glu Val His Ala Val Lys Pro Val Thr Glu Glu Pro Gly Met
            115                 120                 125

Ala Lys Ile Pro Ala Gly Glu Leu Gln Ile Ile Asp Lys Ile Asp Ala
    130                 135                 140

Ala Phe Lys Val Ala Ala Thr Ala Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
            180                 185                 190

Ala Val Lys Gln Ala Tyr Ala Ala Thr Val Ala Ala Ala Pro Gln Val
            195                 200                 205
```

```
Lys Tyr Ala Val Phe Glu Ala Ala Leu Thr Lys Ala Ile Thr Ala Met
    210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                245                 250                 255

Thr Val Ala Ala Gly Gly Tyr Lys Val
            260                 265

<210> SEQ ID NO 355
<211> LENGTH: 295
<212> TYPE: PRT
<213> ORGANISM: Phleum pratense

<400> SEQUENCE: 355

Ser Val Lys Arg Ser Asn Gly Ser Ala Glu Val His Arg Gly Ala Val
1               5                   10                  15

Pro Arg Arg Gly Pro Arg Gly Gly Pro Gly Arg Ser Tyr Ala Ala Asp
                20                  25                  30

Ala Gly Tyr Ala Pro Ala Thr Pro Ala Ala Gly Ala Glu Ala Gly
            35                  40                  45

Lys Ala Thr Thr Glu Glu Gln Lys Leu Ile Glu Asp Ile Asn Val Gly
    50                  55                  60

Phe Lys Ala Ala Val Ala Ala Ala Ser Val Pro Ala Ala Asp Lys
65                  70                  75                  80

Phe Lys Thr Phe Glu Ala Ala Phe Thr Ser Ser Lys Ala Ala Thr
                85                  90                  95

Ala Lys Ala Pro Gly Leu Val Pro Lys Leu Asp Ala Ala Tyr Ser Val
            100                 105                 110

Ala Tyr Lys Ala Ala Val Gly Ala Thr Pro Glu Ala Lys Phe Asp Ser
            115                 120                 125

Phe Val Ala Ser Leu Thr Glu Ala Leu Arg Val Ile Ala Gly Ala Leu
            130                 135                 140

Glu Val His Ala Val Lys Pro Val Thr Glu Glu Pro Gly Met Ala Lys
145                 150                 155                 160

Ile Pro Ala Gly Glu Leu Gln Ile Ile Asp Lys Ile Asp Ala Ala Phe
                165                 170                 175

Lys Val Ala Ala Thr Ala Ala Thr Ala Pro Ala Asp Lys Phe
            180                 185                 190

Thr Val Phe Glu Ala Ala Phe Asn Lys Ala Ile Lys Glu Ser Thr Gly
            195                 200                 205

Gly Ala Tyr Asp Thr Tyr Lys Cys Ile Pro Ser Leu Glu Ala Ala Val
    210                 215                 220

Lys Gln Ala Tyr Ala Ala Thr Val Ala Ala Ala Pro Gln Val Lys Tyr
225                 230                 235                 240

Ala Val Phe Glu Ala Ala Leu Thr Lys Ala Ile Thr Ala Met Ser Glu
                245                 250                 255

Val Gln Lys Val Ser Gln Pro Ala Thr Gly Ala Ala Thr Val Ala Ala
            260                 265                 270

Gly Ala Ala Thr Thr Ala Ala Gly Ala Ala Ser Gly Ala Ala Thr Val
            275                 280                 285

Ala Ala Gly Gly Tyr Lys Val
    290                 295

<210> SEQ ID NO 356
```

```
<211> LENGTH: 312
<212> TYPE: PRT
<213> ORGANISM: Phleum pratense

<400> SEQUENCE: 356

Met Ala Val His Gln Tyr Thr Val Ala Leu Phe Leu Ala Val Ala Leu
1               5                   10                  15

Val Ala Gly Pro Ala Gly Ser Tyr Ala Ala Asp Leu Gly Tyr Gly Pro
            20                  25                  30

Ala Thr Pro Ala Ala Pro Ala Gly Tyr Thr Pro Ala Thr Pro Ala
        35                  40                  45

Ala Pro Ala Gly Ala Glu Pro Ala Gly Lys Ala Thr Thr Glu Glu Gln
    50                  55                  60

Lys Leu Ile Glu Lys Ile Asn Ala Gly Phe Lys Ala Ala Leu Ala Ala
65                  70                  75                  80

Ala Ala Gly Val Pro Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
130                 135                 140

Pro Glu Ala Lys Tyr Asp Ala Tyr Val Ala Thr Val Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Ala Lys Pro Ala Ala Ala Ala
        275                 280                 285

Thr Ala Thr Ala Thr Ala Ala Val Gly Ala Ala Thr Gly Ala Ala Thr
    290                 295                 300

Ala Ala Thr Gly Gly Tyr Lys Val
305                 310

<210> SEQ ID NO 357
<211> LENGTH: 276
<212> TYPE: PRT
<213> ORGANISM: Phleum pratense

<400> SEQUENCE: 357

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
            20                  25                  30
```

```
Lys Ile Asn Asp Gly Phe Lys Ala Ala Leu Ala Ala Ala Gly Val
            35                  40                  45

Pro Pro Ala Asp Lys Tyr Lys Thr Phe Val Ala Thr Phe Gly Ala Ala
 50                  55                  60

Ser Asn Lys Ala Phe Ala Glu Gly Leu Ser Ala Glu Pro Lys Gly Ala
 65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
                100                 105                 110

Tyr Asp Ala Tyr Val Ala Thr Leu Ser Glu Ala Leu Arg Ile Ile Ala
                115                 120                 125

Gly Thr Leu Glu Val His Ala Val Lys Pro Ala Ala Glu Glu Val Lys
            130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
                180                 185                 190

Gly Gly Ala Tyr Glu Ser Tyr Lys Phe Ile Pro Ala Leu Glu Ala Ala
            195                 200                 205

Val Lys Gln Ala Tyr Ala Ala Thr Val Ala Thr Ala Pro Glu Val Lys
            210                 215                 220

Tyr Thr Val Phe Glu Thr Ala Leu Lys Lys Ala Phe Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
                260                 265                 270

Gly Tyr Lys Val
            275

<210> SEQ ID NO 358
<211> LENGTH: 284
<212> TYPE: PRT
<213> ORGANISM: Phleum pratense

<400> SEQUENCE: 358

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
                20                  25                  30

Gly Ala Ala Ala Gly Lys Ala Thr Thr Glu Glu Gln Lys Leu Ile Glu
            35                  40                  45

Asp Ile Asn Val Gly Phe Lys Ala Val Ala Ala Ala Ser Val
            50                  55                  60

Pro Ala Ala Asp Lys Phe Lys Thr Phe Glu Ala Ala Phe Thr Ser Ser
 65                  70                  75                  80

Ser Lys Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
                100                 105                 110

Ala Lys Phe Asp Ser Phe Val Ala Ser Leu Thr Glu Ala Leu Arg Val
```

```
            115                 120                 125
Ile Ala Gly Ala Leu Glu Val His Ala Val Lys Pro Val Thr Glu Glu
            130                 135                 140
Pro Gly Met Ala Lys Ile Pro Ala Gly Glu Leu Gln Ile Ile Asp Lys
145                 150                 155                 160
Ile Asp Ala Ala Phe Lys Val Ala Ala Thr Ala Ala Thr Ala Pro
                    165                 170                 175
Ala Asp Asp Lys Phe Thr Val Phe Glu Ala Ala Phe Asn Lys Ala Ile
                180                 185                 190
Lys Glu Ser Thr Gly Gly Ala Tyr Asp Thr Tyr Lys Cys Ile Pro Ser
                195                 200                 205
Leu Glu Ala Ala Val Lys Gln Ala Tyr Ala Ala Thr Val Ala Ala Ala
            210                 215                 220
Pro Gln Val Lys Tyr Ala Val Phe Glu Ala Ala Leu Thr Lys Ala Ile
225                 230                 235                 240
Thr Ala Met Ser Glu Val Gln Lys Val Ser Gln Pro Ala Thr Gly Ala
                    245                 250                 255
Ala Thr Val Ala Ala Gly Ala Ala Thr Thr Ala Ala Gly Ala Ala Ser
                260                 265                 270
Gly Ala Ala Thr Val Ala Ala Gly Gly Tyr Lys Val
                275                 280

<210> SEQ ID NO 359
<211> LENGTH: 286
<212> TYPE: PRT
<213> ORGANISM: Phleum pratense

<400> SEQUENCE: 359

Ala Asp Leu Gly Tyr Gly Pro Ala Thr Pro Ala Ala Pro Ala Ala Gly
1               5                   10                  15
Tyr Thr Pro Ala Thr Pro Ala Ala Pro Ala Gly Ala Asp Ala Ala Gly
                20                  25                  30
Lys Ala Thr Thr Glu Glu Gln Lys Leu Ile Glu Lys Ile Asn Ala Gly
                35                  40                  45
Phe Lys Ala Ala Leu Ala Gly Ala Gly Val Gln Pro Ala Asp Lys Tyr
        50                  55                  60
Arg Thr Phe Val Ala Thr Phe Gly Pro Ala Ser Asn Lys Ala Phe Ala
65                  70                  75                  80
Glu Gly Leu Ser Gly Glu Pro Lys Gly Ala Ala Glu Ser Ser Ser Lys
                85                  90                  95
Ala Ala Leu Thr Ser Lys Leu Asp Ala Ala Tyr Lys Leu Ala Tyr Lys
                100                 105                 110
Thr Ala Glu Gly Ala Thr Pro Glu Ala Lys Tyr Asp Ala Tyr Val Ala
            115                 120                 125
Thr Leu Ser Glu Ala Leu Arg Ile Ile Ala Gly Thr Leu Glu Val His
            130                 135                 140
Ala Val Lys Pro Ala Ala Glu Glu Val Lys Val Ile Pro Ala Gly Glu
145                 150                 155                 160
Leu Gln Val Ile Glu Lys Val Asp Ala Ala Phe Lys Val Ala Ala Thr
                165                 170                 175
Ala Ala Asn Ala Ala Pro Ala Asn Asp Lys Phe Thr Val Phe Glu Ala
                180                 185                 190
Ala Phe Asn Asp Glu Ile Lys Ala Ser Thr Gly Gly Ala Tyr Glu Ser
                195                 200                 205
```

-continued

```
Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Ala Thr Ala Thr Ala Thr Ala Ala Val Gly Ala
                260                 265                 270

Ala Thr Gly Ala Ala Thr Ala Ala Thr Gly Gly Tyr Lys Val
                275                 280                 285

<210> SEQ ID NO 360
<211> LENGTH: 281
<212> TYPE: PRT
<213> ORGANISM: Phleum pratense

<400> SEQUENCE: 360

Ala Val Pro Arg Arg Gly Pro Arg Gly Gly Pro Gly Arg Ser Tyr Ala
1               5                   10                  15

Ala Asp Ala Gly Tyr Ala Pro Ala Thr Pro Ala Ala Ala Gly Ala Glu
                20                  25                  30

Ala Gly Lys Ala Thr Thr Glu Glu Gln Lys Leu Ile Glu Asp Ile Asn
            35                  40                  45

Val Gly Phe Lys Ala Ala Val Ala Ala Ala Ser Val Pro Ala Gly
    50                  55                  60

Asp Lys Phe Lys Thr Phe Glu Ala Ala Phe Thr Ser Ser Ser Lys Ala
65                  70                  75                  80

Ala Thr Ala Lys Ala Pro Gly Leu Val Pro Lys Leu Asp Ala Ala Tyr
                85                  90                  95

Ser Val Ala Tyr Lys Ala Ala Val Gly Ala Thr Pro Glu Ala Lys Phe
                100                 105                 110

Asp Ser Phe Val Ala Ser Leu Thr Glu Ala Leu Arg Val Ile Ala Gly
            115                 120                 125

Ala Leu Glu Val His Ala Val Lys Pro Val Thr Glu Glu Pro Gly Met
130                 135                 140

Ala Lys Ile Pro Ala Gly Glu Leu Gln Ile Ile Asp Lys Ile Asp Ala
145                 150                 155                 160

Ala Phe Lys Val Ala Ala Thr Ala Ala Thr Ala Pro Ala Asp Asp
                165                 170                 175

Lys Phe Thr Val Phe Glu Ala Ala Phe Asn Lys Ala Ile Lys Glu Ser
                180                 185                 190

Thr Gly Gly Ala Tyr Asp Thr Tyr Lys Cys Ile Pro Ser Leu Glu Ala
            195                 200                 205

Ala Val Lys Gln Ala Tyr Ala Ala Thr Val Ala Ala Pro Gln Val
        210                 215                 220

Lys Tyr Ala Val Phe Glu Ala Ala Leu Thr Lys Ala Ile Thr Ala Met
225                 230                 235                 240

Ser Glu Val Gln Lys Val Ser Gln Pro Ala Thr Gly Ala Ala Thr Val
                245                 250                 255

Ala Ala Gly Ala Ala Thr Thr Ala Thr Gly Ala Ala Ser Gly Ala Ala
                260                 265                 270

Thr Val Ala Ala Gly Gly Tyr Lys Val
                275                 280

<210> SEQ ID NO 361
```

```
<211> LENGTH: 280
<212> TYPE: PRT
<213> ORGANISM: Phleum pratense

<400> SEQUENCE: 361

Met Ala Val Pro Arg Gly Pro Arg Gly Pro Gly Arg Ser Tyr
1               5                   10                  15

Thr Ala Asp Ala Gly Tyr Ala Pro Ala Thr Pro Ala Ala Gly Ala
                20                  25                  30

Ala Ala Gly Lys Ala Thr Thr Glu Glu Gln Lys Leu Ile Glu Asp Ile
            35                  40                  45

Asn Val Gly Phe Lys Ala Ala Val Ala Ala Arg Gln Arg Pro Ala Ala
50                  55                  60

Asp Lys Phe Lys Thr Phe Glu Ala Ala Ser Pro Arg His Pro Arg Pro
65              70                  75                  80

Leu Arg Gln Gly Ala Gly Leu Val Pro Lys Leu Asp Ala Ala Tyr Ser
                85                  90                  95

Val Ala Tyr Lys Ala Ala Val Gly Ala Thr Pro Glu Ala Lys Phe Asp
            100                 105                 110

Ser Phe Val Ala Ser Leu Thr Glu Ala Leu Arg Val Ile Ala Gly Ala
                115                 120                 125

Leu Glu Val His Ala Val Lys Pro Val Thr Glu Glu Pro Gly Met Ala
130                 135                 140

Lys Ile Pro Ala Gly Glu Leu Gln Ile Ile Asp Lys Ile Asp Ala Ala
145                 150                 155                 160

Phe Lys Val Ala Ala Thr Ala Ala Thr Ala Pro Ala Asp Asp Lys
                165                 170                 175

Phe Thr Val Phe Glu Ala Ala Phe Asn Lys Ala Ile Lys Glu Ser Thr
                180                 185                 190

Gly Gly Ala Tyr Asp Thr Tyr Lys Cys Ile Pro Ser Leu Glu Ala Ala
                195                 200                 205

Val Lys Gln Ala Tyr Ala Ala Thr Val Ala Ala Ala Glu Val Lys
            210                 215                 220

Tyr Ala Val Phe Glu Ala Ala Leu Thr Lys Ala Ile Thr Ala Met Ser
225                 230                 235                 240

Glu Val Gln Lys Val Ser Gln Pro Ala Thr Gly Ala Ala Thr Val Ala
                245                 250                 255

Ala Gly Ala Ala Thr Thr Ala Ala Gly Ala Ala Ser Gly Ala Ala Thr
                260                 265                 270

Val Ala Ala Gly Gly Tyr Lys Val
                275                 280

<210> SEQ ID NO 362
<211> LENGTH: 312
<212> TYPE: PRT
<213> ORGANISM: Phleum pratense

<400> SEQUENCE: 362

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
                20                  25                  30

Ala Thr Pro Ala Ala Pro Ala Ala Gly Tyr Thr Pro Ala Thr Pro Ala
            35                  40                  45

Ala Pro Ala Glu Ala Ala Pro Ala Gly Lys Ala Thr Thr Glu Glu Gln
            50                  55                  60
```

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
            85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
            115                 120                 125

Leu Asp Ala Ala Tyr Lys Leu Ala Tyr Lys Thr Ala Glu Gly Ala Thr
            130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Thr Ala Ala Asn Ala Ala Pro
            195                 200                 205

Ala Asn Asp Lys Phe Thr Val Phe Glu Ala Ala Phe Asn Asp Ala Ile
210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
            245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Ala Lys Pro Ala Ala Ala Ala
            275                 280                 285

Thr Ala Thr Ala Thr Ala Ala Val Gly Ala Ala Thr Gly Ala Ala Thr
            290                 295                 300

Ala Ala Thr Gly Gly Tyr Lys Val
305                 310

<210> SEQ ID NO 363
<211> LENGTH: 257
<212> TYPE: PRT
<213> ORGANISM: Phleum pratense

<400> SEQUENCE: 363

Glu Ala Pro Ala Gly Lys Ala Thr Thr Glu Glu Gln Lys Leu Ile Glu
1               5                   10                  15

Lys Ile Asn Ala Gly Phe Lys Ala Ala Leu Ala Arg Arg Leu Gln Pro
            20                  25                  30

Ala Asp Lys Tyr Arg Thr Phe Val Ala Thr Phe Gly Pro Ala Ser Asn
            35                  40                  45

Lys Ala Phe Ala Glu Gly Leu Ser Gly Glu Pro Lys Gly Ala Ala Glu
            50                  55                  60

Ser Ser Lys Ala Ala Leu Thr Ser Lys Leu Asp Ala Ala Tyr Lys
65                  70                  75                  80

Leu Ala Tyr Lys Thr Ala Glu Gly Ala Thr Pro Glu Ala Lys Tyr Asp
            85                  90                  95

Ala Tyr Val Ala Thr Leu Ser Glu Ala Leu Arg Ile Ile Ala Gly Thr
            100                 105                 110

Leu Glu Val His Ala Val Lys Pro Ala Ala Glu Glu Val Lys Val Ile

```
                115                 120                 125
Pro Ala Ala Glu Leu Gln Val Ile Glu Lys Val Asp Ala Ala Phe Lys
    130                 135                 140

Val Ala Ala Thr Ala Ala Asn Ala Ala Pro Ala Asn Asp Lys Phe Thr
145                 150                 155                 160

Val Phe Glu Ala Ala Phe Asn Asp Glu Ile Lys Ala Ser Thr Gly Gly
                165                 170                 175

Ala Tyr Glu Ser Tyr Lys Phe Ile Pro Ala Leu Glu Ala Ala Val Lys
            180                 185                 190

Gln Ala Tyr Ala Ala Thr Val Ala Thr Ala Pro Glu Val Lys Tyr Thr
        195                 200                 205

Val Phe Glu Thr Ala Leu Lys Lys Ala Ile Thr Ala Met Ser Glu Ala
    210                 215                 220

Gln Lys Ala Ala Lys Pro Pro Pro Leu Pro Pro Pro Gln Pro Pro
225                 230                 235                 240

Pro Leu Ala Ala Thr Gly Ala Ala Thr Ala Thr Gly Gly Tyr Lys
                245                 250                 255

Val

<210> SEQ ID NO 364
<211> LENGTH: 312
<212> TYPE: PRT
<213> ORGANISM: Phleum pratense

<400> SEQUENCE: 364

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
        35                  40                  45

Ala Pro Ala Glu Ala Ala Pro Ala Gly Lys Ala Thr Thr Glu Glu Gln
    50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
    130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
```

```
            225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
                260                 265                 270

Thr Ala Met Ser Glu Ala Gln Lys Ala Ala Lys Pro Ala Ala Ala Ala
                275                 280                 285

Thr Ala Thr Ala Thr Ala Ala Val Gly Ala Ala Thr Gly Ala Ala Thr
                290                 295                 300

Ala Ala Thr Gly Gly Tyr Lys Val
305                 310

<210> SEQ ID NO 365
<211> LENGTH: 280
<212> TYPE: PRT
<213> ORGANISM: Phleum pratense

<400> SEQUENCE: 365

Met Ala Val Pro Arg Gly Pro Arg Gly Pro Gly Arg Ser Tyr
1               5                   10                  15

Thr Ala Asp Ala Gly Tyr Ala Pro Ala Thr Pro Ala Ala Gly Ala
                20                  25                  30

Ala Ala Gly Lys Ala Thr Thr Glu Glu Gln Lys Leu Ile Glu Asp Ile
                35                  40                  45

Asn Val Gly Phe Lys Ala Val Ala Ala Arg Gln Arg Pro Ala Ala
                50                  55                  60

Asp Lys Phe Lys Thr Phe Glu Ala Ala Ser Pro Arg His Pro Arg Pro
65                  70                  75                  80

Leu Arg Gln Gly Ala Gly Leu Val Pro Lys Leu Asp Ala Ala Tyr Ser
                85                  90                  95

Val Ala Tyr Lys Ala Ala Val Gly Ala Thr Pro Glu Ala Lys Phe Asp
                100                 105                 110

Ser Phe Val Ala Ser Leu Thr Glu Ala Leu Arg Val Ile Ala Gly Ala
                115                 120                 125

Leu Glu Val His Ala Val Lys Pro Val Thr Glu Glu Pro Gly Met Ala
                130                 135                 140

Lys Ile Pro Ala Gly Glu Leu Gln Ile Ile Asp Lys Ile Asp Ala Ala
145                 150                 155                 160

Phe Lys Val Ala Ala Thr Ala Ala Thr Ala Pro Ala Asp Asp Lys
                165                 170                 175

Phe Thr Val Phe Glu Ala Ala Phe Asn Lys Ala Ile Lys Glu Ser Thr
                180                 185                 190

Gly Gly Ala Tyr Asp Thr Tyr Lys Cys Ile Pro Ser Leu Glu Ala Ala
                195                 200                 205

Val Lys Gln Ala Tyr Ala Ala Thr Val Ala Ala Ala Glu Val Lys
                210                 215                 220

Tyr Ala Val Phe Glu Ala Ala Leu Thr Lys Ala Ile Thr Ala Met Ser
225                 230                 235                 240

Glu Val Gln Lys Val Ser Gln Pro Ala Thr Gly Ala Ala Thr Val Ala
                245                 250                 255

Ala Gly Ala Ala Thr Thr Ala Ala Gly Ala Ala Ser Gly Ala Ala Thr
                260                 265                 270

Val Ala Ala Gly Gly Tyr Lys Val
                275                 280
```

```
<210> SEQ ID NO 366
<211> LENGTH: 285
<212> TYPE: PRT
<213> ORGANISM: Phleum pratense

<400> SEQUENCE: 366

Ala Asp Leu Gly Tyr Gly Pro Ala Thr Pro Ala Pro Ala Ala Gly
1               5                   10                  15

Tyr Thr Pro Ala Thr Pro Ala Ala Pro Ala Gly Ala Asp Ala Gly
            20                  25                  30

Lys Ala Thr Thr Glu Glu Gln Lys Leu Ile Glu Lys Ile Asn Ala Gly
            35                  40                  45

Phe Lys Ala Ala Leu Ala Gly Ala Gly Val Gln Pro Ala Asp Lys Tyr
50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
            115                 120                 125

Thr Leu Ser Glu Ala Leu Arg Ile Ile Ala Gly Thr Leu Glu Val His
    130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Pro Pro Leu Pro Pro Pro Gln Pro Pro Leu Ala Ala
            260                 265                 270

Thr Gly Ala Ala Thr Ala Ala Thr Gly Gly Tyr Lys Val
    275                 280                 285

<210> SEQ ID NO 367
<211> LENGTH: 312
<212> TYPE: PRT
<213> ORGANISM: Phleum pratense

<400> SEQUENCE: 367

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
        35                  40                  45
```

```
Ala Pro Ala Glu Ala Ala Pro Ala Gly Lys Ala Thr Thr Glu Glu Gln
 50                  55                  60

Lys Leu Ile Glu Lys Ile Asn Ala Gly Phe Lys Ala Ala Leu Ala Ala
 65                  70                  75                  80

Ala Ala Gly Val Gln Pro Ala Asp Lys Tyr Arg Thr Phe Val Ala Thr
                 85                  90                  95

Phe Gly Ala Ala Ser Asn Lys Ala Phe Ala Glu Gly Leu Ser Gly Glu
                100                 105                 110

Pro Lys Gly Ala Ala Glu Ser Ser Lys Ala Ala Leu Thr Ser Lys
                115                 120                 125

Leu Asp Ala Ala Tyr Lys Leu Ala Tyr Lys Thr Ala Glu Gly Ala Thr
130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
                180                 185                 190

Val Asp Ala Ala Phe Lys Val Ala Ala Thr Ala Ala Asn Ala Ala Pro
195                 200                 205

Ala Asn Asp Lys Phe Thr Val Phe Glu Ala Ala Phe Asn Asp Ala Ile
210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
                260                 265                 270

Thr Ala Met Ser Glu Ala Gln Lys Ala Ala Lys Pro Ala Ala Ala Ala
                275                 280                 285

Thr Ala Thr Ala Thr Ala Ala Val Gly Ala Ala Thr Gly Ala Ala Thr
                290                 295                 300

Ala Ala Thr Gly Gly Tyr Lys Val
305                 310

<210> SEQ ID NO 368
<211> LENGTH: 138
<212> TYPE: PRT
<213> ORGANISM: Phleum pratense

<400> SEQUENCE: 368

Met Ala Ala His Lys Phe Met Val Ala Met Phe Leu Ala Val Ala Val
 1               5                  10                  15

Val Leu Gly Leu Ala Thr Ser Pro Thr Ala Glu Gly Gly Lys Ala Thr
                 20                  25                  30

Thr Glu Glu Gln Lys Leu Ile Glu Asp Val Asn Ala Ser Phe Arg Ala
                 35                  40                  45

Ala Met Ala Thr Thr Ala Asn Val Pro Pro Ala Asp Lys Tyr Lys Thr
 50                  55                  60

Phe Glu Ala Ala Phe Thr Val Ser Ser Lys Arg Asn Leu Ala Asp Ala
 65                  70                  75                  80

Val Ser Lys Ala Pro Gln Leu Val Pro Lys Leu Asp Glu Val Tyr Asn
                 85                  90                  95

Ala Ala Tyr Asn Ala Ala Asp His Ala Ala Pro Glu Asp Lys Tyr Glu
                100                 105                 110
```

Ala Phe Val Leu His Phe Ser Glu Ala Leu Arg Ile Ile Ala Gly Thr
115                 120                 125

Pro Glu Val His Ala Val Lys Pro Gly Ala
        130                 135

<210> SEQ ID NO 369
<211> LENGTH: 57
<212> TYPE: PRT
<213> ORGANISM: Phleum pratense

<400> SEQUENCE: 369

Ser Lys Ala Pro Gln Leu Val Pro Lys Leu Asp Glu Val Tyr Asn Ala
1               5                   10                  15

Ala Tyr Asn Ala Ala Asp His Ala Ala Pro Glu Asp Lys Tyr Glu Ala
            20                  25                  30

Phe Val Leu His Phe Ser Glu Ala Leu His Ile Ile Ala Gly Thr Pro
        35                  40                  45

Glu Val His Ala Val Lys Pro Gly Ala
    50                  55

<210> SEQ ID NO 370
<211> LENGTH: 80
<212> TYPE: PRT
<213> ORGANISM: Phleum pratense

<400> SEQUENCE: 370

Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
    50                  55                  60

His Ile Ile Ala Gly Thr Pro Glu Val His Ala Val Lys Pro Gly Ala
65                  70                  75                  80

<210> SEQ ID NO 371
<211> LENGTH: 106
<212> TYPE: PRT
<213> ORGANISM: Phleum pratense

<400> SEQUENCE: 371

Thr Glu Glu Gln Lys Leu Ile Glu Asp Val Asn Ala Ser Phe Arg Ala
1               5                   10                  15

Ala Met Ala Thr Thr Ala Asn Val Pro Pro Ala Asp Lys Tyr Lys Thr
            20                  25                  30

Leu Glu Ala Ala Phe Thr Val Ser Ser Lys Arg Asn Leu Ala Asp Ala
        35                  40                  45

Val Ser Lys Ala Pro Gln Leu Val Pro Lys Leu Asp Glu Val Tyr Asn
    50                  55                  60

Ala Ala Tyr Asn Ala Ala Asp His Ala Ala Pro Glu Asp Lys Tyr Glu
65                  70                  75                  80

Ala Phe Val Leu His Phe Ser Glu Ala Leu Arg Ile Ile Ala Gly Thr
                85                  90                  95

Pro Glu Val His Ala Val Lys Pro Gly Ala
        100                 105

<210> SEQ ID NO 372
<211> LENGTH: 138
<212> TYPE: PRT
<213> ORGANISM: Phleum pratense

<400> SEQUENCE: 372

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Ile Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu His Ile Ile Ala Gly Thr
        115                 120                 125

Pro Glu Val His Ala Val Lys Pro Gly Ala
    130                 135

<210> SEQ ID NO 373
<211> LENGTH: 132
<212> TYPE: PRT
<213> ORGANISM: Phleum pratense

<400> SEQUENCE: 373

Met Val Ala Met Phe Leu Ala Val Ala Val Val Leu Gly Leu Ala Thr
1               5                   10                  15

Ser Pro Thr Ala Glu Gly Gly Lys Ala Thr Thr Glu Glu Gln Lys Leu
            20                  25                  30

Ile Glu Asp Val Asn Ala Ser Phe Arg Ala Ala Met Ala Thr Thr Ala
        35                  40                  45

Asn Val Pro Pro Ala Asp Lys Tyr Lys Thr Phe Glu Ala Ala Phe Thr
    50                  55                  60

Val Ser Ser Lys Arg Asn Leu Ala Asp Ala Val Ser Lys Ala Pro Gln
65                  70                  75                  80

Leu Val Pro Lys Leu Asp Glu Val Tyr Asn Ala Ala Tyr Asn Ala Ala
                85                  90                  95

Asp His Ala Ala Pro Glu Asp Lys Tyr Glu Ala Phe Val Leu His Phe
            100                 105                 110

Ser Glu Ala Leu Arg Ile Ile Ala Gly Thr Pro Glu Val His Ala Val
        115                 120                 125

Lys Pro Gly Ala
    130

<210> SEQ ID NO 374
<211> LENGTH: 78
<212> TYPE: PRT
<213> ORGANISM: Phleum pratense

<400> SEQUENCE: 374

Met Ala Asp Asp Met Glu Arg Ile Phe Lys Arg Phe Asp Thr Asn Gly

```
1               5                   10                  15
Asp Gly Lys Ile Ser Leu Ser Glu Leu Thr Asp Ala Leu Arg Thr Leu
            20                  25                  30

Gly Ser Thr Ser Ala Asp Glu Val Gln Arg Met Met Ala Glu Ile Asp
            35                  40                  45

Thr Asp Gly Asp Gly Phe Ile Asp Phe Asn Glu Phe Ile Ser Phe Cys
            50                  55                  60

Asn Ala Asn Pro Gly Leu Met Lys Asp Val Ala Lys Val Phe
65                  70                  75
```

<210> SEQ ID NO 375
<211> LENGTH: 131
<212> TYPE: PRT
<213> ORGANISM: Phleum pratense

<400> SEQUENCE: 375

```
Met Ser Trp Gln Thr Tyr Val Asp Glu His Leu Met Cys Glu Ile Glu
1               5                   10                  15

Gly His His Leu Ala Ser Ala Ala Ile Leu Gly His Asp Gly Thr Val
            20                  25                  30

Trp Ala Gln Ser Ala Asp Phe Pro Gln Phe Lys Pro Glu Glu Ile Thr
            35                  40                  45

Gly Ile Met Lys Asp Phe Asp Glu Pro Gly His Leu Ala Pro Thr Gly
            50                  55                  60

Met Phe Val Ala Gly Ala Lys Tyr Met Val Ile Gln Gly Glu Pro Gly
65                  70                  75                  80

Arg Val Ile Arg Gly Lys Lys Gly Ala Gly Ile Thr Ile Lys Lys
                85                  90                  95

Thr Gly Gln Ala Leu Val Val Gly Ile Tyr Asp Glu Pro Met Thr Pro
            100                 105                 110

Gly Gln Cys Asn Met Val Val Glu Arg Leu Gly Asp Tyr Leu Val Glu
            115                 120                 125

Gln Gly Met
        130
```

<210> SEQ ID NO 376
<211> LENGTH: 227
<212> TYPE: PRT
<213> ORGANISM: Vespula vulgaris

<400> SEQUENCE: 376

```
Met Glu Ile Ser Gly Leu Val Tyr Leu Ile Ile Val Thr Ile Ile
1               5                   10                  15

Asp Leu Pro Tyr Gly Lys Ala Asn Asn Tyr Cys Lys Ile Lys Cys Leu
            20                  25                  30

Lys Gly Gly Val His Thr Ala Cys Lys Tyr Gly Ser Leu Lys Pro Asn
            35                  40                  45

Cys Gly Asn Lys Val Val Ser Tyr Gly Leu Thr Lys Gln Glu Lys
            50                  55                  60

Gln Asp Ile Leu Lys Glu His Asn Asp Phe Arg Gln Lys Ile Ala Arg
65                  70                  75                  80

Gly Leu Glu Thr Arg Gly Asn Pro Gly Pro Gln Pro Pro Ala Lys Asn
                85                  90                  95

Met Lys Asn Leu Val Trp Asn Asp Glu Leu Ala Tyr Val Ala Gln Val
            100                 105                 110

Trp Ala Asn Gln Cys Gln Tyr Gly His Asp Thr Cys Arg Asp Val Ala
```

```
            115                 120                 125
Lys Tyr Gln Val Gly Gln Asn Val Ala Leu Thr Gly Ser Thr Ala Ala
    130                 135                 140

Lys Tyr Asp Asp Pro Val Lys Leu Val Lys Met Trp Glu Asp Glu Val
145                 150                 155                 160

Lys Asp Tyr Asn Pro Lys Lys Lys Phe Ser Gly Asn Asp Phe Leu Lys
                165                 170                 175

Thr Gly His Tyr Thr Gln Met Val Trp Ala Asn Thr Lys Glu Val Gly
            180                 185                 190

Cys Gly Ser Ile Lys Tyr Ile Gln Glu Lys Trp His Lys His Tyr Leu
        195                 200                 205

Val Cys Asn Tyr Gly Pro Ser Gly Asn Phe Met Asn Glu Glu Leu Tyr
210                 215                 220

Gln Thr Lys
225

<210> SEQ ID NO 377
<211> LENGTH: 300
<212> TYPE: PRT
<213> ORGANISM: Vespula maculifrons

<400> SEQUENCE: 377

Gly Pro Lys Cys Pro Phe Asn Ser Asp Thr Val Ser Ile Ile Glu
1               5                   10                  15

Thr Arg Glu Asn Arg Asn Arg Asp Leu Tyr Thr Leu Gln Thr Leu Gln
                20                  25                  30

Asn His Pro Glu Phe Lys Lys Lys Thr Ile Thr Arg Pro Val Val Phe
            35                  40                  45

Ile Thr His Gly Phe Thr Ser Ser Ala Ser Glu Lys Asn Phe Ile Asn
        50                  55                  60

Leu Ala Lys Ala Leu Val Asp Lys Asp Asn Tyr Met Val Ile Ser Ile
65                  70                  75                  80

Asp Trp Gln Thr Ala Ala Cys Thr Asn Glu Tyr Pro Gly Leu Lys Tyr
                85                  90                  95

Ala Tyr Tyr Pro Thr Ala Ala Ser Asn Thr Arg Leu Val Gly Gln Tyr
                100                 105                 110

Ile Ala Thr Ile Thr Gln Lys Leu Val Lys Asp Tyr Lys Ile Ser Met
            115                 120                 125

Ala Asn Ile Arg Leu Ile Gly His Ser Leu Gly Ala His Val Ser Gly
130                 135                 140

Phe Ala Gly Lys Arg Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
                165                 170                 175

Ser Glu Arg Leu Cys Glu Thr Asp Ala Glu Tyr Val Gln Ile Ile His
            180                 185                 190

Thr Ser Asn Tyr Leu Gly Thr Glu Lys Ile Leu Gly Thr Val Asp Phe
        195                 200                 205

Tyr Met Asn Asn Gly Lys Asn Asn Pro Gly Cys Gly Arg Phe Phe Ser
210                 215                 220

Glu Val Cys Ser His Thr Arg Ala Val Ile Tyr Met Ala Glu Cys Ile
225                 230                 235                 240

Lys His Glu Cys Cys Leu Ile Gly Ile Pro Arg Ser Lys Ser Ser Gln
                245                 250                 255
```

-continued

```
Pro Ile Ser Arg Cys Thr Lys Gln Glu Cys Val Cys Val Gly Leu Asn
            260                 265                 270

Ala Lys Lys Tyr Pro Ser Arg Gly Ser Phe Tyr Val Pro Val Glu Ser
        275                 280                 285

Thr Ala Pro Phe Cys Asn Asn Lys Gly Lys Ile Ile
    290                 295                 300

<210> SEQ ID NO 378
<211> LENGTH: 336
<212> TYPE: PRT
<213> ORGANISM: Vespula vulgaris

<400> SEQUENCE: 378

Met Glu Glu Asn Met Asn Leu Lys Tyr Leu Leu Phe Val Tyr Phe
1               5                   10                  15

Val Gln Val Leu Asn Cys Cys Tyr Gly His Gly Asp Pro Leu Ser Tyr
            20                  25                  30

Glu Leu Asp Arg Gly Pro Lys Cys Pro Phe Asn Ser Asp Thr Val Ser
        35                  40                  45

Ile Ile Ile Glu Thr Arg Glu Asn Arg Asn Arg Asp Leu Tyr Thr Leu
    50                  55                  60

Gln Thr Leu Gln Asn His Pro Glu Phe Lys Lys Lys Thr Ile Thr Arg
65                  70                  75                  80

Pro Val Val Phe Ile Thr His Gly Phe Thr Ser Ser Ala Ser Glu Thr
                85                  90                  95

Asn Phe Ile Asn Leu Ala Lys Ala Leu Val Asp Lys Asp Asn Tyr Met
            100                 105                 110

Val Ile Ser Ile Asp Trp Gln Thr Ala Ala Cys Thr Asn Glu Ala Ala
        115                 120                 125

Gly Leu Lys Tyr Leu Tyr Tyr Pro Thr Ala Ala Arg Asn Thr Arg Leu
    130                 135                 140

Val Gly Gln Tyr Ile Ala Thr Ile Thr Gln Lys Leu Val Lys His Tyr
145                 150                 155                 160

Lys Ile Ser Met Ala Asn Ile Arg Leu Ile Gly His Ser Leu Gly Ala
                165                 170                 175

His Ala Ser Gly Phe Ala Gly Lys Lys Val Gln Glu Leu Lys Leu Gly
            180                 185                 190

Lys Tyr Ser Glu Ile Ile Gly Leu Asp Pro Ala Arg Pro Ser Phe Asp
        195                 200                 205

Ser Asn His Cys Ser Glu Arg Leu Cys Glu Thr Asp Ala Glu Tyr Val
    210                 215                 220

Gln Ile Ile His Thr Ser Asn Tyr Leu Gly Thr Glu Lys Thr Leu Gly
225                 230                 235                 240

Thr Val Asp Phe Tyr Met Asn Asn Gly Lys Asn Gln Pro Gly Cys Gly
                245                 250                 255

Arg Phe Phe Ser Glu Val Cys Ser His Ser Arg Ala Val Ile Tyr Met
            260                 265                 270

Ala Glu Cys Ile Lys His Glu Cys Cys Leu Ile Gly Ile Pro Lys Ser
        275                 280                 285

Lys Ser Ser Gln Pro Ile Ser Cys Thr Lys Gln Glu Cys Val Cys
    290                 295                 300

Val Gly Leu Asn Ala Lys Lys Tyr Pro Ser Arg Gly Ser Phe Tyr Val
305                 310                 315                 320

Pro Val Glu Ser Thr Ala Pro Phe Cys Asn Asn Lys Gly Lys Ile Ile
                325                 330                 335
```

<210> SEQ ID NO 379
<211> LENGTH: 331
<212> TYPE: PRT
<213> ORGANISM: Vespula vulgaris

<400> SEQUENCE: 379

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
            20                  25                  30

Asn Ile Lys Arg Asn Ser Lys Asp Asp Phe Gln Gly Asp Lys Ile Ala
        35                  40                  45

Ile Phe Tyr Asp Pro Gly Glu Phe Pro Ala Leu Leu Ser Leu Lys Asp
    50                  55                  60

Gly Lys Tyr Lys Lys Arg Asn Gly Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
            100                 105                 110

Pro Ile Phe Arg Gln Asn Trp Gly Asn Met Lys Ile His Lys Asn Phe
        115                 120                 125

Ser Ile Asp Leu Val Arg Asn Glu His Pro Thr Trp Asn Lys Lys Met
    130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Glu Cys Asp Val Thr Ala Met His Glu Asn Asp Lys Met
        195                 200                 205

Ser Trp Leu Phe Asn Asn Gln Asn Val Leu Leu Pro Ser Val Tyr Val
    210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
        275                 280                 285

Gly Gly Asp Gly Ile Ile Ile Trp Gly Ser Ser Asp Val Asn Ser
    290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
                325                 330

<210> SEQ ID NO 380
<211> LENGTH: 206
<212> TYPE: PRT
<213> ORGANISM: Vespula vidua

<400> SEQUENCE: 380

Lys Val Asn Tyr Cys Lys Ile Cys Leu Lys Gly Val His Thr
1               5                   10                  15

Ala Cys Lys Tyr Gly Thr Ser Thr Lys Pro Asn Cys Gly Lys Met Val
                20                  25                  30

Val Lys Ala Tyr Gly Leu Thr Glu Ala Glu Lys Gln Glu Ile Leu Lys
                35                  40                  45

Val His Asn Asp Phe Arg Gln Lys Val Ala Lys Gly Leu Glu Thr Arg
50                  55                  60

Gly Asn Pro Gly Pro Gln Pro Pro Ala Lys Asn Met Asn Asn Leu Val
65                  70                  75                  80

Trp Asn Asp Glu Leu Ala Asn Ile Ala Gln Val Trp Ala Ser Gln Cys
                85                  90                  95

Asn Tyr Gly His Asp Thr Cys Lys Asp Thr Glu Lys Tyr Pro Val Gly
                100                 105                 110

Gln Asn Ile Ala Lys Arg Ser Thr Thr Ala Ala Leu Phe Asp Ser Pro
                115                 120                 125

Gly Lys Leu Val Lys Met Trp Glu Asn Glu Val Lys Asp Phe Asn Pro
130                 135                 140

Asn Ile Glu Trp Ser Lys Asn Leu Lys Lys Thr Gly His Tyr Thr
145                 150                 155                 160

Gln Met Val Trp Ala Lys Thr Lys Glu Ile Gly Cys Gly Ser Val Lys
                165                 170                 175

Tyr Val Lys Asp Glu Trp Tyr Thr His Tyr Leu Val Cys Asn Tyr Gly
                180                 185                 190

Pro Ser Gly Asn Phe Arg Asn Glu Lys Leu Tyr Glu Lys Lys
                195                 200                 205

<210> SEQ ID NO 381
<211> LENGTH: 160
<212> TYPE: PRT
<213> ORGANISM: Betula pendula

<400> SEQUENCE: 381

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
                20                  25                  30

Lys Val Ala Pro Gln Ala Ile Ser Ser Val Glu Asn Ile Glu Gly Asn
                35                  40                  45

Gly Gly Pro Gly Thr Ile Lys Lys Ile Ser Phe Pro Glu Gly Phe Pro
50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
                100                 105                 110

Ser Ile Leu Lys Ile Ser Asn Lys Tyr His Thr Lys Gly Asp His Glu
                115                 120                 125

Val Lys Ala Glu Gln Val Lys Ala Ser Lys Glu Met Gly Glu Thr Leu
                130                 135                 140

Leu Arg Ala Val Glu Ser Tyr Leu Leu Ala His Ser Asp Ala Tyr Asn
145                 150                 155                 160

```
<210> SEQ ID NO 382
<211> LENGTH: 133
<212> TYPE: PRT
<213> ORGANISM: Betula pendula

<400> SEQUENCE: 382

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130

<210> SEQ ID NO 383
<211> LENGTH: 205
<212> TYPE: PRT
<213> ORGANISM: Betula pendula

<400> SEQUENCE: 383

Met Pro Cys Ser Thr Glu Ala Met Glu Lys Ala Gly His Gly His Ala
1               5                   10                  15

Ser Thr Pro Arg Lys Arg Ser Leu Ser Asn Ser Ser Phe Arg Leu Arg
            20                  25                  30

Ser Glu Ser Leu Asn Thr Leu Arg Leu Arg Arg Ile Phe Asp Leu Phe
        35                  40                  45

Asp Lys Asn Ser Asp Gly Ile Ile Thr Val Asp Glu Leu Ser Arg Ala
    50                  55                  60

Leu Asn Leu Leu Gly Leu Glu Thr Asp Leu Ser Glu Leu Glu Ser Thr
65                  70                  75                  80

Val Lys Ser Phe Thr Arg Glu Gly Asn Ile Gly Leu Gln Phe Glu Asp
                85                  90                  95

Phe Ile Ser Leu His Gln Ser Leu Asn Asp Ser Tyr Phe Ala Tyr Gly
            100                 105                 110

Gly Glu Asp Glu Asp Asn Glu Glu Asp Met Arg Lys Ser Ile Leu
        115                 120                 125

Ser Gln Glu Glu Ala Asp Ser Phe Gly Gly Phe Lys Val Phe Asp Glu
    130                 135                 140

Asp Gly Asp Gly Tyr Ile Ser Ala Arg Glu Leu Gln Met Val Leu Gly
145                 150                 155                 160

Lys Leu Gly Phe Ser Glu Gly Ser Glu Ile Asp Arg Val Glu Lys Met
                165                 170                 175

Ile Val Ser Val Asp Ser Asn Arg Asp Gly Arg Val Asp Phe Phe Glu
            180                 185                 190

Phe Lys Asp Met Met Arg Ser Val Leu Val Arg Ser Ser
```

-continued

```
<210> SEQ ID NO 384
<211> LENGTH: 85
<212> TYPE: PRT
<213> ORGANISM: Betula pendula

<400> SEQUENCE: 384

Met Ala Asp Asp His Pro Gln Asp Lys Ala Glu Arg Glu Arg Ile Phe
1               5                   10                  15

Lys Arg Phe Asp Ala Asn Gly Asp Gly Lys Ile Ser Ala Ala Glu Leu
            20                  25                  30

Gly Glu Ala Leu Lys Thr Leu Gly Ser Ile Thr Pro Asp Glu Val Lys
        35                  40                  45

His Met Met Ala Glu Ile Asp Thr Asp Gly Asp Gly Phe Ile Ser Phe
50                  55                  60

Gln Glu Phe Thr Asp Phe Gly Arg Ala Asn Arg Gly Leu Leu Lys Asp
65                  70                  75                  80

Val Ala Lys Ile Phe
                85

<210> SEQ ID NO 385
<211> LENGTH: 24
<212> TYPE: PRT
<213> ORGANISM: Quercus alba
<220> FEATURE:
<221> NAME/KEY: UNSURE
<222> LOCATION: (5)..(5)
<223> OTHER INFORMATION: Xaa = unknown
<220> FEATURE:
<221> NAME/KEY: UNSURE
<222> LOCATION: (17)..(17)
<223> OTHER INFORMATION: Xaa = unknown

<400> SEQUENCE: 385

Gly Val Phe Thr Xaa Glu Ser Gln Glu Thr Ser Val Ile Ala Pro Ala
1               5                   10                  15

Xaa Leu Phe Lys Ala Leu Phe Leu
            20

<210> SEQ ID NO 386
<211> LENGTH: 40
<212> TYPE: PRT
<213> ORGANISM: Carpinus betulus
<220> FEATURE:
<221> NAME/KEY: UNSURE
<222> LOCATION: (39)..(39)
<223> OTHER INFORMATION: Xaa = unknown

<400> SEQUENCE: 386

Gly Val Phe Asn Tyr Glu Ala Glu Thr Pro Ser Val Ile Pro Ala Ala
1               5                   10                  15

Arg Leu Phe Lys Ser Tyr Val Leu Asp Gly Asp Lys Leu Ile Pro Lys
            20                  25                  30

Val Ala Pro Gln Ala Ile Xaa Lys
        35                  40

<210> SEQ ID NO 387
<211> LENGTH: 44
<212> TYPE: PRT
<213> ORGANISM: Alnus glutinosa

<400> SEQUENCE: 387
```

```
Gly Val Phe Asn Tyr Glu Ala Glu Thr Pro Ser Val Ile Pro Ala Ala
1               5                   10                  15

Arg Leu Phe Lys Ala Phe Ile Leu Asp Gly Asp Lys Leu Leu Pro Lys
            20                  25                  30

Val Ala Pro Glu Ala Val Ser Ser Val Glu Asn Ile
        35                  40

<210> SEQ ID NO 388
<211> LENGTH: 110
<212> TYPE: PRT
<213> ORGANISM: Betula pendula

<400> SEQUENCE: 388

Val Gln Cys Met Gln Val Trp Pro Pro Leu Gly Leu Lys Lys Phe Glu
1               5                   10                  15

Thr Leu Ser Tyr Leu Pro Pro Leu Ser Ser Glu Gln Leu Ala Lys Glu
            20                  25                  30

Val Asp Tyr Leu Leu Arg Lys Asn Leu Ile Pro Cys Leu Glu Phe Glu
        35                  40                  45

Leu Glu His Gly Phe Val Tyr Arg Glu His Asn Arg Ser Pro Gly Tyr
    50                  55                  60

Tyr Asp Gly Arg Tyr Trp Thr Met Trp Lys Leu Pro Met Phe Gly Cys
65                  70                  75                  80

Asn Asp Ser Ser Gln Val Leu Lys Glu Leu Glu Glu Cys Lys Lys Ala
                85                  90                  95

Tyr Pro Ser Ala Phe Ile Arg Ile Ile Gly Phe Asp Asp Lys
            100                 105                 110

<210> SEQ ID NO 389
<211> LENGTH: 626
<212> TYPE: PRT
<213> ORGANISM: Arachis hypogaea

<400> SEQUENCE: 389

Met Arg Gly Arg Val Ser Pro Leu Met Leu Leu Leu Gly Ile Leu Val
1               5                   10                  15

Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
        35                  40                  45

Glu Pro Asp Asp Leu Lys Gln Lys Ala Cys Glu Ser Arg Cys Thr Lys
    50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
    130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175
```

```
Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
        435                 440                 445

Asn Ser Lys Ala Met Val Ile Val Val Asn Lys Gly Thr Gly Asn
    450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Gly Ser Asn Arg Glu
                485                 490                 495

Val Arg Arg Tyr Thr Ala Arg Leu Lys Glu Gly Asp Val Phe Ile Met
            500                 505                 510

Pro Ala Ala His Pro Val Ala Ile Asn Ala Ser Ser Glu Leu His Leu
        515                 520                 525

Leu Gly Phe Gly Ile Asn Ala Glu Asn Asn His Arg Ile Phe Leu Ala
    530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Glu Lys Glu Asp Gln Glu
```

595                 600                 605
Glu Glu Asn Gln Gly Gly Lys Gly Pro Leu Leu Ser Ile Leu Lys Ala
    610                 615                 620
Phe Asn
625

<210> SEQ ID NO 390
<211> LENGTH: 392
<212> TYPE: PRT
<213> ORGANISM: Ambrosia artemisiifolia

<400> SEQUENCE: 390

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Gln Ile
            20                  25                  30

Leu Pro Ser Ala Asn Glu Thr Arg Ser Leu Thr Thr Cys Gly Thr Tyr
        35                  40                  45

Asn Ile Ile Asp Gly Cys Trp Arg Gly Lys Ala Asp Trp Ala Glu Asn
    50                  55                  60

Arg Lys Ala Leu Ala Asp Cys Ala Gln Gly Phe Ala Lys Gly Thr Ile
65                  70                  75                  80

Gly Gly Lys Asp Gly Asp Ile Tyr Thr Val Thr Ser Glu Leu Asp Asp
                85                  90                  95

Asp Val Ala Asn Pro Lys Glu Gly Thr Leu Arg Phe Gly Ala Ala Gln
            100                 105                 110

Asn Arg Pro Leu Trp Ile Ile Phe Ala Arg Asp Met Val Ile Arg Leu
        115                 120                 125

Asp Arg Glu Leu Ala Ile Asn Asn Asp Lys Thr Ile Asp Gly Arg Gly
    130                 135                 140

Ala Lys Val Glu Ile Ile Asn Ala Gly Phe Ala Ile Tyr Asn Val Lys
145                 150                 155                 160

Asn Ile Ile Ile His Asn Ile Ile Met His Asp Ile Val Asn Pro
                165                 170                 175

Gly Gly Leu Ile Lys Ser His Asp Gly Pro Pro Val Pro Arg Lys Gly
            180                 185                 190

Ser Asp Gly Asp Ala Ile Gly Ile Ser Gly Gly Ser Gln Ile Trp Ile
        195                 200                 205

Asp His Cys Ser Leu Ser Lys Ala Val Asp Gly Leu Ile Asp Ala Lys
    210                 215                 220

His Gly Ser Thr His Phe Thr Val Ser Asn Cys Leu Phe Thr Gln His
225                 230                 235                 240

Gln Tyr Leu Leu Leu Phe Trp Asp Phe Asp Glu Arg Gly Met Leu Cys
                245                 250                 255

Thr Val Ala Phe Asn Lys Phe Thr Asp Asn Val Asp Gln Arg Met Pro
            260                 265                 270

Asn Leu Arg His Gly Phe Val Gln Val Val Asn Asn Tyr Glu Arg
        275                 280                 285

Trp Gly Ser Tyr Ala Leu Gly Gly Ser Ala Gly Pro Thr Ile Leu Ser
    290                 295                 300

Gln Gly Asn Arg Phe Leu Ala Ser Asp Ile Lys Lys Glu Val Val Gly
305                 310                 315                 320

Arg Tyr Gly Glu Ser Ala Met Ser Glu Ser Ile Asn Trp Asn Trp Arg
                325                 330                 335

Ser Tyr Met Asp Val Phe Glu Asn Gly Ala Ile Phe Val Pro Ser Gly
            340                 345                 350

Val Asp Pro Val Leu Thr Pro Glu Gln Asn Ala Gly Met Ile Pro Ala
        355                 360                 365

Glu Pro Gly Glu Ala Val Leu Arg Leu Thr Ser Ser Ala Gly Val Leu
    370                 375                 380

Ser Cys Gln Pro Gly Ala Pro Cys
385                 390

<210> SEQ ID NO 391
<211> LENGTH: 397
<212> TYPE: PRT
<213> ORGANISM: Ambrosia artemisiifolia

<400> SEQUENCE: 391

Met Gly Ile Lys His Cys Cys Tyr Ile Leu Tyr Phe Thr Leu Ala Leu
1               5                   10                  15

Val Thr Leu Val Gln Ala Gly Arg Leu Gly Glu Glu Val Asp Ile Leu
            20                  25                  30

Pro Ser Pro Asn Asp Thr Arg Arg Ser Leu Gln Gly Cys Glu Ala His
        35                  40                  45

Asn Ile Ile Asp Lys Cys Trp Arg Cys Lys Pro Asp Trp Ala Glu Asn
    50                  55                  60

Arg Gln Ala Leu Gly Asn Cys Ala Gln Gly Phe Gly Lys Ala Thr His
65                  70                  75                  80

Gly Gly Lys Trp Gly Asp Ile Tyr Met Val Thr Ser Asp Gln Asp Asp
                85                  90                  95

Asp Val Val Asn Pro Lys Glu Gly Thr Leu Arg Phe Gly Ala Thr Gln
            100                 105                 110

Asp Arg Pro Leu Trp Ile Ile Phe Gln Arg Asp Met Ile Ile Tyr Leu
        115                 120                 125

Gln Gln Glu Met Val Val Thr Ser Asp Lys Thr Ile Asp Gly Arg Gly
    130                 135                 140

Ala Lys Val Glu Leu Val Tyr Gly Gly Ile Thr Leu Met Asn Val Lys
145                 150                 155                 160

Asn Val Ile Ile His Asn Ile Asp Ile His Asp Val Arg Val Leu Pro
                165                 170                 175

Gly Gly Arg Ile Lys Ser Asn Gly Gly Pro Ala Ile Pro Arg His Gln
            180                 185                 190

Ser Asp Gly Asp Ala Ile His Val Thr Gly Ser Ser Asp Ile Trp Ile
        195                 200                 205

Asp His Cys Thr Leu Ser Lys Ser Phe Asp Gly Leu Val Asp Val Asn
    210                 215                 220

Trp Gly Ser Thr Gly Val Thr Ile Ser Asn Cys Lys Phe Thr His His
225                 230                 235                 240

Glu Lys Ala Val Leu Leu Gly Ala Ser Asp Thr His Phe Gln Asp Leu
                245                 250                 255

Lys Met His Val Thr Leu Ala Tyr Asn Ile Phe Thr Asn Thr Val His
            260                 265                 270

Glu Arg Met Pro Arg Cys Arg Phe Gly Phe Phe Gln Ile Val Asn Asn
        275                 280                 285

Phe Tyr Asp Arg Trp Asp Lys Tyr Ala Ile Gly Gly Ser Ser Asn Pro
    290                 295                 300

Thr Ile Leu Ser Gln Gly Asn Lys Phe Val Ala Pro Asp Phe Ile Tyr
305                 310                 315                 320

Lys Lys Asn Val Cys Leu Arg Thr Gly Ala Gln Glu Pro Glu Trp Met
                325                 330                 335

Thr Trp Asn Trp Arg Thr Gln Asn Asp Val Leu Glu Asn Gly Ala Ile
            340                 345                 350

Phe Val Ala Ser Gly Ser Asp Pro Val Leu Thr Ala Glu Gln Asn Ala
        355                 360                 365

Gly Met Met Gln Ala Glu Pro Gly Asp Met Val Pro Gln Leu Thr Met
    370                 375                 380

Asn Ala Gly Val Leu Thr Cys Ser Pro Gly Ala Pro Cys
385                 390                 395

<210> SEQ ID NO 392
<211> LENGTH: 397
<212> TYPE: PRT
<213> ORGANISM: Ambrosia artemisiifolia

<400> SEQUENCE: 392

Met Gly Ile Lys Gln Cys Cys Tyr Ile Leu Tyr Phe Thr Leu Ala Leu
1               5                   10                  15

Val Ala Leu Leu Gln Pro Val Arg Ser Ala Glu Gly Val Gly Glu Ile
            20                  25                  30

Leu Pro Ser Val Asn Glu Thr Arg Ser Leu Gln Ala Cys Glu Ala Leu
        35                  40                  45

Asn Ile Ile Asp Lys Cys Trp Arg Gly Lys Ala Asp Trp Glu Asn Asn
    50                  55                  60

Arg Gln Ala Leu Ala Asp Cys Ala Gln Gly Phe Ala Lys Gly Thr Tyr
65                  70                  75                  80

Gly Gly Lys Trp Gly Asp Val Tyr Thr Val Thr Ser Asn Leu Asp Asp
                85                  90                  95

Asp Val Ala Asn Pro Lys Glu Gly Thr Leu Arg Phe Ala Ala Ala Gln
            100                 105                 110

Asn Arg Pro Leu Trp Ile Ile Phe Lys Asn Asp Met Val Ile Asn Leu
        115                 120                 125

Asn Gln Glu Leu Val Val Asn Ser Asp Lys Thr Ile Asp Gly Arg Gly
    130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
                165                 170                 175

Gly Gly Met Ile Lys Ser Asn Asp Gly Pro Pro Ile Leu Arg Gln Ala
            180                 185                 190

Ser Asp Gly Asp Thr Ile Asn Val Ala Gly Ser Ser Gln Ile Trp Ile
        195                 200                 205

Asp His Cys Ser Leu Ser Lys Ser Phe Asp Gly Leu Val Asp Val Thr
    210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
                245                 250                 255

Gly Met Leu Ala Thr Val Ala Phe Asn Met Phe Thr Asp Asn Val Asp
            260                 265                 270

Gln Arg Met Pro Arg Cys Arg Phe Gly Phe Phe Gln Val Val Asn Asn
        275                 280                 285

Asn Tyr Asp Arg Trp Gly Thr Tyr Ala Ile Gly Gly Ser Ser Ala Pro

```
                290             295             300
Thr Ile Leu Cys Gln Gly Asn Arg Phe Leu Ala Pro Asp Asp Gln Ile
305                 310             315                 320

Lys Lys Asn Val Leu Ala Arg Thr Gly Thr Gly Ala Ala Glu Ser Met
                325             330                 335

Ala Trp Asn Trp Arg Ser Asp Lys Asp Leu Leu Glu Asn Gly Ala Ile
                340             345             350

Phe Val Thr Ser Gly Ser Asp Pro Val Leu Thr Pro Val Gln Ser Ala
            355             360             365

Gly Met Ile Pro Ala Glu Pro Gly Glu Ala Ala Ile Lys Leu Thr Ser
        370             375             380

Ser Ala Gly Val Phe Ser Cys His Pro Gly Ala Pro Cys
385                 390             395
```

<210> SEQ ID NO 393
<211> LENGTH: 398
<212> TYPE: PRT
<213> ORGANISM: Ambrosia artemisiifolia

<400> SEQUENCE: 393

```
Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Val Glu Glu Phe
            20                  25                  30

Leu Pro Ser Ala Asn Glu Thr Arg Arg Ser Leu Lys Ala Cys Glu Ala
            35                  40                  45

His Asn Ile Ile Asp Lys Cys Trp Arg Cys Lys Ala Asp Trp Ala Asn
        50                  55                  60

Asn Arg Gln Ala Leu Ala Asp Cys Ala Gln Gly Phe Ala Lys Gly Thr
65                  70                  75                  80

Tyr Gly Gly Lys His Gly Asp Val Tyr Thr Val Thr Ser Asp Lys Asp
                85                  90                  95

Asp Asp Val Ala Asn Pro Lys Glu Gly Thr Leu Arg Phe Ala Ala Ala
            100                 105                 110

Gln Asn Arg Pro Leu Trp Ile Ile Phe Lys Arg Asn Met Val Ile His
            115                 120                 125

Leu Asn Gln Glu Leu Val Val Asn Ser Asp Lys Thr Ile Asp Gly Arg
        130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
            180                 185                 190

Gln Ser Asp Gly Asp Ala Ile Asn Val Ala Gly Ser Ser Gln Ile Trp
            195                 200                 205

Ile Asp His Cys Ser Leu Ser Lys Ala Ser Asp Gly Leu Leu Asp Ile
        210                 215                 220

Thr Leu Gly Ser Ser His Val Thr Val Ser Asn Cys Lys Phe Thr Gln
225                 230                 235                 240

His Gln Phe Val Leu Leu Leu Gly Ala Asp Asp Thr His Tyr Gln Asp
                245                 250                 255

Lys Gly Met Leu Ala Thr Val Ala Phe Asn Met Phe Thr Asp His Val
            260                 265                 270
```

```
Asp Gln Arg Met Pro Arg Cys Arg Phe Gly Phe Phe Gln Val Val Asn
            275                 280                 285

Asn Asn Tyr Asp Arg Trp Gly Thr Tyr Ala Ile Gly Gly Ser Ser Ala
        290                 295                 300

Pro Thr Ile Leu Ser Gln Gly Asn Arg Phe Phe Ala Pro Asp Asp Ile
305                 310                 315                 320

Ile Lys Lys Asn Val Leu Ala Arg Thr Gly Thr Gly Asn Ala Glu Ser
                325                 330                 335

Met Ser Trp Asn Trp Arg Thr Asp Arg Asp Leu Leu Glu Asn Gly Ala
                340                 345                 350

Ile Phe Leu Pro Ser Gly Ser Asp Pro Val Leu Thr Pro Glu Gln Lys
                355                 360                 365

Ala Gly Met Ile Pro Ala Glu Pro Gly Glu Ala Val Leu Arg Leu Thr
            370                 375                 380

Ser Ser Ala Gly Val Leu Ser Cys His Gln Gly Ala Pro Cys
385                 390                 395
```

<210> SEQ ID NO 394
<211> LENGTH: 396
<212> TYPE: PRT
<213> ORGANISM: Ambrosia artemisiifolia

<400> SEQUENCE: 394

```
Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
            20                  25                  30

Leu Pro Val Asn Glu Thr Arg Arg Leu Thr Thr Ser Gly Ala Tyr Asn
            35                  40                  45

Ile Ile Asp Gly Cys Trp Arg Gly Lys Ala Asp Trp Ala Glu Asn Arg
        50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp Asp
                85                  90                  95

Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
            115                 120                 125

Lys Glu Met Val Val Asn Ser Asp Lys Thr Ile Asp Gly Arg Gly Ala
            130                 135                 140

Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
            180                 185                 190

Asp Gly Asp Ala Ile Ser Ile Ser Gly Ser Ser Gln Ile Trp Ile Asp
        195                 200                 205

His Cys Ser Leu Ser Lys Ser Val Asp Gly Leu Val Asp Ala Lys Leu
    210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255
```

```
Met Leu Ala Thr Val Ala Phe Asn Thr Phe Thr Asp Asn Val Asp Gln
            260                 265                 270

Arg Met Pro Arg Cys Arg His Gly Phe Phe Gln Val Asn Asn Asn
        275                 280                 285

Tyr Asp Lys Trp Gly Ser Tyr Ala Ile Gly Ser Ala Ser Pro Thr
        290                 295                 300

Ile Leu Ser Gln Gly Asn Arg Phe Cys Ala Pro Asp Glu Arg Ser Lys
305                 310                 315                 320

Lys Asn Val Leu Gly Arg His Gly Glu Ala Ala Glu Ser Met Lys
                325                 330                 335

Trp Asn Trp Arg Thr Asn Lys Asp Val Leu Glu Asn Gly Ala Ile Phe
                340                 345                 350

Val Ala Ser Gly Val Asp Pro Val Leu Thr Pro Glu Gln Ser Ala Gly
            355                 360                 365

Met Ile Pro Ala Glu Pro Gly Glu Ser Ala Leu Ser Leu Thr Ser Ser
    370                 375                 380

Ala Gly Val Leu Ser Cys Gln Pro Gly Ala Pro Cys
385                 390                 395

<210> SEQ ID NO 395
<211> LENGTH: 373
<212> TYPE: PRT
<213> ORGANISM: Cryptomeria japonica

<400> SEQUENCE: 395

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
                20                  25                  30

Ser Asn Trp Ala Gln Asn Arg Met Lys Leu Ala Asp Cys Ala Val Gly
            35                  40                  45

Phe Gly Ser Ser Thr Met Gly Gly Lys Gly Gly Asp Leu Tyr Thr Val
    50                  55                  60

Thr Asn Ser Asp Asp Pro Val Asn Pro Pro Gly Thr Leu Arg Tyr
65                  70                  75                  80

Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
                100                 105                 110

Asp Gly Arg Gly Ala Gln Val Tyr Ile Gly Asn Gly Gly Pro Cys Val
            115                 120                 125

Phe Ile Lys Arg Val Ser Asn Val Ile His Gly Leu Tyr Leu Tyr
130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Thr Ser Thr Gly Val Thr Ile Ser
        195                 200                 205

Asn Asn Leu Phe Phe Asn His His Lys Val Met Ser Leu Gly His Asp
    210                 215                 220

Asp Ala Tyr Ser Asp Asp Lys Ser Met Lys Val Thr Val Ala Phe Asn
```

```
                225                 230                 235                 240
        Gln Phe Gly Pro Asn Cys Gly Gln Arg Met Pro Arg Ala Arg Tyr Gly
                        245                 250                 255

Leu Val His Val Ala Asn Asn Tyr Asp Pro Trp Thr Ile Tyr Ala
                        260                 265                 270

Ile Gly Gly Ser Ser Asn Pro Thr Ile Leu Ser Glu Gly Asn Ser Phe
                        275                 280                 285

Thr Ala Pro Asn Glu Ser Tyr Lys Lys Gln Val Thr Ile Arg Ile Gly
                290                 295                 300

Cys Lys Thr Ser Ser Cys Ser Asn Trp Val Trp Gln Ser Thr Gln
        305                 310                 315                 320

Asp Val Phe Tyr Asn Gly Ala Tyr Phe Val Ser Ser Gly Lys Tyr Glu
                        325                 330                 335

Gly Gly Asn Ile Tyr Thr Lys Lys Glu Ala Phe Asn Val Glu Asn Gly
                        340                 345                 350

Asn Ala Thr Pro His Leu Thr Gln Asn Ala Gly Val Leu Thr Cys Ser
                        355                 360                 365

Leu Ser Lys Arg Cys
                370

<210> SEQ ID NO 396
<211> LENGTH: 374
<212> TYPE: PRT
<213> ORGANISM: Cryptomeria japonica

<400> SEQUENCE: 396

Met Asp Ser Pro Cys Leu Val Ala Leu Leu Val Leu Ser Phe Val Ile
1               5                   10                  15

Gly Ser Cys Phe Ser Asp Asn Pro Ile Asp Ser Cys Trp Arg Gly Asp
                20                  25                  30

Ser Asn Trp Ala Gln Asn Arg Met Lys Leu Ala Asp Cys Ala Val Gly
            35                  40                  45

Phe Gly Ser Ser Thr Met Gly Gly Lys Gly Gly Asp Leu Tyr Thr Val
    50                  55                  60

Thr Asn Ser Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
                100                 105                 110

Phe Asp Gly Arg Gly Ala Gln Val Tyr Ile Gly Asn Gly Gly Pro Cys
            115                 120                 125

Val Phe Ile Lys Arg Val Ser Asn Val Ile Ile His Gly Leu His Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
                180                 185                 190

Ser Asp Gly Leu Val Asp Val Thr Leu Ser Ser Thr Gly Val Thr Ile
            195                 200                 205

Ser Asn Asn Leu Phe Phe Asn His His Lys Val Met Leu Leu Gly His
    210                 215                 220
```

```
Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
            245                 250                 255

Gly Leu Val His Val Ala Asn Asn Tyr Asp Pro Trp Thr Ile Tyr
        260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
        290                 295                 300

Gly Cys Lys Thr Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
            325                 330                 335

Glu Gly Gly Asn Ile Tyr Thr Lys Lys Glu Ala Phe Asn Val Glu Asn
            340                 345                 350

Gly Asn Ala Thr Pro Gln Leu Thr Lys Asn Ala Gly Val Leu Thr Cys
            355                 360                 365

Ser Leu Ser Lys Arg Cys
            370

<210> SEQ ID NO 397
<211> LENGTH: 514
<212> TYPE: PRT
<213> ORGANISM: Cryptomeria japonica

<400> SEQUENCE: 397

Met Ala Met Lys Leu Ile Ala Pro Met Ala Phe Leu Ala Met Gln Leu
1               5                   10                  15

Ile Ile Met Ala Ala Ala Glu Asp Gln Ser Ala Gln Ile Met Leu Asp
            20                  25                  30

Ser Val Val Glu Lys Tyr Leu Arg Ser Asn Arg Ser Leu Arg Lys Val
        35                  40                  45

Glu His Ser Arg His Asp Ala Ile Asn Ile Phe Asn Val Glu Lys Tyr
    50                  55                  60

Gly Ala Val Gly Asp Gly Lys His Asp Cys Thr Glu Ala Phe Ser Thr
65                  70                  75                  80

Ala Trp Gln Ala Ala Cys Lys Asn Pro Ser Ala Met Leu Leu Val Pro
                85                  90                  95

Gly Ser Lys Lys Phe Val Val Asn Asn Leu Phe Phe Asn Gly Pro Cys
            100                 105                 110

Gln Pro His Phe Thr Phe Lys Val Asp Gly Ile Ile Ala Ala Tyr Gln
        115                 120                 125

Asn Pro Ala Ser Trp Lys Asn Asn Arg Ile Trp Leu Gln Phe Ala Lys
    130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220
```

-continued

```
Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
            245                 250                 255

Cys Val Ala Ile Gly Thr Gly Ser Ser Asn Ile Val Ile Glu Asp Leu
        260                 265                 270

Ile Cys Gly Pro Gly His Gly Ile Ser Ile Gly Ser Leu Gly Arg Glu
    275                 280                 285

Asn Ser Arg Ala Glu Val Ser Tyr Val His Val Asn Gly Ala Lys Phe
290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ile Gln Leu Lys Cys
    370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Glu Asn Met Arg Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Ile Cys Ser Cys His Gly Lys Ile Tyr
            500                 505                 510

His Pro

<210> SEQ ID NO 398
<211> LENGTH: 514
<212> TYPE: PRT
<213> ORGANISM: Cryptomeria japonica

<400> SEQUENCE: 398

Met Ala Met Lys Phe Ile Ala Pro Met Ala Phe Val Ala Met Gln Leu
1               5                   10                  15

Ile Ile Met Ala Ala Ala Glu Asp Gln Ser Ala Gln Ile Met Leu Asp
                20                  25                  30

Ser Asp Ile Glu Gln Tyr Leu Arg Ser Asn Arg Ser Leu Arg Lys Val
            35                  40                  45

Glu His Ser Arg His Asp Ala Ile Asn Ile Phe Asn Val Glu Lys Tyr
        50                  55                  60

Gly Ala Val Gly Asp Gly Lys His Asp Cys Thr Glu Ala Phe Ser Thr
65                  70                  75                  80
```

```
Ala Trp Gln Ala Ala Cys Lys Lys Pro Ser Ala Met Leu Leu Val Pro
                85              90              95
Gly Asn Lys Lys Phe Val Val Asn Asn Leu Phe Phe Asn Gly Pro Cys
            100             105             110
Gln Pro His Phe Thr Phe Lys Val Asp Gly Ile Ile Ala Ala Tyr Gln
        115             120             125
Asn Pro Ala Ser Trp Lys Asn Asn Arg Ile Trp Leu Gln Phe Ala Lys
    130             135             140
Leu Thr Gly Phe Thr Leu Met Gly Lys Gly Val Ile Asp Gly Gln Gly
145             150             155             160
Lys Gln Trp Trp Ala Gly Gln Cys Lys Trp Val Asn Gly Arg Glu Ile
            165             170             175
Cys Asn Asp Arg Asp Arg Pro Thr Ala Ile Lys Phe Asp Phe Ser Thr
        180             185             190
Gly Leu Ile Ile Gln Gly Leu Lys Leu Met Asn Ser Pro Glu Phe His
    195             200             205
Leu Val Phe Gly Asn Cys Glu Gly Val Lys Ile Ile Gly Ile Ser Ile
210             215             220
Thr Ala Pro Arg Asp Ser Pro Asn Thr Asp Gly Ile Asp Ile Phe Ala
225             230             235             240
Ser Lys Asn Phe His Leu Gln Lys Asn Thr Ile Gly Thr Gly Asp Asp
            245             250             255
Cys Val Ala Ile Gly Thr Gly Ser Ser Asn Ile Val Ile Glu Asp Leu
        260             265             270
Ile Cys Gly Pro Gly His Gly Ile Ser Ile Gly Ser Leu Gly Arg Glu
    275             280             285
Asn Ser Arg Ala Glu Val Ser Tyr Val His Val Asn Gly Ala Lys Phe
290             295             300
Ile Asp Thr Gln Asn Gly Leu Arg Ile Lys Thr Trp Gln Gly Gly Ser
305             310             315             320
Gly Met Ala Ser His Ile Ile Tyr Glu Asn Val Glu Met Ile Asn Ser
            325             330             335
Glu Asn Pro Ile Leu Ile Asn Gln Phe Tyr Cys Thr Ser Ala Ser Ala
        340             345             350
Cys Gln Asn Gln Arg Ser Ala Val Gln Ile Gln Asp Val Thr Tyr Lys
    355             360             365
Asn Ile Arg Gly Thr Ser Ala Thr Ala Ala Ile Gln Leu Lys Cys
370             375             380
Ser Asp Ser Met Pro Cys Lys Asp Ile Lys Leu Ser Asp Ile Ser Leu
385             390             395             400
Lys Leu Thr Ser Gly Lys Ile Ala Ser Cys Leu Asn Asp Asn Ala Asn
            405             410             415
Gly Tyr Phe Ser Gly His Val Ile Pro Ala Cys Lys Asn Leu Ser Pro
        420             425             430
Ser Ala Lys Arg Lys Glu Ser Lys Ser His Lys His Pro Lys Thr Val
    435             440             445
Met Val Lys Asn Met Gly Ala Tyr Asp Lys Gly Asn Arg Thr Arg Ile
450             455             460
Leu Leu Gly Ser Arg Pro Pro Asn Cys Thr Asn Lys Cys His Gly Cys
465             470             475             480
Ser Pro Cys Lys Ala Lys Leu Val Ile Val His Arg Ile Met Pro Gln
            485             490             495
```

```
Glu Tyr Tyr Pro Gln Arg Trp Met Cys Ser Arg His Gly Lys Ile Tyr
            500                 505                 510
His Pro

<210> SEQ ID NO 399
<211> LENGTH: 373
<212> TYPE: PRT
<213> ORGANISM: Cryptomeria japonica

<400> SEQUENCE: 399

Met Asp Ser Pro Cys Leu Val Ala Leu Leu Val Ser Phe Val Ile
1                 5                  10                  15

Gly Ser Cys Phe Ser Asp Asn Pro Ile Asp Ser Cys Trp Arg Gly Asp
                20                  25                  30

Ser Asn Trp Ala Gln Asn Arg Met Lys Leu Ala Asp Cys Ala Val Gly
            35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Pro Gly Thr Leu Arg Tyr
65                  70                  75                  80

Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
            100                 105                 110

Asp Gly Arg Gly Ala Gln Val Tyr Ile Gly Asn Gly Gly Pro Cys Val
        115                 120                 125

Phe Ile Lys Arg Val Ser Asn Val Ile Ile His Gly Leu His Leu Tyr
    130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Ser Ser Thr Gly Val Thr Ile Ser
        195                 200                 205

Asn Asn Leu Phe Phe Asn His His Lys Val Met Leu Leu Gly His Asp
    210                 215                 220

Asp Ala Tyr Ser Asp Asp Lys Ser Met Lys Val Thr Val Ala Phe Asn
225                 230                 235                 240

Gln Phe Gly Pro Asn Cys Gly Gln Arg Met Pro Arg Ala Arg Tyr Gly
                245                 250                 255

Leu Val His Val Ala Asn Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
        275                 280                 285

Thr Ala Pro Asn Glu Ser Tyr Lys Lys Gln Val Thr Ile Arg Ile Gly
    290                 295                 300

Cys Lys Thr Ser Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
                325                 330                 335

Gly Gly Asn Ile Tyr Thr Lys Lys Glu Ala Phe Asn Val Glu Asn Gly
            340                 345                 350
```

```
Asn Ala Thr Pro Gln Leu Thr Lys Asn Ala Gly Val Leu Thr Cys Ser
            355                 360                 365

Leu Ser Lys Arg Cys
    370

<210> SEQ ID NO 400
<211> LENGTH: 374
<212> TYPE: PRT
<213> ORGANISM: Cryptomeria japonica

<400> SEQUENCE: 400

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu Tyr Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Thr Ser Thr Gly Val Thr Ile
        195                 200                 205

Ser Asn Asn Leu Phe Phe Asn His His Lys Val Met Ser Leu Gly His
    210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Tyr Asp Pro Trp Thr Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
    290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350
```

-continued

Gly Asn Ala Thr Pro His Leu Thr Gln Asn Ala Gly Val Leu Thr Cys
        355                 360                 365

Ser Leu Ser Lys Arg Cys
    370

<210> SEQ ID NO 401
<211> LENGTH: 174
<212> TYPE: PRT
<213> ORGANISM: Canis familiaris

<400> SEQUENCE: 401

Met Lys Thr Leu Leu Thr Ile Gly Phe Ser Leu Ile Ala Ile Leu
1               5                   10                  15

Gln Ala Gln Asp Thr Pro Ala Leu Gly Lys Asp Thr Val Ala Val Ser
            20                  25                  30

Gly Lys Trp Tyr Leu Lys Ala Met Thr Ala Asp Gln Glu Val Pro Glu
        35                  40                  45

Lys Pro Asp Ser Val Thr Pro Met Ile Leu Lys Ala Gln Lys Gly Gly
    50                  55                  60

Asn Leu Glu Ala Lys Ile Thr Met Leu Thr Asn Gly Gln Cys Gln Asn
65                  70                  75                  80

Ile Thr Val Val Leu His Lys Thr Ser Glu Pro Gly Lys Tyr Thr Ala
                85                  90                  95

Tyr Glu Gly Gln Arg Val Val Phe Ile Gln Pro Ser Pro Val Arg Asp
            100                 105                 110

His Tyr Ile Leu Tyr Cys Glu Gly Glu Leu His Gly Arg Gln Ile Arg
        115                 120                 125

Met Ala Lys Leu Leu Gly Arg Asp Pro Glu Gln Ser Gln Glu Ala Leu
    130                 135                 140

Glu Asp Phe Arg Glu Phe Ser Arg Ala Lys Gly Leu Asn Gln Glu Ile
145                 150                 155                 160

Leu Glu Leu Ala Gln Ser Glu Thr Cys Ser Pro Gly Gly Gln
                165                 170

<210> SEQ ID NO 402
<211> LENGTH: 24
<212> TYPE: PRT
<213> ORGANISM: Canis familiaris

<400> SEQUENCE: 402

Glu Ala Tyr Lys Ser Glu Ile Ala His Arg Tyr Asn Asp Leu Gly Glu
1               5                   10                  15

Glu His Phe Arg Gly Leu Val Leu
            20

<210> SEQ ID NO 403
<211> LENGTH: 265
<212> TYPE: PRT
<213> ORGANISM: Canis familiaris

<400> SEQUENCE: 403

Leu Ser Ser Ala Lys Glu Arg Phe Lys Cys Ala Ser Leu Gln Lys Phe
1               5                   10                  15

Gly Asp Arg Ala Phe Lys Ala Trp Ser Val Ala Arg Leu Ser Gln Arg
            20                  25                  30

Phe Pro Lys Ala Asp Phe Ala Glu Ile Ser Lys Val Val Thr Asp Leu
        35                  40                  45

```
Thr Lys Val His Lys Glu Cys Cys His Gly Asp Leu Leu Glu Cys Ala
 50                  55                  60

Asp Asp Arg Ala Asp Leu Ala Lys Tyr Met Cys Glu Asn Gln Asp Ser
 65                  70                  75                  80

Ile Ser Thr Lys Leu Lys Glu Cys Cys Asp Lys Pro Val Leu Glu Lys
                 85                  90                  95

Ser Gln Cys Leu Ala Glu Val Glu Arg Asp Glu Leu Pro Gly Asp Leu
            100                 105                 110

Pro Ser Leu Ala Ala Asp Phe Val Glu Asp Lys Glu Val Cys Lys Asn
        115                 120                 125

Tyr Gln Glu Ala Lys Asp Val Phe Leu Gly Thr Phe Leu Tyr Glu Tyr
130                 135                 140

Ser Arg Arg His Pro Glu Tyr Ser Val Ser Leu Leu Arg Leu Ala
145                 150                 155                 160

Lys Glu Tyr Glu Ala Thr Leu Glu Lys Cys Cys Ala Thr Asp Asp Pro
                165                 170                 175

Pro Thr Cys Tyr Ala Lys Val Leu Asp Glu Phe Lys Pro Leu Val Asp
            180                 185                 190

Glu Pro Gln Asn Leu Val Lys Thr Asn Cys Glu Leu Phe Glu Lys Leu
        195                 200                 205

Gly Glu Tyr Gly Phe Gln Asn Ala Leu Leu Val Arg Tyr Thr Lys Lys
210                 215                 220

Ala Pro Gln Val Ser Thr Pro Thr Leu Val Val Glu Val Ser Arg Lys
225                 230                 235                 240

Leu Gly Lys Val Gly Thr Lys Cys Cys Lys Lys Pro Glu Ser Glu Arg
                245                 250                 255

Met Ser Cys Ala Asp Asp Phe Leu Ser
            260                 265

<210> SEQ ID NO 404
<211> LENGTH: 180
<212> TYPE: PRT
<213> ORGANISM: Canis familiaris

<400> SEQUENCE: 404

Met Gln Leu Leu Leu Thr Val Gly Leu Ala Leu Ile Cys Gly Leu
 1               5                  10                  15

Gln Ala Gln Glu Gly Asn His Glu Glu Pro Gln Gly Gly Leu Glu Glu
                20                  25                  30

Leu Ser Gly Arg Trp His Ser Val Ala Leu Ala Ser Asn Lys Ser Asp
             35                  40                  45

Leu Ile Lys Pro Trp Gly His Phe Arg Val Phe Ile His Ser Met Ser
 50                  55                  60

Ala Lys Asp Gly Asn Leu His Gly Asp Ile Leu Ile Pro Gln Asp Gly
 65                  70                  75                  80

Gln Cys Glu Lys Val Ser Leu Thr Ala Phe Lys Thr Ala Thr Ser Asn
                 85                  90                  95

Lys Phe Asp Leu Glu Tyr Trp Gly His Asn Asp Leu Tyr Leu Ala Glu
            100                 105                 110

Val Asp Pro Lys Ser Tyr Leu Ile Leu Tyr Met Ile Asn Gln Tyr Asn
        115                 120                 125

Asp Asp Thr Ser Leu Val Ala His Leu Met Val Arg Asp Leu Ser Arg
130                 135                 140

Gln Gln Asp Phe Leu Pro Ala Phe Glu Ser Val Cys Glu Asp Ile Gly
145                 150                 155                 160
```

Leu His Lys Asp Gln Ile Val Val Leu Ser Asp Asp Arg Cys Gln
               165                 170                 175

Gly Ser Arg Asp
            180

<210> SEQ ID NO 405
<211> LENGTH: 187
<212> TYPE: PRT
<213> ORGANISM: Equus caballus

<400> SEQUENCE: 405

Met Lys Leu Leu Leu Leu Cys Leu Gly Leu Ile Leu Val Cys Ala Gln
1               5                   10                  15

Gln Glu Glu Asn Ser Asp Val Ala Ile Arg Asn Phe Asp Ile Ser Lys
            20                  25                  30

Ile Ser Gly Glu Trp Tyr Ser Ile Phe Leu Ala Ser Asp Val Lys Glu
        35                  40                  45

Lys Ile Glu Glu Asn Gly Ser Met Arg Val Phe Val Asp Val Ile Arg
    50                  55                  60

Ala Leu Asp Asn Ser Ser Leu Tyr Ala Glu Tyr Gln Thr Lys Val Asn
65                  70                  75                  80

Gly Glu Cys Thr Glu Phe Pro Met Val Phe Asp Lys Thr Glu Glu Asp
                85                  90                  95

Gly Val Tyr Ser Leu Asn Tyr Asp Gly Tyr Asn Val Phe Arg Ile Ser
            100                 105                 110

Glu Phe Glu Asn Asp Glu His Ile Ile Leu Tyr Leu Val Asn Phe Asp
        115                 120                 125

Lys Asp Arg Pro Phe Gln Leu Phe Glu Phe Tyr Ala Arg Glu Pro Asp
    130                 135                 140

Val Ser Pro Glu Ile Lys Glu Glu Phe Val Lys Ile Val Gln Lys Arg
145                 150                 155                 160

Gly Ile Val Lys Glu Asn Ile Ile Asp Leu Thr Lys Ile Asp Arg Cys
                165                 170                 175

Phe Gln Leu Arg Gly Asn Gly Val Ala Gln Ala
            180                 185

<210> SEQ ID NO 406
<211> LENGTH: 29
<212> TYPE: PRT
<213> ORGANISM: Equus caballus
<220> FEATURE:
<221> NAME/KEY: UNSURE
<222> LOCATION: (3)..(3)
<223> OTHER INFORMATION: Xaa = unknown
<220> FEATURE:
<221> NAME/KEY: UNSURE
<222> LOCATION: (28)..(28)
<223> OTHER INFORMATION: Xaa = unknown

<400> SEQUENCE: 406

Ser Gln Xaa Pro Gln Ser Glu Thr Asp Tyr Ser Gln Leu Ser Gly Glu
1               5                   10                  15

Trp Asn Thr Ile Tyr Gly Ala Ala Ser Asn Ile Xaa Lys
            20                  25

<210> SEQ ID NO 407
<211> LENGTH: 211
<212> TYPE: PRT
<213> ORGANISM: Euroglyphus maynei -continued

```
<400> SEQUENCE: 407

Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
        195                 200                 205

Ile Asn Leu
    210

<210> SEQ ID NO 408
<211> LENGTH: 211
<212> TYPE: PRT
<213> ORGANISM: Euroglyphus maynei

<400> SEQUENCE: 408

Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140
```

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
        195                 200                 205

Ile Asn Leu
    210

<210> SEQ ID NO 409
<211> LENGTH: 211
<212> TYPE: PRT
<213> ORGANISM: Euroglyphus maynei

<400> SEQUENCE: 409

Glu Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
                20                  25                  30

Gly Ser Cys Trp Ala Phe Ser Gly Val Ala Ala Thr Glu Ser Ala Tyr
            35                  40                  45

Leu Ala Tyr Arg Asn Gln Ser Leu Asp Leu Ala Glu Gln Glu Leu Val
50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
                100                 105                 110

Gly Ile Ser Asn Tyr Cys Gln Ile Tyr Pro Pro Asn Ala Asn Lys Ile
            115                 120                 125

Arg Glu Ala Leu Ala Gln Thr His Ser Ala Ile Ala Val Ile Ile Gly
130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175

Gly Tyr Ser Asn Ala Gln Gly Val Asp Tyr Trp Ile Val Arg Asn Ser
            180                 185                 190

Trp Asp Thr Asn Trp Gly Asp Asn Gly Tyr Gly Tyr Phe Ala Ala Asn
        195                 200                 205

Ile Asp Leu
    210

<210> SEQ ID NO 410
<211> LENGTH: 212
<212> TYPE: PRT
<213> ORGANISM: Euroglyphus maynei

<400> SEQUENCE: 410

Glu Thr Ser Ala Cys Arg Ile Asn Ser Val Asn Val Pro Ser Glu Leu
1               5                   10                  15

Asp Leu Arg Ser Leu Arg Thr Val Thr Pro Ile Arg Met Gln Gly Gly
                20                  25                  30

```
Cys Gly Ser Cys Trp Ala Phe Ser Gly Val Ala Ala Thr Glu Ser Ala
         35                  40                  45

Tyr Leu Ala Tyr Arg Asn Thr Ser Leu Asp Leu Ser Glu Gln Glu Leu
 50                  55                  60

Val Asp Cys Ala Ser Gln His Gly Cys His Gly Asp Thr Ile Pro Arg
 65                  70                  75                  80

Gly Ile Glu Tyr Ile Gln Gln Asn Gly Val Val Glu Arg Ser Tyr
                 85                  90                  95

Pro Tyr Val Ala Arg Glu Gln Gln Cys Arg Arg Pro Asn Ser Gln His
                100                 105                 110

Tyr Gly Ile Ser Asn Tyr Cys Gln Ile Tyr Pro Pro Asp Val Lys Gln
                115                 120                 125

Ile Arg Glu Ala Leu Thr Gln Thr His Thr Ala Ile Ala Val Ile Ile
130                 135                 140

Gly Ile Lys Asp Leu Arg Ala Phe Gln His Tyr Asp Gly Arg Thr Ile
145                 150                 155                 160

Ile Gln His Asp Asn Gly Tyr Gln Pro Asn Tyr His Ala Val Asn Ile
                165                 170                 175

Val Gly Tyr Gly Ser Thr Gln Gly Val Asp Tyr Trp Ile Val Arg Asn
                180                 185                 190

Ser Trp Asp Thr Thr Trp Gly Asp Ser Gly Tyr Gly Tyr Phe Gln Ala
                195                 200                 205

Gly Asn Asn Leu
        210

<210> SEQ ID NO 411
<211> LENGTH: 307
<212> TYPE: PRT
<213> ORGANISM: Poa pratensis

<400> SEQUENCE: 411

Met Ala Val Gln Lys Tyr Thr Val Ala Leu Phe Leu Val Ala Leu Val
 1               5                  10                  15

Val Gly Pro Ala Ala Ser Tyr Ala Ala Asp Leu Ser Tyr Gly Ala Pro
                 20                  25                  30

Ala Thr Pro Ala Ala Pro Ala Ala Gly Tyr Thr Pro Ala Ala Pro Ala
             35                  40                  45

Gly Ala Ala Pro Lys Ala Thr Thr Asp Glu Gln Lys Met Ile Glu Lys
 50                  55                  60

Ile Asn Val Gly Phe Lys Ala Ala Val Ala Ala Ala Gly Gly Val Pro
 65                  70                  75                  80

Ala Ala Asn Lys Tyr Lys Thr Phe Val Ala Thr Phe Gly Ala Ala Ser
                 85                  90                  95

Asn Lys Ala Phe Ala Glu Ala Leu Ser Thr Glu Pro Lys Gly Ala Ala
                100                 105                 110

Val Asp Ser Ser Lys Ala Ala Leu Thr Ser Lys Leu Asp Ala Ala Tyr
                115                 120                 125

Lys Leu Ala Tyr Lys Ser Ala Glu Gly Ala Thr Pro Glu Ala Lys Tyr
130                 135                 140

Asp Asp Tyr Val Ala Thr Leu Ser Glu Ala Leu Arg Ile Ile Ala Gly
145                 150                 155                 160

Thr Leu Glu Val His Gly Val Lys Pro Ala Ala Glu Glu Val Lys Ala
                165                 170                 175

Thr Pro Ala Gly Glu Leu Gln Val Ile Asp Lys Val Asp Ala Ala Phe
                180                 185                 190
```

```
Lys Val Ala Ala Thr Ala Ala Asn Ala Ala Pro Ala Asn Asp Lys Phe
            195                 200                 205

Thr Val Phe Glu Ala Ala Phe Asn Asp Ala Ile Lys Ala Ser Thr Gly
        210                 215                 220

Gly Ala Tyr Gln Ser Tyr Lys Phe Ile Pro Ala Leu Glu Ala Ala Val
225                 230                 235                 240

Lys Gln Ser Tyr Ala Ala Thr Val Ala Thr Ala Pro Ala Val Lys Tyr
            245                 250                 255

Thr Val Phe Glu Thr Ala Leu Lys Lys Ala Ile Thr Ala Met Ser Gln
        260                 265                 270

Ala Gln Lys Ala Ala Lys Pro Ala Ala Ala Thr Gly Thr Ala Thr
            275                 280                 285

Ala Ala Val Gly Ala Ala Thr Gly Ala Ala Thr Ala Ala Ala Gly Gly
        290                 295                 300

Tyr Lys Val
305

<210> SEQ ID NO 412
<211> LENGTH: 333
<212> TYPE: PRT
<213> ORGANISM: Poa pratensis

<400> SEQUENCE: 412

Met Ala Val His Gln Tyr Thr Val Ala Leu Phe Leu Ala Val Ala Leu
1               5                   10                  15

Val Ala Gly Pro Ala Ala Ser Tyr Ala Ala Asp Val Gly Tyr Gly Ala
            20                  25                  30

Pro Ala Thr Leu Ala Thr Pro Ala Thr Pro Ala Ala Pro Ala Ala Gly
        35                  40                  45

Tyr Thr Pro Ala Ala Pro Ala Gly Ala Ala Pro Lys Ala Thr Thr Asp
    50                  55                  60

Glu Gln Lys Leu Ile Glu Lys Ile Asn Ala Gly Phe Lys Ala Ala Val
65                  70                  75                  80

Ala Ala Ala Ala Gly Val Pro Ala Val Asp Lys Tyr Lys Thr Phe Val
                85                  90                  95

Ala Thr Phe Gly Thr Ala Ser Asn Lys Ala Phe Ala Glu Ala Leu Ser
            100                 105                 110

Thr Glu Pro Lys Gly Ala Ala Ala Ser Ser Asn Ala Val Leu Thr
        115                 120                 125

Ser Lys Leu Asp Ala Ala Tyr Lys Leu Ala Tyr Lys Ser Ala Glu Gly
    130                 135                 140

Ala Thr Pro Glu Ala Lys Tyr Asp Ala Tyr Val Ala Thr Leu Ser Glu
145                 150                 155                 160

Ala Leu Arg Ile Ile Ala Gly Thr Leu Glu Val His Ala Val Lys Pro
                165                 170                 175

Ala Gly Glu Glu Val Lys Ala Ile Pro Ala Gly Glu Leu Gln Val Ile
            180                 185                 190

Asp Lys Val Asp Ala Ala Phe Lys Val Ala Thr Ala Ala Asn Ala
        195                 200                 205

Ala Pro Ala Asn Asp Lys Phe Thr Val Phe Glu Ala Ala Phe Asn Asp
    210                 215                 220

Ala Ile Lys Ala Ser Thr Gly Gly Ala Tyr Gln Ser Tyr Lys Phe Ile
225                 230                 235                 240

Pro Ala Leu Glu Ala Ala Val Lys Gln Ser Tyr Ala Ala Thr Val Ala
```

```
                    245                 250                 255
Thr Ala Pro Ala Val Lys Tyr Thr Val Phe Glu Thr Ala Leu Lys Lys
                260                 265                 270

Ala Ile Thr Ala Met Ser Gln Ala Gln Lys Ala Ala Lys Pro Ala Ala
            275                 280                 285

Ala Val Thr Ala Thr Ala Thr Gly Ala Val Gly Ala Ala Thr Gly Ala
        290                 295                 300

Val Gly Ala Ala Thr Gly Ala Thr Ala Ala Gly Gly Tyr Lys
305                 310                 315                 320

Thr Gly Ala Ala Thr Pro Thr Ala Gly Gly Tyr Lys Val
                325                 330

<210> SEQ ID NO 413
<211> LENGTH: 373
<212> TYPE: PRT
<213> ORGANISM: Poa pratensis

<400> SEQUENCE: 413

Met Asp Lys Ala Asn Gly Ala Tyr Lys Thr Ala Leu Lys Ala Ala Ser
1               5                   10                  15

Ala Val Ala Pro Ala Glu Lys Phe Pro Val Phe Gln Ala Thr Phe Asp
            20                  25                  30

Lys Asn Leu Lys Glu Gly Leu Ser Gly Pro Asp Ala Val Gly Phe Ala
        35                  40                  45

Lys Lys Leu Asp Ala Phe Ile Gln Thr Ser Tyr Leu Ser Thr Lys Ala
    50                  55                  60

Ala Glu Pro Lys Glu Lys Phe Asp Leu Phe Val Leu Ser Leu Thr Glu
65                  70                  75                  80

Val Leu Arg Phe Met Ala Gly Ala Val Lys Ala Pro Pro Ala Ser Lys
                85                  90                  95

Phe Pro Ala Lys Pro Ala Pro Lys Val Ala Ala Tyr Thr Pro Ala Ala
            100                 105                 110

Pro Ala Gly Ala Ala Pro Lys Ala Thr Thr Asp Glu Gln Lys Leu Ile
        115                 120                 125

Glu Lys Ile Asn Val Gly Phe Lys Ala Ala Val Ala Ala Ala Ala Gly
    130                 135                 140

Val Pro Ala Ala Ser Lys Tyr Lys Thr Phe Val Ala Thr Phe Gly Ala
145                 150                 155                 160

Ala Ser Asn Lys Ala Phe Ala Glu Ala Leu Ser Thr Glu Pro Lys Gly
                165                 170                 175

Ala Ala Val Ala Ser Ser Lys Ala Val Leu Thr Ser Lys Leu Asp Ala
            180                 185                 190

Ala Tyr Lys Leu Ala Tyr Lys Ser Ala Glu Gly Ala Thr Pro Glu Ala
        195                 200                 205

Lys Tyr Asp Ala Tyr Val Ala Thr Leu Ser Glu Ala Leu Arg Ile Ile
    210                 215                 220

Ala Gly Thr Leu Glu Val His Gly Val Lys Pro Ala Ala Glu Glu Val
225                 230                 235                 240

Lys Ala Ile Pro Ala Gly Glu Leu Gln Val Ile Asp Lys Val Asp Ala
                245                 250                 255

Ala Phe Lys Val Ala Ala Thr Ala Ala Asn Ala Ala Pro Ala Asn Asp
            260                 265                 270

Lys Phe Thr Val Phe Glu Ala Ala Phe Asn Asp Ala Ile Lys Ala Ser
        275                 280                 285
```

```
Thr Gly Gly Ala Tyr Gln Ser Tyr Lys Phe Ile Pro Ala Leu Glu Ala
    290                 295                 300

Ala Val Lys Gln Ser Tyr Ala Ala Thr Val Ala Thr Pro Ala Val
305                 310                 315                 320

Lys Tyr Thr Val Phe Glu Thr Ala Leu Lys Lys Ala Ile Thr Ala Met
                325                 330                 335

Ser Gln Ala Gln Lys Ala Ala Lys Pro Ala Ala Val Thr Gly Thr
            340                 345                 350

Ala Thr Ser Ala Val Gly Ala Ala Thr Gly Ala Ala Thr Ala Ala Ala
            355                 360                 365

Gly Gly Tyr Lys Val
    370

<210> SEQ ID NO 414
<211> LENGTH: 685
<212> TYPE: PRT
<213> ORGANISM: Periplaneta americana

<400> SEQUENCE: 414

Met Lys Thr Ala Leu Val Phe Ala Ala Val Ala Phe Val Ala Ala
1               5                   10                  15

Arg Phe Pro Asp His Lys Asp Tyr Lys Gln Leu Ala Asp Lys Gln Phe
                20                  25                  30

Leu Ala Lys Gln Arg Asp Val Leu Arg Leu Phe His Arg Val His Gln
            35                  40                  45

His Asn Ile Leu Asn Asp Gln Val Glu Val Gly Ile Pro Met Thr Ser
        50                  55                  60

Lys Gln Thr Ser Ala Thr Thr Val Pro Pro Ser Gly Glu Ala Val His
65                  70                  75                  80

Gly Val Leu Gln Glu Gly His Ala Arg Pro Arg Gly Pro Phe Ser
                85                  90                  95

Val Asn Tyr Glu Lys His Arg Glu Gln Ala Ile Met Leu Tyr Asp Leu
            100                 105                 110

Leu Tyr Phe Ala Asn Asp Tyr Asp Thr Phe Tyr Lys Thr Ala Cys Trp
        115                 120                 125

Ala Arg Asp Arg Val Asn Glu Gly Met Phe Met Tyr Ser Phe Ser Ile
    130                 135                 140

Ala Val Phe His Arg Asp Asp Met Gln Gly Val Met Leu Pro Pro
145                 150                 155                 160

Tyr Glu Val Tyr Pro Tyr Leu Phe Val Asp His Asp Val Ile His Met
                165                 170                 175

Ala Gln Lys Tyr Trp Met Lys Asn Ala Gly Ser Gly Glu His His Ser
            180                 185                 190

His Val Ile Pro Val Asn Phe Thr Leu Arg Thr Gln Asp His Leu Leu
        195                 200                 205

Ala Tyr Phe Thr Ser Asp Val Asn Leu Asn Ala Phe Asn Thr Tyr Tyr
    210                 215                 220

Arg Tyr Tyr Pro Ser Trp Tyr Asn Thr Thr Leu Tyr Gly His Asn
225                 230                 235                 240

Ile Asp Arg Arg Gly Glu Gln Phe Tyr Thr Tyr Lys Gln Ile Tyr
                245                 250                 255

Ala Arg Tyr Phe Leu Glu Arg Leu Ser Asn Asp Leu Pro Asp Val Tyr
            260                 265                 270

Pro Phe Tyr Tyr Ser Lys Pro Val Lys Ser Ala Tyr Asn Pro Asn Leu
        275                 280                 285
```

Arg Tyr His Asn Gly Glu Glu Met Pro Val Arg Pro Ser Asn Met Tyr
    290                 295                 300

Val Thr Asn Phe Asp Leu Tyr Tyr Ile Ala Asp Ile Lys Asn Tyr Glu
305                 310                 315                 320

Lys Arg Val Glu Asp Ala Ile Asp Phe Gly Tyr Ala Phe Asp Glu His
                325                 330                 335

Met Lys Pro His Ser Leu Tyr His Asp Val His Gly Met Glu Tyr Leu
                340                 345                 350

Ala Asp Met Ile Glu Gly Asn Met Asp Ser Pro Asn Phe Tyr Phe Tyr
            355                 360                 365

Gly Ser Ile Tyr His Met Tyr His Ser Met Ile Gly His Ile Val Asp
370                 375                 380

Pro Tyr His Lys Met Gly Leu Ala Pro Ser Leu Glu His Pro Glu Thr
385                 390                 395                 400

Val Leu Arg Asp Pro Val Phe Tyr Gln Leu Trp Lys Arg Val Asp His
                405                 410                 415

Leu Phe Gln Lys Tyr Lys Asn Arg Leu Pro Arg Tyr Thr His Asp Glu
                420                 425                 430

Leu Ala Phe Glu Gly Val Lys Val Glu Asn Val Asp Val Gly Lys Leu
            435                 440                 445

Tyr Thr Tyr Phe Glu Gln Tyr Asp Met Ser Leu Asp Met Ala Val Tyr
450                 455                 460

Val Asn Asn Val Asp Gln Ile Ser Asn Val Asp Val Gln Leu Ala Val
465                 470                 475                 480

Arg Leu Asn His Lys Pro Phe Thr Tyr Asn Ile Glu Val Ser Ser Asp
                485                 490                 495

Lys Ala Gln Asp Val Tyr Val Ala Val Phe Leu Gly Pro Lys Tyr Asp
                500                 505                 510

Tyr Leu Gly Arg Glu Tyr Asp Leu Asn Asp Arg Arg His Tyr Phe Val
            515                 520                 525

Glu Met Asp Arg Phe Pro Tyr His Val Gly Ala Gly Lys Thr Val Ile
530                 535                 540

Glu Arg Asn Ser His Asp Ser Asn Ile Ile Ala Pro Glu Arg Asp Ser
545                 550                 555                 560

Tyr Arg Thr Phe Tyr Lys Lys Val Gln Glu Ala Tyr Glu Gly Lys Ser
                565                 570                 575

Gln Tyr Tyr Val Asp Lys Gly His Asn Tyr Cys Gly Tyr Pro Glu Asn
                580                 585                 590

Leu Leu Ile Pro Lys Gly Lys Gly Gln Ala Tyr Thr Phe Tyr
            595                 600                 605

Val Ile Val Thr Pro Tyr Val Lys Gln Asp Glu His Asp Phe Glu Pro
610                 615                 620

Tyr Asn Tyr Lys Ala Phe Ser Tyr Cys Gly Val Gly Ser Glu Arg Lys
625                 630                 635                 640

Tyr Pro Asp Asn Lys Pro Leu Gly Tyr Pro Phe Asp Arg Lys Ile Tyr
                645                 650                 655

Ser Asn Asp Phe Tyr Thr Pro Asn Met Tyr Phe Lys Val Ile Ile
                660                 665                 670

Phe His Lys Lys Tyr Asp Glu Val Gly Val Gln Gly His
            675                 680                 685

<210> SEQ ID NO 415
<211> LENGTH: 446

<212> TYPE: PRT
<213> ORGANISM: Periplaneta americana

<400> SEQUENCE: 415

```
Ile Asn Glu Ile His Ser Ile Ile Gly Leu Pro Pro Phe Val Pro Pro
1               5                   10                  15

Ser Arg Arg His Ala Arg Arg Gly Val Gly Ile Asn Gly Leu Ile Asp
            20                  25                  30

Asp Val Ile Ala Ile Leu Pro Val Asp Glu Leu Lys Ala Leu Phe Gln
        35                  40                  45

Glu Lys Leu Glu Thr Ser Pro Asp Phe Lys Ala Leu Tyr Asp Ala Ile
    50                  55                  60

Arg Ser Pro Glu Phe Gln Ser Ile Ile Ser Thr Leu Asn Ala Met Gln
65                  70                  75                  80

Arg Ser Glu His His Gln Asn Leu Arg Asp Lys Gly Val Asp Val Asp
                85                  90                  95

His Phe Ile Gln Leu Ile Arg Ala Leu Phe Gly Leu Ser Arg Ala Ala
            100                 105                 110

Arg Asn Leu Gln Asp Asp Leu Asn Asp Phe Leu His Ser Leu Glu Pro
        115                 120                 125

Ile Ser Pro Arg His Arg His Gly Leu Pro Arg Gln Arg Arg Arg Ser
    130                 135                 140

Ala Arg Val Ser Ala Tyr Leu His Ala Asp Asp Phe His Lys Ile Ile
145                 150                 155                 160

Thr Thr Ile Glu Ala Leu Pro Glu Phe Ala Asn Phe Tyr Asn Phe Leu
                165                 170                 175

Lys Glu His Gly Leu Asp Val Val Asp Tyr Ile Asn Glu Ile His Ser
            180                 185                 190

Ile Ile Gly Leu Pro Pro Phe Val Pro Pro Ser Arg Arg His Ala Arg
        195                 200                 205

Arg Gly Val Gly Ile Asn Gly Leu Ile Asp Asp Val Ile Ala Ile Leu
210                 215                 220

Pro Val Asp Glu Leu Lys Ala Leu Phe Gln Glu Lys Leu Glu Thr Ser
225                 230                 235                 240

Pro Asp Phe Lys Ala Leu Tyr Asp Ala Ile Arg Ser Pro Glu Phe Gln
                245                 250                 255

Ser Ile Ile Ser Thr Leu Asn Ala Met Pro Glu Tyr Gln Glu Leu Leu
            260                 265                 270

Gln Asn Leu Arg Asp Lys Gly Val Asp Val Asp His Phe Ile Arg Val
        275                 280                 285

Asp Gln Gly Thr Leu Arg Thr Leu Ser Ser Gly Gln Arg Asn Leu Gln
    290                 295                 300

Asp Asp Leu Asn Asp Phe Leu Ala Leu Ile Pro Thr Asp Gln Ile Leu
305                 310                 315                 320

Ala Ile Ala Met Asp Tyr Leu Ala Asn Asp Ala Glu Val Gln Glu Leu
                325                 330                 335

Val Ala Tyr Leu Gln Ser Asp Asp Phe His Lys Ile Ile Thr Thr Ile
            340                 345                 350

Glu Ala Leu Pro Glu Phe Ala Asn Phe Tyr Asn Phe Leu Lys Glu His
        355                 360                 365

Gly Leu Asp Val Val Asp Tyr Ile Asn Glu Ile His Ser Ile Ile Gly
    370                 375                 380

Leu Pro Pro Phe Val Pro Pro Ser Gln Arg His Ala Arg Arg Gly Val
385                 390                 395                 400
```

```
Gly Ile Asn Gly Leu Ile Asp Asp Val Ile Ala Ile Leu Pro Val Asp
                405                 410                 415

Glu Leu Lys Ala Leu Phe Gln Glu Lys Leu Glu Thr Ser Pro Asp Phe
                420                 425                 430

Lys Ala Leu Tyr Asp Ala Ile Asp Leu Arg Ser Ser Arg Ala
                435                 440                 445

<210> SEQ ID NO 416
<211> LENGTH: 352
<212> TYPE: PRT
<213> ORGANISM: Blattella germanica

<400> SEQUENCE: 416

Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
                20                  25                  30

Val Phe Ile Asn Thr Gln Tyr Ala Gly Ile Thr Lys Ile Gly Asn Gln
            35                  40                  45

Asn Phe Leu Thr Val Phe Asp Ser Thr Ser Cys Asn Val Val Val Ala
50                  55                  60

Ser Gln Glu Cys Val Gly Gly Ala Cys Val Cys Pro Asn Leu Gln Lys
65                  70                  75                  80

Tyr Glu Lys Leu Lys Pro Lys Tyr Ile Ser Asp Gly Asn Val Gln Val
                85                  90                  95

Lys Phe Phe Asp Thr Gly Ser Ala Val Gly Arg Gly Ile Glu Asp Ser
            100                 105                 110

Leu Thr Ile Ser Asn Leu Thr Thr Ser Gln Gln Asp Ile Val Leu Ala
        115                 120                 125

Asp Glu Leu Ser Gln Glu Val Cys Ile Leu Ser Ala Asp Val Val Val
    130                 135                 140

Gly Ile Ala Ala Pro Gly Cys Pro Asn Ala Leu Lys Gly Lys Thr Val
145                 150                 155                 160

Leu Glu Asn Phe Val Glu Glu Asn Leu Ile Ala Pro Val Phe Ser Ile
                165                 170                 175

His His Ala Arg Phe Gln Asp Gly Glu His Phe Gly Glu Ile Ile Phe
            180                 185                 190

Gly Gly Ser Asp Trp Lys Tyr Val Asp Gly Glu Phe Thr Tyr Val Pro
        195                 200                 205

Leu Val Gly Asp Asp Ser Trp Lys Phe Arg Leu Asp Gly Val Lys Ile
    210                 215                 220

Gly Asp Thr Thr Val Ala Pro Ala Gly Thr Gln Ala Ile Ile Asp Thr
225                 230                 235                 240

Ser Lys Ala Ile Ile Val Gly Pro Lys Ala Tyr Val Asn Pro Ile Asn
                245                 250                 255

Glu Ala Ile Gly Cys Val Val Lys Thr Thr Thr Arg Ile Cys
            260                 265                 270

Lys Leu Asp Cys Ser Lys Ile Pro Ser Leu Pro Asp Val Thr Phe Val
        275                 280                 285

Ile Asn Gly Arg Asn Phe Asn Ile Ser Ser Gln Tyr Tyr Ile Gln Gln
    290                 295                 300

Asn Gly Asn Leu Cys Tyr Ser Gly Phe Gln Pro Cys Gly His Ser Asp
305                 310                 315                 320

His Phe Phe Ile Gly Asp Phe Phe Val Asp His Tyr Tyr Ser Glu Phe
```

```
                    325                 330                 335
Asn Trp Glu Asn Lys Thr Met Gly Phe Gly Arg Ser Val Glu Ser Val
                340                 345                 350

<210> SEQ ID NO 417
<211> LENGTH: 182
<212> TYPE: PRT
<213> ORGANISM: Blattella germanica

<400> SEQUENCE: 417

Ala Val Leu Ala Leu Cys Ala Thr Asp Thr Leu Ala Asn Glu Asp Cys
1               5                   10                  15

Phe Arg His Glu Ser Leu Val Pro Asn Leu Asp Tyr Glu Arg Phe Arg
            20                  25                  30

Gly Ser Trp Ile Ile Ala Ala Gly Thr Ser Glu Ala Leu Thr Gln Tyr
        35                  40                  45

Lys Cys Trp Ile Asp Arg Phe Ser Tyr Asp Asp Ala Leu Val Ser Lys
    50                  55                  60

Tyr Thr Asp Ser Gln Gly Lys Asn Arg Thr Thr Ile Arg Gly Arg Thr
65                  70                  75                  80

Lys Phe Glu Gly Asn Lys Phe Thr Ile Asp Tyr Asn Asp Lys Gly Lys
                85                  90                  95

Ala Phe Ser Ala Pro Tyr Ser Val Leu Ala Thr Asp Tyr Glu Asn Tyr
            100                 105                 110

Ala Ile Val Glu Gly Cys Pro Ala Ala Ala Asn Gly His Val Ile Tyr
        115                 120                 125

Val Gln Ile Arg Phe Ser Val Arg Arg Phe His Pro Lys Leu Gly Asp
    130                 135                 140

Lys Glu Met Ile Gln His Tyr Thr Leu Asp Gln Val Asn Gln His Lys
145                 150                 155                 160

Lys Ala Ile Glu Glu Asp Leu Lys His Phe Asn Leu Lys Tyr Glu Asp
                165                 170                 175

Leu His Ser Thr Cys His
            180

<210> SEQ ID NO 418
<211> LENGTH: 200
<212> TYPE: PRT
<213> ORGANISM: Blattella germanica

<400> SEQUENCE: 418

Tyr Lys Leu Thr Tyr Cys Pro Val Lys Ala Leu Gly Glu Pro Ile Arg
1               5                   10                  15

Phe Leu Leu Ser Tyr Gly Glu Lys Asp Phe Glu Asp Tyr Arg Phe Gln
            20                  25                  30

Glu Gly Asp Trp Pro Asn Leu Lys Pro Ser Met Pro Phe Gly Lys Thr
        35                  40                  45

Pro Val Leu Glu Ile Asp Gly Lys Gln Thr His Gln Ser Val Ala Ile
    50                  55                  60

Ser Arg Tyr Leu Gly Lys Gln Phe Gly Leu Ser Gly Lys Asp Asp Trp
65                  70                  75                  80

Glu Asn Leu Glu Ile Asp Met Ile Val Asp Thr Ile Ser Asp Phe Arg
                85                  90                  95

Ala Ala Ile Ala Asn Tyr His Tyr Asp Ala Asp Glu Asn Ser Lys Gln
            100                 105                 110

Lys Lys Trp Asp Pro Leu Lys Lys Glu Thr Ile Pro Tyr Tyr Thr Lys
```

-continued

```
            115                 120                 125
Lys Phe Asp Glu Val Val Lys Ala Asn Gly Gly Tyr Leu Ala Ala Gly
    130                 135                 140

Lys Leu Thr Trp Ala Asp Phe Tyr Phe Val Ala Ile Leu Asp Tyr Leu
145                 150                 155                 160

Asn His Met Ala Lys Glu Asp Leu Val Ala Asn Gln Pro Asn Leu Lys
                165                 170                 175

Ala Leu Arg Glu Lys Val Leu Gly Leu Pro Ala Ile Lys Ala Trp Val
            180                 185                 190

Ala Lys Arg Pro Pro Thr Asp Leu
        195                 200

<210> SEQ ID NO 419
<211> LENGTH: 15
<212> TYPE: PRT
<213> ORGANISM: Alternaria alternata

<400> SEQUENCE: 419

Glu Val Tyr Gln Lys Leu Lys Ala Leu Ala Lys Lys Thr Tyr Gly
1               5                   10                  15

<210> SEQ ID NO 420
<211> LENGTH: 17
<212> TYPE: PRT
<213> ORGANISM: Alternaria alternata

<400> SEQUENCE: 420

Ala Glu Val Tyr Gln Lys Leu Lys Ala Leu Ala Lys Lys Thr Tyr Gly Gln
1               5                   10                  15
```

PEPTIDE WITH MULTIPLE EPITOPES

FIELD OF THE INVENTION

The present invention relates to peptides comprising multiple MHC Class II-binding T cell epitopes for tolerisation therapy.

BACKGROUND OF THE INVENTION

T-cell antigen recognition requires antigen presenting cells (APCs) to present antigen fragments (peptides) on their cell surface in association with molecules of the major histocompatibility complex (MHC). T cells use their antigen specific T-cell receptors (TCRs) to recognise with high specificity the antigen fragments presented by the APC. Such recognition acts as a trigger to the immune system to generate a range of responses to eradicate the antigen which has been recognized.

Most of the specificity of T cell recognition of the antigen fragments is provided by a smaller subsequence of amino acids within the fragments. This subsequence is known as the T cell epitope. In the case of extracellular allergens and auto- or allo-antigens, the peptides are presented on MHC Class II molecules, which are recognized by CD4 T cells. Accordingly, interest in allergic and auto- or allo-immune disorders has focused on MHC Class II-binding T cell epitopes.

Given their role in the immune system, there is considerable interest in such epitopes for use as therapeutic agents to modulate the immune systems of subjects. For example, administration of peptide epitopes to subjects has been demonstrated to result in the induction of tolerance to the antigen from which the epitope derives. Therapeutic agents based on such an effect have great potential in the prevention and treatment of allergy, and auto- or allo-immune diseases where the down-regulation of an immune response is desirable.

SUMMARY OF THE INVENTION

The minimal amino acid sequence of a T cell epitope required for binding to MHC Class II-molecules can be precisely identified and generally comprises approximately nine amino acids. An epitope sequence typically binds specifically to a particular class of MHC Class II molecule, and does not bind to other MHC Class II molecules. Accordingly, the efficacy of a given epitope sequence varies greatly depending on the MHC Class II type of the individual to whom it is administered. To utilise an epitope for, e.g. the induction of tolerance, it is therefore necessary to undertake time-consuming and costly steps to identify the MHC Class II type of the individual to be tolerised.

The present inventors have made the finding that by incorporating multiple different epitope sequences, it is possible to produce a peptide which binds to multiple different classes of MHC Class II and is therefore effective when administered to a wider range of individuals, reducing the requirement to identify the MHC Class II type of an individual. Two or more epitope sequences may be combined in a peptide in an overlapping configuration, or as two independent sequences separated by amino acids which are not comprised in either epitope, without producing a peptide large enough to possess significant tertiary structure that would enable it to retain the conformation of an IgG or IgE-cross-linking epitope. Consequently the downstream immune responses to antigen caused by such cross-linking do not occur.

Accordingly, the present invention provides:

a peptide which has a length of 10 to 25 amino acids, the peptide comprising a region that comprises at least two different MHC class II-binding T cell epitope sequences, wherein the epitope sequences comprise at least 9 amino acids and derive from an antigenic protein, and wherein each epitope sequence binds to a different MHC class II molecule, and wherein the region is optionally flanked at the N and/or C terminus by additional amino acids which are not part of the epitope sequence. The peptide is typically suitable for use in tolerisation therapy.

Polynucleotides, vectors and cells expressing the peptide of the invention, and methods of making the peptide of the invention are also provided.

DETAILED DESCRIPTION OF THE INVENTION

It is to be understood that references to inserting, deleting, replacing amino acids herein does not require the actual physical insertion, deletion or replacement of amino acids, and instead a peptide can be synthesized comprising sequence which represents (or is the end result of) the insertion, deletion or replacement having occurred.

Amino Acids

The table below shows the properties of amino acids.

| | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged (+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

MHC Class II-Binding T Cell Epitopes

The MHC Class II-binding T cell epitope comprised in the peptides of the invention is typically the minimal amino acid sequence that is capable of binding to Class II molecules and capable of stimulating T cells when presented in to T cells in association with Class II on the cell surface. The epitope is typically one that binds to a human MHC class II molecule.

An MHC Class II molecule consists of two proteins, α and β, each of which is encoded by a different gene. In humans, there are three clusters of genes encoding different α and β proteins. These are the Human Leukocyte Antigen (HLA) clusters, DR, DQ and DP. Each cluster comprises multiple different A genes encoding different variant of the cc protein and multiple different B genes encoding different variants of the β protein. The resulting MHC Class II heterodimers are therefore extremely diverse, and correspondingly so are the T cell epitopes that they bind.

The binding site of MHC Class II molecules is composed of two separate proteins which form a cleft. The cleft is open-ended, which in theory allows a peptide of any length to bind. However, only 9 amino acids can occupy the cleft itself. The identities of the up to 9 amino acids which occupy the cleft define whether or not a given peptide will bind to a given MHC Class II molecule and be available for presentation to T cells. These up to 9 amino acids therefore represent the minimal sequence that is required for MHC Class II-binding. It is generally assumed that such a sequence will be capable of stimulating T cells when presented to T cells in association with Class II on the cell surface. However, this may be confirmed experimentally by methods standard in the art.

Such methods may typically comprise contacting the epitope with T cells in a sample taken from a subject, under conditions which allow the epitope and the T cells to interact; and then determining whether or not any of the T cells are stimulated. Determining whether or not the T cells are stimulated may be achieved by any suitable method, for example by detecting the production of cytokines by the T cells, wherein cytokine production indicates that T cells have been stimulated. Suitable cytokines include interferon gamma and interleukin 13. Cytokine production may be detected by any suitable method, for example an ELISA, ELISPOT assay or a flow cytometric assay. Particularly preferred methods include Multiplex bead array assays as described in, for example de Jager et al; Clinical and Diagnostic Laboratory Immunology, 2003, Vol 10(1) p. 133-139 The T cells in a sample from a subject are typically present in a population of peripheral blood mononuclear cells (PBMCs) isolated from a blood or serum sample taken from the subject.

The MHC Class II-binding T cell epitope of the invention typically consists of 8 or 9 amino acids, but may consist of 7, 10, 11, 12, 13, 14, 15 or 16 amino acids. The amino acid sequence of the epitope may be broadly defined by further reference to the binding site of MHC Class II molecules. This binding site has specific binding pockets, which corresponding to primary and secondary anchor positions in the sequence of the binding peptide epitope. The binding pockets are defined by amino acid positions in the sequence of the MHC Class II molecule, and are generally not absolutely discriminatory for a specific amino acid in the epitope. Therefore the peptide binding specificity of any given MHC molecule is relatively broad. Thus, peptides binding to the same MHC allotype exhibit some degree of similarity, but there is no requirement for identity.

For the most common human MHC Class II type, HLA-DR, the key anchor positions for binding to the binding pockets are at positions 1, 4, 6, 7 and 9 of the peptide epitope (counting from the most N terminal residue occupying the cleft to the most C terminal). Different HLA-DR alleles which have similar amino acids in their binding pockets therefore typically bind peptides with similar amino acids at positions 1, 4, 6, 7 and 9. Accordingly, the region containing an MHC Class II binding T cell epitope preferably has amino acids at positions corresponding to positions 1, 4, 6, 7 and 9 that allow binding to the widest range of HLA-DR alleles. Examples of characteristic binding properties of different HLA-DR alleles are set out below:

DR alleles with Glycine at position 86 of the β chain show strong preferences for large hydrophobic side chains (Trp, Tyr, Phe) at peptide position 1, whereas Valine at position 86 restricts the pocket size and alters the preferences to small hydrophobic side chains (Val and Ala) at this position. Medium sized hydrophobic amino acids Leu and Ile are well accepted in all DR alleles.

DR alleles with Gln at position 70, Lysine at position 71, and Arginine or Gln at position 74 of the β chain have an overall positive charge within pocket 4, which requires negatively charged amino acids Asp and Glu at position 4 of the binding peptide (as in for example, DRB1*0301). DR alleles with this motif are associated with two autoimmune diseases: systematic lupus erythematosus and Hashimoto's thyroiditis.

DR alleles with Gln or Arg at position 70, Arg or Lys at position 71 and Glu or Ala at position 74 of the β chain bind similar peptides to those directly above since the only significant difference is at position 74. However, when Ala is present at position 74, pocket 4 increases in size and can accommodate larger amino acids such as Phe, Trp, and Ile (as in for example DRB1*0401, 04, 05). Alleles bearing Glu at position 74 are expected to allow small polar residues, like Ser and Thr at position 4 of the binding peptide. DR alleles with this motif are associated with a susceptibility to rheumatoid arthritis.

DR alleles with Asp at position 70, Glu or Arg at position 71, and Leu or Ala at position 74 of the β chain exclude peptides with negatively charged amino acids at peptide position 4 (for example DRB1*0402). This is due to the presence of Asp at position 70. DR alleles with this motif are associated with the autoimmune diseases Juvenile rheumatoid arthritis (JRA), pemphigus vulgaris, and allergic bronchopulmonary.

Polymorphisms at position 9 of the β chain define the size of binding pocket 9 in all DR alleles. Alleles with Trp at this position accept only small amino acids in position 9 of the binding peptide, e.g. Ala, Val, Gly, Ser, Thr, Pro (as in for example DRB1*0101 and *1501). Glu at position 9, in combination with Asp at position 57, makes pocket 9 negatively charged, facilitating the accommodation of positively charged amino acids, such as Lys (as in for example DRB1*0401 and *0404) and Histine (as in for example DRB1*0402). In most MHC class II alleles, Asp at position 57 makes a salt-bridged hydrogen bond with Arg at position 76, allowing the pocket to also accommodate aliphatic and polar amino acids. In cases where Asp at position 57 is replaced by Ser (for example DRB1*0405) or Ala (DQ8), the hydrogen bonding network is destroyed and Arg at position 76 can strongly attract negatively charged amino acids such as Asp or Glu at position 9 of the binding peptide (as in for example DRB1*0405).

An example of a preferred sequence for an epitope therefore has Trp, Tyr, Phe, Val or Ala at position 1; Asp, Glu, Ser or Thr at position 4; and Ala, Val, Gly, Ser, Thr, Pro at position 9. A further example of a preferred sequence for an epitope has a large aromatic or hydrophobic amino acid at position 1, for example Tyr, Phe, Trp, Leu, Ile or Val, and a small, non-charged amino acid at position 6, for example Ser, Thr, Ala, Pro, Val, Ile or Met. Approximately 87.5% of peptides binding to all or a combination of the MHC Class II molecules encoded by the DRB1*0101, *0401 and *0701 alleles contain this motif. Furthermore, since T cell epitopes derived from allergens and autoimmune antigens do not typically contain a large number of repeats of a given amino acid or amino acids, preferred epitopes of the invention typically comprise at least 5, 6, 7 or 8 different amino acids.

The precise amino sequence of an epitope may be predicted by computer-based algorithms and confirmed by in vitro biochemical analysis. Suitable commercially available algorithms include the EpiMatrix algorithm (EpiVax Inc.). Other algorithms are available at, for example, the website at the ProPed MHC Class-II Binding Peptide Prediction Server. Analysis with these algorithms typically comprises parsing a larger polypeptide sequence into multiple overlapping small peptides. The sequences of these small peptides are then analysed using the algorithm to identify those which are predicted to bind MHC Class II molecules. The overlapping small peptides are typically 9-mers.

The candidate peptides which score most highly in this analysis are then assessed for the ability to bind a panel of MHC Class II molecules encoded by different Class II alleles in vitro using standard binding assays. For example a competitive MHC class II binding assay may be used, wherein each peptide is analysed for its ability to displace a known control binder from each of the human MHC class II allotypes investigated. In such an assay each peptide is assigned an $IC_{50}$ value (the concentration at which 50% inhibition of control peptide binding is achieved). The lower the $IC_{50}$ the higher the affinity of a peptide for a given MHC class II allotype.

The epitope or epitopes in a polypeptide are taken to be those peptides which show the highest binding affinity to MHC Class II molecules. Particularly preferred epitopes show high affinity binding to different Class II molecules encoded by more than one preferably two, more preferably three, four or five MHC Class II alleles.

It will be appreciated that biochemical assays for the identification of a T cell epitope are not typically able to precisely define the position of the minimal epitope sequence within a larger sequence more accurately than to within approximately 12 amino acids, and more typically 15, 20 or more amino acids. The reason for this is that a large sequence must be physically fragmented into smaller overlapping peptides, or smaller overlapping peptides must be manufactured de novo prior to in vitro assessment of the ability of these peptides to bind MHC Class II molecules. The skilled person will recognise that the smaller the overlapping peptide fragments used, the more time-consuming and labour intensive is the process of manufacture. Hence epitopes are often identified as being contained within a larger polypeptide region. It is envisaged that the epitopes of the invention may be defined as such a larger region.

In all cases, it is envisaged that the epitope sequences of the invention also comprise functional variants of the epitope sequences. A functional variant epitope sequence is any homologous epitope sequence which is able to stimulate a T cell that specifically recognise the native epitope sequence from which the variant derives, or which is able to induce tolerance to the native epitope sequence in an individual. Such a variant typically has at least 55%, preferably 60%, 65%, 70%, 75%, 80%, 85%, 90%, 95% or 99% homology to the native epitope sequence. Suitable methods for determining the stimulatory effect of a variant epitope are known in the art. For example, a sample of peripheral blood mononuclear cells (PBMCs) can be stimulated with the protein from which the native epitope derives at various cell densities. After one week of culture, the T cell cultures are restimulated with autologous antigen presenting cells pulsed with peptides consisting of the native epitope sequence, which produces T cell lines specific for the native epitope sequence. The resulting lines can then be tested to see if they are stimulated by any variant epitope sequence, with stimulation being correlated with, e.g. proliferation or production of cytokines, in particular interferon-gamma, interleukin-13 and interleukin-17.

Regions Containing at Least Two MHC Class II-Binding T Cell Epitopes

As set out above, the bioinformatic techniques used to identify epitopes may identify multiple epitopes in the same polypeptide. Each of these multiple epitopes typically binds to different types of MHC Class II molecule. That is, a first epitope may bind Class II molecules encoded by alleles w, x, and y, whereas a second epitope binds Class II molecules encoded by alleles x, y and z. Since the region of the invention comprises at least two different epitope sequences, the peptides of the invention are capable of binding to a large number of different MHC Class II molecules.

The multiple different epitope sequences may be comprised in a region as two or more overlapping epitopes. For example, in a sequence of 12 amino acids, one epitope corresponds to amino acids 1 to 9 and a second epitope corresponds to amino acids 4 to 12. A peptide region comprising amino acids 1 to 12 will therefore comprise two overlapping epitope sequences since both epitopes comprise the contiguous sequence of amino acids 4 to 9.

The overlap of sequence between any two epitopes may typically comprise a contiguous sequence of upto approximately 10%, 20%, 30%, 40%, 50%, 60%, 65%, 70%, 80% or 90% of the amino acids from the N or C terminus either epitope. Therefore, assuming an epitope length of 9 amino acids, a second epitope may comprise the contiguous sequence of 1, 2, 3, 4, 5, 6, 7 or 8 amino acids at the N terminal of a first epitope, with additional amino acids present at the N terminus of this sequence which are not comprised in the first epitope, or may comprise the contiguous sequence of 1, 2, 3, 4, 5, 6, 7 or 8 amino acids at the C terminal of a first epitope, with additional amino acids present at the C terminus of this sequence which are not comprised in the first epitope.

A preferred overlap of sequence between any two epitopes typically comprises a contiguous sequence of upto approximately 65% of the amino acids from the N or C terminus either epitope. For an epitope length of 9 amino acids, a second epitope may therefore comprise the contiguous sequence of 6 amino acids at the N terminal of a first epitope, with additional amino acids present at the N terminus of this sequence which are not comprised in the first epitope, or may comprise the contiguous sequence of 6 amino acids at the C terminal of a first epitope, with additional amino acids present at the C terminus of this sequence which are not comprised in the first epitope.

Alternatively, the multiple epitopes in the region may be two or more independent sequences. The independent sequences may be consecutive or may be separated by additional amino acids which are not comprised in an epitope. As an example of the former case, in a sequence of 18 amino acids, one epitope corresponds to amino acids 1 to 9 and a second epitope corresponds to amino acids 10 to 18. As an example of the latter case, in a sequence of 19 amino acids, one epitope corresponds to amino acids 1 to 9 and a second epitope corresponds to amino acids 11 to 19. In this example, amino acid 10 is not comprised in either epitope. In general terms, two independent epitope sequences may typically be separated by 1, 2, 3, 4, 5, 6 or 7 additional amino acids which are not comprised in either epitope.

The amino acid sequence separating the epitope sequences ("the additional amino acid(s)") may comprise any amino acid sequence. It is particularly preferred that the additional amino acid(s) comprise a high proportion of hydrophilic amino acids (typically >60%) and comprise no cysteine residues.

In one preferred embodiment, the sequence of the additional amino acid(s) is identical to or homogolous to the sequence of the amino acid(s) which separates the epitope sequences in the native sequence of the protein from which the epitopes derive. If the additional amino acid(s) are homolgous to the native sequence, homology of greater than 55%, 60%, 75%, 80%, 85%, 90% or 95% with the native sequence is preferred. In an alternative embodiment, the sequence of the additional amino acid(s) is not related to the sequence of the amino acid(s) which separates the epitope sequences in the native sequence of the protein from which the epitopes derive. That is, the region may comprise a fusion protein comprising a first epitope, a sequence of additional amino acids, and at least a second epitope.

Alternatively the multiple epitopes may be present in the region as a combination of overlapping or independent epitope sequences.

It will be appreciated that the region may therefore consist entirely of amino acids which are comprised in at least one epitope. Typically, the proportion of amino acids in a region which are comprised in at least one epitope is approximately 70%, 71%, 72%, 73%, 74%, 75%, 80%, 85%, 90% or 95%, or 99%. Preferably, at least 70% of the amino acids in a region are comprised in at least one epitope.

The region therefore typically has a length of approximately 18 amino acids, but may be 10, 11, 12, 13, 14, 15, 16, 17, 18, 19, 20, 21, 22, 23, 24 or 25 amino acids in length.

Peptides

The peptides of the invention may consist entirely of the region as defined above. However, the peptides may optionally comprise additional amino acids flanking the N or C termini of the region. These amino acids are not comprised in an epitope. Typically, the proportion of amino acids in a peptide which are comprised in at least one epitope is approximately 70%, 71%, 72%, 73%, 74%, 75%, 80%, 85%, 90% or 95%, or 99%. Preferably, at least 70% of the amino acids in a peptide are comprised in at least one epitope.

The residues flanking the region typically result in the peptide having a solubility greater than 3.5 mg/ml in aqueous solution at pH 2.0 to 12.0, or pH 2.0 to 11.0, pH 2.0 to 10.0, pH 2.0 to 9.0, pH 2.0 to 8.0 or pH 2.0 to 7.0. The residues flanking the region are preferably:

at the N terminus, at least one, two, three, four, five or six contiguous amino acids corresponding to the at least one, two, three, four, five or six contiguous amino acids immediately N terminal to the region in the natural sequence of the protein from which the region derives; or at the C terminus, at least one, two, three, four, five or six contiguous amino acids corresponding to the at least one, two, three, four, five or six contiguous amino acids immediately C terminal to the epitope sequence in the natural sequence of the protein from which the region derives; or at both the N and C termini, at least one, preferably two, or three amino acids selected from arginine, lysine, histidine, glutamate and aspartate.

Further, the peptide may comprise the region as defined above, but incorporating modification of its native sequence. Particularly preferred modifications regions wherein:

any cysteine residues in the native sequence of the region are replaced with serine; and/or any hydrophobic residues in the up to one, two, preferably three or four amino acids at the N or C terminus of the native sequence of the region which are not comprised in the epitope are deleted; and/or any two consecutive amino acids comprising the sequence Asp-Gly in the up to three or preferably four amino acids at the N or C terminus of the native sequence of the region which are not comprised in the epitope are deleted.

The peptides of the invention typically contain from 10 to 25 amino acids, and may contain 11, 12, 13, 14, 15, 16, 17, 18, 19, 20, 21, 22, 23 or 24 amino acids. Peptides longer than 25 amino acids are likely to possess sufficient tertiary structure to cross-link IgG or IgE on cell surfaces resulting in undesirable immune responses such as B cell activation or mast cell degranulation. Peptides shorter than 10 amino acids are unlikely to contain more than one epitope.

Peptide Synthesis

The peptides of the invention are derived in an intellectual sense from the polypeptide which comprises the epitopes and regions as defined above with additional flanking residues or residues to separate independent epitope sequences. This is done by making use of the amino acid sequence of the region or epitope and synthesising peptides based on the sequence. Peptides may be synthesised using methods well known in the art. Preferred methods include solid-phase peptide synthesis techniques and most preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropyl-ethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, and include t-butyloxycarbonyl (tBoc) and fluorenylmethoxycarbonyl (Fmoc).

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—$NH_2$→—NH(Me) or —N(Me)$_2$).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

Polynucleotides, Vectors and Cells

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the peptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a peptide of the invention.

The present invention thus includes expression vectors that comprise such polynucleotide sequences. Thus, the present invention provides a vector for use in preventing or treating allergy by tolerisation comprising four or more polynucleotide sequences which encode different polypeptides of the invention and optionally one or more further polynucleotide sequences which encode different polypeptides as defined herein. The vector may comprise 4, 5, 6 or 7 polynucleotide sequences which encode different polypeptides of the invention.

Furthermore, it will be appreciated that the compositions and products of the invention may comprise a mixture of polypeptides and polynucleotides. Accordingly, the invention provides a composition or product as defined herein, wherein in place of any one of the polypeptide is a polynucleotide capable of expressing said polypeptide.

Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

Alternatively, polynucleotides of the invention may be expressed in a suitable manner to allow presentation of a peptide of the invention by an MHC class II molecule at the surface of an antigen presenting cell. For example, a polynucleotide, expression cassette or vector of the invention may be targeted to antigen presenting cells, or the expression of encoded peptide may be preferentially stimulated or induced in such cells.

In some embodiments, the polynucleotide, expression cassette or vector will encode an adjuvant, or an adjuvant will otherwise be provided. As used herein, the term "adjuvant" refers to any material or composition capable of specifically or non-specifically altering, enhancing, directing, redirecting, potentiating or initiating an antigen-specific immune response.

Polynucleotides of interest may be used in vitro, ex vivo or in vivo in the production of a peptide of the invention. Such polynucleotides may be administered or used in the prevention or treatment of allergy by tolerisation.

Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

The polypeptides, polynucleotides, vectors or cells of the invention may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins, polynucleotides, cells or dry mass of the preparation.

Formulations and Compositions

The peptides, polynucleotides, vectors and cells of the invention may be provided to an individual either singly or in combination. Each molecule or cell of the invention may be provided to an individual in an isolated, substantially isolated, purified or substantially purified form. For example, a peptide of the invention may be provided to an individual substantially free from the other peptides.

Whilst it may be possible for the peptides, polynucleotides or compositions according to the invention to be presented in raw form, it is preferable to present them as a pharmaceutical formulation. Thus, according to a further aspect of the invention, the present invention provides a pharmaceutical formulation for tolerising an individual to a protein from which a peptide of the invention derives, comprising a composition, vector or product according to the invention together with one or more pharmaceutically acceptable carriers or diluents and optionally one or more other therapeutic ingredients. The carrier(s) must be 'acceptable' in the sense of being compatible with the other ingredients of the formulation and not deleterious to the recipient thereof. Typically, carriers for injection, and the final formulation, are sterile and pyrogen free. The high solubility of the peptide of the invention results in there being little or no requirement for the organic solvents usual in pharmaceutical compositions. Accordingly, the present invention provides a pharmaceutical formulation as defined above comprising less than 5% organic solvent. Subject to this limitation, formulation of a composition comprising the peptide, polynucleotide or cell of the invention can be carried out using standard pharmaceutical formulation chemistries and methodologies all of which are readily available to the reasonably skilled artisan.

For example, compositions containing one or more molecules or cells of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e. g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the peptides or polynucleotides of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of any of the peptides, polynucleotides or cells mentioned herein will depend upon factors such as the nature of the substance and the method of delivery. Any such substance may be administered in a variety of dosage forms.

It may be administered orally (e.g. as tablets, troches, lozenges, aqueous or oily suspensions, dispersible powders or granules), parenterally, subcutaneously, by inhalation, intravenously, intramuscularly, intrasternally, transdermally, intradermally, epicutaneously, sublingually, intranasally, buccally or by infusion techniques. The substance may also be administered as suppositories. A physician will be able to determine the required route of administration for each particular individual.

The compositions of formulations of the invention will comprise a suitable concentration of each peptide/polynucleotide/cell to be effective without causing adverse reaction. Typically, the concentration of each peptide in the composition will be in the range of 0.03 to 200 nmol/ml. More preferably in the range of 0.3 to 200 nmol/ml, 3 to 180 nmol/ml, 10 to 150 nmol/ml or 30 to 120 nmol/ml. Such concentrations are particularly favoured for intradermal administration since an effective dose may be administered in a volume of 60 µl, preferably 50 µl, and most preferably 30 µl. The composition or formulations should have a purity of greater than 95% or 98% or a purity of at least 99%.

A composition may therefore be formulated which comprises a molecule and/or cell of the invention and also one or more other therapeutic molecules. A composition of the invention may alternatively be used simultaneously, sequentially or separately with one or more other therapeutic compositions as part of a combined treatment.

Therapeutic Methods and Individual to be Treated

The present invention relates to peptides, polynucleotides, vectors and cells that are capable of desensitising or tolerising human individuals to proteins from which the peptides of the invention derive. Such proteins are typically allergens or other antigens to which an immune response is undesirable. Examples of such antigens include antigens associated with autoimmune diseases, antigens associated with graft-versus-host disease or transplant rejection (herein referred to as alloimmune conditions) and antigens associated with maternal-foetal immune responses, for example Rhesus D Haemolytic Disease of the Newborn. The peptides of the invention are therefore useful in the prevention or treatment an allergic disease, an autoimmune disease, an alloimmune condition or a maternal-foetal immune response. The invention provides compositions, products, vectors and formulations for use in preventing or treating the above conditions. The invention also provides a method of in preventing or treating a subject having the above conditions, comprising administering, either singly or in combination the polypeptides/polynucleotides/cells of the invention as described above.

The individual to be treated or provided with the composition or formulation of the invention is preferably human. It will be appreciated that the individual to be treated may be known to be sensitised to the particular allergen or antigen, at risk of being sensitised or suspected of being sensitised. The individual can be tested for sensitisation using techniques well known in the art and as described herein. Alternatively, the individual may have a family history of the conditions described above. It may not be necessary to test an individual for sensitisation to allergens because the individual may display symptoms of allergy when brought into proximity to a suitable allergen source. By proximity is meant 10 meters or less, 5 meters or less, 2 meters or less, 1 meter or less, or 0 meters from the source. Symptoms of allergy can include itchy eyes, runny nose, breathing difficulties, red itchy skin or rash. The individual to be treated may be of any age. However, preferably, the individual may be in the age group of 1 to 90, 5 to 60, 10 to 40, or more preferably 18 to 35. Preferably, the individual to be treated is from a population that has MHC allele frequencies within the range of frequencies that are representative of the Caucasian population. Reference population allele frequencies for 11 common DRB1 allele families are shown in Table 1 (Data from HLA Facts Book, Parham and Barber).

TABLE 1

| DRB1 | 1 | 3 | 4 | 7 | 8 | 11 | 12 | 13 | 14 | 15 | 16 |
|---|---|---|---|---|---|---|---|---|---|---|---|
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MHC allele frequencies as the reference population for the alleles referred to Table 1 (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:
4—at least 9%
7—at least 10%
11—at least 8%.

The individual to be treated for allergic disease may have had allergy for at least 2 weeks, 1 month, 6 months, 1 year or 5 years. The individual may suffer from a rash, nasal congestion, nasal discharge and/or coughing caused by the allergy. The individual may or may not have been administered with other compositions/compounds which treat allergy.

Allergens and Antigens

Suitable allergens from which the region containing a MHC Class II-binding T cell epitope may derive can of course be obtained and/or produced using known methods. Classes of suitable allergens include, but are not limited to, pollens, animal dander (in particular cat dander), grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; epidermal allergens can be obtained from house or organic dusts (typically fungal in origin), from arthropods such as house mites (*Dermatophagoides pteronyssinus*), or from animal sources such as feathers, and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major allergen produced by the domestic cat *Felis catus* (*Felis domesticus*) glycoprotein Fel d1, the major and cryptic epitopes of the Der p I allergen (Hoyne et al. (1994) *Immunology* 83190-195), bee venom phospholipase A2 (PLA) (Akdis et al. (1996) *J. Clin. Invest.* 98:1676-1683), birch pollen allergen Bet v 1 (Bauer et al. (1997) *Clin. Exp. Immunol.* 107:536-541), and the multi-epitopic recombinant grass allergen rKBG8.3 (Cao et al. (1997) *Immunology* 90:46-51). These and other suitable allergens are commercially available and/or can be readily prepared as extracts following known techniques.

Preferably, the allergen is selected from the list of allergen sequences and database accession numbers (NCBI Entrez accession numbers) below. NCBI is the National Center for Biotechnology information and is a division of the US National Institutes of Health. Allergen sequences and database accession numbers (NCBI Entrez accession numbers):
House Dust Mite
*Dermatophagoides pteronyssinus*

Der p 1
MKIVLAIASLLALSAVYARPSSIKTFEEYKKAFNKSYATFEDEEAARKNF

LESVKYVQSNGGAINHLSDLSLDEFKNRFLMSAEAFEHLKTQFDLNAETN

ACSINGNAPAEIDLRQMRTVTPIRMQGGCGSCWAFSGVAATESAYLAYRN

QSLDLAEQELVDCASQHGCHGDTIPRGIEYIQHNGVVQESYYRYVAREQS

CRRPNAQRFGISNYCQIYPPNVNKIREALAQTHSAIAVIIGIKDLDAFRH

YDGRTIIQRDNGYQPNYHAVNIVGYSNAQGVDYWIVRNSWDTNWGDNGYG

YFAANIDLMMIEEYPYVVIL (SEQ ID NO: 316)

Der p 2
MMYKILCLSLLVAAVARDQVDVKDCANHEIKKVLVPGCHGSEPCIIHRGK

PFQLEAVFEANQNTKTAKIEIKASIDGLEVDVPGIDPNACHYMKCPLVKG

QQYDIKYTWNVPKIAPKSENVVVTVKVMGDDGVLACAIATHAKIRD
(SEQ ID NO: 317)

Der p 3
MIIYNILIVLLLAINTLANPILPASPNATIVGGEKALAGECPYQISLQSS

SHFCGGTILDEYWILTAAHCVAGQTASKLSIRYNSLKHSLGGEKISVAKI

FAHEKYDSYQIDNDIALIKLKSPMKLNQKNAKAVGLPAKGSDVKVGDQVR

VSGWGYLEEGSYSLPSELRRVDIAVVSRKECNELYSKANAEVTDNMICGG

DVANGGKDSCQGDSGGPVVDVKNNQVVGIVSWGYGCARKGYPGVYTRVGN

FIDWIESKRSQ (SEQ ID NO: 318)

Der p 4
KYXNPHFIGXRSVITXLME (SEQ ID NO: 319)

Der p 5
MKFIIAFFVATLAVMTVSGEDKKHDYQNEFDFLLMERIHEQIKKGELALF

YLQEQINHFEEKPTKEMKDKIVAEMDTIIAMIDGVRGVLDRLMQRKDLDI

FEQYNLEMAKKSGDILERDLKKEEARVKKIEV (SEQ ID NO: 320)

Der p 6
AIGXQPAAEAEAPFQISLMK (SEQ ID NO: 321)

Der p 7
MMKLLLIAAAAFVAVSADPIHYDKITEEINKAVDEAVAAIEKSETFDPMK

VPDHSDKFERHIGIIDLKGELDMRNIQVRGLKQMKRVGDANVKSEDGVVK

AHLLVGVHDDVVSMEYDLAYKLGDLHPNTHVISDIQDFVVELSLEVSEEG

NMTLTSFEVRQFANVVNHIGGLSILDPIFAVLSDVLTAIFQDTVRAEMTK

VLAPAFKKELERNNQ (SEQ ID NO: 322)

Der p9
IVGGSNASPGDAVYQIAL (SEQ ID NO: 323)

*Dermatophagoides farinae*

Der f 1
MKFVLAIASLLVLTVYARPASIKTFEFKKAFNKNYATVEEEEVARKNFLE

SLKYVEANKGAINHLSDLSLDEFKNRYLMSAEAFEQLKTQFDLNAETSAC

RINSVNVPSELDLRSLRTVTPIRMQGGCGSCWAFSGVAATESAYLAYRNT

SLDLSEQELVDCASQHGCHGDTIPRGIEYIQQNGVVEERSYPYVAREQRC

RRPNSQHYGISNYCQIYPPDVKQIREALTQTHTAIAVIIGIKDLRAFQHY

DGRTIIQHDNGYQPNYHAVNIVGYGSTQGDDYWIVRNSWDTTWGDSGYGY

FQAGNNLMMIEQYPYVVIM (SEQ ID NO: 324)

Der f 2
MISKILCLSLLVAAVVADQVDVKDCANNEIKKVMVDGCHGSDPCIIHRGK

PFTLEALFDANQNTKTAKIEIKASLDGLEIDVPGIDTNACHFMKCPLVKG

QQYDIKYTWNVPKIAPKSENVVVTVKLIGDNGVLACAIATHGKIRD
(SEQ ID NO: 325)

Der f 3
MMILTIVVLLAANILATPILPSSPNATIVGGVKAQAGDCPYQISLQSSSH

FCGGSILDEYWILTAAHCVNGQSAKKLSIRYNTLKHASGGEKIQVAEIYQ

HENYDSMTIDNDVALIKLKTPMTLDQTNAKPVPLPAQGSDVKVGDKIRVS

GWGYLQEGSYSLPSELQRVDIDVVSREQCDQLYSKAGADVSENMICGGDV

ANGGVDSCQGDSGGPVVDVATKQIVGIVSWGYGCARKGYPGVYTRVGNFV

DWIESKRSQ (SEQ ID NO: 326)

Der f 4
AVGGQDADLAEAPFQISLLK (SEQ ID NO: 327)

Der f 7
MMKFLLIAAVAFVAVSADPIHYDKITEEINKAIDDAIAAIEQSETIDPMK

VPDHADKFERHVGIVDFKGELAMRNIEARGLKQMKRQGDANVKGEEGIVK

AHLLIGVHDDIVSMEYDLAYKLGDLHPTTHVISDIQDFVVALSLEISDEG

NITMTSFEVRQFANVVNHIGGLSILDPIFGVLSDVLTAIFQDTVRKEMTK

VLAPAFKRELEKN (SEQ ID NO: 328)

Additional mite allergen sequences (NCBI entrez accession): 1170095; 1359436; 2440053; 666007; 487661; 1545803; 84702; 84699; 625532; 404370; 1091577; 1460058; 7413; 9072; 387592.
Cat
*Felis* Sequences (NCBI Entrez Accession):
539716; 539715; 423193; 423192; 423191; 423190; 1364213; 1364212; 395407; 163827; 163823; 163825; 1169665; 232086; 1169666.

Latex

*Hevea* Sequences:

Hev b 1
MAEDEDNQQGQGEGLKYLGFVQDAATYAVTTFSNVYLFAKDKSGPLQPGV
DIIEGPVKNVAVPLYNRFSYIPNGALKFVDSTVVASVTIIDRSLPPIVKD
ASIQVVSAIRAAPEAARSLASSLPGQTKILAKVFYGEN (SEQ ID NO: 329)

Hev b 3
MAEEVEEERLKYLDFVRAAGVYAVDSFSTLYLYAKDISGPLKPGVDTIEN
VVKTVVTPVYYIPLEAVKFVDKTVDVSVTSLDGVVPPVIKQVSAQTYSVA
QDAPRIVLDVASSVFNTGVQEGAKALYANLEPKAEQYAVITWRALNKLPL
VPQVANVVVPTAVYFSEKYNDVVRGTTEQGYRVSSYLPLLPTEKITKVFG
DEAS (SEQ ID NO: 330)

Additional *Hevea* Sequences (NCBI Entrez Accession):
3319923; 3319921; 3087805; 1493836; 1480457; 1223884; 3452147; 3451147; 1916805; 232267; 123335; 2501578; 3319662; 3288200; 1942537; 2392631; 2392630; 1421554; 1311006; 494093; 3183706; 3172534; 283243; 1170248; 1708278; 1706547; 464775; 266892; 231586; 123337; 116359; 123062; 2213877; 542013; 2144920; 1070656; 2129914; 2129913; 2129912; 100135; 82026; 1076559; 82028; 82027; 282933; 280399; 100138; 1086972; 108697; 1086976; 1086978; 1086978; 1086976; 1086974; 1086972; 913758; 913757; 913756; 234388; 1092500; 228691; 1177405; 18839; 18837; 18835; 18833; 18831; 1209317; 1184668; 168217; 168215; 168213; 168211; 168209; 348137.

Rye Grass

*Lolium* Sequences:

126385 Lol p 1
MASSSSVLLVVALFAVFLGSAHGIAKVPPGPNITAEYGDKWLDAKSTWYG
KPTGAGPKDNGGACGYKNVDKAPFNGMTGCGNTPIFKDGRGCGSCFEIKC
TKPESCSGEAVTVTITDDNEEPIAPYHFDLSGHAFGSMAKKGEEQNVRSA
GELELQFRRVKCKYPDDTKPTFHVEKASNPNYLAILVKYVDGDGDVVAVD
IKEKGKDKWIELKESWGAVWRIDTPDKLTGPFTVRYTTEGGTKSEFEDVI
PEGWKADTSYSAK (SEQ ID NO: 331)

126386 Lol p 2a
AAPVEFTVEKGSDEKNLALSIKYNKEGDSMAEVELKEHGSNEWLALKKNG
DGVWEIKSDKPLKGPFNFRFVSEKGMRNVFDDVVPADFKVGTTYKPE
(SEQ ID NO: 332)

126387 Lol p 3
TKVDLTVEKGSDAKTLVLNIKYTRPGDTLAEVELRQHGSEEWEPMTKKGN
LWEVKSAKPLTGPMNFRFLSKGGMKNVFDEVIPTAFTVGKTYTPEYN
(SEQ ID NO: 333)

2498581 Lol p 5a
MAVQKYTVALFLRRGPRGGPGRSYAADAGYTPAAAATPATPAATPAGGWR
EGDDRRAEAAGGRQRLASRQPWPPLPTPLRRTSSRSSRPPSPSPPRASSP
TSAAKAPGLIPKLDTAYDVAYKAAEAHPRGQVRRLRHCPHRSLRVIAGAL
EVHAVKPATEEVLAAKIPTGELQIVDKIDAAFKIAATAANAAPTNDKFTV
FESAFNKALNECTGGAMRPTSSSPPSRPRSSRPTPPPSPAAPEVKYAVFE
AALTKAITAMTQAQKAGKPAAAAATAAATVATAAATAAAVLPPPLLVVQS
LISLLIYY (SEQ ID NO: 334)

2498582 Lol p 5b
MAVQKHTVALFLAVALVAGPAASYAADAGYAPATPATPAAPATAATPATP
ATPATPAAVPSGKATTEEQKLIEKINAGFKAAVAAAAVVPPADKYKTFVE
TFGTATNKAFVEGLASGYADQSKNQLTSKLDAALKLAYEAAQGATPEAKY
DAYVATLTEALRVIAGTLEVHAVKPAAEEVKVGAIPAAEVQLIDKVDAAY
RTAATAANAAPANDKFTVFENTFNNAIKVSLGAAYDSYKFIPTLVAAVKQ
AYAAKQATAPEVKYTVSETALKKAVTAMSEAEKEATPAAAATATPTPAAA
TATATPAAAYATATPAAATATATPAAATATPAAAGGYKV (SEQ ID NO: 335)

455288 Lol p isoform 9
MAVQKHTVALFLAVALVAGPAASYAADAGYAPATPATPAAPATAATPATP
ATPATPAAVPSGKATTEEQKLIEKINAGFKAAVAAAAVVPPADKYKTFVE
TFGTATNKAFVEGLASGYADQSKNQLTSKLDAALKLAYEAAQGATPEAKY
DAYVATLTEALRVIAGTLEVHAVKPAAEEVKVGAIPAAEVQLIDKVDAAY
RTAATAANAAPANDKFTVFENTFNNAIKVSLGAAYDSYKFIPTLVAAVKQ
AYAAKQATAPEVKYTVSETALKKAVTAMSEAEKEATPAAAATATPTPAAA
TATATPAAAYATATPAAATATATPAAATATPAAAGGYKV (SEQ ID NO: 336)

1582249 Lol p 11
DKGPGFVVTGRVYCDPCRAGFETNVSHNVEGATVAVDCRPFDGGESKLKA
EATTDKDGWYKIEIDQDHQEEICEVVLAKSPDKSCSEIEEFRDRARVPLT
SNXGIKQQGIRYANPIAFFRKEPLKECGGILQAY (SEQ ID NO: 337)

Additional *Lolium* Sequences (NCBI Entrez Accession):
135480; 417103; 687261; 687259; 1771355; 2388662; 631955; 542131; 542130; 542129; 100636; 626029; 542132; 320616; 320615; 320614; 100638; 100634; 82450; 626028; 100639; 283345; 542133; 1771353; 1763163; 1040877; 1040875; 250525; 551047; 515377; 510911; 939932; 439950; 2718; 168316; 168314; 485371; 2388664; 2832717; 2828273; 548867.

Olive Tree

Olive Sequences

416610 Ole e 1
EDIPQPPVSQFHIQGQVYCDTCRAGFITELSEFIPGASLRLQCKDKENGD
VTFTEVGYTRAEGLYSMLVERDHKNEFCEITLISSGRKDCNEIPTEGWAK
PSLKFKLNTVNGTTRTVNPLGFFKKEALPKCAQVYNKLGMYPPNM
(SEQ ID NO: 338)

*Parietaria*

*Parietaria* Sequences:

2497750 Par j P2
MRTVSMAALVVIAAALAWTSSAEPAPAPAPGEEACGKVVQDIMPCLHFVK
GEEKEPSKECCSGTKKLSEEVKTTEQKREACKCIVRATKGISGKINELVA
EVPKKCDIKTTLPPITADFDCSKIQSTIFRGYY (SEQ ID NO: 339)

1352506 Par j P5
MVRALMPCLPFVQGKEKEPSKGCCSGAKRLDGETKTGPQRVHACECIQTA
MKTYSDIDGKLVSEVPKHCGIVDSKLPPIDVNMDCKTVGVVPRQPQLPVS
LRHGPVTGPSDPAHKARLERPQIRVPPPAPEKA (SEQ ID NO: 340)

1532056 Par j P8
MRTVSMAALVVIAAALAWTSSAELASAPAPGEGPCGKVVHHIMPCLKFVK

GEEKEPSKSCCSGTKKLSEEVKTTEQKREACKCIVAATKGISGIKNELVA

EVPKKCGITTTLPPITADFDCSKIESTIFRGYY (SEQ ID NO: 341)

1532058 Par j P9
MRTVSAPSAVALVVIVAAGLAWTSLASVAPPAPAPGSEETCGTVVRALMP

CLPFVQGKEKEPSKGCCSGAKRLDGETKTGLQRVHACECIQTAMKTYSDI

DGKLVSEVPKHCGIVDSKLPPIDVNMDCKTLGVVPRQPQLPVSLRHGPVT

GPSDPAHKARLERPQIRVPPPAPEKA (SEQ ID NO: 342)

2497749 Par j P9
MRTVSARSSVALVVIVAAVLVWTSSASVAPAPAPGSEETCGTVVGALMPC

LPFVQGKEKEPSKGCCSGAKRLDGETKTGPQRVHACECIQTAMKTYSDID

GKLVSEVPKHCGIVDSKLPPIDVNMDCKTLGVLHYKGN (SEQ ID NO: 343)

1086003 Par j 1
MVRALMPCLPFVQGKEKEPSKGCCSGAKRLDGETKTGPQRVHACECIQTA

MKTYSDIDGKLVSEVPKHCGIVDSKLPPIDVNMDCKTVGVVPRQPQLPVS

LRHGPVTGPSRSRPPTKHGWRDPRLEFRPPHRKKPNPAFSTLG (SEQ ID NO: 344)

Additional *Parietaria* Sequences (NCBI Entrez Accession): 543659; 1836011; 1836010; 1311513; 1311512; 1311511; 1311510; 1311509; 240971.

Timothy Grass

*Phleum* Sequences:

Phl p 1
MASSSSVLLVVVLFAVFLGSAYGIPKVPPGPNITATYGDKWLDAKSTWYG

KPTGAGPKDNGGACGYKDVDKPPFSGMTGCGNTPIFKSGRGCGSCFEIKC

TKPEACSGEPVVVHITDDNEEPIAPYHFDLSGHAFGAMAKKGDEQKLRSA

GELELQFRRVKCKYPEGTKVTFHVEKGSNPNYLALLVKYVNGDGDVVAVD

IKEKGKDKWIELKESWGAIWRIDTPDKLTGPFTVRYTTEGGTKTEAEDVI

PEGWKADTSYESK (SEQ ID NO: 345)

Phl p 1
MASSSSVLLVVALFAVFLGSAHGIPKVPPGPNITATYGDKWLDAKSTWYG

KPTAAGPKDNGGACGYKDVDKPPFSGMTGCGNTPIFKSGRGCGSCFEIEK

CTKPACSGEPVVVHITDDNEEPIAAYHFDLSGIAFGSMAKKGDEQKLQFR

RSAGEVEIRVKCKYPEGTKVTFHVEKGSNPNYLALLVKFSGDGDVVKWIA

VDIKEKGKDALKESWGAIWRIDTPEVLKGPFTVRYTTEGGTKARAKDVIP

EGWKADTAYESK (SEQ ID NO: 346)

Phlp 2
MSMASSSSSSLLAMAVLAALFAGAWCVPKVTFTVEKGSNEKHLAVLVKYE

GDTMAEVELREHGSDEWVAMTKGEGGVWTFDSEEPLQGPFNFRFLTEKGM

KNVFDDVVPEKYTIGATYAPEE (SEQ ID NO: 347)

Phl p 5
ADLGYGGPATPAAPAEAAPAGKATTEEQKLIEKINDGFKAALAAAAGVPP

ADKYKTFVATFGAASNKAFAEGLSAEPKGAAESSSKAALTSKLDAAYKLA

YKTAEGATPEAKYDAYVATLSEALRIIAGTLEVHAVKPAAEEVKVIPAGE

LQVIEKVDSAFKVAATAANAAPANDKFTVFEAAFNNAIKASTGGAYESYK

FIPALEAAVKQAYAATVATAPEVKYTVFETALKKAFTAMSEAQKAAKPAT

EATATATAAVGAATGAATAATGGYKV (SEQ ID NO: 348)

Phl p 5
ADLGYGGPATPAAPAEAAPAGKATTEEQKLIEKINDGFKAALAAAAGVPP

ADKYKTFVATFGAASNKAFAEGLSAEPKGAAESSSKAALTSKLDAAYKLA

YKTAEGATPEAKYDAYVATLSEALRIIAGTLEVHAVKPAAEEVKVIPAGE

KLQVIEVDSAFKVAATAANAAPANDKFTVFEAAFNNAIKASTGGAYESYK

FIPALEAAVKQAYAATVATAPEVKYTVFETALKKAITAMSEAQKAAKPAT

EATATATAAVGAATGAATAATGGYKV (SEQ ID NO: 349)

Phl p 5b
AAAAVPRRGPRGGPGRSYTADAGYAPATPAAAGAAAGKATTEEQKLIEDI

NVGFKAAVAAAASVPAADKFKTFEAAFTSSSKAAAAKAPGLVPKLDAAYS

VAYKAAVGATPEAKFDSFVASLTEALRVIAGALEVHAVKPVTEEPGMAKI

PAGELQIIDKIDAAFKVAATAAATAPADDKFTVFEAAFNKAIKESTGGAY

DTYKCIPSLEAAVKQAYAATVAAAPQVKYAVFEAALTKAITAMSEVQKVS

QPATGAATVAAGAATTAAGAASGAATVAAGGYKV (SEQ ID NO: 350)

Phl p 5a
ADLGYGPATPAAPAAGYTPATPAAPAGADAAGKATTEEQKLIEKINAGFK

AALAGAGVQPADKYRTFVATFGPASNKAFAEGLSGEPKGAAESSSKAALT

SKLDAAYKLAYKTAEGATPEAKYDAYVATLSEALRIIAGTLEVHAVKPAA

EEVKVIPAGELQVIEKVDAAFKVAATAANAAPANDKFTVFEAAFNDEIKA

STGGAYESYKFIPALEAAVKQAYAATVATAPEVKYTVFETALKKAITAMS

EAQKAAKPAAAATATATAAVGAATGAATAATGGYKV (SEQ ID NO: 351)

Phl p 5
MAVQKYTVALFLAVALVAGPAASYAADAGYAPATPAAAGAEAGKATTEEQ

KLIEDINVGFKAAVAAAASVPAADKFKTFEAAFTSSSKAATAKAPGLVPK

LDAAYSVSYKAAVGATPEAKFDSFVASLTEALRVIAGALEVHAVKPVTEE

MPGAKIPAGELQIIDKIDAAFKVAATAAATAPADTVFEAAFNKAIKESTG

GAYDTYKCIPSLEAAVKQAYAATVAAAPQVKYAVFEAALTKAITAMSEVQ

KVSQPATGAATVAAGAATTAAGAASGAATVAAGGYKV (SEQ ID NO: 352)

Phl p 5
MAVQKYTVALFLAVALVAGPAASYAADAGYAPATPAAAGAEAGKATTEEQ

KLIEDINVGFKAAVAAAASVPAADKFKTFEAAFTSSSKAATAKAPGLVPK

LDAAYSVAYKAAVGATPEAKFDSFVASLTEALRVIAGALEVHAVKPVTED

PAWPKIPAGELQIIDKIDAAFKVAATAAATAPADDKFTVFEAAFNKAIKE

STGGAYDTYKCIPSLEAAVKQAYAATVAAAPQVKYAVFEAALTKAITAMS

EVQKVSQPATGAATVAAGAATTATGAASGAATVAAGGYKV (SEQ ID NO: 353)

Phl p 5
ADAGYAPATPAAAGAEAGKATTEEQKLIEDINVGFKAAVAAAASVPAADK

FKTFEAAFTSSSKAATAKAPGLVPKLDAAYSVAYKAAVGATPEAKFDSFV

ASLTEALRVIAGALEVHAVKPVTEEPGMAKIPAGELQIIDKIDAAFKVAA

-continued

TAAATAPADDKFTVFEAAFNKAIKESTGGAYDTYKCIPSLEAAVKQAYAA

TVAAAPQVKYAVFEAALTKAITAMSEVQKVSQPATGAATVAAGAATTAAG

AASGAATVAAGGYKV (SEQ ID NO: 354)

Phl p 5
SVKRSNGSAEVHRGAVPRRGPRGGPGRSYAADAGYAPATPAAAGAEAGKA

TTEEQKLIEDINVGFKAAVAAAASVPAADKFKTFEAAFTSSSKAATAKAP

GLVPKLDAAYSVAYKAAVGATPEAKFDSFVASLTEALRVIAGALEVHAVK

EPVTEPGMAKIPAGELQIIDKIDAAFKVAATAAATAPADDKFTVFEAAFN

KAIKESTGGAYDTYKCIPSLEAAVKQAYAATVAAAPQVKYAVFEAALTKA

ITAMSEVQKVSQPATGAATVAAGAATTAAGAASGAATVAAGGYKV
(SEQ ID NO: 355)

Phl p 5
MAVHQYTVALFLAVALVAGPAGSYAADLGYGPATPAAPAAGYTPATPAAP

AGAEPAGKATTEEQKLIEKINAGFKAALAAAAGVPPADKYRTFVATFGAA

SNKAFAEGLSGEPKGAAESSSKAALTSKLDAAYKLAYKTAEGATPEAKYD

AYVATVSEALRIIAGTLEVHAVKPAAEEVKVIPAGELQVIEKVDAAFKVA

ATAANAAPANDKFTVFEAAFNDAIKASTGGAYESYKFIPALEAAVKQAYA

ATVATATAPEVKYTVFETALKKAITAMSEAQKAAKPAAAATATATAAVGAAT

GAATAATGGYKV (SEQ ID NO: 356)

Phl p 5
ADLGYGGPATPAAPAEAAPAGKATTEEQKLIEKINDGFKAALAAAAGVPP

ADKYKTFVATFGAASNKAFAEGLSAEPKGAAESSSKAALTSKLDAAYKLA

YKTAEGATPEAKYDAYVATLSEALRIIAGTLEVHAVKPAAEEVKVIPAGE

LQVIEKVDSAFKVAATAANAAPANDKFTVFEAAFNNAIKASTGGAYESYK

FIPALEAAVKQAYAATVATAPEVKYTVFETALKKAFTAMSEAQKAAKPAT

TEATATAAAVGAATGAATAATGGYKV (SEQ ID NO: 357)

Phl p 5b
AAAAVPRRGPRGGPGRSYTADAGYAPATPAAAGAAAGKATTEEQKLIEDI

NVGFKAAVAAAASVPAADKFKTFEAAFTSSSKAAAAKAPGLVPKLDAAYS

VAYKAAVGATPEAKFDSFVASLTEALRVIAGALEVHAVKPVTEEPGMAKI

PAGELQIIDKIDAAFKVAATAAATAPADDKFTVFEAAFNKAIKESTGGAY

DTYKCIPSLEAAVKQAYAATVAAAPQVKYAVFEAALTKAITAMSEVQKVS

QPATGAATVAAGAATTAAGAASGAATVAAGGYKV (SEQ ID NO:
358)

Phl p 5a
ADLGYGPATPAAPAAGYTPATPAAPAGADAAGKATTEEQKLIEKINAGFK

AALAGAGVQPADKYRTFVATFGPASNKAFAEGLSGEPKGAAESSSKAALT

SKLDAAYKLAYKTAEGATPEAKYDAYVATLSEALRIIAGTLEVHAVKPAA

EEVKVIPAGELQVIEKVDAAFKVAATAANAAPANDKFTVFEAAFNDEIKA

STGGAYESYKFIPALEAAVKQAYAATVATAPEVKYTVFETALKKAITAMS

EAQKAAKPAAAATATATAAVGAATGAATAATGGYKV (SEQ ID NO:
359)

Phl p 5
AVPRRGPRGGPGRSYAADAGYAPATPAAAGAEAGKATTEEQKLIEDINVG

FKAAVAAAASVPAGDKFKTFEAAFTSSSKAATAKAPGLVPKLDAAYSVAY

KAAVGATPEAKFDSFVASLTEALRVIAGALEVHAVKPVTEEPGMAKIPAG

ELQIIDKIDAAFKVAATAAATAPADDKFTVFEAAFNKAIKESTGGAYDTY

EKCIPSLAAVKQAYAATVAAAPQVKYAVFEAALTKAITAMSEVQKVSQPA

AATGAATVGAATTATGAASGAATVAAGGYKV (SEQ ID NO: 360)

Phl p 5b
MAVPRRGPRGGPGRSYTADAGYAPATPAAAGAAAGKATTEEQKLIEDINV

GFKAAVAARQRPAADKFKTFEAASPRHPRPLRQGAGLVPKLDAAYSVAYK

AAVGATPEAKFDSFVASLTEALRVIAGALEVHAVKPVTEEPGMAKIPAGE

LQIIDKIDAAFKVAATAAATAPADDKFTVFEAAFNKAIKESTGGAYDTYK

CIPSLEAAVKQAYAATVAAAAEVKYAVFEAALTKAITAMSEVQKVSQPAT

GAATVAAGAATTAAGAASGAATVAAGGYKV (SEQ ID NO: 361)

Phl p 5
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAA

SNKAFAEGLSGEPKGAAESSSKAALTSKLDAAYKLAYKTAEGATPEAKYD

AYVATLSEALRIIAGTLEVHAVKPAAEEVKVIPAGELQVIEKVDAAFKVA

ATAANAAPANDKFTVFEAAFNDAIKASTGGAYESYKFIPALEAAVKQAYA

ATVATAPEVKYTVFETALKKAITAMSEAQKAAKPAAAATATATAAVGAAT

GAATAATGGYKV (SEQ ID NO: 362)

Phl p 5
EAPAGKATTEEQKLIEKINAGFKAALARRLQPADKYRTFVATFGPASNKA

FAEGLSGEPKGAAESSSKAALTSKLDAAYKLAYKTAEGATPEAKYDAYVA

TLSEALRIIAGTLEVHAVKPAAEEVKVIPAAELQVIEKVDAAFKVAATAA

NAAPANDKFTVFEAAFNDEIKASTGGAYESYKFIPALEAAVKQAYAATVA

TAPEVKYTVFETALKKAITAMSEAQKAAKPPPLPPPPQPPPLAATGAATA

ATGGYKV (SEQ ID NO: 363)

Phl p 5
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAA

SNKAFAEGLSGEPKGAAESSSKAALTSKLDAAYKLAYKTAEGATPEAKYD

AYVATLSEALRIIAGTLEVHAVKPAAEEVKVIPAGELQVIEKVDAAFKVA

ATAANAAPANDKFTVFEAAFNDAIKASTGGAYESYKFIPALEAAVKQAYA

AATVATPEVKYTVFETALKKAITAMSEAQKAAKPAAAATATATAAVGAAT

GAATAATGGYKV (SEQ ID NO: 364)

Phl p 5b
MAVPRRGPRGGPGRSYTADAGYAPATPAAAGAAAGKATTEEQKLIEDINV

GFKAAVAARQRPAADKFKTFEAASPRHPRPLRQGAGLVPKLDAAYSVAYK

AAVGATPEAKFDSFVASLTEALRVIAGALEVHAVKPVTEEPGMAKIPAGE

LQIIDKIDAAFKVAATAAATAPADDKFTVFEAAFNKAIKESTGGAYDTYK

ACIPSLEAVKQAYAATVAAAAEVKYAVFEAALTKAITAMSEVQKVSQPAT

GAATVAAGAATTAAGAASGAATVAAGGYKV (SEQ ID NO: 365)

-continued

Phl p 5a
ADLGYGPATPAAPAAGYTPATPAAPAGADAAGKATTEEQKLIEKINAGFK

AALAGAGVQPADKYRTFVATFGPASNKAFAEGLSGEPKGAAESSSKAALT

SKLDAAYKLAYKTAEGATPEAKYDAYVATLSEALRIIAGTLEVHAVKPAA

EEVKVIPAGELQVIEKVDAAFKVAATAANAAPANDKFTVFEAAFNDEIKA

STGGAYESYKFIPALEAAVKQAYAATVATAPEVKYTVFETALKKAITAMS

AEAQKAKPPPLPPPPQPPPLAATGAATAATGGYKV (SEQ ID NO:
366)

Phl p 5
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAA

SNKAFAEGLSGEPKGAAESSSKAALTSKLDAAYKLAYKTAEGATPEAKYD

AYVATLSEALRIIAGTLEVHAVKPAAEEVKVIPAGELQVIEKVDAAFKVA

ATAANAAPANDKFTVFEAAFNDAIKASTGGAYESYKFIPALEAAVKQAYA

AATVATPEVKYTVFETALKKAITAMSEAQKAAKPAAAATATATAAVGAAT

GAATAATGGYKV (SEQ ID NO: 367)

Phl p 6
MAAHKFMVAMFLAVAVVLGLATSPTAEGGKATTEEQKLIEDVNASFRAAM

ATTANVPPADKYKTFEAAFTVSSKRNLADAVSKAPQLVPKLDEVYNAAYN

AADHAAPEDKYEAFVLHFSEALRIIAGTPEVHAVKPGA (SEQ ID NO:
368)

Phl p 6
SKAPQLVPKLDEVYNAAYNAADHAAPEDKYEAFVLHFSEALHIIAGTPEV

HAVKPGA (SEQ ID NO: 369)

Phl p 6
ADKYKTFEAAFTVSSKRNLADAVSKAPQLVPKLDEVYNAAYNAADHAAPE

DKYEAFVLHFSEALHIIAGTPEVHAVKPGA (SEQ ID NO: 370)

Phl p 6
TEEQKLIEDVNASFRAAMATTANVPPADKYKTLEAAFTVSSKRNLADAVS

KAPQLVPKLDEVYNAAYNAADHAAPEDKYEAFVLHFSEALRIIAGTPEVH

AVKPGA (SEQ ID NO: 371)

Phl p 6
MAAHKFMVAMFLAVAVVLGLATSPTAEGGKATTEEQKLIEDINASFRAAM

ATTANVPPADKYKTFEAAFTVSSKRNLADAVSKAPQLVPKLDEVYNAAYN

AADHAAPEDKYEAFVLHFSEALHIIAGTPEVHAVKPGA (SEQ ID NO:
372)

Phl p 6
MVAMFLAVAVVLGLATSPTAEGGKATTEEQKLIEDVNASFRAAMATTANV

PPADKYKTFEAAFTVSSKRNLADAVSKAPQLVPKLDEVYNAAYNAADHAA

PEDKYEAFVLHFSEALRIIAGTPEVHAVKPGA (SEQ ID NO: 373)

Phl p 7
MADDMERIFKRFDTNGDGKISLSELTDALRTLGSTSADEVQRMMAEIDTD

GDGFIDFNEFISFCNANPGLMKDVAKVF (SEQ ID NO: 374)

Phl p 11
MSWQTYVDEHLMCEIEGHHLASAAILGHDGTVWAQSADFPQFKPEEITGI

MKDFDEPGHLAPTGMFVAGAKYMVIQGEPGRVIRGKKGAGGITIKKTGQA

LVVGIYDEPMTPGQCNMVVERLGDYLVEQGM (SEQ ID NO: 375)

Additional *Phleum* Sequences (NCBI Entrez Accession):
458878; 548863; 2529314; 2529308; 2415702; 2415700;
2415698; 542168; 542167; 626037; 542169; 541814;
542171; 253337; 253336; 453976; 439960.

Wasp (and Related)

*Vespula* Sequences:

465054 ALLERGEN VES V 5
MEISGLVYLIIIVTIIDLPYGKANNYCKIKCLKGGVHTACKYGSLKPNCG

NKVVVSYGLTKQEKQDILKEHNDFRQKIARGLETRGNPGPQPPAKNMKNL

VWNDELAYVAQVWANQCQYGHDTCRDVAKYQVGQNVALTGSTAAKYDDPV

KLVKMWEDEVKDYNPKKKFSGNDFLKTGHYTQMVWANTKEVGCGSIKYIQ

EKWHKHYLVCNYGPSGNFMNEELYQTK (SEQ ID NO: 376)

1709545 ALLERGEN VES M 1
GPKCPFNSDTVSIIIETRENRNRDLYTLQTLQNHPEFKKKTITRPVVFIT

HGFTSSASEKNFINLAKALVDKDNYMVISIDWQTAACTNEYPGLKYAYYP

RTAASNTLVGQYIATITQKLVKDYKISMANIRLIGHSLGAHVSGFAGKRV

YQELKLGKSEIIGLDPARPSFDSNHCSERLCETDAEYVQIIHTSNYLGTE

KILGTVDFYMNNGKNNPGCGRFFSEVCSHTRAVIYMAECIKHECCLIGIP

RSKSSQPISRCTKQECVCVGLNAKKYPSRGSFYVPVESTAPFCNNKGKII
(SEQ ID NO: 377)

1352699 ALLERGEN VES V 1
MEENMNLKYLLLFVYFVQVLNCCYGHGDPLSYELDRGPKCPFNSDTVSII

IETRENRNRDLYTLQTLQNHPEFKKKTITRPVVFITHGFTSSASETNFIN

LAKALVDKDNYMVISIDWQTAACTNEAAGLKYLYYPTAARNTRLVGQYIA

TITQKLVKHYKISMANIRLIGHSLGAHASGFAGKKVQELKLGKYSEIIGL

DPARPSFDSNHCSERLCETDAEYVQIIHTSNYLGTEKTLGTVDFYMNNGK

NQPGCGRFFSEVCSHSRAVIYMAECIKHECCLIGIPKSKSSQPISSCTKQ

ECVCVGLNAKKYPSRGSFYVPVESTAPFCNNKGKII (SEQ ID NO:
378)

1346323 ALLERGEN VES V 2
SERPKRVFNIYWNVPTFMCHQYDLYFDEVTNFNIKRNSKDDFQGDKIAIF

YDPGEFPALLSLKDGKYKKRNGGVPQEGNITIHLQKFIENLDKIYPNRNF

SGIGVIDFERWRPIFRQNWGNMKIHKNFSIDLVRNEHPTWNKKMIELEAS

KRFEKYARFFMEETLKLAKKTRKQADWGYYGYPYCFNMSPNNLVPECDVT

AMHENDKMSWLFNNQNVLLPSVYVRQELTPDQRIGLVQGRVKEAVRISNN

LKHSPKVLSYWWYVYQDETNTFLTETDVKKTFQEIVINGGDGIIIWGSSS

DVNSLSKCKRLQDYLLTVLGPIAINVTEAVN (SEQ ID NO: 379)

549194 ALLERGEN VES VI
5KVNYCKIKCLKGGVHTACKYGTSTKPNCGKMVVKAYGLTEAEKQEILKV

HNDFRQKVAKGLETRGNPGPQPPAKNMMNNLVWNDELANIAQVWASQCNYG

HDTCKDTEKYPVGQNIAKRSTTAALFDSPGKLVKMWENEVKDFNPNIEWS

KNNLKKTGHYTQMVWAKTKEIGCGSVKYVKDEWYTHYLVCNYGPSGNFRN

EKLYEKK (SEQ ID NO: 380)

Additional *Vespula* Sequences (NCBI Entrez Accession):
549193; 549192; 549191; 549190; 549189; 117414; 126761;
69576; 625255; 627189; 627188; 627187; 482382; 112561;
627186; 627185; 1923233; 897645; 897647; 745570;
225764; 162551.

Tree Allergen Sequences (Mainly Birch) Sequences:

114922 Bet v 1
MGVFNYETETTSVIPAARLFKAFILDGDNLFPKVAPQAISSVENIEGNGG
PGTIKKISFPEGFPFKYVKDRVDEVDHTNFKYNYSVIEGGPIGDTLEKIS
NEIKIVATPDGGSILKISNKYHTKGDHEVKAEQVKASKEMGETLLRAVES
YLLAHSDAYN (SEQ ID NO: 381)

130975 Bet v 2
MSWQTYVDEHLMCDIDGQASNSLASAIVGHDGSVWAQSSSFPQFKPQEIT
GIMKDFEEPGHLAPTGLHLGGIKYMVIQGEAGAVIRGKKGSGGITIKKTG
QALVFGIYEEPVTPGQCNMVVERLGDYLIDQGL (SEQ ID NO: 382)

1168696 Bet v 3
MPCSTEAMEKAGHGHASTPRKRSLSNSSFRLRSESLNTLRLRRIFDLFDK
NSDGIITVDELSRALNLLGLETDLSELESTVKSFTREGNIGLQFEDFISL
FHQSLNDSYAYGGEDEDDNEEDMRKSILSQEEADSFGGFKVFDEDGDGYI
SARELQMVLGKLGFSEGSEIDRVEKMIVSVDSNRDGRVDFFEFKDMMRSV
LVRSS (SEQ ID NO: 383)

809536 Bet v 4
MADDHPQDKAERERIFKRFDANGDGKISAAELGEALKTLGSITPDEVKHM
MAEIDTDGDGFISFQEFTDFGRANRGLLKDVAKIF (SEQ ID NO: 384)

543675 Que a I - *Quercus alba* = oak trees (fragment)
GVFTXESQETSVIAPAXLFKALFL (SEQ ID NO: 385)

543509 Car b I - *Carpinus betulus* = hornbeam trees (fragment)
GVFNYEAETPSVIPAARLFKSYVLDGDKLIPKVAPQAIXK (SEQ ID NO: 386)

543491 Aln g I - *Alnus glutinosa* = alder trees (fragment)
GVFNYEAETPSVIPAARLFKAFILDGDKLLPKVAPEAVSSVENI (SEQ ID NO: 387)

1204056 Rubisco
VQCMQVWPPLGLKKFETLSYLPPLSSEQLAKEVDYLLRKNLIPCLEFELE
HGFVYREHNRSPGYYDGRYWTMWKLPMFGCNDSSQVLKELEECKKAYPSA
FIRIIGFDDK (SEQ ID NO: 388)

Additional Tree Allergen Sequences (NCBI Entrez Accession Number):
131919; 128193; 585564; 1942360; 2554672; 2392209; 2414158; 1321728; 1321726; 1321724; 1321722; 1321720; 1321718; 1321716; 1321714; 1321712; 3015520; 2935416; 464576; 1705843; 1168701; 1168710; 1168709; 1168708; 1168707; 1168706; 1168705; 1168704; 1168703; 1168702; 1842188; 2564228; 2564226; 2564224; 2564222; 2564220; 2051993; 1813891; 1536889; 534910; 534900; 534898; 1340000; 1339998; 2149808; 66207; 2129477; 1076249; 1076247; 629480; 481805; 81443; 1361968; 1361967; 1361966; 1361965; 1361964; 1361963; 1361962; 1361961; 1361960; 1361959; 320546; 629483; 629482; 629481; 541804; 320545; 81444; 541814; 629484; 474911; 452742; 1834387; 298737; 298736; 1584322; 1584321; 584320; 1542873; 1542871; 1542869; 1542867; 1542865; 1542863; 1542861; 1542859; 1542857; 1483232; 1483230; 1483228; 558561; 551640; 488605; 452746; 452744; 452740; 452738; 452736; 452734; 452732; 452730; 452728; 450885; 17938; 17927; 17925; 17921; 297538; 510951; 289331; 289329; 166953.

Peanut
Peanut Sequences

1168391 Ara h 1
MRGRVSPLMLLLGILVLASVSATHAKSSPYQKKTENPCAQRCLQSCQQEP
DDLKQKACESRCTKLEYDPRCVYDPRGHTGTTNQRSPPGERTRGRQPGDY
DDDRRQPRREEGGRWGPAGPREREREEDWRQPREDWRRPSHQQPRKIRPE
GREGEQEWGTPGSHVREETSRNNPFYFPSRRFSTRYGNQNGRIRVLQRFD
QRSRQFQNLQNHRIVQIEAKPNTLVLPKHADADNILVIQQGQATVTVANG
NNRKSFNLDEGHALRIPSGFISYILNRHDNQNLRVAKISMPVNTPGQFED
FFPASSRDQSSYLQGFSRNTLEAAFNAEFNEIRRVLLEENAGGEQEERGQ
RRWSTRSSENNEGVIVKVSKEHVEELTKHAKSVSKKGSEEEGDITNPINL
REGEPDLSNNFGKLFEVKPDKKNPQLQDLDMMLTCVEIKEGALMLPHFNS
KAMVIVVVNKGTGNLELVAVRKEQQQRGRREEEEDEDEEEGSNREVRRY
TARLKEGDVFPIMPAAHPVAINASSELHLLGFGINAENNHRIFLAGDKDNV
IDQIEKQAKDLAFPGSGEQVEKLIKNQKESHFVSARPQSQSQSPSSPEKE
SPEKEDQEEENQGGKGPLLSILKAFN (SEQ ID NO: 389)

Ragweed
*Ambrosia* Sequences

113478 Amb a 1
MGIKHCCYILYFTLALVTLLQPVRSAEDLQQILPSANETRSLTTCGTYNI
IDGCWRGKADWAENRKALADCAQGFAKGTIGGKDGDIYTVTSELDDDVAN
PKEGTLRFGAAQNRPLWIIFARDMVIRLDRELAINNDKTIDGRGAKVEII
NAGFAIYNVKNIIHNIIMHDIVVNPGGLIKSHDGPPVPRKGSDGDAIGI
SGGSQIWIDHCSLSKAVDGLIDAKHGSTHFTVSNCLFTQHQYLLLFWDFD
ERGMLCTVAFNKFTDNVDQRMPNLRHGFVQVVNNNYERWGSYALGGSAGP
KTILSQGNRFLASDIKEVVGRYGESAMSESINWNWRSYMDVFENGAIFVP
SGVDPVLTPEQNAGMIPAEPGEAVLRLTSSAGVLSCQPGAPC (SEQ ID NO: 390)

113479 Amb a 2
MGIKHCCYILYFTLALVTLVQAGRLGEEVDILPSPNDTRRSLQGCEAHNI
CIDKWRCKPDWAENRQALGNCAQGFGKATHGGKWGDIYMVTSDQDDDVVN
PKEGTLRFGATQDRPLWIIFQRDMIIYLQQEMVVTSDKTIDGRGAKVELV
YGGITLMNVKNVIIHNIDIHDVRVLPGGRIKSNGGPAIPRHQSDGDAIHV
TGSSDIWIDHCTLSKSFDGLVDVNWGSTGVTISNCKFTHHEKAVLLGASD
THFQDLKMHVTLAYNIFTNTVHERMPRCRFGFFQIVNNFYDRWDKYAIGG
SSNPTILSQGNKFVAPDFIYKKNVCLRTGAQEPEWMTWNWRTQNDVLENG
AIFVASGSDPVLTAEQNAGMMQAEPGDMVPQLTMNAGVLTCSPGAPC (SEQ ID NO: 391)

113477 Amb a 1.3
MGIKQCCYILYFTLALVALLQPVRSAEGVGEILPSVNETRSLQACEALNI
IDKCWRGKADWENNRQALADCAQGFAKGTYGGKWGDVYTVTSNLDDDVAN
PKEGTLRFAAAQNRPLWIIFKNDMVINLNQELVVNSDKTIDGRGVKVEII
NGGLTLMNVKNIIIHNINIHDVKVLPGGMIKSNDGPPILRQASDGDTINV
IAGSSQIWDHCSLSKSFDGLVDVTLGSTHVTISNCKFTQQSKAILLGADD

```
ATVATHVQDKGMLFNMFTDNVDQRMPRCRFGFFQVVNNNYDRWGTYAIGG
SSAPTILCQGNRFLAPDDQIKKNVLARTGTGAAESMAWNWRSDKDLLENG
SAGAIFVTSGSDPVLTPVQMIPAEPGEAAIKLTSSAGVFSCHPGAPC
(SEQ ID NO: 392)
1113476 Amb a 1.2
MGIKHCCYILYFTLALVTLLQPVRSAEDVEEFLPSANETRRSLKACEAHN
IIDKCWRCKADWANNRQALADCAQGFAKGTYGGKHGDVYTVTSDKDDDVA
NPKEGTLRFAAAQNRPLWIIFKRNMVIHLNQELVVNSDKTIDGRGVKVNI
VNAGLTLMNVKNIIIHNINIHDIKVCPGGMIKSNDGPPILRQQSDGDAIN
VAGSSQIWIDHCSLSKASDGLLDITLGSSHVTVSNCKFTQHQFVLLLGAD
DTHYQDKGMLATVAFNMFTDHVDQRMPRCRFGFFQVVNNNYDRWGTYAIG
GSSAPTILSQGNRFFAPDDIIKKNVLARTGTGNAESMSWNWRTDRDLLEN
GAIFLPSGSDPVLTPEQKAGMIPAEPGEAVLRLTSSAGVLSCHQGAPC
(SEQ ID NO: 393)
113475 Amb a 1.1
MGIKHCCYILYFTLALVTLLQPVRSAEDLQEILPVNETRRLTTSGAYNII
WDGCRGKADWAENRKALADCAQGFGKGTVGGKDGDIYTVTSELDDDVANP
KEGTLRFGAAQNRPLWIIFERDMVIRLDKEMVVNSDKTIDGRGAKVEIIN
AGFTLNGVKNVIIHNINMHDVKVNPGGLIKSNDGPAAPRAGSDGDAISIS
GSSQIWIDHCSLSKSVDGLVDAKLGTTRLTVSNSLFTQHQFVLLFGAGDE
ANIEDRGMLTVAFNTFTDNVDQRMPRCRHGFFQVVNNNYDKWGSYAIGGS
NASPTILSQGRFCAPDERSKKNVLGRHGEAAAESMKWNWRTNKDVLENGA
IFVASGVDPVLTPEQSAGMIPAEPGESALSLTSSAGVLSCQPGAPC
(SEQ ID NO: 394)
```

*Cedar* Sequences

```
493634 Cry j IB precursor
MDSPCLVALLVFSFVIGSCFSDNPIDSCWRGDSNWAQNRMKLADCAVGFG
SSTMGGKGGDLYTVTNSDDDPVNPPGTLRYGATRDRPLWIIFSGNMNIKL
KMPMYIAGYKTFDGRGAQVYIGNGGPCVFIKRVSNVIIHGLYLYGCSTSV
LGNVLINESFGVEPVHPQDGDALTLRTATNIWIDHNSFSNSSDGLVDVTL
NTSTGVTISNLFFNHHKVMSLGHDDAYSDDKSMKVTVAFNQFGPNCGQRM
VHPRARYGLVANNNYDPWTIYAIGGSSNPTILSEGNSFTAPNESYKKQVT
IRIGCKTSSSCSNWVWQSTQDVFYNGAYFVSSGKYEGGNIYTKKEAFNVE
NGNATPHLTQNAGVLTCSLSKRC (SEQ ID NO: 395)
493634 Cry j IA precursor
MDSPCLVALLVLSFVIGSCFSDNPIDSCWRGDSNWAQNRMKLADCAVGFG
SSTMGGKGGDLYTVTNSDDDPVNPAPGTLRYGATRDRPLWIIFSGNMNIK
LKMPMYIAGYKTFDGRGAQVYIGNGGPCVFIKRVSNVIIHGLHLYGCSTS
VLGNVLINESFGVEPVHPQDGDALTLRTATNIWIDHNSFSNSSDGLVDVT
LSSTGVTISNLFFNHHKVMLLGHDDAYSDDKSMKVTVAFNQFGPNCGQR
MPRARYGLVHVANNNYDPWTIYAIGGSSNPTILSEGNSFTAPNESYKKQV
TIRIGCKTSSSCSNWVWQSTQDVFYNGAYFVSSGKYEGGNIYTKKEAFNV
ENGNATPQLTKNAGVLTCSLSKRC (SEQ ID NO: 396)
1076242 Cry j II precursor-Japanese cedar
MAMKLIAPMAFLAMQLIIMAAAEDQSAQIMLDSVVEKYLRSNRSLRKVEH
SRHDAINIFNVEKYGAVGDGKHDCTEAFSTAWQAACKNPSAMLLVPGSKK
FVVNNLFFNGPCQPHFTFKVDGIIAAYQNPASWKNNRIWLQFAKLTGFTL
MGKGVIDGQGKQWWAGQCKWVNGREICNDRDRPTAIKFDFSTGLIIQGLK
LMNSPEFHLVFGNCEGVKIIGISITAPRDSPNTDGIDIFASKNFHLQKNT
AIGTGDDCVIGTGSSNIVIEDLICGPGHGISIGSLGRENSRAEVSYVHVN
GAKFIDTQNGLRIKTWQGGSGMASHIIYENVEMINSENPILINQFYCTSA
SACQNQRSAVQIQDVTYKNIRGTSATAAAIQLKCSDSMPCKDIKLSDISL
SKLTSGKIASCLNDNANGYFGHVIPACKNLSPSAKRKESKSHKHPKTVMV
ENMRAYDKGNRTRILLGSRPPNCTNKCHGCSPCKAKLVIVHRIMPQEYYP
QRWICSCHGKIYHP (SEQ ID NO: 397)
1076241 Cry j II protein-Japanese cedar
MAMKFIAPMAFVAMQLIIMAAAEDQSAQIMLDSDIEQYLRSNRSLRKVEH
SRHDAINIFNVEKYGAVGDGKHDCTEAFSTAWQAACKKPSAMLLVPGNKK
FVVNNLFFNGPCQPHFTFKVDGIIAAYQNPASWKNNRIWLQFAKLTGFTL
KMGGVIDGQGKQWWAGQCKWVNGREICNDRDRPTAIKFDFSTGLIIQGLK
LMNSPEFHLVFGNCEGVKIIGISITAPRDSPNTDGIDIFASKNFHLQKNT
AIGTGDDCVIGTGSSNIVIEDLICGPGHGISIGSLGRENSRAEVSYVHVN
GAKFIDTQNGLRIKTWQGGSGMASHIIYENVEMINSENPILINQFYCTSA
SACQNQRSAVQIQDVTYKNIRGTSATAAAIQLKCSDSMPCKDIKLSDISL
KLTSGKIASCLNDNANGYFSGHVIPACKNLSPSAKRKESKSHKHPKTVMV
KNMGAYDKGNRTRILLGSRPPNCTNKCHGCSPCKAKLVIVHRIMPQEYYP
QRWMCSRHGKIYHP (SEQ ID NO: 398)
541803 Cry j I precursor-Japanese cedar
MDSPCLVALLVLSFVIGSCFSDNPIDSCWRGDSNWAQNRMKLADCAVGFG
SSTMGGKGGDLYTVTNSDDDPVNPPGTLRYGATRDRPLWIIFSGNMNIKL
KMPMYIAGYKTFDGRGAQVYIGNGGPCVFIKRVSNVIIHGLHLYGCSTSV
LGNVLINESFGVEPVHPQDGDALTLRTATNIWIDHNSFSNSSDGLVDVTL
SSTGVTISNNLFFNHHKVMLLGHDDAYSDDKSMKVTVAFNQFGPNCGQRM
PRARYGLVHVANNNYDPWTIYAIGGSSNPTILSEGNSFTAPNESYKKQVT
IRIGCKTSSSCSNWVWQSTQDVFYNGAYFVSSGKYEGGNIYTKKEAFNVE
NGNATPQLTKNAGVLTCSLSKRC (SEQ ID NO: 399)
541802 Cry j I precursor-Japanese cedar
MDSPCLVALLVFSFVIGSCFSDNPIDSCWRGDSNWAQNRMKLADCAVGFG
SSTMGGKGGDLYTVTNSDDDPVNPAPGTLRYGATRDRPLWIIFSGNMNIK
LKMPMYIAGYKTFDGRGAQVYIGNGGPCVFIKRVSNVIIHGLHLYGCSTS
VLGNVLINESFGVEPVHPQDGDALTLRTATNIWIDHNSFSNSSDGLVDVT
LTSTGVTISNNLFFNHHKVMSLGHDDAYSDDKSMKVTVAFNQFGPNCGQR
MPRARYGLVHVANNNYDPWTIYAIGGSSNPTILSEGNSFTAPNESYKKQV
TIRIGCKTSSSCSNWVWQSTQDVFYNGAYFVSSGKYEGGNIYTKKEAFNV
ENGNATPHLTQNAGVLTCSLSKRC (SEQ ID NO: 400)
```

Dog
*Canis* Sequences:

```
Can f 1
MKTLLLTIGFSLIAILQAQDTPALGKDTVAVSGKWYLKAMTADQEVPEKP
DSVTPMILKAQKGGNLEAKITMLTNGQCQNITVVLHKTSEPGKYTAYEGQ
RVVFIQPSPVRDHYILYCEGELHGRQIRMAKLLGRDPEQSQEALEDFREF
SRAKGLNQEILELAQSETCSPGGQ (SEQ ID NO: 401)
```

Serum Albumin Fragment

```
        EAYKSEIAHRYNDLGEEHFRGLVL  (SEQ ID NO: 402)
```

Serum Albumin Fragment

```
LSSAKERFKCASLQKFGDRAFKAWSVARLSQRFPKADFAEISKVVTDLTK
VHKECCHGDLLECADDRADLAKYMCENQDSISTKLKECCDKPVLEKSQCL
AEVERDELPGDLPSLAADFVEDKEVCKNYQEAKDVFLGTFLYEYSRRHPE
YSVSLLLRLAKEYEATLEKCCATDDPPTCYAKVLDEFKPLVDEPQNLVKT
NCELFEKLGEYGFQNALLVRYTKKAPQVSTPTLVVEVSRKLGKVGTKCCK
KPESERMSCADDFLS (SEQ ID NO: 403)
Can f 2
MQLLLLTVGLALICGLQAQEGNHEEPQGGLEELSGRWHSVALASNKSDLI
KPWGHFRVFIHSMSAKDGNLHGDILIPQDGQCEKVSLTAFKTATSNKFDL
EYWGHNDLYLAEVDPKSYLILYMINQYNDDTSLVAHLMVRDLSRQQDFLP
AFESVCEDIGLHKDQIVVLSDDDRCQGSRD (SEQ ID NO: 404)
```

Additional Dog Allergen Protein (NCBI Entrez Accession): 1731859

Horse
*Equus* Sequences:

```
1575778 Equ c1
MKLLLLCLGLILVCAQQEENSDVAIRNFDISKISGEWYSIFLASDVKEKI
EENGSMRVFVDVIRALDNSSLYAEYQTKVNGECTEFPMVFDKTEEDGVYS
LNYDGYNVFRISEFENDEHIILYLVNFDKDRPFQLFEFYAREPDVSPEIK
EEFVKIVQKRGIVKENIIDLTKIDRCFQLRGNGVAQA (SEQ ID NO:
405)
3121755 Equ c 2
SQXPQSETDYSQLSGEWNTIYGAASNIXK (SEQ ID NO: 406)
```

*Euroglyphus* (Mite)
*Euroglyphus* Sequences:

```
Eur m 1 (variant)
                                (SEQ ID NO: 407)
TYACSINSVSLPSELDLRSLRTVTPIRMQGGCGSCWAFSGVASTESAYLA
YRNMSLDLAEQELVDCASQNGCHGDTIPRGIEYIQQNGVVQEHYYPYVAR
EQSCHRPNAQRYGLKNYCQISPPDSNKIRQALTQTHTAVAVIIGIKDLNA
FRHYDGRTIMQHDNGYQPNYHAVNIVGYGNTQGVDYWIVRNSWDTTWGDN
GYGYFAANINL
Eur m 1 (variant)
                                (SEQ ID NO: 408)
TYACSINSVSLPSELDLRSLRTVTPIRMQGGCGSCWAFSGVASTESAYLA
YRNMSLDLAEQELVDCASQNGCHGDTIPRGIEYIQQNGVVQEHYYPYVAR
EQSCHRPNAQRYGLKNYCQISPPDSNKIRQALTQTHTAVAVIIGIKDLNA
FRHYDGRTIMQHDNGYQPNYHAVNIVGYGNTQGVDYWIVRNSWDTTWGDN
GYGYFAANINL
Eur m 1 (variant)
                                (SEQ ID NO: 409)
ETNACSINGNAPAEIDLRQMRTVTPIRMQGGCGSCWAFSGVAATESAYLA
YRNQSLDLAEQELVDCASQHGCHGDTIPRGIEYIQHNGVVQESYYRYVAR
EQSCRRPNAQRFGISNYCQIYPPNANKIREALAQTHSAIAVIIGIKDLDA
FRHYDGRTIIQRDNGYQPNYHAVNIVGYSNAQGVDYWIVRNSWDTNWGDN
GYGYFAANIDL
Eur m 1 (variant)
                                (SEQ ID NO: 410)
ETSACRINSVNVPSELDLRSLRTVTPIRMQGGCGSCWAFSGVAATESAYL
AYRNTSLDLSEQELVDCASQHGCHGDTIPRGIEYIQQNGVVEERSYPYVA
REQQCRRPNSQHYGISNYCQIYPPDVKQIREALTQTHTAIAVIIGIKDLR
AFQHYDGRTIIQHDNGYQPNYHAVNIVGYGSTQGVDYWIVRNSWDTTWGD
SGYGYFQAGNNL
```

*Poa* (Grass) Sequences

```
113562 POLLEN ALLERGEN POA P 9
                                (SEQ ID NO: 411)
MAVQKYTVALFLVALVVGPAASYAADLSYGAPATPAAPAAGYTPAAPAGA
APKATTDEQKMIEKINVGFKAAVAAAGGVPAANKYKTFVATFGAASNKAF
AEALSTEPKGAAVDSSKAALTSKLDAAYKLAYKSAEGATPEAKYDDYVAT
LSEALRIIAGTLEVHGVKPAAEEVKATPAGELQVIDKVDAAFKVAATAAN
AAPANDKFTVFEAAFNDAIKASTGGAYQSYKFIPALEAAVKQSYAATVAT
APAVKYTVFETALKKAITAMSQAQKAAKPAAAATGTATAAVGAATGAATA
AAGGYKV
113561 POA P 9
                                (SEQ ID NO: 412)
MAVHQYTVALFLAVALVAGPAASYAADVGYGAPATLATPATPAAPAAGYT
PAAPAGAAPKATTDEQKLIEKINAGFKAAVAAAAGVPAVDKYKTFVATFG
TASNKAFAEALSTEPKGAAAASSNAVLTSKLDAAYKLAYKSAEGATPEAK
YDAYVATLSEALRIIAGTLEVHAVKPAGEEVKAIPAGELQVIDKVDAAFK
VAATAANAAPANDKFTVFEAAFNDAIKASTGGAYQSYKFIPALEAAVKQS
YAATVATAPAVKYTVFETALKKAITAMSQAQKAAKPAAAVTATATGAVGA
ATGAVGAATGAATAAAGGYKTGAATPTAGGYKV
113560 POA P 9
                                (SEQ ID NO: 413)
MDKANGAYKTALKAASAVAPAEKFPVFQATFDKNLKEGLSGPDAVGFAKK
LDAFIQTSYLSTKAAEPKEKFDLFVLSLTEVLRFMAGAVKAPPASKFPAK
PAPKVAAYTPAAPAGAAPKATTDEQKLIEKINVGFKAAVAAAAGVPAASK
```

-continued

YKTFVATFGAASNKAFAEALSTEPKGAAVASSKAVLTSKLDAAYKLAYKS

AEGATPEAKYDAYVATLSEALRIIAGTLEVHGVKPAAEEVKAIPAGELQV

IDKVDAAFKVAATAANAAPANDKFTVFEAAFNDAIKASTGGAYQSYKFIP

ALEAAVKQSYAATVATAPAVKYTVFETALKKAITAMSQAQKAAKPAAAVT

GTATSAVGAATGAATAAAGGYKV

Cockroach Sequences

2833325 Cr p1
(SEQ ID NO: 414)
MKTALVFAAVVAFVAARFPDHKDYKQLADKQFLAKQRDVLRLFHRVHQHN

ILNDQVEVGIPMTSKQTSATTVPPSGEAVHGVLQEGHARPRGEPFSVNYE

KHREQAIMLYDLLYFANDYDTFYKTACWARDRVNEGMFMYSFSIAVFHRD

DMQGVMLPPPYEVYPYLFVDHDVIHMAQKYWMKNAGSGEHHSHVIPVNFT

LRTQDHLLAYFTSDVNLNAFNTYYRYYYPSWYNTTLYGHNIDRRGEQFYY

TYKQIYARYFLERLSNDLPDVYPFYYSKPVKSAYNPNLRYHNGEEMPVRP

SNMYVTNFDLYYIADIKNYEKRVEDAIDFGYAFDEHMKPHSLYHDVHGME

YLADMIEGNMDSPNFYFYGSIYHMYHSMIGHIVDPYHKMGLAPSLEHPET

FVLRDPVYQLWKRVDHLFQKYKNRLPRYTHDELAFEGVKVENVDVGKLYT

MYFEQYDSLDMAVYVNNVDQISNVDVQLAVRLNHKPFTYNIEVSSDKAQD

VYVAVFLGPKYDYLGREYDLNDRRHYFVEMDRFPYHVGAGKTVIERNSHD

SNIIAPERDSYRTFYKKVQEAYEGKSQYYVDKGHNYCGYPENLLIPKGKK

GGQAYTFYVIVTPYVKQDEHDFEPYNYKAFSYCGVGSERKYPDNKPLGYP

FDRKIYSNDFYTPNMYFKDVIIFHKKYDEVGVQGH

2231297 Cr p2
(SEQ ID NO: 415)
INEIHSIIGLPPFVPPSRRHARRGVGINGLIDDVIAILPVDELKALFQEK

LETSPDFKALYDAIRSPEFQSIISTLNAMQRSEHHQNLRDKGVDVDHFIQ

RALIRALFGLSARNLQDDLNDFLHSLEPISPRHRHGLPRQRRRSARVSAY

ILHADDFHKIITTEALPEFANFYNFLKEHGLDVVDYINEIHSIIGLPPFV

PPSRRHARRGVGINGLIDDVIAILPVDELKALFQEKLETSPDFKALYDAI

RSPEFQSIISTLNAMPEYQELLQNLRDKGVDVDHFIRVDQGTLRTLSSGQ

MRNLQDDLNDFLALIPTDQILAIADYLANDAEVQELVAYLQSDDFHKIIT

TIEALPEFANFYNFLKEHGLDVVDYINEIHSIIGLPPFVPPSQRHARRGV

GINGLIDDVIAILPVDELKALFQEKLETSPDFKALYDAIDLRSSRA

1703445 Bla g 2
(SEQ ID NO: 416)
MIGLKLVTVLFAVATITHAAELQRVPLYKLVHVFINTQYAGITKIGNQNF

FLTVDSTSCNVVVASQECVGGACVCPNLQKYEKLKPKYISDGNVQVKFFD

VTGSAGRGIEDSLTISNLTTSQQDIVLADELSQEVCILSADVVVGIAAPG

CPNALKGKTVLENFVEENLIAPVFSIHHARFQDGEHFGEIIFGGSDWKYV

DGEFTYVPLVGDDSWKFRLDGVKIGDTTVAPAGTQAIIDTSKAIIVGPKA

YVNPINEAIGCVVEKTTTRRICKLDCSKIPSLPDVTFVINGRNFNISSQY

YIQQNGNLCYSGFQPCGHSDHFFIGDFFVDHYYSEFNWENKTMGFGRSVE

SV

1705483 Bla g 4
(SEQ ID NO: 417)
AVLALCATDTLANEDCFRHESLVPNLDYERFRGSWIIAAGTSEALTQYKC

WIDRFSYDDALVSKYTDSQGKNRTTIRGRTKFEGNKFTIDYNDKGKAFSA

PYSVLATDYENYAIVEGCPAAANGHVIYVQIRFSVRRFHPKLGDKEMIQH

YTLDQVNQHKKAIEEDLKHFNLKYEDLHSTCH

2326190 Bla g 5
(SEQ ID NO: 418)
YKLTYCPVKALGEPIRFLLSYGEKDFEDYRFQEGDWPNLKPSMPFGKTPV

LEIDGKQTHQSVAISRYLGKQFGLSGKDDWENLEIDMIVDTISDFRAAIA

NYHYDADENSKQKKWDPLKKETIPYYTKKFDEVVKANGGYLAAGKLTWAD

FYFVAILDYLNHMAKEDLVANQPNLKALREKVLGLPAIKAWVAKRPPTDL

Additional Cockroach Sequences (NCBI Entrez Accession Numbers):
2580504; 1580797; 1580794; 1362590; 544619; 544618; 1531589; 1580792; 1166573; 1176397; 2897849.
Allergen (General) Sequences:
NCBI Accession Numbers
2739154; 3719257; 3703107; 3687326; 3643813; 3087805; 1864024; 1493836; 1480457; 2598976; 2598974; 1575778; 763532; 746485; 163827; 163823; 3080761; 163825; 3608493; 3581965; 2253610; 2231297; 2897849; 3409499; 3409498; 3409497; 3409496; 3409495; 3409494; 3409493; 3409492; 3409491; 3409490; 3409489; 3409488; 3409487; 3409486; 3409485; 3409484; 3409483; 3409482; 3409481; 3409480; 3409479; 3409478; 3409477; 3409476; 3409475; 3409474; 3409473; 3409472; 3409471; 3409470; 3409469; 3409468; 3409467; 3409466; 3409465; 3409464; 3409463; 3409462; 3409461; 3409460; 3409459; 3409458; 3409457; 3409456; 3318885; 3396070; 3367732; 1916805; 3337403; 2851457; 2851456; 1351295; 549187; 136467; 1173367; 2499810; 2498582; 2498581; 1346478; 1171009; 126608; 114091; 2506771; 1706660; 1169665; 1169531; 232086; 416898; 114922; 2497701; 1703232; 1703233; 1703233; 1703232; 3287877; 3122132; 3182907; 3121758; 3121756; 3121755; 3121746; 3121745; 3319925; 3319923; 3319921; 3319651; 3318789; 3318779; 3309647; 3309047; 3309045; 3309043; 3309041; 3309039; 3288200; 3288068; 2924494; 3256212; 3256210; 3243234; 3210053; 3210052; 3210051; 3210050; 3210049; 3210048; 3210047; 3210046; 3210045; 3210044; 3210043; 3210042; 3210041; 3210040; 3210039; 3210038; 3210037; 3210036; 3210035; 3210034; 3210033; 3210032; 3210031; 3210030; 3210029; 3210028; 3210027; 3210026; 3210025; 3210024; 3210023; 3210022; 3210021; 3210020; 3210019; 3210018; 3210017; 3210016; 3210015; 3210014; 3210013; 3210012; 3210011; 3210010; 3210009; 3210008; 3210007; 3210006; 3210005; 3210004; 3210003; 3210002; 3210001; 3210000; 3209999; 3201547; 2781152; 2392605; 2392604; 2781014; 1942360; 2554672; 2392209; 3114481; 3114480; 2981657; 3183706; 3152922; 3135503; 3135501; 3135499; 3135497; 2414158; 1321733; 1321731; 1321728; 1321726; 1321724; 1321722; 1321720; 1321718; 1321716; 1321714; 1321712; 3095075; 3062795; 3062793; 3062791; 2266625; 2266623; 2182106; 3044216; 2154736; 3021324; 3004467; 3005841; 3005839; 3004485; 3004473; 3004471; 3004469; 3004465; 2440053; 1805730; 2970629; 2959898; 2935527; 2935416; 809536; 730091; 585279; 584968; 2498195; 2833325; 2498604; 2498317; 2498299; 2493414; 2498586; 2498585; 2498576; 2497749; 2493445; 1513216; 729944; 2498099; 548449; 465054; 465053; 465052; 548671; 548670; 548660; 548658; 548657;

2832430; 232084; 2500822; 2498118; 2498119; 2498119; 2498118; 1708296; 1708793; 416607; 416608; 416608; 416607; 2499791; 2498580; 2498579; 2498578; 2498577; 2497750; 1705483; 1703445; 1709542; 1709545; 1710589; 1352699; 1346568; 1346323; 1346322; 2507248; 11352240; 1352239; 1352237; 1352229; 1351935; 1350779; 1346806; 1346804; 1346803; 1170095; 1168701; 1352506; 1171011; 1171008; 1171005; 1171004; 1171002; 1171001; 1168710; 1168709; 1168708; 1168707; 1168706; 1168705; 1168704; 1168703; 1168702; 1168696; 1168391; 1168390; 1168348; 1173075; 1173074; 1173071; 1169290; 1168970; 1168402; 729764; 729320; 729979; 729970; 729315; 730050; 730049; 730048; 549194; 549193; 549192; 549191; 549190; 549189; 549188; 549185; 549184; 549183; 549182; 549181; 549180; 549179; 464471; 585290; 416731; 1169666; 113478; 113479; 113477; 113476; 113475; 130975; 119656; 113562; 113561; 113560; 416610; 126387; 126386; 126385; 132270; 416611; 416612; 416612; 416611; 730035; 127205; 1352238; 125887; 549186; 137395; 730036; 133174; 114090; 131112; 126949; 129293; 124757; 129501; 416636; 2801531; 2796177; 2796175; 2677826; 2735118; 2735116; 2735114; 2735112; 2735110; 2735108; 2735106; 2735104; 2735102; 2735100; 2735098; 2735096; 2707295; 2154730; 2154728; 1684720; 2580504; 2465137; 2465135; 2465133; 2465131; 2465129; 2465127; 2564228; 2564226; 2564224; 2564222; 2564220; 2051993; 1313972; 1313970; 1313968; 1313966; 2443824; 2488684; 2488683; 2488682; 2488681; 2488680; 2488679; 2488678; 2326190; 2464905; 2415702; 2415700; 2415698; 2398759; 2398757; 2353266; 2338288; 1167836; 414703; 2276458; 1684718; 2293571; 1580797; 1580794; 2245508; 2245060; 1261972; 2190552; 1881574; 511953; 1532058; 1532056; 1532054; 1359436; 666007; 487661; 217308; 1731859; 217306; 217304; 1545803; 1514943; 577696; 516728; 506858; 493634; 493632; 2154734; 2154732; 543659; 1086046; 1086045; 2147643; 2147642; 1086003; 1086002; 1086001; 543675; 543623; 543509; 543491; 1364099; 2147108; 2147107; 1364001; 1085628; 631913; 631912; 631911; 2147092; 477301; 543482; 345521; 542131; 542130; 542129; 100636; 2146809; 480443; 2114497; 2144915; 72355; 71728; 319828; 1082946; 1082945; 1082944; 539716; 539715; 423193; 423192; 423191; 423190; 1079187; 627190; 627189; 627188; 627187; 482382; 1362656; 627186; 627185; 627182; 482381; 85299; 85298; 2133756; 2133755; 1079186; 627181; 321044; 321043; 112559; 112558; 1362590; 2133564; 1085122; 1078971; 627144; 627143; 627142; 627141; 280576; 102835; 102834; 102833; 102832; 84703; 84702; 84700; 84699; 84698; 84696; 477888; 477505; 102575; 102572; 478272; 2130094; 629813; 629812; 542172; 542168; 542167; 481432; 320620; 280414; 626029; 542132; 320615; 320614; 100638; 100637; 100635; 82449; 320611; 320610; 280409; 320607; 320606; 539051; 539050; 539049; 539048; 322803; 280407; 100501; 100498; 100497; 100496; 1362137; 1362136; 1362135; 1362134; 1362133; 1362132; 1362131; 1362130; 1362129; 1362128; 100478; 2129891; 1076531; 1362049; 1076486; 2129817; 2129816; 2129815; 2129814; 2129813; 2129812; 2129805; 2129804; 2129802; 2129801; 2129800; 2129799; 479902; 479901; 2129477; 1076247; 629480; 1076242; 1076241; 541803; 541802; 280372; 280371; 1361968; 1361967; 1361966; 1361965; 1361964; 1361963; 1361962; 1361961; 1361960; 1361959; 320546; 2119763; 543622; 541804; 478825; 478824; 478823; 421788; 320545; 81444; 626037; 626028; 539056; 483123; 481398; 481397; 100733; 100732; 100639; 625532; 1083651; 322674; 322673; 81719; 81718; 2118430; 2118429; 2118428; 2118427; 419801; 419800; 419799; 419798; 282991; 100691; 322995; 322994; 101824; 626077; 414553; 398830; 1311457; 1916292; 1911819; 1911818; 1911659; 1911582; 467629; 467627; 467619; 467617; 915347; 1871507; 1322185; 1322183; 897645; 897647; 1850544; 1850542; 1850540; 288917; 452742; 1842045; 1839305; 1836011; 1836010; 1829900; 1829899; 1829898; 1829897; 1829896; 1829895; 1829894; 1825459; 1808987; 159653; 1773369; 1769849; 1769847; 608690; 1040877; 1040875; 1438761; 1311513; 1311512; 1311511; 1311510; 1311509; 1311689; 1246120; 1246119; 1246118; 1246117; 1246116; 1478293; 1478292; 1311642; 1174278; 1174276; 1086972; 1086974; 1086976; 1086978; 1086978; 1086976; 1086974; 1086972; 999009; 999356; 999355; 994866; 994865; 913758; 913757; 913756; 913285; 913283; 926885; 807138; 632782; 601807; 546852; 633938; 544619; 544618; 453094; 451275; 451274; 407610; 407609; 404371; 409328; 299551; 299550; 264742; 261407; 255657; 250902; 250525; 1613674; 1613673; 1613672; 1613671; 1613670; 1613304; 1613303; 1613302; 1613240; 1613239; 1613238; 1612181; 1612180; 1612179; 1612178; 1612177; 1612176; 1612175; 1612174; 1612173; 1612172; 1612171; 1612170; 1612169; 1612168; 1612167; 1612166; 1612165; 1612164; 1612163; 1612162; 1612161; 1612160; 1612159; 1612158; 1612157; 1612156; 1612155; 1612154; 1612153; 1612152; 1612151; 1612150; 1612149; 1612148; 1612147; 1612146; 1612145; 1612144; 1612143; 1612142; 1612141; 1612140; 1612139; 1093120; 447712; 447711; 447710; 1587177; 158542; 1582223; 1582222; 1531589; 1580792; 886215; 1545897; 1545895; 1545893; 1545891; 1545889; 1545887; 1545885; 1545883; 1545881; 1545879; 1545877; 1545875; 166486; 1498496; 1460058; 972513; 1009442; 1009440; 1009438; 1009436; 1009434; 7413; 1421808; 551228; 452606; 32905; 1377859; 1364213; 1364212; 395407; 22690; 22688; 22686; 22684; 488605; 17680; 1052817; 1008445; 1008443; 992612; 706811; 886683; 747852; 939932; 19003; 1247377; 1247375; 1247373; 862307; 312284; 999462; 999460; 999458; 587450; 763064; 886209; 1176397; 1173557; 902012; 997915; 997914; 997913; 997912; 997911; 997910; 99790; 997908; 997907; 997906; 997905; 997904; 997903; 997902; 997901; 997900; 997899; 997898; 997897; 997896; 997895; 997894; 997893; 997892; 910984; 910983; 910982; 910981; 511604; 169631; 169629; 169627; 168316; 168314; 607633; 555616; 293902; 485371; 455288; 166447; 166445; 166443; 166435; 162551; 160780; 552080; 156719; 156715; 515957; 515956; 515955; 515954; 515953; 459163; 166953; 386678; 169865.

Particularly preferred T cell epitopes are derived from the allergens: cat dander protein Fel d1; House dust mite proteins Der P1, Der P2 and Der P7; Ragweed protein amb a 1.1, a 1.2, a1.3 or a1.4; Rye grass proteins lol p1 and lol p5; Timothy grass proteins phl p1 and phl p5; Bermuda grass protein Cyn d 5; *Alternaria* alternate proteins Alt a 1, Alt a 2 and Enolase (Alt a 6); Birch protein Bet v1 and P14; German Cockroach proteins Bla g 1, Bla g 2, Bla g 3, Bla g 4, Bla g 5 and Bla g 6; Mugwort protein Art v 1; Russian thistle protein Sal k 1 and Sal k 2; peanut Ara h1, Ara h2, Ara h3, Ara h4, Ara h5, Ara h6, plant profilins or lipid transfer proteins or a human leukocyte antigen.

Suitable autoimmune antigens from which the MHC Class II-binding T cell epitope may derive can of course be obtained and/or produced using known methods. Suitable autoimmune antigens include the major antigens in the following autoimmune diseases: Acute disseminated encephalomyelitis (ADEM); Addison's disease; Ankylosing spondylitis; Antiphospholipid antibody syndrome (APS); Aplastic anemia; Autoimmune hepatitis; Autoimmune Oophoritis; Coeliac disease; Crohn's disease; Diabetes mellitus type 1; Gestational pemphigoid; Goodpasture's syndrome; Graves' disease; Guillain-Barré syndrome (GBS); Hashimoto's disease; Idiopathic thrombocytopenic purpura; Kawasaki's Disease; Lupus erythematosus; Multiple sclerosis; Myasthenia gravis; Opsoclonus myoclonus syndrome (OMS); Optic neuritis; Ord's thyroiditis; Pemphigus; Pernicious anaemia; Polyarthritis in dogs; Primary biliary cirrhosis; Rheumatoid arthritis; Reiter's syndrome; Sjögren's syndrome; Takayasu's arteritis; Temporal arteritis (also known as "giant cell arteritis"); Warm autoimmune hemolytic anemia; Wegener's granulomatosis.

Other preferred eptiopes may be derived from antigens involved with maternal-foetal immunes responses, for example Rhesus D antigens involved in Rhesus D Haemolytic Disease of the Newborn.

Other preferred epitopes may be derived from antigens involved in graft-versus-host disease or transplant rejection (alloimmune responses), for example from MHC Class I molecules (otherwise referred to as human leukocyte antigens—HLA), preferably from the α3 domain and/or transmembrane domain of MHC Class I molecules, most preferably from the human MHC Class I molecule HLA-A2.

The epitopes may be of proteins which are administered to the individual, for example for therapy. Such proteins may act as neoantigens in the individual, such as for example in the situation where the individual does not express the protein. The therapeutic protein may be factor IIX or salcatonin.

Particularly suitable proteins from which to derive the epitope sequences of the invention are those which have a low frequency of epitopes per amino acid residue, i.e. the ratio of amino acids in the minimal binding sequence of an epitope, relative to the total number of amino acids in the protein ("the epitope ratio") is low. A protein with a low frequency of epitopes per amino acid residue typically has an epitope ratio of 1:35, 1:40, 1:45, 1:50, 1:55, 1:60 or 1:65. These proteins are preferred sources of epitope sequences of the invention because a high proportion of the different epitope sequences derived from such proteins typically overlap. In general, the percentage of epitope sequences which overlap with at least one other epitope sequence, as a proportion of the total number of epitopes in a protein with a low epitope ratio as defined above, is greater than 60%, 65%, 70%, 80% or 90%.

The following Examples illustrate the invention:

Example 1

House Dust Mite Peptides from Der p 1, Der p2 and Der p 7

MHC Class II Binding Search

The aim of this study is to identify peptides with strong affinities for the seven most common human MHC Class II HLA-DRB1* allotypes (covering in total around 63% of the allotypes found in the average Caucasian population). In order to identify binding peptides in the House Dust Mite (HDM) allergens, Der p 1, Der p 2 and Der p 7, in vitro binding assays have been performed on a subset of peptides from these allergenic proteins. Peptides for testing in the binding assays were initially identified by an in silico approach known as "peptide threading" (carried out by Biovation, Ltd., Aberdeen, Scotland, UK). This is a bioinformatic analysis of consecutive peptides from a sequence for the potential to be accommodated within the binding groove of MHC class II HLA-DR molecules. This subset of peptides was pre-screened for solubility in an aqueous, acidic milieu and a final panel of 44 peptides selected for testing in an in vitro MHC Class II binding assay.

Methods

The assay employed is a competitive MHC class II binding assay, wherein each peptide is analysed for its ability to displace a known control binder from each of the human MHC class II allotypes investigated. The allotypes and control peptides used in this study are shown in the table below.

Control Peptides Used in the In Vitro Binding Assays

| Allotype | Control Peptide | Sequence |
| --- | --- | --- |
| DRB1*0101 | Influenza haemagglutinin 307-319 | PKYVKQNTLKLAT (SEQ ID NO: 1) |
| DRB1*0301 | Myco. tuberculosis/leprae hsp 65 2-16 | AKTIAYDEEARRGLE (SEQ ID NO: 2) |
| DRB1*0401 | Influenza haemagglutinin 307-319 | PKYVKQNTLKLAT (SEQ ID NO: 1) |
| DRB1*0701 | Influenza haemagglutinin 307-319 | PKYVKQNTLKLAT (SEQ ID NO: 1) |
| DRB1*1101 | Influenza haemagglutinin 307-319 | PKYVKQNTLKLAT (SEQ ID NO: 1) |
| DRB1*1301 | HLA-DQB1*0603 21-36 | TERVRLVTRHIYNREE (SEQ ID NO: 3) |
| DRB1*1501 | Human myelin basic protein 85-99 | ENPVVHFFKNIVTPR (SEQ ID NO: 4) |
| DQB1*0602 | Human Insulin B 1-15 | FVNQHLCGSHLVEAL (SEQ ID NO: 5) |

Each of the 44 HDM peptides (which are shown in Tables A and B) were analysed in the competition assay and screened for relative binding compared to the control peptide. Due to the nature of the competitive assay the data for each peptide is represented as a ratio of its own IC50 to that of the control peptide. Thus, a peptide that has an IC50 value that is parity to the control peptide has an identical binding affinity, while peptides with a ratio less than one have a higher affinity and those with a ratio greater than one have a lower affinity.

Results

Solubility in aqueous solution is an essential criterion for a peptide to be an effective therapeutic agent. Therefore, as a consequence of the solubility screen we will have eliminated very hydrophobic peptides with a high frequency of large hydrophobic amino acid residues in multiple binding registers. This is a characteristic of promiscuous HLA-DRB1* binders. The data from the binding assays is shown in Table 3B. The relative binding of each peptide is shown for each of the allotypes in the study. The data shows that 24 of the 44 peptides tested bound to one or more of the MHC Class II allotypes. A range of cross-reactivity is seen with 5 peptides binding only one allotype, 8 peptides binding two, 9 peptides binding three and two peptides binding four different MHC Class II allotypes (red). It would also be expected that such peptides would have the ability to bind similar allotypes that have not been tested through the homology of MHC structures. This can be seen in the cross-reactivity of peptides for DRB1*0101, *0401, *0701 and *1101 in several cases here. Also shown is the solubility status of the peptide at the highest concentrations in the aqueous solution of the binding assay.

The value illustrates the lowest concentration at which an insoluble white precipitate is seen. There appears to be no significant nonspecific effect of the formation of precipitate in the assays. Several peptides that precipitate at high concentrations also bind to MHC class II; however, several also show no ability to compete with the control peptides. It is to be expected that peptides liable to form precipitates may exhibit high affinity and promiscuous binding due to the presence of many hydrophobic residues.

The % purity of the peptides is indicated in Table 3A. This is of significance as purities were seen to vary from 60-90%. This would have a considerable effect on the ability of a peptide to compete if it is relatively impure. For example, HDM23A and HDM32 show low affinity binding; however, they are of reduced purity (66.7% and 68.7% respectively) compared to other HDM peptides. Therefore, if purity is taken into consideration, they may in fact have an equivalent affinity to a peptide of a higher purity.

It can be seen that some MHC Class II allotypes bind to more peptides than others; this is probably to be expected as there is variability between the pocket positions in the different MHC class II binding grooves. There are however, also a number of well-characterised differences between the affinities of the various control peptides. Clearly a high affinity control peptide will be more difficult to displace by the competing HDM peptide resulting in the identification of fewer binding peptides. This can be illustrated by the data presented here. For example, the Influenza Haemagglutinin 307-319 control peptide, has varying affinity according to the allotype, where DRB1*0101>*0401>*0701>*1101. This is reflected in the number of binders to each of the allotypes, where DRB1*0101 has the lowest number of binders (5) and DRB1*1101 has the highest (14). Furthermore, the binding assay for DRB1*1501 is very stringent due to the high affinity of Myelin Basic Protein 85-99 for this allotype. In the high stringency screen the Fel d 1 peptide EQVAQYKALPVV-LENA (SEQ ID NO:6), that was tested in an earlier study, gave a ratio of 0.97 indicating that high affinity binders could be identified at this stringency.

In addition, to identify lower affinity binders, the assay was also carried out under less stringent conditions. All the Der p binding peptides were seen to have a high ratio when tested against this allotype, showing they were low affinity binders compared to the control peptide. The DQA1*0102/DQB1*0602 binding assay uses a peptide from the B-chain of human insulin which is of lower affinity compared to those used in the DR assays. This dictates that the DQ assay is very sensitive and tends to produce very low ratio values for the strongest binders to this MHC Class II allotype. This sensitivity also accounts for the relatively higher number of DQ binding peptides within the panel screened. Finally, on closer analysis, the peptides identified as ligands for the DRB1*0101,*0401, *0701 superfamily, are found to incorporate a motif that is characteristic of promiscuous binders to this family of allotypes where: P1=Y, F, W, L, I, V, or M (Large aromatic or hydrophobic residue), P6=S, T, C, A, P, V, I, M (small, non-charged residue)

Out of the 16 peptides (e.g. HDM 21B RGK-PFQLEAVFEANQNT SEQ ID NO: 26) identified as binders to all or a combination of these 3 allotypes, 14 (87.5%) contain this motif, which suggests that these are promiscuous binders with a range of affinities for the 1-4-7 allotypes.

CONCLUSIONS

A range of peptides have been shown to have the capacity to bind the MHC Class II allotypes and are considered to represent T cell epitopes. Thus the inventors were able to identify sequences comprising T cell epitopes which are close together in the overall protein sequence and therefore construct peptides which comprise overlapping epitopes. A number of such sequences will be apparent to the skilled person when considering Tables 1A and 1B. Specific illustrative examples include:

HDM01 (residues 112-124) and HDM02 (118-130). Providing a combination of these two sequences, the inventors devised a longer sequence spanning residues 112 to 130. In order to reduce dimer formation by this longer peptide, the cysteine at position 129 is replaced with serine to give new peptide HDM01A: IDLRQMRTVTPIRMQGGSG (SEQ ID NO: 7) (HDM01=underlined, HDM02=bold).

HDM34 (residues 74-88) and HDM35 (79-91). Providing a combination of these two sequences, the inventors devised a longer sequence spanning residues 72 to 89. Residues 72 and 73 were added, and residues 90 and 91 removed in order to improve solubility for the new peptide, HDM207: DM RNIQVRGLKQMKRVGD (SEQ ID NO: 8) (HDM34=underlined, HDM35=bold).

Evidence that these new peptides are suitable for tolerisation to house dust mite allergens is shown in Table 1C. Table 1C presents results from a cytokine release assay performed on four house dust mite allergic individuals for HDM01A compared to HDM01 and HDM02, and on three house dust mite allergic individuals for HDM34, HDM35 and HDM207.

Cytokine secretion profiles from PBMC's were analysed in response to the peptide stimulation using the above peptides. Supernatants from the cytokine release assay were tested for the presence of 2 cytokines, IFN-γ and IL-13, using either an ELISA assay or a multiplex bead array assay.

A typical cytokine release assay requires $40 \times 10^6$ PBMC's per subject. In more detail, 250 µl of a 200 µg/ml solution of the appropriate antigen or peptide concentration is distributed into the appropriate wells of 48 well plates. Plates are the incubated in a humidified 5% $CO_2$ incubator at 37° C. for a maximum of 4 hours. 250 µl of a $5 \times 10^6$ cell/ml PBMC suspension is then added to each well and the plates returned to the incubator for 5 days. Following stimulation, samples of culture supernatant are harvested for testing by ELISA or multiplex bead assay according to standard protocols.

As can be seen, the new peptides HDM01A and HDM207 give rise to significantly higher cytokine production in all patients tested than the original "single epitope" peptides from which they derive.

TABLE 1A

| Peptide | Sequence | Residues in parent molecule | % purity | Solubility test | Precipitation in assay | SEQ ID NO |
|---|---|---|---|---|---|---|
| HDM01 | IDLRQMRTVTPIR | 112-124 | 79.2 | YES | None | 9 |
| HDM02 | RTVTPIRMQGCG | 118-130 | 79.6 | YES | None | 10 |
| HDM03C | RNQSLDLAEQELVDCASQH | 149-167 | 60.1 | YES | None | 11 |
| HDM05 | EYIQHNGVVQESY | 179-191 | 77.5 | YES | None | 12 |
| HDM06 | RYVAREQSCRRPN | 193-205 | 79.7 | YES | None | 13 |
| HDM07 | PNVNKIREALAQT | 220-232 | 88.6 | YES | None | 14 |
| HDM08 | NKIREALAQTHSA | 223-235 | 87.6 | YES | None | 15 |
| HDM09A | REALAQTHSAIAVI | 226-239 | 69.6 | YES | 1000 µM (2.9 mg/ml) | 16 |
| HDM11 | IGIKDLDAFRHYD | 240-252 | 77.6 | YES | None | 17 |
| HDM12 | KDLDAFRHYDGRT | 243-255 | 72.9 | YES | None | 18 |
| HDM13 | RTIIQRDNGYQPNY | 254-267 | 70.7 | NO | None | 19 |
| HDM16A | RNSWDTNWGDNGYG | 287-300 | 70.0 | YES | None | 20 |
| HDM17 | NSVNVPSELDLRSLRT | 105-120 | 74.5 | YES | None | 21 |
| HDM19 | DQVDVKDCANHEIKK | 18-32 | 81.4 | YES | None | 22 |
| HDM20 | CIIHRGKPFQLEA | 44-56 | 77.4 | YES | None | 23 |
| HDM21 | KPFQLEAVFEANQNT | 50-64 | 88.7 | YES | 200 µM (0.3 mg/ml) | 24 |
| HDM21A | KPFQLEAVFEANQNTK | 50-65 | 90.1 | YES | 5000 µM (9.3 mg/ml) | 25 |
| HDM21B | RGKPFQLEAVFEANQNT | 48-64 | 82.6 | YES | 1000 µM (1.98 mg/ml) | 26 |
| HDM22A | EAVFEANQNTKTAK | 55-68 | 90.3 | YES | None | 27 |
| HDM23A | DGLEVDVPGIDPNACH | 76-88 | 66.7 | YES | None | 28 |
| HDM26A | DGVLACAIATHAKIR | 131-145 | | | 1000 µM (1.5 mg/ml) | 29 |
| HDM27 | AKIEIKASLDGLE | 67-79 | 65.9 | YES | 1000 µM (1.4 mg/ml) | 30 |
| HDM28 | KAVDEAVAAIEKS | 31-43 | 86.8 | YES | 1000 µM (1.3 mg/ml) | 31 |
| HDM29 | ETFDPMKVPDHSD | 44-56 | 84.7 | YES | None | 32 |
| HDM29A | ETFDPMKVPDHSDK | 44-57 | 91.7 | YES | None | 33 |
| HDM29B | KSETFDPMKVPDHSD | 42-56 | 92.5 | YES | 1000 µM (1.7 mg/ml) | 34 |
| HDM30 | DKFERHIGIIDLK | 56-68 | 81.4 | YES | 5000 µM (7.9 mg/ml) | 35 |
| HDM31 | IGIIDLKGELDMRN | 62-75 | | | 1000 µM (1.8 mg/ml) | 36 |
| HDM31A | HIGIIDLKGELDMRN | 61-75 | 66.4 | YES | 1000 µM (1.7 mg/ml) | 37 |
| HDM32 | IDLKGELDMRNIQ | 65-77 | 68.7 | YES | 5000 µM (7.7 mg/ml) | 38 |
| HDM32A | IDLKGELDMRNIQVR | 65-79 | 85.2 | YES | 5000 µM (9.0 mg/ml) | 39 |
| HDM33 | LDMRNIQVRGLKQ | 71-83 | 70.3 | YES | None | 40 |
| HDM34 | RNIQVRGLKQMKRVG | 74-88 | 74.7 | YES | None | 41 |
| HDM35 | RGLKQMKRVGDAN | 79-91 | 84.0 | YES | None | 42 |
| HDM36 | KRVGDANVKSEDG | 85-97 | 82.9 | YES | None | 43 |
| HDM37 | ANVKSEDGVVKAH | 90-102 | 76.5 | YES | None | 44 |
| HDM39 | DDVVSMEYDLAYK | 109-121 | 84.9 | NO* | None | 45 |
| HDM39A | HDDVVSMEYDLAYKL | 108-121 | 80.9 | YES | 1000 µM (1.8 mg/ml) | 46 |

TABLE 1A-continued

| Peptide | Sequence | Residues in parent molecule | % purity | Solubility test | Precipitation in assay | SEQ ID NO |
|---|---|---|---|---|---|---|
| HDM40A | VSMEYDLAYKLGDLH | 112-124 | 66.9 | YES | 1000 μM (1.8 mg/ml) | 47 |
| HDM48 | TAIFQDTVRAEMTK | 187-200 | 79.1 | YES | 1000 μM (1.6 mg/ml) | 48 |
| HDM49 | DTVRAEMTKVLAP | 192-204 | 69.5 | YES | None | 49 |

Peptides HDM01 to 116A are from Der p1; peptide HDM17 is from Der f1.
Peptides HDM19 to 26A are from Der p 2; peptide HDM37 is from Der f2.
Peptides HDM 28 to 49 are from Der p 7.
The sequence of Der p 1 from which the "residues in parent" positions are derived is the publically available sequence with NCBI Accession No. P08176.
The corresponding sequences for Der p 2 and Der p 7 are NCBI Accession Nos. P49278 and P49273, respectively.

TABLE 1B

| Peptide | DRB1*0101 | DRB1*0301 | DRB1*0401 | DRB1*0701 | DRB1*1101 | DRB1*1301 | DRB1*1501 | DQA1*0102 DQB1*0602 |
|---|---|---|---|---|---|---|---|---|
| HDM01 | | 19.23 | | 16 | | | | |
| HDM02 | | | | | | | 80 | 0.03 |
| HDM03C | | | | | | | | 0.16 |
| HDM05 | | | | | | | | |
| HDM06 | | | | | 30.36 | | | 0.86 |
| HDM07 | | | | | | | | |
| HDM08 | | | | | | | | |
| HDM09A | | | | 0.49 | 21.15 | | 200 | |
| HDM11 | | | | | | | | |
| HDM12 | | | | | | | | |
| HDM13 | | | | | | | | |
| HDM16A | | | | | | | | |
| HDM17 | | | | | | | | |
| HDM19 | | | | | | | | |
| HDM20 | | | | 1.1 | 28 | | 242.11 | 2.37 |
| HDM21 | 92 | | 11.15 | | 11.73 | | | |
| HDM21A | 200 | | 52.17 | | 10.27 | | | |
| HDM21B | 13.5 | | 0.78 | | 4.1 | | | |
| HDM22A | | | 328.6 | | 80 | | | |
| HDM23A | | 347 | | | | | | 0.76 |
| HDM26A | 42.3 | | | 16.28 | | | | 0.61 |
| HDM27 | | | | | | | | |
| HDM28 | | | | | | | | |
| HDM29 | | | | | | | | |
| HDM29A | | | | | | | | |
| HDM29B | | | | | | | | |
| HDM30 | | | | 6.2 | | | | |
| HDM31 | | | | | | | | |
| HDM31A | | | | | | | | |
| HDM32A | | | | | | | | |
| HDM33 | | | | 46.51 | 41.5 | 263.16 | | |
| HDM34 | | | | | 3.38 | 3.7 | 769.23 | |
| HDM35 | | | | | 1.26 | | | |
| HDM36 | | | | | | | | |
| HDM37 | | | | | | | | |
| HDM39 | | | | | | | | |
| HDM39A | | | 76.19 | 0.71 | | | | 0.1 |
| HDM40A | | | 2.29 | 6 | | | | |
| HDM48 | | 211.26 | 15.71 | 13.57 | | | | |
| HDM49 | | | | | | | 671.43 | 1.7 |
| HDM50 | | | | | | | | |
| HDM51 | | | 20.93 | 30.91 | | | | |

TABLE 1C (cytokine levels shown in pg/ml)

| Subject | Cytokine | HDM01 | HDM02 | HDM01A |
|---|---|---|---|---|
| 1 | Il-13 | 73 | 61 | 502 |
| | IFN-γ | 139 | 350 | 459 |
| 2 | Il-13 | 47 | 11 | 82 |
| | IFN-γ | 63 | 58 | 166 |
| 3 | Il-13 | 26 | 24 | 57 |
| | IFN-γ | 0 | 22 | 44 |

TABLE 1C-continued (cytokine levels shown in pg/ml)

| 4 | Il-13 | 81 | 37 | 135 |
| | IFN-γ | 31 | 0 | 44 |

| | | HDM34 | HDM35A | HDM207 |
|---|---|---|---|---|
| A | Il-13 | 0 | 0 | 11 |
| | IFN-γ | 0 | 0 | 72 |
| B | Il-13 | 0 | 0 | 169 |
| | IFN-γ | 26 | 20 | 341 |
| C | Il-13 | 4 | 25 | 676 |
| | IFN-γ | 113 | 247 | 609 |

Example 2

Grass Peptides

The Timothy Grass pollen allergen Phl p 5 Accession number 2003342A was analysed by methods analogous to those used in Example 1. A number of peptides sequences containing MHC Class II binding epitopes were identified. As above, the inventors were able to identify sequences comprising T cell epitopes which are close together in the overall protein sequence and therefore construct peptides which comprise overlapping epitopes.

A specific example is peptide Tim10B, which consists of residues 260 to 277 of Phl p5. This peptide was constructed by extending peptide Tim10C (residues 268 to 276 of Phl p5) to include a second, third and fourth T cell epitope (As confirmed in the further in silico analysis of Phl p 5 in Example 5). Production of IL13 in response to both peptides was measured as in Example 1. As shown in FIG. 1, Tim 10B demonstrates consistently greater cytokine production in the panel of subjects tested than the "single epitope" peptide Tim 10C.

| | Start position | | End position |
|---|---|---|---|
| Tim 10B | 260 | KYTVFETALKKAITAMSE (SEQ ID NO: 50) | 277 |
| Tim 10C | 268 | LKKAITAMS (SEQ ID NO: 51) | 276 |

Example 3

Peptides Comprising Multiple Epitopes from House Dust Mite Allergens der p1

The peptides listed in this Example were identified as containing T cell epitopes by an in silico MHC binding analysis. The peptides identified have strong affinities for the seven most common human MHC Class II HLA-DRB1* allotypes (covering in total around 63% of the allotypes found in the average Caucasian population).

In order to identify additional binding peptides in the House dust mite allergen der p 1, the inventors used an in silico approach known as "peptide threading" using the commercially available EpiMatrix algorithm (EpiVax Inc.) This is a bioinformatic analysis of peptides from a sequence for the potential to be accommodated within the binding groove of MHC class II HLA-DR molecules. EpiMatrix is a matrix-based algorithm that ranks amino acid segments from any polypeptide sequence by estimated probability of binding to each of the selected MHC molecules. (De Groot et al., AIDS Research and Human Retroviruses 13:539-41 (1997)). The procedure for developing matrix motifs was published by Schafer et al, 16 Vaccine 1998 (1998). In this Example, binding potential for HLA DR1, DR2, DR3, DR4, DR7, DR8, DR11, DR13 and DR15 is assessed. Putative MHC ligands are selected by scoring each 9-mer frame in a protein sequence. This score is derived by comparing the sequence of the 9-mer to the matrix of amino acid sequences known to bind to each MHC allele. Retrospective studies have demonstrated that EpiMatrix accurately predicts published MHC ligands (Jesdale et al., in Vaccines '97 (Cold Spring Harbor Press, Cold Spring Harbor, N.Y., 1997)). Successful prediction of peptides which bind to multiple MHC molecules has also been confirmed. The tables shown below show Epivax data for consecutive 9-mers in specific regions of each of the above allergen proteins. The regions are identified by "Frame start" and "Frame stop" values, which refer to the amino acid positions in the published sequences of each protein (the protein concerned and the relevant public database accession number for its sequence is shown at the top of each table). Flanking amino acids, added to stabilize the cluster during in-vitro testing, are shown underlined. Epivax also analysed hydrophobicity of peptides containing epitopes. Scores of greater than 1 are considered to be unsuitable for administration and/or manufacture.

The "Z-score" under each HLA allele indicates the potential of a given 9-mer to bind to that HLA allele. All scores in the Top 5% (Z-Score>=1.64) are considered "Hits". "Hits" in each 9 mer scoring above 1.64 are considered to comprise T cell epitopes (summarised in the "Hits" column). Thus the inventors were able to identify sequences which are close together in the overall protein sequence and therefore construct peptides which comprise overlapping epitopes. Examples of such sequences are provided beneath the Table for the relevant section of each protein. Where such sequences comprise greater than two epitopes, it will be appreciated that any fragment of these sequences comprising at least two overlapping epitopes would also be suitable.

| | | | \multicolumn{8}{c}{DER P 1: Accession No. P08176} | | |
|---|---|---|---|---|---|---|---|---|---|---|---|---|
| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
| 51 | LESVKYVQS | 59 | | | | | | | | 1.31 | 0 | 52 |
| 52 | ESVKYVQSN | 60 | | | | | | | | | 0 | 53 |
| 53 | SVKYVQSNG | 61 | | | | | 1.37 | | | | 0 | 54 |
| 54 | VKYVQSNGG | 62 | 1.43 | 1.84 | 1.97 | 1.63 | 1.53 | 1.28 | | 2.37 | 3 | 55 |

-continued

| | Sequence | Frame Stop | | | | | | | | | SEQ ID NO |
|---|---|---|---|---|---|---|---|---|---|---|---|
| 55 | KYVQSNGGA | 63 | | | | | | | | 0 | 56 |
| 56 | YVQSNGGAI | 64 | 2.24 | | 2.88 | 1.45 | | | 2.04 | 3 | 57 |
| 57 | VQSNGGAIN | 65 | 1.54 | | | | | | | 0 | 58 |
| 58 | QSNGGAINH | 66 | | | | | | | | 0 | 59 |

Suitable sequence HDM_1_ME1 = VKYVQSNGGAI (SEQ ID NO: 60) (residues 54-64) [epitope 1 = bold, epitope 2 = underlined]

DER P 1: Accession No. P08176

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 72 | LDEFKNRFL | 80 | | | | | | | | | 0 | 61 |
| 73 | DEFKNRFLM | 81 | | | | | 1.61 | 1.49 | | | 0 | 62 |
| 74 | EFKNRFLMS | 82 | | | | | | | | | 0 | 63 |
| 75 | FKNRFLMSA | 83 | | | | | 2.19 | 2.20 | | 2.28 | 3 | 64 |
| 76 | KNRFLMSAE | 84 | | | | | | | | | 0 | 65 |
| 77 | NRFLMSAEA | 85 | 2.21 | | 2.26 | | | 1.87 | | | 3 | 66 |
| 78 | RFLMSAEAF | 86 | | | | | | | | | 0 | 67 |
| 79 | FLMSAEAFE | 87 | 1.53 | | | | 1.56 | 1.28 | | | 0 | 68 |

Suitable sequence HDM_1_ME2 = FKNRFLMSAEA (SEQ ID NO: 69) (residues 75-85) [epitope 1 = bold, epitope 2 = underlined]

DER P 1: Accession No. P08176

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 114 | LRQMRTVTP | 122 | 2.44 | 2.22 | 2.66 | 1.37 | 1.77 | 2.45 | | 1.78 | 6 | 70 |
| 115 | RQMRTVTPI | 123 | | | | | | | | | 0 | 71 |
| 116 | QMRTVTPIR | 124 | | | | | | | | | 0 | 72 |
| 117 | MRTVTPIRM | 125 | 1.78 | 2.04 | 1.37 | 2.16 | | | 1.97 | 2.36 | 5 | 73 |
| 118 | RTVTPIRMQ | 126 | | | | | | | | | 0 | 74 |
| 119 | TVTPIRMQG | 127 | | | | | 1.28 | | | | 0 | 75 |
| 120 | VTPIRMQGG | 128 | | | | | | | | | 0 | 76 |
| 121 | TPIRMQGGC | 129 | | | | | | | | | 0 | 77 |
| 122 | PIRMQGGCG | 130 | 1.29 | | | | | | | | 0 | 78 |
| 123 | IRMQGGCGS | 131 | 2.85 | | 2.26 | 1.36 | | 1.98 | 2.22 | 1.65 | 5 | 79 |
| 124 | RMQGGCGSC | 132 | | | | | | | | | 0 | 80 |

Suitable sequence HDM_1_ME3 = LRQMRTVTP_IRMQGGCGS_ (SEQ ID NO: 81) (residues 114-131)
[epitope 1 = bold, epitope 2 = underlined, epitope 3 = italic]

DER P 1: Accession No. P08176

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 144 | AYLAYRNQS | 152 | | 1.95 | | | 1.39 | | | | 1 | 82 |
| 145 | YLAYRNQSL | 153 | 1.95 | | 1.52 | 1.81 | 1.81 | | | 3.13 | 4 | 83 |

-continued

| | | | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 146 | LAYRNQSLD | 154 | | | | 2.22 | | | | | 1 | 84 |
| 147 | AYRNQSLDL | 155 | 1.42 | | | 1.79 | | | | 1.67 | 2 | 85 |
| 148 | YRNQSLDLA | 156 | 1.52 | 1.80 | 1.87 | | | 1.69 | 1.36 | | 3 | 86 |
| 149 | RNQSLDLAE | 157 | | | | | | | | | 0 | 87 |

Suitable sequence HDM_1_ME4 = A*YLAYRNQSL*DLA (SEQ ID NO: 88) (residues 144-156)
[epitope 1 = bold, epitope 2 = underlined, epitope 3 = italic, epitope 4 = grey background, epitope 5 = last 9 amino acids]

DER P 1: Accession No. P08176

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 190 | SYYRYVARE | 198 | | | | | | | | | 0 | 89 |
| 191 | YYRYVAREQ | 199 | 1.96 | | 1.51 | 1.41 | 2.67 | 2.08 | 1.38 | 1.49 | 3 | 90 |
| 192 | YRYVAREQS | 200 | 1.90 | 2.57 | 1.85 | 1.90 | 2.92 | 3.69 | 2.31 | | 7 | 91 |
| 193 | RYVAREQSC | 201 | | | | | | | | | 0 | 92 |
| 194 | YVAREQSCR | 202 | | 1.29 | | 1.28 | 2.24 | | 1.68 | | 2 | 93 |
| 195 | VAREQSCRR | 203 | | | | | | | | | 0 | 94 |
| 196 | AREQSCRRP | 204 | | | | | | | | | 0 | 95 |
| 197 | REQSCRRPN | 205 | | | | | | | | | 0 | 96 |
| 198 | EQSCRRPNA | 206 | | | | | 2.03 | 1.29 | 1.71 | | 2 | 97 |
| 199 | QSCRRPNAQ | 207 | | | | | | | | | 0 | 98 |

Suitable sequence HDM_1_ME5 = YR*YVAREQ*SCRRPNA (SEQ ID NO: 99) (residues 191-206)
[epitope 1 = bold, epitope 2 = underlined, epitope 3 = italic, epitope 4 = grey background]

DER P 1: Accession No. P08176

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 298 | GYGYFAANI | 306 | | | | | | | | | 0 | 100 |
| 299 | YGYFAANID | 307 | 1.44 | | | | 2.74 | | 1.65 | | 2 | 101 |
| 300 | GYFAANIDL | 308 | 1.40 | | | 1.78 | | | 1.94 | | 2 | 102 |
| 301 | YFAANIDLM | 309 | | | 1.55 | 1.53 | | | | | 0 | 103 |
| 302 | FAANIDLMM | 310 | 1.41 | 1.50 | 1.87 | | | 1.46 | 1.74 | 1.83 | 3 | 104 |
| 303 | AANIDLMMI | 311 | | | | | | | | | 0 | 105 |
| 304 | ANIDLMMIE | 312 | | | | | | | | | 0 | 106 |

Suitable sequence HDM_1_ME6 = (SEQ ID NO: 107) (residues 299-310)
[epitope 1 = bold, epitope 2 = underlined, epitope 3 = italic, epitope 4 = grey background]

Example 4

Peptides Comprising Multiple Epitopes from Birch Pollen Allergens

The peptides listed in this Example were identified as in Example 3.

| | | | | BET V 1: Accession No. 1FM4A | | | | | | | | |
|---|---|---|---|---|---|---|---|---|---|---|---|---|
| Frame Start | Sequence | Frame Stop | Hydro- pho- bicity | DRB1* 0101 Z- Score | DRB1* 0301 Z- Score | DRB1* 0401 Z- Score | DRB1* 0701 Z- Score | DRB1* 0801 Z- Score | DRB1* 1101 Z- Score | DRB1* 1301 Z- Score | DRB1* 1501 Z- Score | Hits | SEQ ID NO |
| 14 | PAARMFKAF | 22 | .07 | | | | | | | | | 0 | 108 |
| 15 | AARMFKAFI | 23 | 1.00 | 1.41 | 1.86 | | | | 1.33 | 1.91 | | 2 | 109 |
| 16 | ARMFKAFIL | 24 | 1.22 | 2.26 | | | 1.99 | | | 1.68 | 3.25 | 4 | 110 |
| 17 | RMFKAFILD | 25 | .14 | | | | | | | | | 0 | 111 |

Suitable sequence BET_1_ME1 = AARMFKAFIL (SEQ ID NO: 112) (residues 15-24) [epitope 1 = bold, epitope 2 = underlined]

| | | | | BET V 1: CAA04829.1 | | | | | | | | |
|---|---|---|---|---|---|---|---|---|---|---|---|---|
| Frame Start | Sequence | Frame Stop | Hydro- pho- bicity | DRB1* 0101 Z- Score | DRB1* 0301 Z- Score | DRB1* 0401 Z- Score | DRB1* 0701 Z- Score | DRB1* 0801 Z- Score | DRB1* 1101 Z- Score | DRB1* 1301 Z- Score | DRB1* 1501 Z- Score | Hits | SEQ ID NO |
| 2 | VFNYEIGAT | 10 | .09 | | | | | | | | 2.11 | 1 | 113 |
| 3 | FNYEIGATS | 11 | -.12 | 2.27 | | 2.09 | | | 1.46 | | | 2 | 114 |
| 4 | NYEIGATSV | 12 | .03 | | | | | | | | | 0 | 115 |
| 5 | YEIGATSVI | 13 | .92 | 2.11 | 1.91 | 1.87 | 1.77 | | | | 1.69 | 5 | 116 |
| 6 | EIGATSVIP | 14 | .19 | | | | | | | | | 0 | 117 |
| 7 | IGATSVIPA | 15 | .32 | | | 1.90 | 1.42 | | | | 1.45 | 1 | 118 |
| 8 | GATSVIPAA | 16 | .25 | | | | | | | | | 0 | 119 |

Suitable sequence BET_1_ME2 = VFNYEIGATSVIPA (SEQ ID NO: 120) (residues 2-15) [epitope 1 = bold, epitope 2 = underlined, epitope 3 = italic, epitope 4 = grey background]

| | | | BET V 1: Accession No. P43186 | | | | | | | | |
|---|---|---|---|---|---|---|---|---|---|---|---|---|
| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
| 63 | SPFKYVKER | 71 | -.86 | -1.47 | -1.35 | -.95 | -.31 | -1.42 | -.48 | | 0 | 121 |
| 64 | PFKYVKERV | 72 | -.85 | .85 | -1.38 | -.65 | .85 | -.16 | 1.15 | .85 | 0 | 122 |
| 65 | FKYVKERVD | 73 | .71 | .71 | .05 | .62 | 2.34 | 1.79 | 1.15 | .15 | 2 | 123 |
| 66 | KYVKERVDE | 74 | -.77 | .51 | -1.53 | -.65 | 2.29 | .47 | .86 | -.47 | 1 | 124 |
| 67 | YVKERVDEV | 75 | 1.89 | .79 | 2.27 | 1.72 | .09 | .42 | -.83 | -.09 | 3 | 125 |
| 68 | VKERVDEVD | 76 | -1.55 | -.39 | -.95 | -.52 | 1.50 | -.80 | .28 | .19 | 0 | 126 |
| 69 | KERVDEVDH | 77 | -.75 | -.15 | .00 | -.26 | .20 | .99 | -.28 | -.35 | 0 | 127 |

Suitable sequence BET_1_ME3 = FKYVKERVDEV (SEQ ID NO: 314) (residues 65-75) [epitope 1 = bold, epitope 2 = underlined, epitope 3 = italic]

| | | | BET V 1: Accession No. P43186 | | | | | | | | |
|---|---|---|---|---|---|---|---|---|---|---|---|---|
| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
| 79 | NFKYSYSMI | 87 | -.16 | -.59 | -1.04 | -.25 | -.18 | -1.28 | -.47 | 1.09 | 0 | 128 |
| 80 | FKYSYSMIE | 88 | .81 | .41 | 1.87 | 1.30 | 1.46 | 1.32 | -.15 | 1.43 | 1 | 129 |
| 81 | KYSYSMIEG | 89 | -1.13 | -.38 | -.95 | -1.37 | .65 | -1.20 | .13 | .41 | 0 | 130 |
| 82 | YSYSMIEGG | 90 | .26 | .69 | 1.34 | 1.35 | .56 | .82 | -.05 | -.51 | 0 | 131 |
| 83 | SYSMIEGGA | 91 | .21 | .42 | -.24 | -.94 | .28 | 1.51 | -1.01 | .48 | 0 | 132 |

| | | | | | | | | | | | |
|---|---|---|---|---|---|---|---|---|---|---|---|
| 84 | YSMIEGGAL | 92 | | .11 | .67 | | .28 | 1.26 | −.63 | 1.93 | 3 | 133 |
| 85 | SMIEGGALG | 93 | 1.26 | .23 | .75 | −1.29 | .23 | .14 | −.86 | −.68 | 0 | 134 |

Suitable sequence BET_1_ME4 = FKYSYSMIEGGAL (SEQ ID NO: 135) (residues 80-92)
[epitope 1 = bold, epitope 2 = underlined]

BET V 1: Accession No. P43177

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 143 | ALLRAVESY | 151 | −.81 | .35 | −.34 | .29 | −.06 | −.84 | 1.00 | −.32 | 0 | 136 |
| 144 | LLRAVESYL | 152 | 1.26 | 1.52 | .46 | 1.47 | .78 | .46 | .90 | 1.73 | 1 | 137 |
| 145 | LRAVESYLL | 153 | | 1.91 | 1.66 | | 1.36 | 1.73 | 1.51 | | 6 | 138 |
| 146 | RAVESYLLA | 154 | .65 | −.01 | .83 | −.65 | −.88 | −.23 | −.76 | .09 | 0 | 139 |
| 147 | AVESYLLAH | 155 | −1.28 | −.03 | .05 | −.69 | −.71 | .28 | −.36 | −.38 | 0 | 140 |
| 148 | VESYLLAHS | 156 | −.53 | .94 | −.18 | −2.13 | 1.08 | .59 | 1.28 | 1.06 | 0 | 141 |
| 149 | ESYLLAHSD | 157 | .75 | −1.02 | .25 | .44 | 1.28 | .13 | −.18 | −1.41 | 0 | 142 |
| 150 | SYLLAHSDA | 158 | .44 | .48 | .81 | −.78 | .66 | 1.33 | .17 | .28 | 0 | 143 |
| 151 | YLLAHSDAY | 159 | 1.61 | 1.73 | 1.83 | 1.48 | .14 | .13 | .88 | .83 | 2 | 144 |

Suitable sequence BET_1_ME5 = LLRAVESYLL*AHSDAY* (SEQ ID NO: 145) (residues 144-151)
[epitope 1 = bold, epitope 2 = underlined, epitope 3 = italic]

Example 5

Peptides Comprising Multiple Epitopes from Timothy Grass Pollen Allergens

The peptides listed in this Example were identified as in Example 3.

Phl P 1: Accession No. P43213

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 142 | GDEQKLRSA | 150 | −.62 | −.54 | −1.14 | −2.14 | −1.22 | −.15 | .20 | −1.31 | 0 | 146 |
| 143 | DEQKLRSAG | 151 | −.71 | .34 | −1.29 | −1.40 | 1.88 | .74 | .42 | −.25 | 1 | 147 |
| 144 | EQKLRSAGE | 152 | 1.04 | .00 | 1.00 | −.03 | 1.42 | .61 | −.03 | −.85 | 0 | 148 |
| 145 | QKLRSAGEL | 153 | .85 | .25 | −.69 | 2.11 | 1.23 | .54 | .74 | 2.14 | 2 | 149 |
| 146 | KLRSAGELE | 154 | −.07 | −.03 | −.17 | .56 | −.13 | −.63 | −.74 | −.84 | 0 | 150 |
| 147 | LRSAGELEL | 155 | 1.80 | 1.91 | 1.14 | 2.02 | 1.17 | .86 | 1.89 | 2.40 | 5 | 151 |
| 148 | RSAGELELQ | 156 | −1.14 | .12 | −.35 | −.95 | −.18 | −.28 | −1.20 | −.57 | 0 | 152 |

Suitable sequence Phl_1_ME1 = DEQKLRSAGELEL (SEQ ID NO: 153) (residues 143-155)
[epitope 1 = bold, epitope 2 = underlined, epitope 3 = italic]

Phl P 1: Accession No. P43213

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 181 | NYLALLVKY | 189 | .08 | 1.23 | −.26 | −.23 | −.14 | −.20 | .89 | .20 | 0 | 154 |
| 182 | YLALLVKYV | 190 | 2.74 | −.32 | 1.97 | 2.80 | 1.32 | 1.50 | .23 | .48 | 3 | 155 |

-continued

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 183 | LALLVKYVN | 191 | 1.27 | 1.27 | -.08 | -.19 | 2.09 | 1.78 | .99 | .97 | 2 | 156 |
| 184 | ALLVKYVNG | 192 | .65 | .48 | .31 | .38 | .43 | .57 | .33 | .98 | 0 | 157 |

Suitable sequence Phl_1_ME2 = YLALLVKYVN (SEQ ID NO: 158) (residues 182-191) [epitope 1 = bold, epitope 2 = underlined]

Phl P 1: Accession No. P43213

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 215 | SWGAIWRID | 223 | -.68 | -1.26 | -1.15 | -.21 | .08 | -1.12 | -.91 | -1.80 | 0 | 159 |
| 216 | WGAIWRIDT | 224 | 1.95 | 1.28 | 1.03 | 2.16 | 1.37 | 1.93 | .83 | 1.35 | 3 | 160 |
| 217 | GAIWRIDTP | 225 | -1.73 | -1.00 | .04 | -.45 | -1.91 | -.96 | -.46 | -1.40 | 0 | 161 |
| 218 | AIWRIDTPD | 226 | -1.52 | -1.01 | -1.25 | -1.34 | .35 | -1.57 | -.66 | .32 | 0 | 162 |
| 219 | IWRIDTPDK | 227 | .79 | .96 | 1.81 | .21 | .13 | 1.44 | .52 | .69 | 1 | 163 |
| 220 | WRIDTPDKL | 228 | 1.97 | 2.87 | 2.36 | 2.86 | 1.13 | .63 | .28 | 1.09 | 4 | 164 |
| 221 | RIDTPDKLT | 229 | -.75 | -2.52 | -1.02 | -.36 | -1.45 | -1.27 | -1.42 | -.12 | 0 | 165 |

Suitable sequence Phl_1_ME3 = WGA_IWRIDTPDKL_ (SEQ ID NO: 166) (residues 216-228) [epitope 1 = bold, epitope 2 = underlined, epitope 3 = italic]

Phl P 1: Accession No. P43213

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 142 | GDEQKLRSA | 150 | -.62 | -.54 | -1.14 | -2.14 | -1.22 | -.15 | .20 | -1.31 | 0 | 167 |
| 143 | DEQKLRSAG | 151 | -.71 | .34 | -1.29 | -1.40 | 1.88 | .74 | .42 | -.25 | 1 | 168 |
| 144 | EQKLRSAGE | 152 | 1.04 | .00 | 1.00 | -.03 | 1.42 | .61 | -.03 | -.85 | 0 | 169 |
| 145 | QKLRSAGEL | 153 | .85 | .25 | -.69 | 2.11 | 1.23 | .54 | .74 | 2.14 | 2 | 170 |
| 146 | KLRSAGELE | 154 | -.07 | -.03 | -.17 | .56 | -.13 | -.63 | -.74 | -.84 | 0 | 171 |
| 147 | LRSAGELEL | 155 | 1.80 | 1.91 | 1.14 | 2.02 | 1.17 | .86 | 1.89 | 2.40 | 5 | 172 |
| 148 | RSAGELELQ | 156 | -1.14 | .12 | -.35 | -.95 | -.18 | -.28 | -1.20 | -.57 | 0 | 173 |

Suitable sequence Phl_1_ME4 = (residues 143-155) [epitope 1 = bold, epitope 2 = underlined, epitope 3 = italic]

Phl P 5: Accession No. 2003342A

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 69 | KINAGFKAA | 77 | .34 | -.85 | .04 | -.03 | -.48 | -.24 | -.55 | -.41 | 0 | 174 |
| 70 | INAGFKAAL | 78 | 1.39 | 2.68 | -.06 | -.20 | 1.06 | 1.08 | 1.32 | 1.38 | 1 | 175 |
| 71 | NAGFKAALA | 79 | 1.10 | -.02 | .67 | -1.09 | .41 | .72 | .23 | .50 | 0 | 176 |
| 72 | AGFKAALAA | 80 | .67 | .42 | .52 | -.36 | .93 | .68 | 1.11 | 1.15 | 0 | 177 |
| 73 | GFKAALAAA | 81 | .26 | .83 | .22 | -1.54 | .06 | .51 | .51 | -.07 | 0 | 178 |
| 74 | FKAALAAAA | 82 | 3.20 | 2.30 | 2.70 | 1.16 | 1.80 | 2.26 | 1.93 | 1.53 | 6 | 179 |
| 75 | KAALAAAAG | 83 | 1.74 | .29 | 1.03 | -.47 | 1.34 | 1.29 | .25 | -.64 | 1 | 180 |
| 76 | AALAAAAGV | 84 | 1.74 | .84 | .69 | .63 | .24 | .26 | .52 | .51 | 1 | 181 |
| 77 | ALAAAAGVQ | 85 | 1.05 | .43 | .84 | 1.31 | 1.09 | 1.08 | -.09 | 1.39 | 0 | 182 |

Suitable sequence Phl_5_ME1 = INAG_FKAAL_AAAAGV (SEQ ID NO: 183) (residues 70-84) [epitope 1 = bold, epitope 2 = underlined, epitope 3 = italic, epitope 4 = grey background]

Phl P 5: Accession No. 2003342A

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 89 | KYRTFVATF | 97 | .31 | −.73 | .91 | .36 | −.58 | −.03 | −.25 | −.91 | 0 | 184 |
| 90 | YRTFVATFG | 98 | 2.56 | 1.50 | 2.20 | 1.06 | 1.84 | 1.45 | 1.32 | 2.45 | 4 | 185 |
| 91 | RTFVATFGA | 99 | 1.13 | .96 | 1.02 | .76 | .59 | 1.08 | 1.23 | 1.74 | 1 | 186 |
| 92 | TFVATFGAA | 100 | −.30 | −.25 | −.40 | −.34 | −.54 | −.03 | −.74 | .03 | 0 | 315 |
| 93 | FVATFGAAS | 101 | 2.41 | .66 | 2.30 | .87 | 1.30 | 1.96 | 1.09 | 1.34 | 3 | 187 |
| 94 | VATFGAASN | 102 | 1.00 | .22 | .20 | −.81 | .98 | .25 | .45 | 1.07 | 0 | 188 |

Suitable sequence Phl_5_ME2 = YRTFVATFGA*AS* (SEQ ID NO: 189) (residues 90-101)
[epitope 1 = bold, epitope 2 = underlined, epitope 3 = italic]

Phl P 5: Accession No. 2003342A

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 126 | TSKLDAAYK | 134 | .83 | −.45 | .60 | −.78 | .26 | .86 | −.47 | −1.50 | 0 | 190 |
| 127 | SKLDAAYKL | 135 | 1.53 | 2.11 | 1.00 | 1.99 | .61 | .03 | −.16 | 1.07 | 2 | 191 |
| 128 | KLDAAYKLA | 136 | .44 | −1.45 | −.32 | −.26 | −1.06 | −.83 | −1.13 | −.32 | 0 | 192 |
| 129 | LDAAYKLAY | 137 | .53 | 2.43 | .00 | −.42 | .69 | .59 | 2.39 | 1.24 | 2 | 193 |
| 130 | DAAYKLAYK | 138 | −1.58 | −.35 | −1.07 | −2.56 | .28 | −.30 | .03 | −.49 | 0 | 194 |
| 131 | AAYKLAYKT | 139 | .54 | −.12 | −.68 | −.01 | .70 | .09 | .05 | .80 | 0 | 195 |
| 132 | AYKLAYKTA | 140 | 1.09 | −.95 | .16 | .08 | −.27 | .33 | −.38 | −.04 | 0 | 196 |
| 133 | YKLAYKTAE | 141 | 1.65 | 2.54 | 1.18 | .69 | 2.43 | 1.44 | 1.79 | 1.30 | 4 | 197 |
| 134 | KLAYKTAEG | 142 | .38 | .66 | .85 | −1.04 | 1.73 | .49 | 1.01 | .72 | 1 | 198 |
| 135 | LAYKTAEGA | 143 | .64 | 1.05 | .61 | .12 | 1.26 | .93 | 1.35 | .61 | 0 | 199 |

Suitable sequence Phl_5_ME3 = SKLDAAYKLAY*KTA*EG (SEQ ID NO: 200) (residues 127-142)
[epitope 1 = bold, epitope 2 = underlined, epitope 3 = italic, epitope 4 = grey background]

Phl P 5: Accession No. 2003342A

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 192 | KVDAAFKVA | 200 | .00 | −1.20 | −.30 | −.37 | −.82 | −.58 | −.89 | −.73 | 0 | 201 |
| 193 | VDAAFKVAA | 201 | .90 | 2.21 | .46 | −.23 | .91 | 1.28 | 1.84 | 1.53 | 2 | 202 |
| 194 | DAAFKVAAT | 202 | .48 | −.86 | .42 | −.65 | −.18 | −.26 | −.59 | .03 | 0 | 203 |
| 195 | AAFKVAATA | 203 | .70 | .50 | .26 | −1.24 | 1.02 | .90 | .86 | .09 | 0 | 204 |
| 196 | AFKVAATAA | 204 | 1.13 | .81 | .68 | −.03 | −.78 | .50 | .28 | 1.14 | 0 | 205 |
| 197 | FKVAATAAN | 205 | 2.18 | 1.37 | 2.22 | .91 | 1.95 | 1.38 | 1.03 | .89 | 3 | 206 |
| 198 | KVAATAANA | 206 | 2.23 | 1.24 | 1.72 | .20 | .84 | 1.29 | .91 | .57 | 2 | 207 |
| 199 | VAATAANAA | 207 | 1.63 | 1.24 | 1.78 | 1.50 | .63 | .94 | 1.23 | 2.07 | 2 | 208 |
| 200 | AATAANAAP | 208 | .33 | .10 | .73 | −1.15 | −.38 | −.33 | −.20 | −.12 | 0 | 209 |

Suitable sequence Phl_5_ME4 = VDAAFKV*AA*TAANAA (SEQ ID NO: 210) (residues 193-207)
[epitope 1= bold, epitope 2 = underlined, epitope 3 = italic, epitope 4 = grey background]

Phl P 5: Accession No. 2003342A

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 234 | SYKFIPALE | 242 | .10 | -.05 | -.16 | -1.19 | 1.21 | -.12 | .19 | -.10 | 0 | 211 |
| 235 | YKFIPALEA | 243 | 3.30 | 1.48 | 3.23 | 2.19 | 1.37 | 2.79 | 1.24 | 2.12 | 5 | 212 |
| 236 | KFIPALEAA | 244 | -1.07 | -.16 | -.36 | -.59 | -.58 | -.16 | .31 | -.52 | 0 | 213 |
| 237 | FIPALEAAV | 245 | 1.33 | 1.18 | .76 | .60 | .94 | .96 | .84 | .47 | 0 | 214 |
| 238 | IPALEAAVK | 246 | 1.26 | .59 | 1.04 | -.36 | .69 | 1.29 | .54 | -.55 | 0 | 215 |
| 239 | PALEAAVKQ | 247 | 1.37 | .40 | 1.65 | .90 | .74 | .92 | -.70 | .20 | 1 | 216 |
| 240 | ALEAAVKQA | 248 | .50 | -.89 | .43 | -.03 | -.94 | -.71 | -.58 | -.17 | 0 | 217 |
| 241 | LEAAVKQAY | 249 | .95 | 2.96 | .15 | -.19 | 1.07 | .99 | 1.71 | 1.41 | 2 | 218 |
| 242 | EAAVKQAYA | 250 | .83 | .63 | .22 | -.67 | .51 | 1.62 | .47 | -.66 | 0 | 219 |

Suitable sequence Phl_5_ME5 = YKFIP<u>ALEA</u>*AVKQAY* (SEQ ID NO: 220) (residues 235-249)
[epitope 1 = bold, epitope 2 = underlined, epitope 3 = italic]

Phl P 5: Accession No. 2003342A

| Frame Start | Sequence | Frame Stop | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|
| 260 | KYTVFETAL | 268 | .18 | .07 | -.69 | .38 | -.89 | -.24 | -.44 | .55 | 0 | 221 |
| 261 | YTVFETALK | 269 | 1.27 | .76 | 2.24 | .19 | 1.77 | 1.87 | .98 | .70 | 3 | 222 |
| 262 | TVFETALKK | 270 | 1.34 | .66 | 1.84 | .52 | .44 | .87 | -.11 | .09 | 1 | 223 |
| 263 | VFETALKKA | 271 | -.26 | -.71 | -.35 | -.32 | -.39 | .18 | .33 | .53 | 0 | 224 |
| 264 | FETALKKAI | 272 | 1.66 | 1.28 | .09 | 1.25 | 1.50 | 1.16 | 1.52 | 1.32 | 1 | 225 |
| 265 | ETALKKAIT | 273 | 1.19 | .67 | .08 | -.69 | 1.38 | 1.82 | .62 | -.43 | 1 | 226 |
| 266 | TALKKAITA | 274 | .51 | -.01 | .23 | -.09 | .89 | .16 | .48 | .62 | 0 | 227 |
| 267 | ALKKAITAM | 275 | -.55 | .17 | -.37 | -.50 | -.39 | -.70 | .15 | .32 | 0 | 228 |
| 268 | LKKAITAMS | 276 | 2.13 | 2.14 | 2.85 | .58 | 1.67 | 2.00 | 1.77 | 1.25 | 6 | 229 |
| 269 | KKAITAMSE | 277 | .70 | -.73 | .82 | -.09 | .93 | .99 | -1.11 | .57 | 0 | 230 |

Suitable sequence Phl_5_ME6 = YTV<i>FETALKK</i>*AI*TAMS (SEQ ID NO: 231) (residues 261-276)
[epitope 1 = bold, epitope 2 = underlined, epitope 3 = italic, epitope 4 = grey background, epitope 5 = last 9 amino acids]

Example 6

Peptides Comprising Multiple Epitopes from *Alternaria* Allergens

The peptides listed in this Example were identified as in Example 3.

ALT A 1: Accession No. AAD00097

| Frame Start | Sequence | Frame Stop | Hydro-pho-bicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 40 | QLLMLSAKR | 48 | .06 | 1.52 | | | | | | | | 0 | 232 |
| 41 | LLMLSAKRM | 49 | .87 | 2.83 | | 1.44 | 2.17 | 1.46 | 1.71 | 1.47 | 1.33 | 3 | 233 |

-continued

| Frame Start | Sequence | Frame Stop | Hydro-pho-bicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 42 | LMLSAKRMK | 50 | .01 | | | 1.62 | | | | 2.04 | 1.49 | 1 | 234 |
| 43 | MLSAKRMKV | 51 | .06 | 1.29 | 1.49 | | | 1.65 | 1.83 | 1.28 | 2.34 | 3 | 235 |
| 44 | LSAKRMKVA | 52 | .04 | | | | | | | | | 0 | 236 |
| 45 | SAKRMKVAF | 53 | −.07 | | | | | | | | | 0 | 237 |
| 46 | AKRMKVAFK | 54 | −.41 | | | 1.67 | | | 1.38 | | | 1 | 238 |
| 47 | KRMKVAFKL | 55 | −.19 | 1.81 | | | 1.79 | 1.81 | | 1.37 | 1.96 | 4 | 239 |
| 48 | RMKVAFKLD | 56 | −.14 | | | | | | | | | 0 | 240 |
| 49 | MKVAFKLDI | 57 | .86 | 1.82 | 2.87 | | | 1.74 | 1.49 | 2.82 | 2.60 | 5 | 241 |
| 50 | KVAFKLDIE | 58 | .05 | | | | | | | | | 0 | 242 |

Suitable sequence ALT_1_ME1 = LLMLSAKRMKV (SEQ ID NO: 234) (residues 41-51) [epitope 1 = bold, epitope 2 = underlined, epitope 3 = italic]
Suitable sequence ALT_1_ME2 = AKR*MKVAFKL*DI (SEQ ID NO: 244) (residues 46-57) [epitope 1 = bold, epitope 2 = underlined, epitope 3 = italic]
Sequences ALT_1_ME1 and ALT_1_ME2 may also be combined to create
ALT_1_ME3 = LLMLSAKRMKVAFKLDI (SEQ ID NO: 245) containing 6 epitopes ALT A 1: Accession No. AAD00097

| Frame Start | Sequence | Frame Stop | Hydro-pho-bicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 77 | GFKRCLQFT | 85 | −.03 | | | | | | | | | 0 | 246 |
| 78 | FKRCLQFTL | 86 | .34 | 1.63 | | | 1.84 | 2.35 | | 1.96 | | 3 | 247 |
| 79 | KRCLQFTLY | 87 | −.11 | | | | | | | | | 0 | 248 |
| 80 | RCLQFTLYR | 88 | −.18 | | | | | | | 1.31 | | 0 | 249 |
| 81 | CLQFTLYRP | 89 | .14 | | | | | | | | | 0 | 250 |
| 82 | LQFTLYRPR | 90 | −.63 | 1.31 | | | | | | 1.73 | | 1 | 251 |
| 83 | QFTLYRPRD | 91 | −1.44 | | | | | 2.03 | | | | 1 | 252 |
| 84 | FTLYRPRDL | 92 | −.63 | 1.92 | | | 1.65 | 1.57 | | 1.92 | 1.97 | 4 | 253 |
| 85 | TLYRPRDLL | 93 | −.52 | | | | | | | | | 0 | 254 |
| 86 | LYRPRDLLS | 94 | −.53 | | | 1.28 | | | | 1.71 | | 1 | 255 |
| 87 | YRPRDLLSL | 95 | −.53 | 1.37 | | | 2.34 | 2.46 | 1.58 | 1.93 | 2.44 | 4 | 256 |
| 88 | RPRDLLSLL | 96 | .01 | | | | | | | | | 0 | 257 |

Suitable sequence ALT_1_ME4 = FKRCLQFTLYRPRDL (SEQ ID NO: 258) (residues 78-92) [epitope 1 = bold, epitope 2 = underlined, epitope 3 = italic, epitope 4 = grey background]
Suitable sequence ALT_1_ME5 = FTLYRPRDLLSL (SEQ ID NO: 259) (residues 84-95) [epitope 1 = bold, epitope 2 = underlined, epitope 3 = italic]
Sequences ALT_1_ME4 and ALT_1_ME5 may also be combined to create
ALT_1_ME6 = FKRCLQFTLYRPRDLLSL (SEQ ID NO: 260) (residues 78-95) containing 6 epitopes ALT A 2: Accession No. AAM90320

| Frame Start | Sequence | Frame Stop | Hydro-pho-bicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 53 | TYYNSLGFN | 61 | −.12 | | | | | | | | | 0 | 261 |
| 54 | YYNSLGFNI | 62 | .03 | 2.47 | | | 2.66 | | | 1.94 | | 3 | 262 |
| 55 | YNSLGFNIK | 63 | −.26 | | | 1.48 | | | | | | 0 | 263 |
| 56 | NSLGFNIKA | 64 | .09 | | | | | | | | | 0 | 264 |

-continued

| | Sequence | Frame Stop | Hydro-phobicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 57 | SLGFNIKAT | 65 | .40 | | | | | | | | | 0 | 265 |
| 58 | LGFNIKATN | 66 | .10 | | 1.72 | | | 2.04 | 1.82 | 1.62 | | 3 | 266 |
| 59 | GFNIKATNG | 67 | -.37 | | | | | | | | | 0 | 267 |
| 60 | FNIKATNGG | 68 | -.37 | | 1.58 | 1.92 | | 2.97 | 1.50 | 1.48 | 1.55 | 2 | 268 |
| 61 | NIKATNGGT | 69 | -.76 | | | | | | | | | 0 | 269 |
| 62 | IKATNGGTL | 70 | .06 | 1.96 | | 2.71 | | | | | 2.94 | 3 | 270 |
| 63 | KATNGGTLD | 71 | -.18 | | | | | | | | | 0 | 271 |

Suitable sequence ALT_1_ME7 = (SEQ ID NO: 272) (residues 54-70) [epitope 1 = bold, epitope 2 = underlined, epitope 3 = italic, epitope 4 = grey background,]

ALT A 2: Accession No. AAM90320

| Frame Start | Sequence | Frame Stop | Hydro-phobicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 115 | DITYVATAT | 123 | .13 | | | | | | | | | 0 | 273 |
| 116 | ITYVATATL | 124 | 1.41 | 2.04 | 1.81 | 1.54 | 1.65 | | 1.73 | 1.62 | 1.59 | 4 | 274 |
| 117 | TYVATATLP | 125 | .73 | | | | | | | | | 0 | 275 |
| 118 | YVATATLPN | 126 | .42 | 2.17 | | 2.84 | 2.45 | 2.11 | 1.74 | | 1.92 | 6 | 276 |
| 119 | VATATLPNY | 127 | .42 | | 2.10 | | | | | 1.87 | | 2 | 277 |
| 120 | ATATLPNYC | 128 | .23 | | | | | | | | | 0 | 278 |

Suitable sequence ALT_1_ME8 = ITY*VATATLPN*Y (SEQ ID NO: 279) (residues 116-127) [epitope 1 = bold, epitope 2 = underlined, epitope 3 = italic]

ALT A 2: Accession No. AAM90320

| Frame Start | Sequence | Frame Stop | Hydro-phobicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 146 | AYITLVTLP | 154 | .33 | | | | | | | | | 0 | 280 |
| 147 | YITLVTLPK | 155 | .90 | 1.80 | | 2.79 | 1.47 | 1.67 | 2.15 | | | 4 | 281 |
| 148 | ITLVTLPKS | 156 | .96 | | 1.70 | | | | 2.21 | 1.63 | 1.66 | 3 | 282 |
| 149 | TLVTLPKSS | 157 | .08 | | | | | | | | | 0 | 283 |

Suitable sequence ALT_1_ME9 = YITLVTLPKS (SEQ ID NO: 284) (residues 147-156) [epitope 1 = bold, epitope 2 = underlined]

ALT A 6: Accession No. Q9HDT3

| Frame Start | Sequence | Frame Stop | Hydro-phobicity | DRB1* 0101 Z-Score | DRB1* 0301 Z-Score | DRB1* 0401 Z-Score | DRB1* 0701 Z-Score | DRB1* 0801 Z-Score | DRB1* 1101 Z-Score | DRB1* 1301 Z-Score | DRB1* 1501 Z-Score | Hits | SEQ ID NO |
|---|---|---|---|---|---|---|---|---|---|---|---|---|---|
| 188 | EVYQKLKAL | 196 | -.06 | | | | | | | | | 0 | 285 |
| 189 | VYQKLKALA | 197 | .31 | | 1.90 | | | 2.13 | 2.02 | 2.21 | | 4 | 286 |
| 190 | YQKLKALAK | 198 | -.59 | 2.57 | | 2.63 | 1.84 | 1.92 | 2.40 | | | 5 | 287 |
| 191 | QKLKALAKK | 199 | -.88 | | | | | | | | | 0 | 288 |
| 192 | KLKALAKKT | 200 | -.57 | 1.74 | | | 1.47 | | | | | 1 | 289 |

| | | | | | | | | | | | |
|---|---|---|---|---|---|---|---|---|---|---|---|
| 193 | LKALAKKTY | 201 | -.28 | 1.49 | 1.97 | | 1.69 | 1.87 | 2.45 | | 4 | 290 |
| 194 | KALAKKTY<u>G</u> | 202 | -.16 | | 1.44 | | | | | | 0 | 291 |

Suitable sequence ALT_1_ME10 = (SEQ ID NO: 292) (residues 189-201) [epitope 1 = bold, epitope 2 = underlined, epitope 3 = italic, epitope 4 = grey background]

ALT A 6: Accession No. Q9HDT3

| Frame Start | Sequence | Frame Stop | Hydro-pho-bicity | DRB1*0101 Z-Score | DRB1*0301 Z-Score | DRB1*0401 Z-Score | DRB1*0701 Z-Score | DRB1*0801 Z-Score | DRB1*1101 Z-Score | DRB1*1301 Z-Score | DRB1*1501 Z-Score | Hits | SEQ ID NO |
|---|---|---|---|---|---|---|---|---|---|---|---|---|---|
| 236 | <u>G</u>YTGKIKIA | 244 | .00 | | | | | | | | | 0 | 293 |
| 237 | YTGKIKIAM | 245 | .28 | | 1.57 | | | 2.68 | 1.60 | 2.02 | | 2 | 294 |
| 238 | TGKIKIAMD | 246 | .03 | | | | | | | | | 0 | 295 |
| 239 | GKIKIAMDV | 247 | .58 | | | | | 1.40 | | | 1.65 | 1 | 296 |
| 240 | KIKIAMDVA | 248 | .82 | | | | | | | | | 0 | 297 |
| 241 | IKIAMDVAS | 249 | 1.17 | 1.56 | 1.88 | 2.15 | | | 1.39 | 1.52 | 2.28 | 3 | 298 |
| 242 | KIAMDVASS | 250 | .58 | 1.53 | | 1.92 | | | 1.63 | | | 1 | 299 |
| 243 | IAMDVASSE | 251 | .62 | | 2.53 | | | 1.54 | | | | 1 | 300 |
| 244 | AMDVASSE<u>F</u> | 252 | .09 | | | | | | | | | 0 | 301 |

Suitable sequence ALT_1_ME11 = YTGK*IKIAMDV*<u>AS</u>SE (SEQ ID NO: 302) (residues 237-251)
[epitope 1 = bold, epitope 2 = underlined, epitope 3 = italic, epitope 4 = grey background, epitope 5 = last nine amino acids]

ALT A 6: Accession No. Q9HDT3

| Frame Start | Sequence | Frame Stop | Hydro-pho-bicity | DRB1*0101 Z-Score | DRB1*0301 Z-Score | DRB1*0401 Z-Score | DRB1*0701 Z-Score | DRB1*0801 Z-Score | DRB1*1101 Z-Score | DRB1*1301 Z-Score | DRB1*1501 Z-Score | Hits | SEQ ID NO |
|---|---|---|---|---|---|---|---|---|---|---|---|---|---|
| 364 | <u>A</u>FGAGWGVM | 372 | .25 | | | | | | | | | 0 | 303 |
| 365 | FGAGWGVMV | 373 | 1.42 | 2.11 | | | 1.55 | | | | 1.90 | 2 | 304 |
| 366 | GAGWGVMVS | 374 | 1.02 | | | 1.47 | | | | | | 0 | 305 |
| 367 | AGWGVMVSH | 375 | .71 | | | | | | | | | 0 | 306 |
| 368 | GWGVMVSHR | 376 | .01 | | | | | | | | | 0 | 307 |
| 369 | WGVMVSHRS | 377 | -.03 | 2.54 | | 3.16 | 1.50 | 1.56 | 2.57 | | | 3 | 308 |
| 370 | GVMVSHRSG | 378 | .02 | | | | | 1.44 | 1.97 | 1.59 | | 1 | 309 |
| 371 | VMVSHRSGE | 379 | -.32 | | 1.85 | | | | | | | 1 | 310 |
| 372 | MVSHRSGET | 380 | -.87 | | | | 2.20 | | | | 1.65 | 2 | 311 |
| 373 | VSHRSGET<u>E</u> | 381 | -.31 | | | | | | | | | 0 | 312 |

Suitable sequence ALT_1_ME11 = FGAGW<i>GVMVSHRS</i>GET (SEQ ID NO: 313)(residues 365-381)
[epitope 1 = bold, epitope 2 = underlined, epitope 3 = italic, epitope 4 = grey background, epitope 5 = last nine amino acids]

---

The invention claimed is:

1. A composition comprising a peptide which has a length of 13 to 25 amino acids and which comprises a region having the sequence of SEQ ID NO:292, a pharmaceutically acceptable carrier and an adjuvant.

2. The composition of claim 1, wherein the region has the sequence SEQ ID NO: 419 or SEQ ID NO: 420.

3. A composition comprising a peptide which has a length of 13 to 25 amino acids and which comprises a region having the sequence of SEQ ID NO:292, an effective amount of a preservative and a pharmaceutically acceptable carrier.

4. The composition of claim 3, wherein the region has the sequence SEQ ID NO: 419 or SEQ ID NO: 420.

* * * * *